US012653839B2

(12) United States Patent      (10) Patent No.:   US 12,653,839 B2

Hung et al.            (45) Date of Patent:     Jun. 16, 2026

(54) PROTEIN PAYLOAD RELEASE

(71) Applicant: SENTI BIOSCIENCES, INC., South San Francisco, CA (US)

(72) Inventors: Michelle Elizabeth Hung, South San Francisco, CA (US); Russell Morrison Gordley, San Francisco, CA (US); Gary Lee, Castro Valley, CA (US)

(73) Assignee: Senti Biosciences, Inc., South San Francisco, CA (US)

( * ) Notice: Subject to any disclaimer, the term of this patent is extended or adjusted under 35 U.S.C. 154(b) by 390 days.

(21) Appl. No.: 18/143,338

(22) Filed: May 4, 2023

(65) Prior Publication Data

US 2024/0082303 A1      Mar. 14, 2024

Related U.S. Application Data

(63) Continuation of application No. PCT/US2021/058134, filed on Nov. 4, 2021.

(60) Provisional application No. 63/193,004, filed on May 25, 2021, provisional application No. 63/109,812, filed on Nov. 4, 2020.

(51) Int. Cl.

| | |
|---|---|
| *A61K 35/17* | (2025.01) |
| *A61K 40/11* | (2025.01) |
| *A61K 40/15* | (2025.01) |
| *A61K 40/31* | (2025.01) |
| *A61K 40/42* | (2025.01) |
| *C07K 14/54* | (2006.01) |

(52) U.S. Cl.

CPC .............. *A61K 35/17* (2013.01); *A61K 40/11* (2025.01); *A61K 40/15* (2025.01); *A61K 40/31* (2025.01); *A61K 40/4234* (2025.01); *C07K 14/5434* (2013.01); *C07K 14/5443* (2013.01); *A61K 2239/21* (2023.05); *A61K 2239/22* (2023.05); *C07K 2319/50* (2013.01)

(58) Field of Classification Search

CPC ........ A61K 35/17; A61K 40/11; A61K 40/15; A61K 40/31; A61K 40/4234; C07K 14/5434; C07K 14/5443

See application file for complete search history.

(56) References Cited

U.S. PATENT DOCUMENTS

| | | | |
|---|---|---|---|
| 2016/0033490 A1* | 2/2016 | Berget | G01N 33/573 |
| | | | 536/23.53 |
| 2016/0264665 A1 | 9/2016 | Lim et al. | |
| 2020/0102363 A1 | 4/2020 | Mishra et al. | |
| 2022/0056092 A1* | 2/2022 | Ols | C07K 16/2803 |

FOREIGN PATENT DOCUMENTS

| | | |
|---|---|---|
| JP | 2018-506293 | 3/2018 |
| WO | WO 2018/237022 A1 | 12/2018 |
| WO | WO 2019/099689 A1 | 5/2019 |
| WO | WO 2019/118518 A2 | 6/2019 |
| WO | WO 2020/118076 A1 | 6/2020 |
| WO | WO 2020/123716 A1 | 6/2020 |

OTHER PUBLICATIONS

Jing Y et al. "Identification of an ADAM17 Cleavage Region in Human CD16 (FcγRIII) and the Engineering of a Non-Cleavable Version of the Receptor in NK Cells." PLoS One. Mar. 27, 2015;10(3):e0121788 (Year: 2015).*

Notice of Reasons for Rejection for Japanese Application No. 2023-527260 mailed Oct. 2, 2025, 12 pages.

Zhou, et al., "Simultaneous Expression of Displayed and Secreted Antibodies for Antibody Screen," PLOS ONE, vol. 8, Issue 11, Nov. 11, 2013, 7 pages.

Sharma, et al., "Membrane-bound and soluble forms of an NMDA receptor extracellular domain retain epitopes targeted in autoimmune encephalitis," BMC Biotechnology, vol. 18, No. 1, Jun. 27, 2018, 9 pages.

Extended European Search Report for EP21890098.3 mailed Sep. 16, 2024, 15 pages.

Office Action and Search Report for TW110141197 mailed Apr. 11, 2025, 18 pages.

International Search Report and Written Opinion for PCT/US2021/058134 mailed Feb. 15, 2022, 12 pages.

* cited by examiner

*Primary Examiner* — Lora E Barnhart Driscoll

(74) *Attorney, Agent, or Firm* — DLA Piper LLP (US)

(57) ABSTRACT

Described herein are chimeric proteins, specifically membrane-cleavable chimeric systems. Also described herein are nucleic acids, cells, and methods directed to the same.

30 Claims, 7 Drawing Sheets

Specification includes a Sequence Listing.

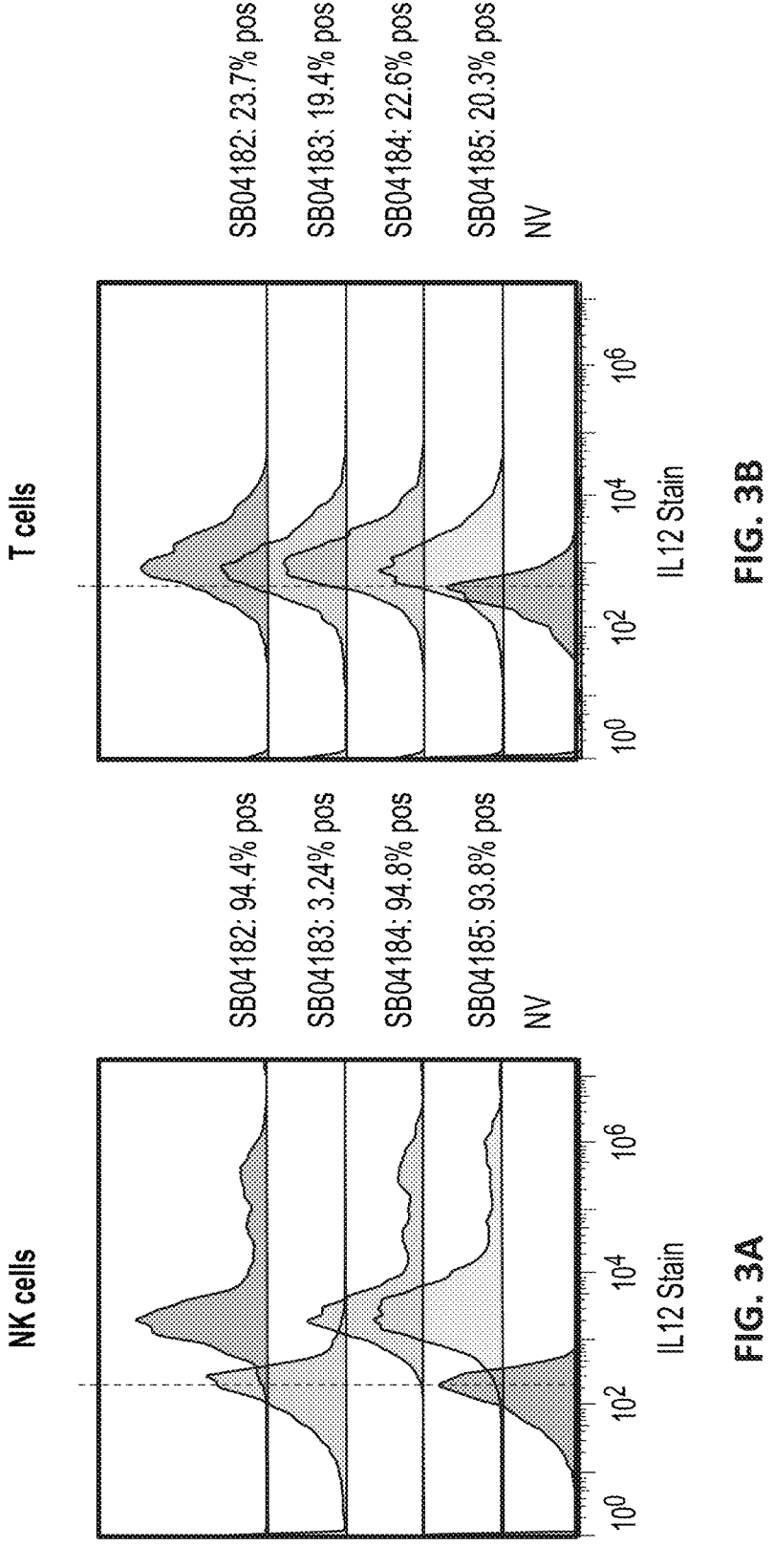

Sample - labels in order from top to bottom

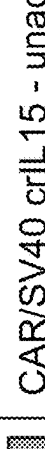

CAR/SV40 crIL15 - unactivated

CAR/SV40 crIL15 - target cell 1 activated

CAR/SV40 crIL15 - target cell 2 activated

CAR/NFAT crIL15+IL-15Rsushi - unactivated

CAR/NFAT crIL15+IL-15Rsushi - target cell 1 activated

CAR/NFAT crIL1+IL-15Rsushi - target cell 2 activated

CAR/NFAT crIL15 - unactivated

CAR/NFAT crIL15 - target cell 1 activated

CAR/NFAT crIL15 - target cell 2 activated

Untransduced - unactivated

Untransduced - target cell 1 activated

Untransduced - target cell 2 activated

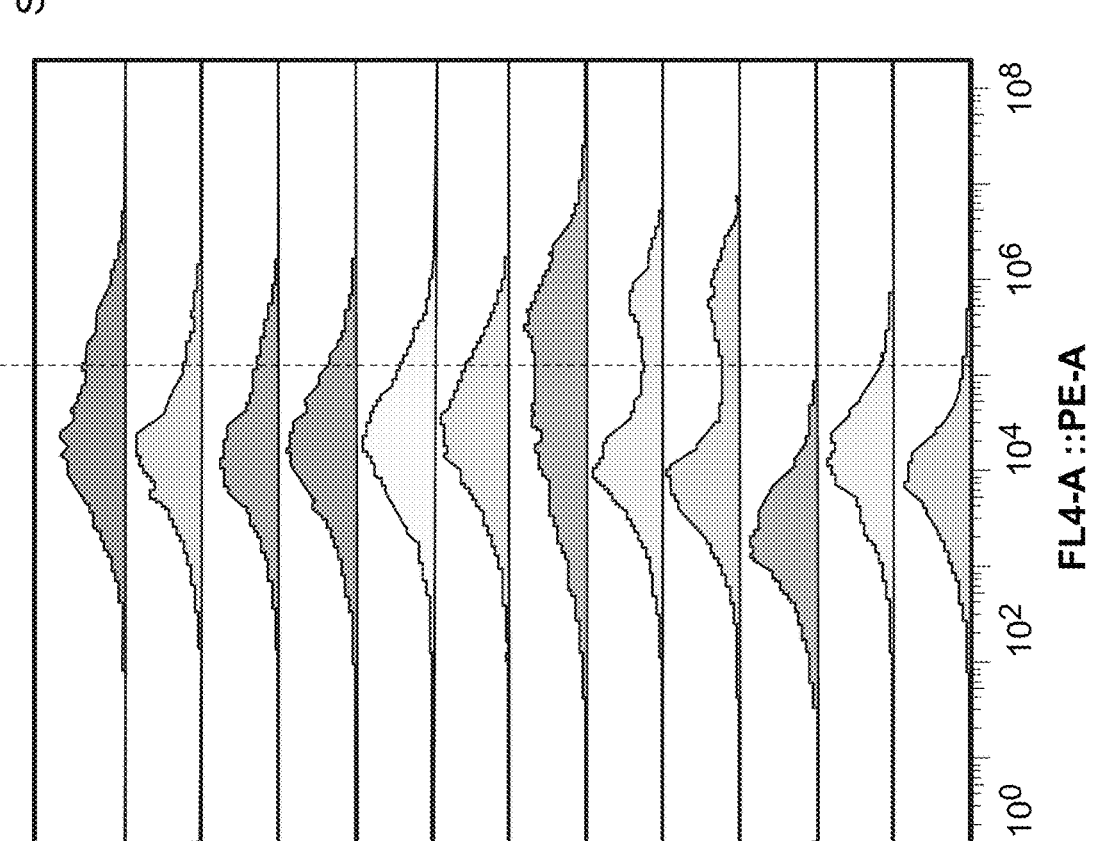

PROTEIN PAYLOAD RELEASE

CROSS REFERENCE TO RELATED APPLICATIONS

This application is a continuation of International Application No. PCT/US2021/058134, filed Nov. 4, 2023, which claims the benefit of U.S. Provisional Application Nos. 63/193,004 filed May 25, 2021 and 63/109,812 filed Nov. 4, 2020, each of which is hereby incorporated in their entirety by reference for all purposes.

SEQUENCE LISTING

The instant application contains a Sequence Listing which has been submitted electronically in xml format and is hereby incorporated by reference in its entirety. Said xml. copy, created on 24 May 2023, is named STB-024WOC1 and is 3,23,502 bytes in size.

BACKGROUND

Cell-based therapy platforms provide promising avenues for treating a variety of diseases. One such promising platform is CAR-T based therapies in the treatment of cancer. Given their promise, improvements in cell-based therapies are needed. An active area of exploration is engineering cell-based therapies to produce and/or secrete effector molecules such as cytokines, a process referred to as armoring, that enhance the cell-based therapy. For example, unarmored CAR-T therapies have poor efficacy in solid tumors and armoring can impact the entire cancer immunity cycle and boost the activity of CAR-T. However, uncontrolled or unregulated armoring strategies can have negative impacts on treatment, such as off-target effects and toxicity in subjects. Thus, additional methods of controlling and regulating the armoring of cell-based therapies, such as regulating production and/or secretion of payload effector molecules, are required.

SUMMARY

Provided herein, in some embodiments, is a cell-based therapy platform involving regulated armoring of the cell-based therapy, such as regulated secretion of payload effector molecules. Also provided herein, in some embodiments, is a combinatorial cell-based immunotherapy involving regulated armoring for the targeted treatment of cancer, such as ovarian cancer, breast cancer, colon cancer, lung cancer, and pancreatic cancer.

The therapy provided herein, however, can limit systemic toxicity of armoring. For example, the immunotherapy provided herein can be tumor-specific and effective while limiting systemic toxicity and/or other off-target effects due to armoring. These therapies deliver proteins of interest, such as immunomodulatory effector molecules, in a regulated manner, including regulation of secretion kinetics, cell state specificity, and cell or tissue specificity. The design of the delivery vehicle is optimized to improve overall function in cell-based therapies, such as cancer therapy, including, but not limited to, optimization of the membrane-cleavage sites, promoters, linkers, signal peptides, delivery methods, combination, regulation, and order of the immunomodulatory effector molecules.

Non-limiting examples of effector molecules encompassed by the present disclosure include cytokines, antibodies, chemokines, nucleotides, peptides, enzymes, and oncolytic viruses. For example, cells may be engineered to express and secrete in a regulated manner at least one, two, three or more of the following effector molecules: IL-12, IL-16, IFN-β, IFN-γ, IL-2, IL-15, IL-7, IL-36γ, IL-18, IL-1β, IL-21, OX40-ligand, CD40L, anti-PD-1 antibodies, anti-PD-L1 antibodies, anti-CTLA-4 antibodies, anti-TGFβ antibodies, anti-TNFR2, MIP1α (CCL3), MIP1β (CCL5), CCL21, CpG oligodeoxynucleotides, and anti-tumor peptides (e.g., anti-microbial peptides having anti-tumor activity, see, e.g., Gaspar, D. et al. *Front Microbiol.* 2013; 4: 294; Chu, H. et al. PLoS One. 2015; 10(5): e0126390, and website:aps.unmc.edu/AP/main.php).

Provided for herein is an engineered nucleic acid comprising an expression cassette comprising a promoter and an exogenous polynucleotide sequence encoding a membrane-cleavable chimeric protein, oriented from N-terminal to C-terminal, having the formula: S-C-MT or MT-C-S, wherein S comprises a secretable effector molecule, C comprises a protease cleavage site, and MT comprises a cell membrane tethering domain, wherein the promoter is operably linked to the exogenous polynucleotide sequence, and wherein S-C-MT or MT-C-S is configured to be expressed as a single polypeptide.

Also provided for herein is a membrane-cleavable chimeric protein, oriented from N-terminal to C-terminal, having the formula: S-C-MT or MT-C-S, wherein S comprises a secretable effector molecule, C comprises a protease cleavage site, and MT comprises a cell membrane tethering domain, wherein S-C-MT or MT-C-S is configured to be expressed as a single polypeptide.

Also provided for herein is an isolated cell comprising an engineered nucleic acid, wherein the engineered nucleic acid comprises an expression cassette comprising a promoter and an exogenous polynucleotide sequence encoding a membrane-cleavable chimeric protein, oriented from N-terminal to C-terminal, having the formula: S-C-MT or MT-C-S, wherein S comprises a secretable effector molecule, C comprises a protease cleavage site, and MT comprises a cell membrane tethering domain, wherein the promoter is operably linked to the exogenous polynucleotide sequence, and wherein S-C-MT or MT-C-S is configured to be expressed as a single polypeptide.

Also provided for herein is an isolated cell comprising a membrane-cleavable chimeric protein, wherein the membrane-cleavable chimeric protein, oriented from N-terminal to C-terminal, has the formula: S-C-MT or MT-C-S, wherein S comprises a secretable effector molecule, C comprises a protease cleavage site, and MT comprises a cell membrane tethering domain, and wherein S-C-MT or MT-C-S is configured to be expressed as a single polypeptide.

Also provided for herein is a method of inducing release of a membrane-tethered effector molecule, comprising: a) providing a cell, wherein the cell comprises a membrane-bound protease and a membrane-cleavable chimeric protein, oriented from N-terminal to C-terminal, having the formula: S-C-MT or MT-C-S, wherein S comprises a secretable effector molecule, C comprises a cognate protease cleavage site of the membrane-bound protease, wherein S-C-MT or MT-C-S is configured to be expressed as a single polypeptide; and b) culturing the cell under conditions suitable for expression of the membrane-bound protease and the membrane-cleavable chimeric protein, wherein upon expression, the membrane-cleavable chimeric protein is tethered to the cell membrane of the cell, and wherein, upon expression, the membrane-bound protease cleaves the cognate membrane-bound protease cleavage site of the membrane-cleavable chimeric protein, thereby releasing the secretable effector molecule from the cell membrane.

In some aspects, the promoter is a constitutive promoter. In some aspects, the constitutive promoter is selected from the group consisting of: CAG, HLP, CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb. In some aspects, the promoter is an inducible promoter. In some aspects, the inducible promoter comprises a minimal promoter and a responsive element selected from the group consisting of: NFkB response element, CREB response element, NFAT response element, SRF response element 1, SRF response element 2, AP1 response element, TCF-LEF response element promoter fusion, Hypoxia responsive element, SMAD binding element, STAT3 binding site, inducer molecule responsive promoters, and tandem repeats thereof.

In some aspects, the promoter is a synthetic promoter. In some aspects, the synthetic promoter comprises an activation-conditional control polypeptide- (ACP-) binding domain sequence and a promoter sequence. In some aspects, the promoter sequence is derived from a promoter selected from the group consisting of: minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, minCMV, YB_TATA, minTK, inducer molecule responsive promoters, and tandem repeats thereof. In some aspects, the ACP-binding domain comprises one or more zinc finger binding sites. In some aspects, the synthetic promoter is regulatable by an activation-conditional control polypeptide (ACP) that binds to the ACP-binding domain of the synthetic promoter.

In some aspects, the ACP is a transcriptional modulator. In some aspects, the ACP is a transcriptional repressor. In some aspects, the ACP is a transcriptional activator. In some aspects, the ACP further comprises a repressible protease and one or more cognate cleavage sites of the repressible protease. In some aspects, the ACP further comprises a hormone-binding domain of estrogen receptor (ERT2 domain).

In some aspects, the ACP is a transcription factor. In some aspects, the transcription factor is a zinc-finger-containing transcription factor. In some aspects, the ACP comprises a DNA-binding zinc finger protein domain (ZF protein domain) and a transcriptional effector domain. In some aspects, the ZF protein domain is modular in design and is composed of zinc finger arrays (ZFA). In some aspects, the ZF protein domain comprises one to ten ZFA.

In some aspects, the effector domain is selected from the group consisting of: a Herpes Simplex Virus Protein 16 (VP16) activation domain; an activation domain comprising four tandem copies of VP16, a VP64 activation domain; a p65 activation domain of NFkB; an Epstein-Barr virus R transactivator (Rta) activation domain; a tripartite activator comprising the VP64, the p65, and the Rta activation domains (VPR activation domain); a histone acetyltransferase (HAT) core domain of the human E1A-associated protein p300 (p$^{300}$ HAT core activation domain); a Krüppel associated box (KRAB) repression domain; a Repressor Element Silencing Transcription Factor (REST) repression domain; a WRPW (SEQ ID NO: 224) motif of the hairy-related basic helix-loop-helix repressor proteins, the motif is known as a WRPW (SEQ ID NO: 224) repression domain;

a DNA (cytosine-5)-methyltransferase 3B (DNMT3B) repression domain; and an HP1 alpha chromoshadow repression domain.

In some aspects, the one or more cognate cleavage sites of the repressible protease are localized between the ZF protein domain and the effector domain. In some aspects, the repressible protease is hepatitis C virus (HCV) nonstructural protein 3 (NS3). In some aspects, the cognate cleavage site comprises an NS3 protease cleavage site. In some aspects, the NS3 protease cleavage site comprises a NS3/NS4A, a NS4A/NS4B, a NS4B/NS5A, or a NS5A/NS5B junction cleavage site. In some aspects, the NS3 protease can be repressed by a protease inhibitor. In some aspects, the protease inhibitor is selected from the group consisting of: simeprevir, danoprevir, asunaprevir, ciluprevir, boceprevir, sovaprevir, paritaprevir, telaprevir, grazoprevir, glecaprevir, and voxiloprevir.

In some aspects, the ACP is capable of undergoing nuclear localization upon binding of the ERT2 domain to tamoxifen or a metabolite thereof. In some aspects, the tamoxifen metabolite is selected from the group consisting of: 4-hydroxytamoxifen, N-desmethyltamoxifen, tamoxifen-N-oxide, and endoxifen.

In some aspects, the ACP further comprises a degron domain, and wherein the degron domain is operably linked to the ACP. In some aspects, the degron domain is derived from a degron selected from the group consisting of HCV NS4 degron, PEST (two copies of residues 277-307 of human IkBα), GRR (residues 352-408 of human p105), DRR (residues 210-295 of yeast Cdc34), SNS (tandem repeat of SP2 and NB (SP2-NB-SP2 of influenza A or influenza B), RPB (four copies of residues 1688-1702 of yeast RPB), SPmix (tandem repeat of SP1 and SP2 (SP2-SP1-SP2-SP1-SP2 of influenza A virus M2 protein), NS2 (three copies of residues 79-93 of influenza A virus NS protein), ODC (residues 106-142 of ornithine decarboxylase), Nek2A, mouse ODC (residues 422-461), mouse ODC_DA (residues 422-461 of mODC including D433A and D434A point mutations), an APC/C degron, a COP1 E3 ligase binding degron motif, a CRL4-Cdt2 binding PIP degron, an actinfilin-binding degron, a KEAP1 binding degron, a KLHL2 and KLHL3 binding degron, an MDM2 binding motif, an N-degron, a hydroxyproline modification in hypoxia signaling, a phytohormone-dependent SCF-LRR-binding degron, an SCF ubiquitin ligase binding phosphodegron, a phytohormone-dependent SCF-LRR-binding degron, a DSGxxS phospho-dependent degron, an Siah binding motif, an SPOP SBC docking motif, and a PCNA binding PIP box. In some aspects, the degron domain comprises a cereblon (CRBN) polypeptide substrate domain capable of binding CRBN in response to an immunomodulatory drug (IMiD) thereby promoting ubiquitin pathway-mediated degradation of the ACP. In some aspects, the CRBN polypeptide substrate domain is selected from the group consisting of: IKZF1, IKZF3, CK1a, ZFP91, GSPT1, MEIS2, GSS E4F1, ZN276, ZN517, ZN582, ZN653, ZN654, ZN692, ZN787, and ZN827, or a fragment thereof that is capable of drug-inducible binding of CRBN. In some aspects, the CRBN polypeptide substrate domain is a chimeric fusion product of native CRBN polypeptide sequences. In some aspects, the CRBN polypeptide substrate domain is a IKZF3/ZFP91/IKZF3 chimeric fusion product having the amino acid sequence of FNVLMVHKRSHT-GERPLQCEICGFTCRQKGNLLRHIKLHT-GEKPFKCHLCNYACQRR DAL (SEQ ID NO: 175). In some aspects, the IMiD is an FDA-approved drug. In some aspects, the IMiD is selected from the group consisting of:

thalidomide, lenalidomide, and pomalidomide. In some aspects, the degron domain is N-terminal of the repressible protease, C-terminal of the repressible protease, N-terminal of the ZF protein domain, C-terminal of the ZF protein domain, N-terminal of the effector domain, or C-terminal of the effector domain.

In some aspects, the promoter is a tissue-specific promoter.

In some aspects, the secretable effector molecule comprises a signal peptide or a signal-anchor sequence. In some aspects, the signal peptide comprises a native signal peptide native to the secretable effector molecule. In some aspects, the signal peptide comprises a non-native signal peptide or the signal-anchor sequence comprises a non-native signal-anchor sequence non-native to the secretable effector molecule. In some aspects, the non-native signal peptide or the non-native signal-anchor sequence is selected from the group consisting of: IL-12, IL-2, optimized IL-2, trypsion-gen-2, *Gaussia* luciferase, CD5, human IgKVII, murine IgKVII, VSV-G, prolactin, serum albumin preprotein, azurocidin preprotein, osteonectin, CD33, IL6, IL8, CCL2, TIMP2, VEGFB, osteoprotegerin, serpin E1, GROalpha, CXCL12, IL21, CD8, NKG2D, TNFR2, and GMCSF.

In some aspects, the secretable effector molecule is selected from a therapeutic class, wherein the therapeutic class is selected from the group consisting of: a cytokine, a chemokine, a homing molecule, a growth factor, a co-activation molecule, a tumor microenvironment modifier, a ligand, an antibody, a peptide, and an enzyme. In some aspects, the cytokine is selected from the group consisting of: IL-1-beta, IL-2, IL-4, IL-6, IL-7, IL-10, IL-12, an IL-12p70 fusion protein, IL-15, IL-17A, IL-18, IL-21, IL-22, Type I interferons, Interferon-gamma, and TNF-alpha. In some aspects, the secretable effector molecule comprises IL-15, IL-12, or an IL-12p70 fusion protein. In some aspects, the secretable effector molecule comprises IL-15. In some aspects, the secretable effector molecule comprises IL-15 having the amino acid sequence of SEQ ID NO: 199. In some aspects, the secretable effector molecule comprises IL-15 and an IL-15Rα sushi domain. In some aspects, the secretable effector molecule comprises and IL-15/IL-15Rα sushi domain fusion protein having the amino acid sequence of SEQ ID NO: 202. In some aspects, the secretable effector molecule consists of IL-15 and IL-15Rα sushi domain. In some aspects, the secretable effector molecule comprises IL-12. In some aspects, the secretable effector molecule comprises an IL-12p70 fusion protein. In some aspects, the secretable effector molecule comprises an IL-12p70 fusion protein having the amino acid sequence of SEQ ID NO: 203. In some aspects, the secretable effector molecule consists of IL-12. In some aspects, the secretable effector molecule consists of an IL-12p70 fusion protein. In some aspects, the secretable effector molecule is IL-15. In some aspects, the chemokine is selected from the group consisting of: CCL21a, CXCL10, CXCL11, CXCL13, a CXCL10-CXCL11 fusion protein, CCL19, CXCL9, and XCL1. In some aspects, the homing molecule is selected from the group consisting of: anti-integrin alpha4,beta7; anti-MAdCAM; SDF1; and MMP-2. In some aspects, the growth factor is selected from the group consisting of: FLT3L and GM-CSF. In some aspects, the co-activation molecule is selected from the group consisting of: 4-1BBL and CD40L. In some aspects, the tumor microenvironment modifier is selected from the group consisting of: adenosine deaminase, a TGFbeta inhibitor, an immune checkpoint inhibitor, a VEGF inhibitor, and HPGE2. In some aspects, the TGFbeta inhibitor is selected from the group consisting of: an anti-TGFbeta peptide, an anti-TGFbeta antibody, a TGFb-TRAP, and a combination thereof. In some aspects, the immune checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody. In some aspects, the VEGF inhibitor comprises an anti-VEGF antibody, an anti-VEGF peptide, or a combination thereof. In some aspects, the secretable effector molecule is a human-derived effector molecule.

In some aspects, the protease cleavage site is selected from the group consisting of: a Type 1 transmembrane protease cleavage site, a Type II transmembrane protease cleavage site, a GPI anchored protease cleavage site, an ADAM8 protease cleavage site, an ADAM9 protease cleavage site, an ADAM10 protease cleavage site, an ADAM12 protease cleavage site, an ADAM15 protease cleavage site, an ADAM17 protease cleavage site, an ADAM19 protease cleavage site, an ADAM20 protease cleavage site, an ADAM21 protease cleavage site, an ADAM28 protease cleavage site, an ADAM30 protease cleavage site, an ADAM33 protease cleavage site, a BACE1 protease cleavage site, a BACE2 protease cleavage site, a SIP protease cleavage site, an MT1-MMP protease cleavage site, an MT3-MMP protease cleavage site, an MT5-MMP protease cleavage site, a furin protease cleavage site, a PCSK7 protease cleavage site, a matriptase protease cleavage site, a matriptase-2 protease cleavage site, an MMP9 protease cleavage site, and an NS3 protease cleavage site. In some aspects, the protease cleavage site is cleavable by a protease selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, an MMP9 protease, and an NS3 protease.

In some aspects, the protease cleavage site is cleavable by an ADAM17 protease. In some aspects, the protease cleavage site comprises a first region having the amino acid sequence of PRAE (SEQ ID NO: 176). In some aspects, the protease cleavage site comprises a second region having the amino acid sequence of KGG (SEQ ID NO: 177). In some aspects, the first region is located N-terminal to the second region. In some aspects, the protease cleavage site comprises the amino acid sequence of PRAEX1X2KGG (SEQ ID NO: 219), wherein X1 is A, Y, P, S, or F, and wherein X2 is V, L, S, I, Y, T, or A. In some aspects, the protease cleavage site comprises the amino acid sequence of PRAEX1X2KGG (SEQ ID NO: 178), wherein X1 is A, Y, P, S, or F, and wherein X2 is V, L, S, I, Y, or T. In some aspects, the protease cleavage site comprises the amino acid sequence of PRAEAVKGG (SEQ ID NO: 179). In some aspects, the protease cleavage site comprises the amino acid sequence of PRAEALKGG (SEQ ID NO: 180). In some aspects, the protease cleavage site comprises the amino acid sequence of PRAEYSKGG (SEQ ID NO: 181). In some aspects, the protease cleavage site comprises the amino acid sequence of PRAEPIKGG (SEQ ID NO: 182). In some aspects, the protease cleavage site comprises the amino acid sequence of PRAEAYKGG (SEQ ID NO: 183). In some aspects, the protease cleavage site comprises the amino acid sequence of PRAESSKGG (SEQ ID NO: 184). In some aspects, the protease cleavage site comprises the amino acid sequence of PRAEFTKGG (SEQ ID NO: 185). In some aspects, the protease cleavage site comprises the amino acid sequence of PRAEAAKGG (SEQ ID NO: 186). In some aspects, the protease cleavage site comprises the amino acid sequence of DEPHYSQRR (SEQ ID NO: 187). In some aspects, the protease cleavage site comprises the amino acid sequence of PPLGPIFNPG (SEQ ID NO: 188). In some aspects, the protease cleavage site comprises the amino acid sequence of PLAQAYRSS (SEQ ID NO: 189). In some aspects, the protease cleavage site comprises the amino acid sequence of TPIDSSFNPD (SEQ ID NO: 190). In some aspects, the protease cleavage site comprises the amino acid sequence of VTPEPIFSLI (SEQ ID NO: 191). In some aspects, the protease cleavage site comprises the amino acid sequence of ITQGLAVSTISSFF (SEQ ID NO: 198)

In some aspects, the cell membrane tethering domain comprises a transmembrane-intracellular domain or a transmembrane domain. In some aspects, the transmembrane-intracellular domain and/or transmembrane domain is derived from PDGFR-beta, CD8, CD28, CD3zeta-chain, CD4, 4-1BB, OX40, ICOS, CTLA-4, PD-1, LAG-3, 2B4, LNGFR, NKG2D, EpoR, TNFR2, B7-1, or BTLA. In some aspects, the cell membrane tethering domain comprises a cell surface receptor, or a cell membrane-bound portion thereof.

In some aspects, the cell membrane tethering domain comprises a post-translational modification tag, or motif capable of post-translational modification to modify the chimeric protein to include a post-translational modification tag, where the post-translational modification tag is capable of association with a cell membrane. In some aspects, the post-translational modification tag comprises a lipid-anchor domain, optionally wherein the lipid-anchor domain is selected from the group consisting of: a GPI lipid-anchor, a myristoylation tag, and a palmitoylation tag.

In some aspects, when expressed in a cell, the secretable effector molecule is tethered to a cell membrane of the cell. In some aspects, when expressed in a cell expressing a protease capable of cleaving the protease cleavage site, the secretable effector molecule is released from the cell membrane. In some aspects, the protease expressed on the cell membrane is endogenous to the cell. In some aspects, the protease is selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, and an MMP9 protease. In some aspects, the protease is an ADAM17 protease.

In some aspects, the protease expressed on the cell membrane is heterologous to the cell. In some aspects, the protease is hepatitis C virus (HCV) nonstructural protein 3

(NS3). In some aspects, the protease cleavage site comprises an NS3 protease cleavage site. In some aspects, the NS3 protease cleavage site comprises a NS3/NS4A, a NS4A/NS4B, a NS4B/NS5A, or a NS5A/NS5B junction cleavage site. In some aspects, the protease can be repressed by a protease inhibitor. In some aspects, the protease inhibitor is selected from the group consisting of: simeprevir, danoprevir, asunaprevir, ciluprevir, boceprevir, sovaprevir, paritaprevir, telaprevir, grazoprevir, glecaprevir, and voxiloprevir. In some aspects, expression and/or localization of the protease is capable of regulation. In some aspects, the expression and/or localization is regulated by a cell state of the cell.

In some aspects, the engineered nucleic acid is a single-stranded or double-stranded nucleic acid selected from the group consisting of: a DNA, cDNA, an RNA, an mRNA, and a naked plasmid.

In some aspects, the isolated cell is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, a mesenchymal stromal cell (MSC), an induced pluripotent stem cell (iPSC), and an iPSC-derived cell. In some aspects, the isolated cell is a Natural Killer (NK) cell.

In some aspects, the isolated cell is autologous. In some aspects, the isolated cell is allogeneic. In some aspects, the isolated cell is a tumor cell selected from the group consisting of: a bladder tumor cell, a brain tumor cell, a breast tumor cell, a cervical tumor cell, a colorectal tumor cell, an esophageal tumor cell, a glioma cell, a kidney tumor cell, a liver tumor cell, a lung tumor cell, a melanoma cell, an ovarian tumor cell, a pancreatic tumor cell, a prostate tumor cell, a skin tumor cell, a thyroid tumor cell, and a uterine tumor cell.

In some aspects, the isolated cell was engineered via transduction with an oncolytic virus.

In some aspects, the isolated cell further comprises a protease capable of cleaving the protease cleavage site. In some aspects, the protease is an endogenous protease. In some aspects, the endogenous protease is selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, and an MMP9 protease. In some aspects, the endogenous protease is an ADAM17 protease. In some aspects, the protease is a heterologous protease. In some aspects, the heterologous protease is hepatitis C virus (HCV) nonstructural protein 3 (NS3). In some aspects, the protease is expressed on the cell membrane of the isolated cell. In some aspects, the protease is capable of cleaving the protease cleavage site. In some aspects, cleavage of the protease cleavage site releases the secretable effector molecule from the cell membrane of the isolated cell.

In some aspects, the protease cleavage site comprises a first region having the amino acid sequence of PRAE (SEQ ID NO: 176). In some aspects, the protease cleavage site comprises a second region having the amino acid sequence of KGG (SEQ ID NO: 177). In some aspects, the first region is located N-terminal to the second region. In some aspects, the protease cleavage site comprises the amino acid sequence of PRAEX1X2KGG (SEQ ID NO: 219), wherein X1 is A, Y, P, S, or F, and wherein X2 is V, L, S, I, Y, T, or A. In some aspects, the protease cleavage site comprises the amino acid sequence of PRAEX1X2KGG (SEQ ID NO: 178), wherein X1 is A, Y, P, S, or F, and wherein X2 is V, L, S, I, Y, or T. In some aspects, the protease cleavage site comprises the amino acid sequence of PRAEAVKGG (SEQ ID NO: 179). In some aspects, the protease cleavage site comprises the amino acid sequence of PRAEALKGG (SEQ ID NO: 180). In some aspects, the protease cleavage site comprises the amino acid sequence of PRAEYSKGG (SEQ ID NO: 181). In some aspects, the protease cleavage site comprises the amino acid sequence of PRAEPIKGG (SEQ ID NO: 182). In some aspects, the protease cleavage site comprises the amino acid sequence of PRAEAYKGG (SEQ ID NO: 183). In some aspects, the protease cleavage site comprises the amino acid sequence of PRAESSKGG (SEQ ID NO: 184). In some aspects, the protease cleavage site comprises the amino acid sequence of PRAEFTKGG (SEQ ID NO: 185). In some aspects, the protease cleavage site comprises the amino acid sequence of PRAEAAKGG (SEQ ID NO: 186). In some aspects, the protease cleavage site comprises the amino acid sequence of DEPHYSQRR (SEQ ID NO: 187). In some aspects, the protease cleavage site comprises the amino acid sequence of PPLGPIFNPG (SEQ ID NO: 188). In some aspects, the protease cleavage site comprises the amino acid sequence of PLAQAYRSS (SEQ ID NO: 189). In some aspects, the protease cleavage site comprises the amino acid sequence of TPIDSSFNPD (SEQ ID NO: 190). In some aspects, the protease cleavage site comprises the amino acid sequence of VTPEPIFSLI (SEQ ID NO: 191). In some aspects, the protease cleavage site comprises the amino acid sequence of ITQGLAVSTISSFF (SEQ ID NO: 198).

In some aspects, the isolated cell further comprises an antigen recognizing receptor. In some aspects, the antigen recognizing receptor recognizes an antigen selected from the group consisting of: 5T4, ADAM9, AFP, AXL, B7-H3, B7-H4, B7-H6, C4.4, CA6, Cadherin 3, Cadherin 6, CCR4, CD123, CD133, CD138, CD142, CD166, CD25, CD30, CD352, CD37, CD38, CD44, CD56, CD66e, CD70, CD71, CD74, CD79b, CD80, CEA, CEACAM5, Claudin18.2, cMet, CSPG4, CTLA, DLK1, DLL3, DR5, EGFR, ENPP3, EpCAM, EphA2, Ephrin A4, ETBR, FGFR2, FGFR3, FRal-pha, FRb, GCC, GD2, GFRa4, gpA33, GPC3, gpNBM, GPRC5, HER2, IL-13R, IL-13Ra, IL-13Ra2, IL-8, IL-15, IL1RAP, Integrin aV, KIT, L1CAM, LAMP1, Lewis Y, LeY, LIV-1, LRRC, LY6E, MCSP, Mesothelin, MUC1, MUC16, MUC1C, NaPi2B, Nectin 4, NKG2D, NOTCH3, NY ESO 1, Ovarin, P-cadherin, pan-Erb2, PSCA, PSMA, PTK7, ROR1, S Aures, SCT, SLAMF7, SLITRK6, SSTR2, STEAP1, Survivin, TDGF1, TIM1, TROP2, and WT1. In some aspects, the antigen recognizing receptor comprises an antigen-binding domain. In some aspects, the antigen-binding domain comprises an antibody, an antigen-binding fragment of an antibody, a F(ab) fragment, a F(ab') fragment, a single chain variable fragment (scFv), or a single-domain antibody (sdAb). In some aspects, the antigen-binding domain comprises a single chain variable fragment (scFv). In some aspects, the scFv comprises a heavy chain variable domain (VH) and a light chain variable domain (VL). In some aspects, the VH and VL are separated by a peptide linker. In some aspects, the scFv comprises the structure VH-L-VL or VL-L-VH, wherein VH is the heavy chain variable domain, L is the peptide linker, and VL is the light chain variable domain. In some aspects, the antigen recognizing receptor is a chimeric antigen receptor (CAR) or T cell receptor (TCR).

In some aspects, the antigen recognizing receptor is a CAR. In some aspects, the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain. In some aspects, the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain. In some aspects, the CAR comprises a spacer region between the antigen-binding domain and the transmembrane domain.

Also provided for herein is a composition comprising any of the isolated cells described herein, and a pharmaceutically acceptable carrier.

Also provided for herein is a method of treating a subject in need thereof, the method comprising administering a therapeutically effective dose of any of the isolated cells described herein or any of the compositions described herein. In some aspects, the isolated cell is derived from the subject. In some aspects, the isolated cell is allogeneic with reference to the subject. In some aspects, the method further comprises administering a checkpoint inhibitor. In some aspects, the checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody. In some aspects, the method further comprises administering an anti-CD40 antibody.

Also provided for herein is a lipid-based structure comprising any of the engineered nucleic acids described herein, or any of the expression vectors described herein, or any of the membrane-cleavable chimeric proteins described herein. In some aspects, the lipid-based structure comprises an extracellular vesicle, a lipid nanoparticle, a micelle, or a liposome. In some aspects, the extracellular vesicle is selected from the group consisting of: a nanovesicle and an exosome. In some aspects, the lipid-based structure comprises a lipid nanoparticle or a micelle. In some aspects, the lipid-based structure comprises a liposome.

Also provided for herein is a composition comprising any of the lipid-based structures described herein, and a pharmaceutically acceptable carrier.

Also provided for herein is a method of treating a subject in need thereof, the method comprising administering a therapeutically effective dose of any of the lipid-based structures described herein or any of the compositions described herein. In some aspects, the administering comprises systemic administration. In some aspects, the lipid-based structure is capable of engineering a cell in the subject. In some aspects, the method further comprises administering a checkpoint inhibitor. In some aspects, the checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody. In some aspects, the method further comprises administering an anti-CD40 antibody.

Also provided for herein is a nanoparticle comprising any of the engineered nucleic acids described herein or any of the membrane-cleavable chimeric proteins described herein. In some aspects, the nanoparticle comprises an inorganic material.

Also provided for herein is a composition comprising any of the nanoparticles described herein.

Also provided for herein is a method of treating a subject in need thereof, the method comprising administering a therapeutically effective dose of any of the nanoparticles described herein, or any of the compositions described herein. In some aspects, the administering comprises systemic administration. In some aspects, the nanoparticle is capable of engineering a cell in the subject. In some aspects, the method further comprises administering a checkpoint inhibitor. In some aspects, the checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody. In some aspects, the method further comprises administering an anti-CD40 antibody.

Also provided for herein is a virus engineered to comprise any of the engineered nucleic acids described herein or any of the expression vectors described herein. In some aspects, the virus is selected from the group consisting of: a lentivirus, a retrovirus, an oncolytic virus, an adenovirus, an adeno-associated virus (AAV), and a virus-like particle (VLP).

Also provided for herein is a composition comprising any of the engineered viruses described herein, and a pharmaceutically acceptable carrier.

Also provided for herein is a method of treating a subject in need thereof, the method comprising administering a therapeutically effective dose of any of the engineered viruses described herein, or any of the compositions described herein. In some aspects, the administering comprises systemic administration. In some aspects, the engineered virus infects a cell in the subject and expresses the expression cassette. In some aspects, the method further comprises administering a checkpoint inhibitor. In some aspects, the checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody. In some aspects, the method further comprises administering an anti-CD40 antibody.

BRIEF DESCRIPTION OF THE DRAWINGS

FIGS. 3A-3C provide membrane-bound expression and secretion of IL-12 Membrane-Cleavable systems. FIG. 3A indicates membrane-bound expression of each Membrane-Cleavable IL-12 system in NK cells, as measured by flow cytometry. FIG. 3B indicates membrane-bound expression of each Membrane-Cleavable IL-12 system in T cells, as measured by flow cytometry. FIG. 3C shows IL-12 secretion for each Membrane-Cleavable IL-12 system expressed in NK cells and T cells.

FIGS. 4A-4B provide membrane-bound NK cell expression and secretion of various IL-15 Membrane-Cleavable systems. FIG. 4A indicates membrane-bound expression of each Membrane-Cleavable IL-15 system in NK cells, as measured by flow cytometry. FIG. 4B shows IL-15 secretion for each Membrane-Cleavable IL-15 system expressed in NK cells.

DETAILED DESCRIPTION

Figure 1A:
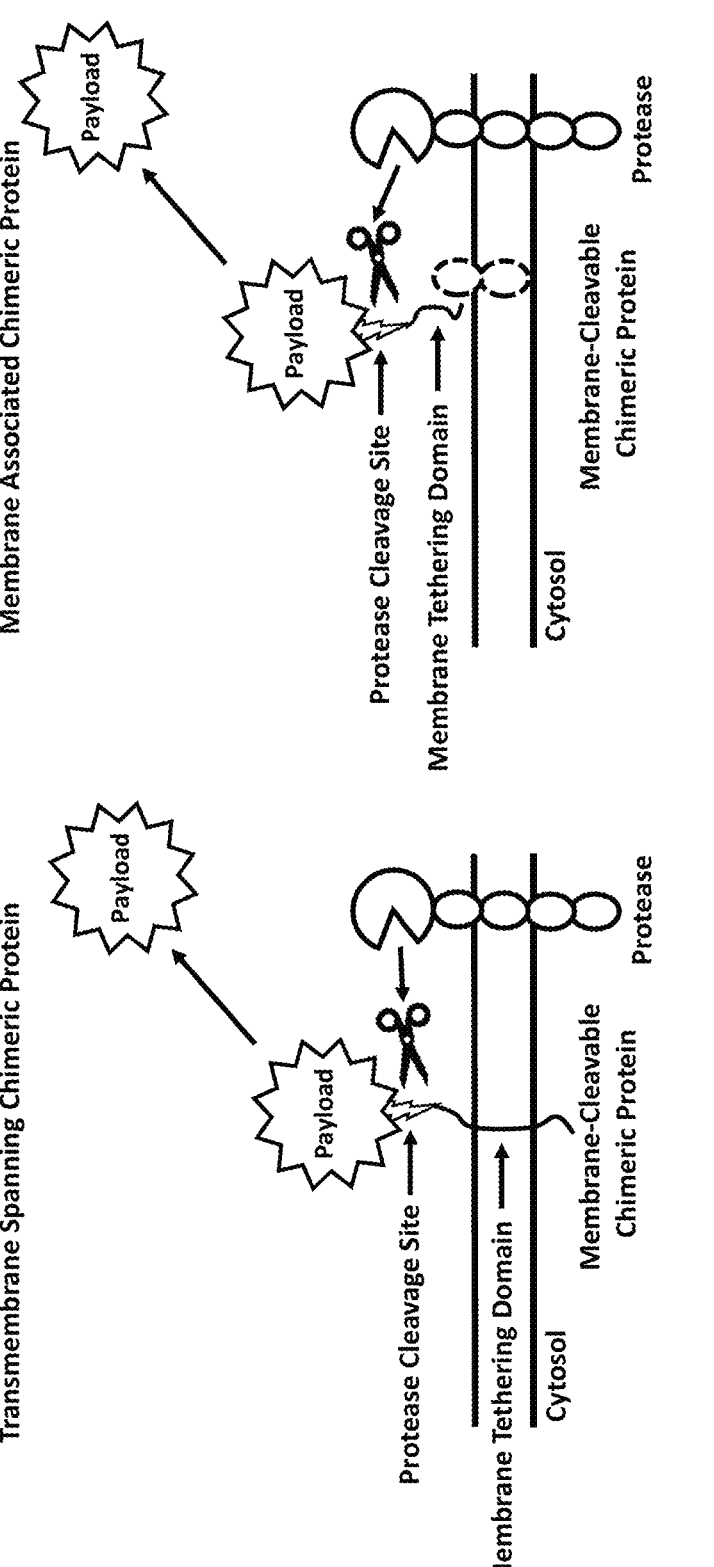
FIG. 1A illustrates a schematic of the Membrane-Cleavable system described herein in which a desired payload is expressed as a chimeric protein in which a protease cleavage site is inserted between the payload and membrane-tethering domain. The left panel illustrates a schematic of the Membrane-Cleavable system using a transmembrane spanning architecture (e.g., the chimeric protein contains a transmembrane domain). The right panel illustrates a schematic of the Membrane-Cleavable system using a membrane-associated architecture (e.g., the chimeric protein contains a post-translational modification tag allowing association with a cell membrane).

Chimeric proteins (or engineered nucleic acids encoding the chimeric proteins) are provided for herein having the formula S-C-MT or MT-C-S, oriented from N-terminal to C-terminal and expressed as a single polypeptide. S refers to a secretable effector molecule. C refers to a protease cleavage site. MT refers to a cell membrane tethering domain. The membrane-cleavable chimeric protein is engineered such that secretion of the effector molecule can be regulated in a protease-dependent manner. Specifically, the membrane-cleavable chimeric protein is engineered such that secretion of the effector molecule can be regulated as part of a "Membrane-Cleavable" system, where incorporation of a protease cleavage site ("C") and a cell membrane tethering domain ("MT") allow for regulated secretion of an effector molecule in a protease-dependent manner. Without wishing to be bound by theory, the components of the Membrane-Cleavable system present in the membrane-cleavable chimeric protein generally regulate secretion through the below cellular processes:

MT: The cell membrane tethering domain contains a transmembrane domain (or a transmembrane-intracellular domain) that directs cellular-trafficking of the chimeric protein such that the protein is inserted into, or otherwise associated with, a cell membrane ("tethered")

C: Following expression and localization of the chimeric protein into the cell membrane, the protease cleavage site directs cleavage of the chimeric protein such that the effector molecule is released ("secreted") into the extracellular space. Generally, the protease cleavage site is protease-specific, including sites engineered to be protease-specific. The protease cleavage site can be selected or engineered to achieve optimal protein expression, cell-type specific cleavage, cell-state specific cleavage, and/or cleavage and release of the payload at desired kinetics (e.g., ratio of membrane-bound to secreted chimeric protein levels)

In some aspects, membrane-cleavable chimeric proteins (or engineered nucleic acids encoding the membrane-cleavable chimeric proteins) are provided for herein having a protein of interest (e.g., any of the effector molecules described herein), a protease cleavage site, and a cell membrane tethering domain.

An "effector molecule," refers to a molecule (e.g., a nucleic acid such as DNA or RNA, or a protein (polypeptide) or peptide) that binds to another molecule and modulates the biological activity of that molecule to which it binds. For example, an effector molecule may act as a ligand to increase or decrease enzymatic activity, gene expression, or cell signaling. Thus, in some embodiments, an effector molecule modulates (activates or inhibits) different immunomodulatory mechanisms. By directly binding to and modulating a molecule, an effector molecule may also indirectly modulate a second, downstream molecule.

In certain embodiments described herein (e.g., in general, for all membrane-cleavable chimeric proteins described herein), an effector molecule is a secretable effector molecule (e.g., referred to as "S" in the formula S-C-MT or MT-C-S for membrane-cleavable chimeric proteins described herein). Non-limiting examples of effector molecules include cytokines, chemokines, enzymes that modulate metabolite levels, growth factors, co-activation molecules, tumor microenvironment modifiers, ligands, peptides, enzymes, antibodies, antibodies or decoy molecules that modulate cytokines, homing molecules, and/or integrins.

The term "modulate" encompasses maintenance of a biological activity, inhibition (partial or complete) of a biological activity, and stimulation/activation (partial or complete) of a biological activity. The term also encompasses decreasing or increasing (e.g., enhancing) a biological activity. Two different effector molecules are considered to "modulate different tumor-mediated immunosuppressive mechanisms" when one effector molecule modulates a tumor-mediated immunosuppressive mechanism (e.g., stimulates T cell signaling) that is different from the tumor-mediated immunosuppressive mechanism modulated by the other effector molecule (e.g., stimulates antigen presentation and/or processing).

Modulation by an effector molecule may be direct or indirect. Direct modulation occurs when an effector molecule binds to another molecule and modulates activity of that molecule. Indirect modulation occurs when an effector molecule binds to another molecule, modulates activity of that molecule, and as a result of that modulation, the activity of yet another molecule (to which the effector molecule is not bound) is modulated.

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in an increase in an immunostimulatory and/or anti-tumor immune response by at least 20%, at least 30%, at least 40%, at least 50%, at least 60%, at least 70%, at least 80%, at least 90%, at least 100%. In some embodiments, modulation of a tumor-mediated immunosuppressive mechanism results in an increase in an immunostimulatory and/or anti-tumor immune response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "an increase" in an immunostimulatory and/or anti-tumor immune response, for example, systemically or in a tumor microenvironment, is relative to the immunostimulatory and/or anti-tumor immune response that would otherwise occur, in the absence of the effector molecule(s).

In some embodiments, modulation of a tumor-mediated immunosuppressive mechanism by at least one effector molecule results in an increase in an immunostimulatory and/or anti-tumor immune response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in an increase in an immunostimulatory and/or anti-tumor immune response by at least 3 fold, at least 5 fold, at least 10 fold, at least 20 fold, at least 50 fold, or at least 100 fold. In some embodiments, modulation of a tumor-mediated immunosuppressive mechanism results in an increase in an immunostimulatory and/or anti-tumor immune response by 2-10, 2-20, 2-30, 2-40, 2-50, 2-60, 2-70, 2-80, 2-90, or 2-100 fold.

Non-limiting examples of immunostimulatory and/or anti-tumor immune mechanisms include T cell signaling, activity and/or recruitment, antigen presentation and/or processing, natural killer cell-mediated cytotoxic signaling, activity and/or recruitment, dendritic cell differentiation and/or maturation, immune cell recruitment, pro-inflammatory macrophage signaling, activity and/or recruitment, stroma degradation, immunostimulatory metabolite production, stimulator of interferon genes (STING) signaling (which increases the secretion of IFN and Th1 polarization, promoting an anti-tumor immune response), and/or Type I interferon signaling. An effector molecule may stimulate at least one (one or more) of the foregoing immunostimulatory mechanisms, thus resulting in an increase in an immunostimulatory response. Changes in the foregoing immunostimulatory and/or anti-tumor immune mechanisms may be assessed, for example, using in vitro assays for T cell proliferation or cytotoxicity, in vitro antigen presentation assays, expression assays (e.g., of particular markers), and/or cell secretion assays (e.g., of cytokines).

In some embodiments, modulation of a tumor-mediated immunosuppressive mechanism by at least one effector molecule results in a decrease in an immunosuppressive response (e.g., systemically or in the tumor microenvironment) by at least 10% (e.g., 10%, 20%, 30%, 40%, 50%, 60%, 70%, 80%, 90%, 100%, or 200%). For example, modulation of a tumor-mediated immunosuppressive mechanism may result in a decrease in an immunosuppressive response by at least 20%, at least 30%, at least 40%, at least 50%, at least 60%, at least 70%, at least 80%, at least 90%, at least 100%. In some embodiments, modulation of a tumor-mediated immunosuppressive mechanism results in a decrease in an immunosuppressive response 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%. It should be understood that "a decrease" in an immunosuppressive response, for example, systemically or in a tumor microenvironment, is relative to the immunosuppressive response that would otherwise occur, in the absence of the effector molecule(s).

In some embodiments, modulation of a tumor-mediated immunosuppressive mechanism by at least one effector molecule results in a decrease in an immunosuppressive response (e.g., systemically or in the tumor microenvironment) by at least 2 fold (e.g., 2, 3, 4, 5, 10, 25, 20, 25, 50, or 100 fold). For example, modulation of a tumor-mediated immunosuppressive mechanism may result in a decrease in an immunosuppressive response by at least 3 fold, at least 5 fold, at least 10 fold, at least 20 fold, at least 50 fold, or at least 100 fold. In some embodiments, modulation of a tumor-mediated immunosuppressive mechanism results in a decrease in an immunosuppressive response by 2-10, 2-20, 2-30, 2-40, 2-50, 2-60, 2-70, 2-80, 2-90, or 2-100 fold.

Non-limiting examples of immunosuppressive mechanisms include negative costimulatory signaling, pro-apoptotic signaling of cytotoxic cells (e.g., T cells and/or NK cells), T regulatory (Treg) cell signaling, tumor checkpoint molecule production/maintenance, myeloid-derived suppressor cell signaling, activity and/or recruitment, immunosuppressive factor/metabolite production, and/or vascular endothelial growth factor signaling. An effector molecule may inhibit at least one (one or more) of the foregoing immunosuppressive mechanisms, thus resulting in a decrease in an immunosuppressive response. Changes in the foregoing immunosuppressive mechanisms may be assessed, for example, by assaying for an increase in T cell proliferation and/or an increase in IFNγ production (negative co-stimulatory signaling, $T_{reg}$ cell signaling and/or MDSC); Annexin V/PI flow staining (pro-apoptotic signaling); flow staining for expression, e.g., PDL1 expression (tumor checkpoint molecule production/maintenance); ELISA, LUMINEX®, RNA via qPCR, enzymatic assays, e.g., IDO tryptophan catabolism (immunosuppressive factor/metabolite production); and phosphorylation of PI3K, Akt, p38 (VEGF signaling).

In some embodiments, effector molecules function additively: the effect of two effector molecules, for example, may be equal to the sum of the effect of the two effector molecules functioning separately. In other embodiments, effector molecules function synergistically: the effect of two effector molecules, for example, may be greater than the combined function of the two effector molecules.

Effector molecules that modulate tumor-mediated immunosuppressive mechanisms and/or modify tumor microenvironments may be, for example, secreted factors (e.g., cytokines, chemokines, antibodies, and/or decoy receptors that modulate extracellular mechanisms involved in the immune system), inhibitors (e.g., antibodies, antibody fragments, ligand TRAP and/or small blocking peptides), intracellular factors that control cell state (e.g., microRNAs and/or transcription factors that modulate the state of cells to enhance pro-inflammatory properties), factors packaged into exosomes (e.g., microRNAs, cytosolic factors, and/or extracellular factors), surface displayed factors (e.g., checkpoint inhibitors, TRAIL), and and/or metabolic genes (e.g., enzymes that produce/modulate or degrade metabolites or amino acids).

In some embodiments, at least one of the effector molecules stimulates an immunostimulatory mechanism in the tumor microenvironment and/or inhibits an immunosuppressive mechanism in the tumor microenvironment.

In some embodiments, at least one of the effector molecules (a) stimulates T cell signaling, activity and/or recruitment, (b) stimulates antigen presentation and/or processing, (c) stimulates natural killer cell-mediated cytotoxic signaling, activity and/or recruitment, (d) stimulates dendritic cell differentiation and/or maturation, (e) stimulates immune cell recruitment, (f) stimulates pro-inflammatory macrophage signaling, activity and/or recruitment or inhibits anti-inflammatory macrophage signaling, activity and/or recruitment, (g) stimulates stroma degradation, (h) stimulates immunostimulatory metabolite production, (i) stimulates Type I interferon signaling, (j) inhibits negative costimulatory signaling, (k) inhibits pro-apoptotic signaling of anti-tumor immune cells, (l) inhibits T regulatory ($T_{reg}$) cell signaling, activity and/or recruitment, (m) inhibits tumor checkpoint molecules, (n) stimulates stimulator of interferon genes (STING) signaling, (o) inhibits myeloid-derived suppressor cell signaling, activity and/or recruitment, (p) degrades immunosuppressive factors/metabolites, (q) inhibits vascular endothelial growth factor signaling, and/or (r) directly kills tumor cells.

In some embodiments, effector molecules may be selected from the following non-limiting classes of molecules: cytokines, antibodies, chemokines, nucleotides, peptides, and enzymes. Non-limiting examples of the foregoing classes of effector molecules are listed in Table 1 and specific sequences encoding exemplary effector molecules are listed in Table 2. Effector molecules can be human, such as those listed in Table 1 or Table 2 or human equivalents of murine effector molecules listed in Table 1 or Table 2. Effector molecules can be human-derived, such as the endogenous human effector molecule or an effector molecule modified and/or optimized for function, e.g., codon optimized to improve expression, modified to improve stability, or modified at its signal sequence (see below). Various programs and algorithms for optimizing function are known to those skilled in the art and can be selected based on the improvement desired, such as codon optimization for a specific species (e.g., human, mouse, bacteria, etc.).

In some embodiments, the effector molecule comprises interleukin 12 (IL-12), for example, p35 and p40 as a dimer that is generally referred to in the art as IL12p70. In some embodiments, the first effector molecule comprises an IL12p70 fusion protein. In some embodiments, the IL12p70 fusion protein is a human IL12p70 fusion protein. In some embodiments, the human IL12p70 fusion protein comprises the sequence shown in SEQ ID NO: 203.

In some embodiments, the effector molecule comprises interleukin 15 (IL-15). In some embodiments, the effector molecule consists of IL-15 (see, e.g., SEQ ID NO: 199). In some embodiments, the effector molecule comprises a fusion protein including IL-5 and an extracellular portion of IL-15 Receptor α (IL-15Rα), such as the sushi domain as shown in SEQ ID NO: 201. An exemplary IL-15/IL-15Rα sushi domain fusion is provided as SEQ ID NO: 202.

TABLE 1

Exemplary Effector Molecules

| Effector name | Category | Function |
|---|---|---|
| anti-CD40 or CD40 Ligand | Agonist antibody | Stimulates B-cells and antigen presenting cells. |
| Flt3L | Ligand agonist | Stimulates myeloid cells and antigen presenting cells |
| CXCL10-11 fusion | Chemokine | Attracts T-cells |
| TGFb blocking peptides | Antagonist peptides | Inhibit TGFb pathway, TME modifier |
| Adenosine deaminase (ADA) | TME modifier | Degradation of suppressive adenosine in the TME |
| Kyneurinase | TME modifier | Degradation of kyneurine |
| HPGE2 | TME modifier | Degradation of PGE2 |
| CXCL13 | Chemokine | Attracts B-cells |
| anti PD-1/PD-L1 | Agonist antibody | Remove checkpoint |
| anti-CTLA-4 | Agonist antibody | Remove checkpoint |
| anti-VEGF | Antagonist antibody | Neutralizes an immunosuppressive/ angiogenesis factor |
| anti-TNFa | Antagonist antibody | Neutralizes cytokine/pro-tumor factor |
| anti-IL-10 | Antagonist antibody | Neutralizes immunosuppressive cytokine |
| anti-SDF1/CXCL12 | Antagonist antibody | Neutralizes pro-tumor chemokine |
| (TβRII)2 trap | Capture trap | Neutralizes an immunosuppressive cytokine |
| CCL21 | Chemokine | Attracts leukocytes/NK |
| CCL1 | Chemokine | Attracts leukocytes/NK |

TABLE 1-continued

Exemplary Effector Molecules

| Effector name | Category | Function |
|---|---|---|
| CCL17 | Chemokine | Attracts leukocytes/NK |
| CCL19 | Chemokine | Attracts leukocytes/NK |
| CCL21 | Chemokine | Attracts leukocytes/NK |
| CCL20 | Chemokine | Attracts leukocytes/NK |
| CCL21a | Chemokine | Attracts leukocytes/NK |
| MIP1b (CCL5) | Chemokine | Attracts leukocytes/NK |
| CXCL10 | Chemokine | Attracts leukocytes/NK |
| CXCL11 | Chemokine | Attracts leukocytes/NK |
| CCL2 | Chemokine | Attracts monocytes |
| MIP-1alpha (CCL3) | Chemokine | Attracts leukocytes/NK |
| XCL1 | Chemokine | Attracts leukocytes/NK |
| IFNbeta | Cytokine | T cell response, tumor cell killing |
| IFNgamma | Cytokine | T cell response, tumor cell killing |
| IL-12 | Cytokine | T cells, NK cells |
| IL-1beta | Cytokine | T cells, NK cells |
| IL-15 | Cytokine | Stimulates T-cells and NK |
| IL-2 | Cytokine | Stimulates T-cells and NK |
| IL-21 | Cytokine | Stimulates T-cells |
| IL-24 | Cytokine | Stimulates T-cells |
| IL36-gamma | Cytokine | Stimulates T-cells |
| IL-7 | Cytokine | Stimulates T-cells |
| IL-22 | Cytokine | Stimulates T-cells |
| IL-18 | Cytokine | Stimulates T-cells |
| Granzymes/Perforin | Enzyme | Direct tumor cell killing |
| OX86 (anti-OX40) | ligand | Stimulates T-cells |
| anti-TGFbeta | Neutralizing antibody | Neutralizes an Immunosuppressive cytokine |
| TRAIL | Receptor/ligand | Direct tumor cell killing |
| FASL (CD49L) | Receptor/ligand | Direct tumor cell killing |
| OX40-L | Receptor/Ligand | Stimulates T-cells |
| cGAS | secreted molecule | Stimulates antigen-presenting cells |
| 41BBL | secreted molecule | Co-activation of T-cells |
| CD40L | secreted molecule | Stimulates T-cells |
| GM-CSF | secreted molecule | Growth factor for monocytes |
| STING | secreted molecule | Stimulates antigen-presenting cells |
| HAC-V 'microbody'_PD1 | Antagonist antibody | inhibits checkpoint |
| yCD | Pro-drug | Converts to cytotoxic molecule upon activation |
| CpG/Nucleotides | Nucleotides | STING agonist |

TABLE 2

Exemplary effector molecule sequences

```
IL-12 (Human) (SEQ ID NO: 56)
ATGTGCCATCAGCAGCTTGTCATATCTTGGTTTTTCACTTGTATTCCTGGCCAGCCCTTTGGTTGC
GATCTGGGAGCTCAAGAAGGATGTGTACGTTGTAGAGCTGGACTGGTACCCCGATGCTCCCGGT
GAGATGGTCGTTTTGACATGTGACACTCCAGAAGAGGACGGTATTACGTGGACTCTGGACCAGT
CCTCCGAAGTTCTTGGTTCTGGTAAGACTCTGACTATCCAGGTGAAAGAATTTGGGGATGCGGG
ACAATACACATGCCACAAGGGAGGCGAGGTGTTGTCTCATAGTTTGCTGCTTCTCCACAAGAAA
GAGGATGGAATCTGGAGCACCGACATACTCAAGGATCAAAAGGAACCCAAAAATAAGACATTT
CTGCGATGTGAGGCTAAGAACTATAGTGGCCGCTTCACTTGTTGGTGGCTGACTACCATCAGCA
CAGATCTCACGTTTTCAGTAAAAAGTAGTAGAGGTTCAAGTGATCCTCAAGGGGTAACGTGCGG
TGCTGCAACACTGTCTGCTGAACGCGTAAGAGGAGATAATAAGGAGTACGAGTATTCCGTAGA
ATGCCAAGAGGACAGTGCTTGTCCTGCGGCCGAGGAGTCTCTCCCAATAGAAGTGATGGTGGA
CGCGGTGCATAAACTGAAATATGAGAACTACACAAGCAGTTTTTTTATAAGAGATATCATCAAG
CCCGATCCGCCGAAGAATTTGCAACTTAAACCGCTTAAAAACTCACGCCAGGTTGAAGTATCCT
GGGAGTATCCGGATACATGGTCAACACCACACAGCTATTTTTCCCTTACCTTCTGTGTGCAGGTC
CAAGGGAAGAGCAAAAGGGAGAAGAAGGACAGGGTATTCACTGATAAAACTTCCGCGACGGT
CATCTGCCGAAAAAACGCTAGTATATCTGTACGGGCGCAGGATAGGTACTATAGTTCTTCTTGG
TCTGAGTGGGCCTCAGTTCCGTGCTCTGGGGGAGGAAGTGGAGGAGGGTCCGGCGGTGGAAGC
GGGGGAGGGGAGTCGCAACTTGCCAGTGGCTACACCAGATCCAGGCATGTTTCCATGTCTGCATC
ATTCCCAGAATCTCCTGAGAGCGGTGTCAAATATGCTCCAAAAAGCGAGACAACACTGGAAT
TTTACCCGTGTACCAGTGAGGAGATTGATCACGAGGACATAACCAAGGACAAGACCTCAACTG
TAGAAGCGTGTTTGCCGCTGGAGTTGACTAAGAATGAGTCCTGCCTCAATTCCAGAGAAACTTC
ATTCATTACTAACGGCAGTTGTCTTGCATCCCGGAAAAACGTCCTTTATGATGGCCCTTTGCCTTA
GTTCAATTTACGAGGATCTTAAAATGTATCAAGTGGAGTTTAAAACCATGAATGCTAAACTTCT
TATGGACCCCAAACGACAAATTTTTCTGGATCAGAATATGCTTGCCGTGATAGACGAACTCATG
```

TABLE 2-continued

Exemplary effector molecule sequences

CAGGCGCTTAATTTTAACTCCGAAACAGTTCCACAAAAATCTAGCCTTGAAGAACCTGATTTTT
ATAAAACGAAGATTAAACTGTGTATCCTGCTGCATGCCTTTCGCATCCGAGCTGTCACAATCGA
TAGGGTTATGTCCTACCTTAACGCGAGCtaG

IL-12p70 (Human; codon optimized; bold denotes signal sequence)
(SEQ ID NO: 57)
ATGTGCCATCAGCAACTCGTCATCTCCTGGTTCTCCCTTGTGTTCCTCGCTTCCCCTCTGG
TCGCCATTTGGGAACTGAAGAAGGACGTCTACGTGGTCGAGCTGGATTGGTACCCGGACGCCC
CTGGAGAAATGGTCGTGCTGACTTGCGATACGCCAGAAGAGGACGGCATAACCTGGACCCTGG
ATCAGAGCTCCGAGGTGCTCGGAAGCGGAAAGACCCTGACCATTCAAGTCAAGGAGTTCGGCG
ACGCGGGCCAGTACACTTGCCACAAGGGTGGCGAAGTGCTGTCCCACTCCCTGCTGCTGCTGCA
CAAGAAAGAGGATGGAATCTGGTCCACTGACATCCTCAAGGACCAAAAAGAACCGAAGAACA
AGACCTTCCTCCGCTGCGAAGCCAAGAACTACAGCGGTCGGTTCACCTGTTGGTGGCTGACGAC
AATCTCCACCGACCTGACTTTCTCCGTGAAGTCGTCACGGGGATCAAGCGATCCTCAGGGCGTG
ACCTGTGGAGCCGCCACTCTGTCCGCCGAGAGAGTCAGGGGAGACAACAAGGAATATGAGTAC
TCCGTGGAATGCCAGGAGGACAGCGCCTGCCCTGCCGCGGAAGAGTCCCTGCCTATCGAGGTC
ATGGTCGATGCCGTGCATAAGCTGAAATACGAGAACTACACTTCCTCCTTCTTTATCCGCGACA
TCATCAAGCCTGACCCCCCCAAGAACTTGCAGCTGAAGCCACTCAAGAACTCCCGCCAAGTGGA
AGTGTCTTGGGAATATCCAGACACTTGGAGCACCCCGCACTCATACTTCTCGCTCACTTTCTGTG
TGCAAGTGCAGGGAAAGTCCAAACGGGAGAAGAAAGACCGGGTGTTCACCGACAAAACCTCCG
CCACTGTGATTTGTCGGAAGAACGCGTCAATCAGCGTCCGGGCGCAGGATAGATACTACTCGTC
CTCCTGGAGCGAATGGGCCAGCGTGCCTTGTTCCGGTGGCGGATCAGGCGGAGGTTCAGGAGG
AGGCTCCGGAGGAGGTTCCCGGAACCTCCCTGTGGCAACCCCCGACCCTGGAATGTTCCCGTGC
CTACACCACTCCCAAAACCTCCTGAGGGCTGTGTCGAACATGTTGCAGAAGGCCCGCCAGACCC
TTGAGTTCTACCCCTGCACCTCGGAAGAAATTGATCACGAGGACATCACCAAGGACAAGACCTC
GACCGTGGAAGCCTGCCTGCCGCTGGAACTGACCAAGAACGAATCGTGTCTGAACTCCCGCGA
GACAAGCTTTATCACTAACGGCAGCTGCCTGGCGTCGAGAAAGACCTCATTCATGATGGCGCTC
TGTCTTTCCTCGATCTACGAAGATCTGAAGATGTATCAGGTCGAGTTCAAGACCATGAACGCCA
AGCTGCTCATGGACCCGAAGCGGCAGATCTTCCTGGACCAGAATATGCTCGCCGTGATTGATGA
ACTGATGCAGGCCCTGAATTTCAACTCCGAGACTGTGCCTCAAAAGTCCAGCCTGGAAGAACCG
GACTTCTACAAGACCAAGATCAAGCTGTGCATCCTGTTGCACGCTTTCCGCATTCGAGCCGTGA
CCATTGACCGCGTGATGTCCTACCTGAACGCCAGT IL-12(Mouse)(SEQ ID NO: 58)
ATGTGTCCACAGAAGCTGACAATAAGTTGGTTTGCCATTGTGTCCTCCTGGTGGAGCCCCACTCATGG
CAATGTGGGAACTCGAAAAGGATGTCTACGTGGTAGAAGTAGATTGGACTCCAGACGCGCCAG
GGGAGACAGTGAATTTGACATGTGACACACCAGAAGAAGATGACATTACATGGACATCTGACC
AACGCCATGGCGTAATAGGGAGTGGGAAAACACTCACGATCACAGTTAAAGAGTTCTTGGATG
CTGGTCAATATACTTGCCATAAAGGCGGCGAGACACTCAGCCACTCACATTTGCTTTTGCATAA
AAAAGAGAATGGCATTTGGAGCACTGAAATACTTAAGAACTTTAAGAACAAGACATTTTCTCAA
GTGTGAGGCCCCTAATTACAGCGGCAGGTTCACGTGCTCATGGCTGGTCCAGCGCAACATGGAC
CTCAAGTTTAACATAAAATCTTCTTCCTCTTCACCTGACTCCAGAGCTGTTACTTGCGGCATGGC
TTCTCTGAGCGCAGAAAAAGTAACGTTGGATCAAAGAGACTACGAAAAGTACTCTGTTTCTTGT
CAAGAGGATGTTACGTGCCCGACGGCCGAAGAAACGCTTCCAATTGAACTCGCGTTGGAAGCT
CGCCAACAAAACAAGTATGAAAACTACAGTACAAGCTTCTTTATACGGGATATAATTAAACCCG
ATCCCCCCAAGAACTTGCAAATGAAACCACTTAAGAACAGCCAGGTGGAAGTTTCCTGGGAGT
ATCCAGACTCATGGAGTACTCCTCACAGCTATTTTTCTCTGAAATTCTTTGTAAGGATACAACGG
AAGAAAGAGAAGATGAAAGAGACCGAGGAGGGTTGTAATCAGAAGGGAGCGTTTCTCGTGGA
GAAAACGTCTACCGAAGTCCAATGTAAAGGTGGCAATGTGTGCGTCCAAGCTCAGGATAGATA
CTATAATTCAAGTTGCTCCAAGTGGGCCTGTGTTCCATGCCGCGTTCGGAGCGGGGGAGGTAGC
GGAGGAGGTAGTGGGGGTGGGTCAGGAGGAGGGAGTCGAGTTATCCCGGTGTCAGGCCCCGCA
CGCTGCTTGAGCCAGAGTCGCAACCTCCTTAAGACAACAGATGACATGGTGAAAACAGCACGC
GAAAAGCTTAAACACTACTCTTGTACGGCGGAGGATATTGATCACGAGGATATTACCCGAGACC
AAACTAGCACTTTGAAAAACCTGTCTGCCCCTTGAACTTCATAAAAATGAGAGCTGTCTGGCTAC
ACGAGAGACGTCAAGTACGACTAGGGGCAGCTGTCTCCCGCCGCAAAAGACAAGCCTCATGAT
GACGCTCTGTTTGGGTTCCATTTACGAGGACTTGAAAATGTATCAAACGGAGTTCCAGGCTATA
AATGCGGCGTTGCAGAACCATAACCATCAACAAATTATACTTGATAAAGGCATGTTGGTGGCGA
TTGATGAACTCATGCAGAGTCTCAATCACAACGGGGAAACGTTGAGACAGAAACCCCCAGTCG
GTGAAGCGGACCCATATCGAGTAAAAATGAAGCTCTGCATTCTGCTTCACGCATTCAGCACTAG
AGTTGTTACCATCAACCGGGTAATGGGATATCTCTCCAGTGCGtaG IL21(Human; codon optimized; bold denotes signal sequence)
(SEQ ID NO: 59)
ATGGAACGCATTGTGATCTGCCTGATGGTCATCTTCCTGGGCACCTTAGTGCACAAGTCG
AGCAGCCAGGGACAGGACAGGCACATGATTAGAATGCGCCAGCTCATCGATATCGTGGACCAG
TTGAAGAACTACGTGAACGACCTGGTGCCCGAGTTCCTGCCGGCCCCCGAAGATGTGGAAACC
AATTGCGAATGGTCGGCATTTTCCTGCTTTCAAAAGGCACAGCTCAAGTCCGCTAACACCGGGA
ACAACGAACGGATCATCAACGTGTCCATCAAAAAGCTGAAGCGGAAGCCTCCCTCCACCAACG
CCGGACGGAGGCAGAAGCATAGGCTGACTTGCCCGTCATGCGACTCCTACGAGAAGAAGCCGC
CGAAGGAGTTCCTGGAGCGGTTCAAGTCGCTCCTGCAAAAGATGATTCATCAGCACCTGTCCTC
CCGGACTCATGGGTCTGAGGATTCA IL-12p70_T2A_IL21(Human; codon optimized; bold denotes signal
sequences)(SEQ ID NO: 60)
ATGTGCCATCAGCAACTCGTCATCTCCTGGTTCTCCCTTGTGTTCCTCGCTTCCCCTCTGG
TCGCCATTTGGGAACTGAAGAAGGACGTCTACGTGGTCGAGCTGGATTGGTACCCGGACGCCC
CTGGAGAAATGGTCGTGCTGACTTGCGATACGCCAGAAGAGGACGGCATAACCTGGACCCTGG
ATCAGAGCTCCGAGGTGCTCGGAAGCGGAAAGACCCTGACCATTCAAGTCAAGGAGTTCGGCG TABLE 2-continued Exemplary effector molecule sequences

```
ACGCGGGCCAGTACACTTGCCACAAGGGTGGCGAAGTGCTGTCCCACTCCCTGCTGCTGCTGCA
CAAGAAAGAGGATGGAATCTGGTCCACTGACATCCTCAAGGACCAAAAAGAACCGAAGAACA
AGACCTTCCTCCGCTGCGAAGCCAAGAACTACAGCGGTCGGTTCACCTGTTGGTGGCTGACGAC
AATCTCCACCGACCTGACTTTCTCCGTGAAGTCGTCACGGGGATCAAGCGATCCTCAGGGCGTG
ACCTGTGGAGCCGCCACTCTGTCCGCCGAGAGAGTCAGGGGAGACAACAAGGAATATGAGTAC
TCCGTGGAATGCCAGGAGGACAGCGCCTGCCCTGCCGCGGAAGAGTCCCTGCCTATCGAGGTC
ATGGTCGATGCCGTGCATAAGCTGAAATACGAGAACTACACTTCCTCCTTCTTTATCCGCGACA
TCATCAAGCCTGACCCCCCCAAGAACTTGCAGCTGAAGCCACTCAAGAACTCCCGCCAAGTGGA
AGTGTCTTGGGAATATCCAGACACTTGGAGCACCCCGCACTCATACTTCTCGCTCACTTTCTGTG
TGCAAGTGCAGGGAAAGTCCAAACGGGAGAAGAAAGACCGGGTGTTCACCGACAAAACCTCCG
CCACTGTGATTTGTCGGAAGAACGCGTCAATCAGCGTCCGGGCGCAGGATAGATACTACTCGTC
CTCCTGGAGCGAATGGGCCAGCGTGCCTTGTTCCGGTGGCGGATCAGGCGGAGGTTCAGGAGG
AGGCTCCGGAGGAGGTTCCCGGAACCTCCCTGTGGCAACCCCCGACCCTGGAATGTTCCCGTGC
CTACACCACTCCCAAAACCTCCTGAGGGCTGTGTCGAACATGTTGCAGAAGGCCCGCCAGACCC
TTGAGTTCTACCCCTGCACCTCGGAAGAAATTGATCACGAGGACATCACCAAGGACAAGACCTC
GACCGTGGAAGCCTGCCTGCCGCTGGAACTGACCAAGAACGAATCGTGTCTGAACTCCCGCGA
GACAAGCTTTATCACTAACGGCAGCTGCCTGGCGTCGAGAAGACCTCATTCATGATGGCGCTC
TGTCTTTCCTCGATCTACGAAGATCTGAAGATGTATCAGGTCGAGTTCAAGACCATGAACGCCA
AGCTGCTCATGGACCCGAAGCGGCAGATCTTCCTGGACCCAGAATATGCTCGCCGTGATTGATGA
ACTGATGCAGGCCCTGAATTTCAACTCCGAGACTGTGCCTCAAAAGTCCAGCCTGGAAGAACCG
GACTTCTACAAGACCAAGATCAAGCTGTGCATCCTGTTGCACGCTTTCCGCATTCGAGCCGTGA
CCATTGACCGCGTGATGTCCTACCTGAACGCCAGTAGACGGGAAACGCGGAAGCGGAGAGGGCA
GAGGGCTCGCTGCTTACATGCGGGGACGTGGAAGAGAACCCCGGTCCGATGGAACGCATTGTG
ATCTGCCTGATGGTCATCTTCCTGGGCACCTTAGTGCACAAGTCGAGCAGCCAGGGACAG
GACAGGCACATGATTAGAATGCGCCAGCTCATCGATATCGTGGACCAGTTGAAGAACTACGTG
AACGACCTGGTGCCCGAGTTCCTGCCGGCCCCCGAAGATGTGGAAACCAATTGCGAATGGTCG
GCATTTTCCTGCTTTCAAAAGGCACAGCTCAAGTCCGCTAACCACCGGGAACAACGAACGGATCA
TCAACGTGTCCATCAAAAAGCTGAAGCGGAAGCCTCCCTCCACCAACGCCGGACGGAGGCAGA
AGCATAGGCTGACTTGCCCGTCATGCGACTCCTACGAGAAGAAGCGCCGAAGGAGTTCCTGG
AGCGGTTCAAGTCGCTCCTGCAAAAGATGATTCATCAGCACCTGTCCTCCCGGACTCATGGGTC
TGAGGATTCA
```

IL-12_2A_CCL21a(Human)(SEQ ID NO: 61)
```
ATGTGCCATCAGCAGCTTGTCATATCTTGGTTTTCACTTGTATTCCTGGCCAGCCCTTTGGTTGC
GATCTGGGGAGCTCAAGAAGGATGTGTACGTTGTAGAGCTGGACTGGTACCCCGATGCTCCCGGT
GAGATGGTCGTTTTGACATGTGACACTCCAGAAGAGGACGGTATTACGTGGACTCTGGACCAGT
CCTCCGAAGTTCTTGGTTCTGGTAAGACTCTGACTATCCAGGTGAAAGAATTTGGGGATGCGGG
ACAATACACATGCCACAAGGGAGGCGAGGTGTTGTCTCATAGTTTGCTGCTTCTCCACAAGAAA
GAGGATGGAATCTGGAGCACCGACATACTCAAGGATCAAAAGGAACCCAAAAATAAGACATTT
CTGCGATGTGAGGCTAAGAACTATAGTGGCCGCTTCACTTGTTGGTGGCTGACTACCATCAGCA
CAGATCTCACGTTTTCAGTAAAAAGTAGTAGAGGTTCAAGTGATCCTCAAGGGGTAACGTGCGG
TGCTGCAACACTGTCTGCTGAACGCGTAAGAGGAGATAATAAGGAGTACGAGTATTCCGTAGA
ATGCCAAGAGGACAGTGCTTGTCCTGCGGCCGAGGAGTCTCTCCCAATAGAAGTGATGGTGGA
CGCGGTGCATAAACTGAAATATGAGAACTACACAAGCAGTTTTTTTATAAGAGATATCATCAAG
CCCGATCCGCCGAAGAATTTGCAACTTAAACCGCTTAAAAACTCACGCCAGGTTGAAGTATCCT
GGGAGTATCCGGATACATGGTCAACACCACACAGCTATTTTTCCCTTACCTTCTGTGTGCAGGTC
CAAGGGAAGAGCAAAAGGGAGAAGAAGGACAGGGTATTCACTGATAAACTTCCGCGACGGT
CATCTGCCGAAAAAACGCTAGTATATCTGTACGGGCGCAGGATAGGTACTATAGTTCTTCTTGG
TCTGAGTGGGCCTCAGTTCCGTGCTCTGGGGGAGGAAGTGGAGGAGGGTCCGGCGGTGGAAGC
GGGGGAGGGAGTCGCAACTTGCCAGTGGCTACACCAGATCCAGGCATGTTTCCATGTCTGCATC
ATTCCCAGAATCTCCTGAGAGCGGTGTCAAATATGCTCCAAAAAGCGAGACAAACACTGGAAT
TTTACCCGTGTACCAGTGAGGAGATTGATCACGAGGACATAACCAAGGACAAGACCTCAACTG
TAGAAGCGTGTTTGCCGCTGGAGTTGACTAAGAATGAGTCCTGCCTCAATTCCAGAGAAACTTC
ATTCATTACTAACGGCAGTTGTCTTGCATCCCGGAAACGTCCTTTATGATGGCCCTTTGCCTTA
GTTCAATTTACGAGGATCTTAAAATGTATCAAGTGGAGTTTAAAACCATGAATGCTAAACTTCT
TATGGACCCCAAACGACAAATTTTTCTGGATCAGAATATGCTTGCCGTGATAGACGAACTCATG
CAGGCGCTTAATTTTAACTCCGAAACAGTTCCACAAAAATCTAGCCTTGAAGAACCTGATTTTT
ATAAAACGAAGATTAAACTGTGTATCCTGCTGCATGCCTTTCGCATCCGAGCTGTCACAATCGA
TAGGGTTATGTCCTACCTTAACGCGAGCCGGCGCAAGAGGGGTTCCGGAGAGGGAAGGGGTAG
TCTGCTCACCTGCGGCGATGTTGAAGAAAATCCTGGTCCCATGGCGCAAAGTCTGGCTCTTTCA
CTCCTGATCCTGGTCTTGGCCTTCGGGATTCCGAGGACCCAAGGAAGTGATGGTGGCGCCCAAG
ATTGTTGCCTTAAATACAGCCAGCGGAAAATACCCGCGAAAGTGGTCAGGAGTTTATAGAAAAC
AGGAGCCTTCCCTGGGTTGTAGTATCCCCGCCATACTTTTCCTCCCGAGAAAACGGAGCCAGGC
CGAACTGTGCGCTGACCCTAAGGAACTTTGGGTGCAACAACTTATGCAACACCTGGATAAGACA
CCTTCTCCTCAAAAGCCAGCTCAGGGCTGCCGAAAAGATAGAGGCGCCTCAAAAACCGGAAAA
AAGGGCAAAGGTTCTAAAGGATGTAAGCGGACTGAACGCTCTCAAACGCCTAAAGGGCCGtaG
```

IL-12_2A_CCL21a(Mouse)(SEQ ID NO: 62)
```
ATGTGTCCACAGAAGCTGACAATAAGTTGGTTTGCCATTGTCCTCCTGGTGAGCCCACTCATGG
CAATGTGGGAACTCGAAAAGGATGTCTACGTGGTAGAAGTAGATTGGACTCCAGACGCGCCAG
GGGAGACAGTGAATTTGACATGTGACACACCAGAAGAAGATGACATTACATGGACATCTGACC
AACGCCATGGCGTAATAGGGAGTGGGAAAACACTCACGATCACAGTTAAAGAGTTCTTGGATG
CTGGTCAATATACTTGCCATAAAGGCGGCGAGACACTCAGCCACTCACATTTGCTTTTGCATAA
AAAAGAGAATGGCATTTGGAGCACTGAAATACTTAAGAACTTTAAGAACAAGACATTTCTCAA
GTGTGAGGCCCCTAATTACAGCGGCAGGTTCACGTGCTCATGGCTGGTCAGCGCAACATGGAC
CTCAAGTTTAACATAAAATCTTCTTCCTCTTCACCTGACTCCAGAGCTGTTACTTGCGGCATGGC
TTCTCTGAGCGCAGAAAAAGTAACGTTGGATCAAAGAGACTACGAAAGTACTCTGTTTCTTGT
CAAGAGGATGTTACGTGCCCGACGGCCGAAGAAACGCTTCCAATTGAACTCGCGTTGGAAGCT
```

TABLE 2-continued

Exemplary effector molecule sequences

```
CGCCAACAAAACAAGTATGAAAACTACAGTACAAGCTTCTTTATACGGGATATAATTAAACCCG
ATCCCCCCAAGAACTTGCAAATGAAACCACTTAAGAACAGCCAGGTGGAAGTTTCCTGGGAGT
ATCCAGACTCATGGAGTACTCCTCACAGCTATTTTTCTCTGAAATTCTTTGTAAGGATACAACGG
AAGAAAGAGAAGATGAAAGAGACCGAGGAGGGTTGTAATCAGAAGGGAGCGTTTCTCGTGGA
GAAAACGTCTACCGAAGTCCAATGTAAAGGTGGCAATGTGTGCGTCCAAGCTCAGGATAGATA
CTATAATTCAAGTTGCTCCAAGTGGGCCTGTGTTCCATGCCGCGTTCGGAGCGGGGGAGGTAGC
GGAGGAGGTAGTGGGGGTGGGTCAGGAGGAGGGAGTCGAGTTATCCCGGTGTCAGGCCCCGCA
CGCTGCTTGAGCCAGAGTCGCAACCTCCTTAAGCACAACAGATGACATGGTGAAAACAGCACGC
GAAAAGCTTAAACACTACTCTTGTACGGCGGAGGATATTGATCACGAGGATATTACCCGAGACC
AAACTAGCACTTTGAAAACCTGTCTGCCCCTTGAACTTCATAAAAATGAGAGCTGTCTGGCTAC
ACGAGAGACGTCAAGTACGACTAGGGGCAGCTGTCTCCCGCCGCAAAAGACAAGCCTCATGAT
GACGCTCTGTTTGGGTTCCATTTACGAGGACTTGAAAATGTATCAAACGGAGTTCCAGGCTATA
AATGCGGCGTTGCAGAACCATAACCATCAACAAATTATACTTGATAAAGGCATGTTGGTGGCGA
TTGATGAACTCATGCAGAGTCTCAATCACAACGGGGAAACGTTGAGACAGAAACCCCCAGTCG
GTGAAGCGGACCCATATCGAGTAAAAATGAAGCTCTGCATTCTGCTTCACGCATTCAGCACTAG
AGTTGTTACCATCAACCGGGTAATGGGATATCTCTCCAGTGCGCGGCGCAAGAGGGGTTCCGGA
GAGGGAAGGGGTAGTCTGCTCACCTGCGGCGATGTTGAAGAAATCCTGGTCCCATGGCGCAA
ATGATGACCCTTTCCCTGCTGAGTCTTGTCCTCGCGCTCTGCATCCCGTGGACGCAGGGGTCTGA
TGGGGGGGGCCAAGACTGTTGCCTGAAGTATTCACAAAAAAAGATACCGTACTCTATTGTCAGA
GGGTACAGGAAGCAAGAACCCTCCTTGGGTTGCCCTATACCAGCAATTCTTTTCTCCCCACGCA
AGCATTCCAAACCAGAACTGTGTGCGAACCCCGAGGAGGGTTGGGTACAGAACTTGATGCGAA
GGCTTGACCAGCCCCCAGCCCCTGGCAAGCAGTCACCTGGGTGCAGAAAAAACAGAGGTACTT
CAAAGAGCGGCAAGAAAGGCAAAGGGAGTAAAGGATGTAAAAGAACGGAGCAGACCCAGCCT
TCACGAGGCtaG

CCL21a_2A_IL-12(Mouse)(SEQ ID NO: 63)
ATGGCGCAAATGATGACCCTTTCCCTGCTGAGTCTTGTCCTCGCGCTCTGCATCCCGTGGACGCA
GGGGTCTGATGGGGGGGGGCCAAGACTGTTGCCTGAAGTATTCACAAAAAAAGATACCGTACTC
TATTGTCAGAGGGTACAGGAAGCAAGAACCCTCCTTGGGTTGCCCTATACCAGCAATTCTTTTC
TCCCCACGCAAGCATTCCAAACCAGAACTGTGTGCGAACCCCGAGGAGGGTTGGGTACAGAAC
TTGATGCGAAGGCTTGACCAGCCCCCAGCCCCTGGCAAGCAGTCACCTGGGTGCAGAAAAAAC
AGAGGTACTTCAAAGAGCGGCAAGAAAGGCAAAGGGAGTAAAGGATGTAAAAGAACGGAGCA
GACCCAGCCTTCACGAGGCCGGCGCAAGAGGGGTTCCGGAGAGGGAAGGGGTAGTCTGCTCAC
CTGCGGCGATGTTGAAGAAATCCTGGTCCCATGTGTCCACAGAAGCTGACAATAAGTTGGTTT
GCCATTGTCCTCCTGGTGAGCCCACTCATGGCAATGTGGGAACTCGAAAAGGATGTCTACGTGG
TAGAAGTAGATTGGACTCCAGACGCGCCAGGGGAGACAGTGAATTTGACATGTGACACACCAG
AAGAAGATGACATTACATGGACATCTGACCAACGCCATGGCGTAATAGGGAGTGGGAAAACAC
TCACGATCACAGTTAAAGAGTTCTTGGATGCTGGTCAATATACTTGCCATAAAGGCGGCGAGAC
ACTCAGCCACTCACATTTGCTTTTGCATAAAAAAGAGAATGGCATTTGGAGCACTGAAATACTT
AAGAACTTTAAGAACAAGACATTTCTCAAGTGTGAGGCCCCTAATTACAGCGGCAGGTTCACGT
GCTCATGGCTGGTCCAGCGCAACATGGACCTCAAGTTTAACATAAAATCTTCTTCCTCTTCACCT
GACTCCAGAGCTGTTACTTGCGGCATGGCTTCTCTGAGCGCAGAAAAGTAACGTTGGATCAAA
GAGACTACGAAAAGTACTCTGTTTCTTGTCAAGAGGATGTTACGTGCCCGACGGCCGAAGAAAC
GCTTCCAATTGAACTCGCGTTGGAAGCTCGCCAACAAAACAAGTATGAAAACTACAGTACAAG
CTTCTTTATACGGGATATAATTAAACCCGATCCCCCCAAGAACTTGCAAATGAAACCACTTAAG
AACAGCCAGGTGGAAGTTTCCTGGGAGTATCCAGACTCATGGAGTACTCCTCACAGCTATTTTT
CTCTGAAATTCTTTGTAAGGATACAACGGAAGAAAGAGAAGATGAAAGAGACCGAGGAGGGTT
GTAATCAGAAGGGAGCGTTTCTCGTGGAGAAAACGTCTACCGAAGTCCAATGTAAAGGTGGCA
ATGTGTGCGTCCAAGCTCAGGATAGATACTATAATTCAAGTTGCTCCAAGTGGGCCTGTGTTCC
ATGCCGCGTTCGGAGCGGGGGAGGTAGCGGAGGAGGTAGTGGGGGTGGGTCAGGAGGAGGGA
GTCGAGTTATCCCGGTGTCAGGCCCCGCACGCTGCTTGAGCCAGAGTCGCAACCTCCTTAAGAC
AACAGATGACATGGTGAAAACAGCACGCGAAAAGCTTAAACACTACTCTTGTACGGCGGAGGA
TATTGATCACGAGGATATTACCCGAGACCAAACTAGCACTTTGAAAACCTGTCTGCCCCTTGAA
CTTCATAAAAATGAGAGCTGTCTGGCTACACGAGAGACGTCAAGTACGACTAGGGGCAGCTGT
CTCCCGCCGCAAAAGACAAGCCTCATGATGACGCTCTGTTTGGGTTCCATTTACGAGGACTTGA
AAATGTATCAAACGGAGTTCCAGGCTATAAATGCGGCGTTGCAGAACCATAACCATCAACAAC GG
GGAAACGTTGAGACAGAAACCCCCAGTCGGTGAAGCGGACCCATATCGAGTAAAAATGAAGCT
CTGCATTCTGCTTCACGCATTCAGCACTAGAGTTGTTACCATCAACCGGGTAATGGGATATCTCT
CCAGTGCGtaG IL7(Mouse)(SEQ ID NO: 64)
ATGTTTCATGTGTCCTTCAGGTACATATTTGGTATCCCACCACTTATATTGGTGCTCTTGCCTGTA
ACCAGCTCTGAATGTCATATAAAAGACAAGGAGGGCAAAGCATACGAGTCCGTATTGATGATC
TCAATCGATGAACTTGACAAGATGACAGGGACCGATTCTAATTGTCAAATAACGAGCCAAACT
TCTTTCGGAAACACGTGTGTGATGATACAAAAGAAGCTGCTTTTCTTAACAGAGCTGCCAGAAA
ACTCAAGCAGTTCCTCAAGATGAATATATCCGAGGAATTTAACGTGCATCTCCTCACAGTATCT
CAGGGAACTCAAACCCTTGTAAACTGCACTTCTAAGGAGGAGAAGAATGTCAAAGAGCAGAAG
AAAAATGATGCATGTTTTTTGAAACGGCTGTTGAGGGAGATCAAAACATGCTGGAATAAAATCC
TCAAGGGCTCAATTtaG IL-15 (Human)(SEQ ID NO: 65)
ATGGAAACAGACACATTGCTGCTTTGGGTATTGTTGCTCTGGGTGCCTGGATCAACAGGAAACT
GGGTAAACGTAATTTCAGATCTGAAGAAGATCGAGGACCTTATTCAATCCATGCACATCGATGC
CACTCTCTACACCGAAAGCGACGTTCACCCATCTTGCAAGGTGACCGCTATGAAATGTGAATTG
TTGGAACTTCAGGTAATTTCTCTGGAGAGCGGCGATGCCTCAATACATGACACCGTTGAAAATC
TTATCATCCTTGCTAATGATTCACTCTCTAGTAATGGGAACGTAACAGAGAGCGGGTGTAAGGA
GTGTGAAGAACTGGAGGAGAAAAACATTAAGGAATTTTTGCAGTCATTCGTCCATATAGTGCAA
```

TABLE 2-continued

Exemplary effector molecule sequences

```
ATGTTCATAAACACTTCCAGAAGAAAGCGAGGCTCTGGGGAGGGGCGAGGCTCTCTGCTGACC
TGTGGGGATGTAGAAGAGAATCCAGGTCCCATGGACCGGCTGACCAGCTCATTCCTGCTTCTGA
TTGTGCCAGCCTACGTGCTCTCCATCACATGTCCTCCCCCAATGAGCGTCGAGCATGCTGACATC
TGGGTGAAGTCATACTCCTTGTACAGCAGAGAGAGATACATTTGTAATTCCGGATTCAAGCGCA
AGGCCGGCACCTCCTCTCTGACAGAGTGCGTCCTTAACAAAGCAACCAACGTAGCACATTGGAC
CACACCATCCTTGAAGTGCATACGAGAACCTAAATCTTGCGATAAGACTCATACTTGTCCACCT
TGTCCAGCCCCAGAACTGCTTGGCGGACCCTCAGTATTTTTGTTCCCACCAAAGCCAAAAGACA
CACTCATGATATCCAGAACTCCTGAGGTGACCTGTGTCGTTGTAGACGTTTCCCACGAAGATCC
TGAAGTAAAATTCAACTGGTACGTGGATGGGGTCGAAGTCCATAACGCCAAGACTAAACCAAG
GGAGGAACAGTATAACTCTACTTACCGAGTAGTTTCTGTGTTGACCGTGCTGCACCAGGACTGG
TTGAACGGGAAGGAGTACAAATGCAAGGTGAGCAATAAAGCTCTGCCCGCACCAATCGAAAAG
ACAATATCTAAGGCCAAGGGGCAGCCACGAGAGCCCCAGGTATACACACTGCCACCCTCACGC
GATGAATTGACTAAGAACCAGGTTTCCCTGACCTGTCTTGTAAAAGGTTTCTACCCTTCCGACAT
AGCTGTTGAGTGGGAAAGTAACGGGCAGCCAGAGAACAATTACAAGACAACTCCACCCGTTCT
TGATAGCGATGGATCATTTTTTCTGTATTCCAAACTCACTGTCGATAAAAGTCGCTGGCAGCAA
GGCAATGTTTTTAGCTGCTCAGTCATGCACGAAGCACTGCATAATCACTACACACAAAAAAGTT
TGTCCCTTAGCCCTGGTAAGtaG
```

IL-15(Human)(SEQ ID NO: 66)
```
ATGTACTCAATGCAGTTGGCCTCCTGTGTAACATTGACCTTGGTCCTCTTGGTCAACAGCAATTG
GATCGATGTACGCTACGACTTGGAGAAGATTGAGTCCCTTATACAGAGTATACACATAGATACA
ACCTTGTATACTGACAGTGACTTCCATCCCAGCTGTAAAGTGACTGCAATGAACTGTTTTTTGTT
GGAGTTGCAAGTAATTCTGCATGAATACAGCAACATGACCCTCAATGAACGTTAGGAATGTC
CTTTATCTCGCAAATTCTACTCTGAGTAGCAATAAGAATGTTGCCGAAAGCGGCTGCAAGGAGT
GCGAAGAACTGGAGGAAAAAACTTTCACCGAGTTTCTCCAGAGTTTCATCAGAATTGTCCAAAT
GTTCATTAATACAAGTAGTGGTGGTGGGAGCGGGGGTGGAGGCAGTGGGGGAGGTGGGAGCGG
AGGTGGAGGGTCCGGAGGGGGGAGCCTTCAAGGCACTACTTGTCCTCCACCCGTATCCATCGAG
CACGCCGATATTCGAGTTAAAAATTATAGTGTTAATAGCAGAGAACGATACGTCTGCAACTCAG
GGTTTAAGAGAAAGGCCGGAACTTCAACTCTCATAGAATGCGTGATTAATAAGAATACTAACGT
CGCACATTGGACTACTCCCAGTCTCAAGTGCATACGCGATCCATCTCTCGCTCATTACTCACCAG
TACCTACAGTGGTTACTCCTAAGGTGACCTCTCAGCCCGAATCACCATCTCCCAGCGCAAAAGA
GCCTGAGGCCTTTTCTCCTAAATCAGACACTGCTATGACTACAGAAACAGCCATAATGCCAGGA
AGCCGGCTGACACCATCTCAAACTACCAGCGCAGGCACAACTGGGACTGGCTCCCACAAAAGC
TCACGCGCACCAAGTCTCGCCGCAACAATGACATTGGAGCCTACAGCCAGCACATCTCTTAGAA
TCACAGAAATTTCTCCCCACAGTAGCAAGATGACCAAGGTGGCAATTAGTACCAGCGTCCTTCT
TGTAGGAGCTGGAGTTGTGATGGCATTTTTGGCATGGTATATCAAAAGCAGGtaG
```

IL-15(Mouse)(SEQ ID NO: 67)
```
ATGAAGATCCTCAAGCCATACATGCGAAACACTAGTATTAGCTGTTACTTGTGTTTTCTGCTGAA
TAGTCATTTTTTGACTGAAGCAGGAATCCATGTATTTATACTGTTACTTGTGTGTCTGTAGGTCTGC
CAAAGACTGAGGCTAATTGGATTGACGTGCGCTATGATCTTGAAAAAATAGAGTCCTTGATTCA
ATCAATACACATCGATACCACTCTCTACACCGACAGTGATTTCCATCCTTCCTGCAAGGTAACA
GCTATGAATTGCTTCCTCCTGGAGCTCCAAGTCATTCTCCATGAGTACTCCAACATGACTTTGAA
CGAAACTGTAAGAAACGTATTGTATCTGGCTAATAGCACCTTGTCTAGTAACAAAAATGTGGCA
GAGAGCGGCTGCAAAGAATGTGAAGAATTGGAAGAGAAAACATTTACAGAGTTCCTGCAATCC
TTTATTCGCATCGTCCAAATGTTTATCAATACCTCTtaG
```

IL-15(Mouse)(SEQ ID NO: 68)
```
ATGTATTCCATGCAACTTGCCAGTTGTGTGTAACCCTTACTCTCGTCCTGCTCGTTAATTCCGCTGG
TGCTAACTGGATAGATGTTCGATACGATCTGGAAAAGATTGAGTCCCTTATCCAATCCATTCAT
ATAGATACCACCCTTTATACTGACAGCGACTTCCATCCTTCTTGCAAGGTGACCGCTATGAATTG
TTTCCTGCTGGAACTCCAAGTTATTCTGCATGAATACTCTAATATGACACTTAACGAGACCGTAA
GAAATGTTCTCTATCTCGCTAATAGTACTTTGAGCTCAAATAAGAACGTGGCCGAGTCTGGGTG
TAAGGAATGCGAAGAGCTGGAAGAAAAGACATTCACCGAGTTTCTCCAGTCTTTCATACGGATT
GTGCAGATGTTTATCAACACATCAGATTACAAAGACGACGATGATAAGtaG
```

IL-18(Mouse)(SEQ ID NO: 69)
```
ATGGCAGCCATGTCTGAGGACTCTTGTGTGAACTTTAAAGAAATGATGTTCATAGACAATACAC
TCTACTTTATACCTGAGGAGAATGGAGATTTGGAATCTGACAACTTTGGCAGGCTGCATTGCAC
TACCGCAGTTATCCGAAACATCAACGATCAGGTACTGTTTGTTGATAAAAGACAACCTGTATTC
GAGGACATGACCGACATAGATCAGTCTGCCTCAGAGCCCCAGACTAGGCTTATCATCTATATGT
ACAAGGACAGCGAAGTACGAGGCCTGGCTGTTACACTCTCAGTCAAAGACTCTAAGATGAGCA
CCCTGTCATGCAAGAACAAAATTATCAGTTTTGAGGAGATGGACCCACCTGAAAACATAGATG
ACATTCAGTCAGACCTCATTTTTTTTCAAAAGCGGGTACCAGGACACAACAAAATGGAATTTGA
ATCATCACTCTACGAAGGACATTTCCTTGCATGCCAGAAAGAGGATGACGCATTCAAATTGATC
CTGAAAAAAAAGGACGAAAATGGTGATAAATCAGTCATGTTTACATTGACCAATCTTCACCAA
AGTtaG
```

IL-18(Mouse)(SEQ ID NO: 70)
```
ATGGCTGCAATGTCTGAAGATAGCTGTGTCAACTTTAAGGAGATGATGTTCATTGATAATACTT
TGTACTTTATACCTGAAGAAAATGGAGACCTTGAGTCAGACAACTTCGGGAGACTGCACTGCAC
AACTGCCGTTATCCGAAACATAAATGATCAAGTATTGTTCGTGGACAAAAGACAACCAGTCTTT
GAGGATATGACAGACATCGACCAATCCGCATCTGAACCTCAGACTAGGCTGATCATCTATATGT
ACGCCGACTCCGAAGTAAGAGGCCTTGCTGTGACACTTAGTGTTAAGGATAGTAAGATGAGCA
CACTGTCCTGTAAGAATAAGATTATATCTTTTGAAGAGATGGACCCTCCCGAGAACATAGATGA
CATCCAGAGCGACTTGATCTTCTTTCAGAAGCGAGTGCCAGGCCATAACAAGATGGAATTTGAA
```

TABLE 2-continued

---

Exemplary effector molecule sequences

---

TCATCTCTTTATGAAGGCCATTTCCTCGCATGTCAAAAGGAGGACGATGCCTTCAAGCTCATTCT
GAAAAAAAAAGACGAGAACGGTGATAAGAGCGTGATGTTCACTCTGACAAATCTGCACCAGTC
AtaG

IL-18(Human)(SEQ ID NO: 71)
ATGTATCGCATGCAACTCCTGTCCTGCATTGCTCTGAGCTTGGCTTTGGTAACCAACTCATACTT
CGGGAAACTGGAGAGTAAACTCTCCGTAATCAGGAATCTTAATGACCAAGTATTGTTTATTGAC
CAGGGCAACCGCCCGTTGTTCGAGGATATGACTGATTCTGACTGTCGGGATAACGCTCCGAGAA
CTATCTTTATCATTTCAATGTACAAGGACAGCCAACCGCGGGGTATGGCTGTGACAATCAGTGT
CAAATGTGAGAAGATTTCCACGCTGTCCTGCGAAAACAAGATAATTTCTTTCAAAGAAATGAAC
CCCCCTGACAATATAAAGGATACAAAGAGTGATATCATCTTCTTTCAGAGGTCCGTGCCCGGCC
ACGATAATAAGATGCAATTTGAAAGTTCATCTTATGAGGGGTACTTTTTGGCATGCGAGAAAGA
AAGGGATCTCTTCAAGTTGATCCTGAAGAAGGAGGACGAATTGGGCGACCGCTCCATCATGTTC
ACAGTCCAGAACGAGGACtaG IL-18(Human)(SEQ ID NO: 72)
ATGTACCGCATGCAGCTCCTGAGTTGTATTGCCCTTTCCCTCGCTCTCGTTACCAATTCTTACTTC
GGTAAGCTTGCCTCTAAACTCTCTGTTATTAGGAACTTGAACGACCAAGTCCTTTTCATAGACCA
AGGGAACAGACCCACTGTTTGAAGATATGACGGATAGCGATTGCCGAGATAATGCCCCTAGGAC
GATTTTTATCATTAGTATGTATGCGGACTCTCAACCGAGGGGGATGGCCGTTACTATAAGTGTG
AAATGCGAGAAAATATCAACGCTCAGTTGTGAGAACAAAATCATAAGTTTCAAGGAGATGAAT
CCACCTGATAACATCAAAGACACTAAGTCTGATATTATATTTTTCCAACGAAGTGTTCCGGGAC
ACGATAACAAAATGCAATTTGAGAGCTCCTCATACGAGGGCTACTTCCTCGCGTGTGAGAAGA
AAGGGATTTGTTTAAGCTTATCCTCAAGAAAGAGGACGAGTTGGGGGATCGGAGCATAATGTTT
ACCGTACAGAATGAGGACtaG IL-21(Mouse)(SEQ ID NO: 73)
ATGGAGCGGACACTCGTGTGTGTCTTGTCGTAATTTTTCTCGGGACAGTCGCACACAAGTCCTCAC
CCCAGGGTCCTGATCGCCTTCTCATACGCCTCCGACATTTGATCGACATTGTAGAGCAGCTCAA
AATTTACGAGAATGACCTCGATCCCGAGCTTTTGAGTGCTCCCCAAGACGTTAAGGGTCATTGC
GAGCACGCAGCTTTTGCTTGCTTCCAGAAGGCCAAGTTGAAACCAAGCAACCCTGGTAATAATA
AGACTTTCATCATCGACTTGGTCGCCCAACTCCGAAGGAGGCTGCCTGCCCGGCGCGGAGGAAA
AAAACAAAAGCATATTGCAAAGTGTCCTTCATGTGATTCATACGAAAAGCGGACTCCCAAAGA
GTTCTTGGAAAGGTTGAAATGGCTTCTTCAGAAGATGATTCATCAACATTTGTCAtaG IFN-beta(Human)(SEQ ID NO: 74)
ATGACCAACAAATGCCTTTTGCAAATTGCCCTGCTTTTGTGTTTTAGCACTACCGCATTGAGCAT
GTCATATAACCTCCTCGGCTTCCTTCAGAGATCATCAAACTTTCAGTGTCAGAAACTGCTTTGGC
AACTTAATGGCAGGCTCGAATATTGTCTGAAAGATCGGATGAATTTCGACATTCCAGAAGAAAT
AAAACAGCTTCAACAATTCCAGAAAGAGGACGCCGCCCTGACTATTTACGATGCTCCAGAA
TATCTTCGCCATTTTCCGGCAGGACAGCTCATCCACGGGGTGGAATGAGACTATTGTAGAAAAT
CTTCTGGCTAATGTGTACCATCAAATTAATCACCTCAAAACGGTGCTTGAGGAAAAACTTGAAA
AGGAAGATTTCACACGGGGCAAGTTGATGTCCTCCCTGCACCTTAAACGATACTACGGCAGGAT
TCTTCATTACTTGAAGGCTAAGGAGTATAGCCATTGCGCGTGGCAATTGTACGGGTAGAAATA
CTGCGAAACTTTTATTTCATCAACCGGCTCACTGGATACCTTAGAAATtaG IFN-beta(Mouse)(SEQ ID NO: 75)
ATGAACAATCGGTGGATACTCCACGCCGCATTTCTCCTCTGCTTTAGCACGACGGCCCTGTCCAT
CAACTACAAACAGCTTCAGTTGCAGGAGCGGACTAACATAAGGAAGTGCCAGGAACTGCTGGA
ACAGCTTAATGGTAAAATTAATCTTACATACCGAGCTGACTTCAAAATTCCTATGGAAATGACC
GAGAAGATGCAGAAATCCTACACGGCATTCGCCATCCAGGAAATGCTCCAGAACGTATTTCTCG
TGTTCCGCAATAATTTCTCTTCTACGGGTTGGAACGAAACCATTGTTGTTAGACTGCTTGACGAA
CTGCATCAGCAAACCGTGTTCCTTAAAACCGTGCTTGAGGAGAAGCAGGAGGAGCGCCTGACTT
GGGAGATGTCTAGTACCGCACTTCACTTGAAATCCTACTACTGGCGCGTTCAGCGGTATCTGAA
GCTGATGAAGTATAACTCATACGCCTGGATGGTAGTGCGCGCAGAGATCTTCAGAAACTTTCTT
ATCATCCGGCGACTGACCCGAAACTTTCAGAATtaG IFN-gamma(Human)(SEQ ID NO: 76)
ATGAAGTACACTAGCTATATATTGGCCTTCCAGCTTTGCATCGTATTGGGTAGCCTCGGATGCTA
TTGCCAAGACCCGTATGTCAAAGAAGCCGAAAATCTCAAAAAGTAATTTCAATGCCGGACACTCA
GACGTCGCGGATAACGGTACACTGTTTCTTGGCATCCTGAAAAATTGGAAGGAAGAGAGTGAC
AGAAAAATAATGCAGTCACAAATAGTGTCCTTTTACTTTAAGCTGTTCAAAAATTTCAAGGATG
ACCAAAGTATCCAGAAGAGTGTTGAAACTATCAAAGAGGACATGAATGTGAAATTCTTTAACA
GTAATAAGAAGAAGCGCGATGACTTCGAGAAACTCACTAATTACAGCGTAACGGATCTTAACG
TCCAACGCAAGGCAATCCACGAGCTTATACAGGTAATGGCTGAGCTTAGTCCCGCAGCCAAGA
CAGGGAAGAGAAAAAGGTCTCAAATGCTTTTTCGGGGCCGGCGAGCTTCACAAtaG IFN-gamma(Mouse)(SEQ ID NO: 77)
ATGAACGCTACGCATTGCATCCTCGCACTCCAATTGTTCCTCATGGCTGTGTCAGGGTGTTACTG
TCACGGTACTGTCATAGAAAGCCTCGAATCCCTGAATAACTATTTTAACAGTAGCGGTATAGAT
GTAGAAGAAAAGTCTCTCTTTCTTGACATCTGGAGGAATTGGCAAAAGGATGGAGACATGAAG
ATTCTCCAATCTCAGATTATATCATTTTACTTGAGGCTTTTTGAGGTTCTGAAGGATAACCAGGC
GATCAGCAATAATATCAGCGTAATTGAATCTCACCTTATTCAACATTTTTCTCAAATTCCAAGG
CAAAGAAAGATGCTTTCATGTCTATCGCGAAATTTGAGGTGAACAATCCTCAGGTACAAAGGCA
AGCCTTTAACGAGCTGATTAGAGTTGTACATCAGTTGTTGCCCGAAAGTAGTCTTAGAAAACGC
AAACGGAGCCGATGCtaG TABLE 2-continued Exemplary effector molecule sequences IFN-alpha(Mouse)(SEQ ID NO: 78)
ATGGCAAGGTTGTGCGCTTTTCTCATGGTACTGGCTGTGCTCTCCTATTGGCCTACTTGTTCTCTG
GGATGCGACTTGCCACAGACCCACAATCTGCGGAATAAGAGGGCTCTGACTCTGCTGGTGCAA
ATGAGACGGCTCTCTCCACTTAGCTGTTTGAAAGATAGAAAGGATTTCGGGTTCCCCCAGGAGA
AGGTGGATGCCCAGCAGATCAAGAAGGCACAGGCTATCCCCGTCCTTTCCGAGCTGACCCAGC
AAATTTTGAACATCTTTACAAGTAAGGATAGTTCAGCTGCATGGAATACCACACTTTTGGATTCT
TTTTGTAACGATCTGCATCAGCAGCTGAACGATCTCCAGGGATGCCTGATGCAGCAAGTCGGCG
TGCAAGAATTTCCACTCACCCAGGAGGACGCTCTGCTCGCAGTGCGAAAGTATTTTCACCGAAT
TACCGTGTACCTCCGGGAGAAAAAGCATTCACCCTGCGCTTGGGAAGTAGTCAGGGCCGAAGT
ATGGAGAGCCCTTAGTAGCTCCGCTAATGTACTGGGCCGGTTGCGGGAAGAGAAAtaG CCL21(Human)(SEQ ID NO: 79)
ATGGCGCAAAGTCTGGCTCTTTCACTCCTGATCCTGGTCTTGGCCTTCGGGATTCCGAGGACCCA
AGGAAGTGATGGTGGCGCCCAAGATTGTTGCCTTAAATACAGCCAGCGGAAAATACCCGCGAA
AGTGGTCAGGAGTTATAGAAAACAGGAGCCTTCCCTGGGTTGTAGTATCCCCGCCATACTTTTC
CTCCCGAGAAAACGGAGCCAGGCCGAACTGTGCGCTGACCCTAAGGAACTTTGGGTGCAACAA
CTTATGCAACACCTGGATAAGACACCTTCTCCTCAAAAGCCAGCTCAGGGCTGCCGAAAAGATA
GAGGCGCCTCAAAAACCGGAAAAAAGGGCAAAGGTTCTAAAGGATGTAAGCGGACTGAACGC
TCTCAAACGCCTAAAGGGCCGtaG CCL21a(Mouse)(SEQ ID NO: 80)
ATGGCGCAAATGATGACCCTTTCCCTGCTGAGTCTTGTCCTCGCGCTCTGCATCCCGTGGACGCA
GGGGTCTGATGGGGGGGGCCAAGACTGTTGCCTGAAGTATTCACAAAAAAAGATACCGTACTC
TATTGTCAGAGGGTACAGGAAGCAAGAACCCTCCTTGGGTTGCCCTATACCAGCAATTCTTTTC
TCCCCACGCAAGCATTCCAAACCAGAACTGTGTGCGAACCCCGAGGAGGGTTGGGTACAGAAC
TTGATGCGAAGGCTTGACCAGCCCCCAGCCCCTGGCAAGCAGTCACCTGGGTGCAGAAAAAAC
AGAGGTACTTCAAAGAGCGGCAAGAAAGGCAAAGGGAGTAAAGGATGTAAAAGAACGGAGCA
GACCCAGCCTTCACGAGGCtaG Tail-less CCL21(Human)(SEQ ID NO: 81)
ATGGCGCAAAGTCTGGCTCTTTCACTCCTGATCCTGGTCTTGGCCTTCGGGATTCCGAGGACCCA
AGGAAGTGATGGTGGCGCCCAAGATTGTTGCCTTAAATACAGCCAGCGGAAAATACCCGCGAA
AGTGGTCAGGAGTTATAGAAAACAGGAGCCTTCCCTGGGTTGTAGTATCCCCGCCATACTTTTC
CTCCCGAGAAAACGGAGCCAGGCCGAACTGTGCGCTGACCCTAAGGAACTTTGGGTGCAACAA
CTTATGCAACACCTGGATAAGACACCTTCTCCTCAAAAGCCAGCTCAGGGCtaG Tail-less CCL21(Mouse)(SEQ ID NO: 82)
ATGGCGCAAATGATGACCCTTTCCCTGCTGAGTCTTGTCCTCGCGCTCTGCATCCCGTGGACGCA
GGGGTCTGATGGGGGGGGCCAAGACTGTTGCCTGAAGTATTCACAAAAAAAGATACCGTACTC
TATTGTCAGAGGGTACAGGAAGCAAGAACCCTCCTTGGGTTGCCCTATACCAGCAATTCTTTTC
TCCCCACGCAAGCATTCCAAACCAGAACTGTGTGCGAACCCCGAGGAGGGTTGGGTACAGAAC
TTGATGCGAAGGCTTGACCAGCCCCCAGCCCCTGGCAAGCAGTCACCTGGGtaG CCL19(Mouse)(SEQ ID NO: 83)
ATGGCACCCCGCGTCACACCCTTGCTTGCTTTTTTCTCTGCTTGTCCTCTGGACCTTCCCCGCTCCT
ACCCTTGGAGGAGCCAATGATGCCGAGGATTGCTGCCTGAGTGTTACACAAAGGCCAATACCA
GGGAATATAGTGAAGGCATTCCGGTATCTGCTCAATGAAGATGGGTGCAGAGTCCCCGCAGTTG
TCTTTACAACATTGCGAGGTTACCAGCTTTGTGCTCCCCCAGACCAGCCTTGGGTAGATCGCATT
ATTCGCCGGTTGAAGAAGAGCTCAGCAAAGAATAAGGGCAATTCCACACGGAAGCCCCGTC
TCCtaG CCL19(Mouse)(SEQ ID NO: 84)
ATGAAATCAGCAGTCCTTTTCTTGCTCGGGATTATTTTTCTGGAACAATGTGGAGTGAGGGGAA
CACTCGTAATAAGAAACGCTCGGTGCTCATGCATATCAACATCACGGGGCACTATCCACTACAA
ATCCCTGAAGGATCTGAAGCAGTTCGCCCCAAGCCCTAACTGTAACAAGACCGAAATTATCGCA
ACTCTCAAAAATGGAGATCAGACTTGTCTTGACCCAGATTCAGCAAATGTCAAGAAGCTGATGA
AAGAGTGGGAAAAGAAGATTTCACAAAAAAAAAAGCAAAAACGCGGCAAGAAACATCAAAAG
AACATGAAAAACAGGAAACCTAAGACTCCCCAGTCAAGGAGAAGATCCCGCAAGACAACCtaG CXCL11(Mouse)(SEQ ID NO: 85)
ATGAACAGAAAAGTTACCGCTATAGCACTTGCTGCCATAATATGGGCCACCGCAGCTCAAGGGT
TCCTGATGTTCAAGCAGGGCCGATGCCTCTGCATTGGCCCTGGAATGAAGGCCGTGAAAATGGC
CGAAATAGAAAAAGCTAGTGTCATATACCCCTCTAACGGTTGCGATAAAGTCGAGGTTATAGTC
ACAATGAAAGCTCATAAACGCCAACGCTGCCTCGACCCCCGGTCTAAGCAGGCTAGGCTCATA
ATGCAAGCAATCGAGAAGAAAAACTTTCTTAGACGGCAAAACATGtaG CXCL10(Mouse)(SEQ ID NO: 86)
ATGAACCCATCTGCCGCCGTTATTTTCTGTCTGATACTCCTTGGGCTGAGTGGCACACAAGGCAT
ACCCCTCGCCCGCACAGTCCGGTGTAATTGTATACATATTGACGACGGCCCTGTTAGAATGCGG
GCCATCGGTAAGCTGGAGATTATACCAGCAAGCCTTAGTTGTCCCAGGGTTGAAATCATAGCAA
CTATGAAAAAAAACGACGAACAAAGATGTTTGAATCCCGAGAGCAAGACAATCAAAAACCTTA
TGAAAGCATTTAGTCAAAAACGCTCTAAACGCGCTCCAtaG CXCL10(Human)(SEQ ID NO: 87)
ATGAATCAGACGGCAATCCTTATATGCTGCCTTATATTCCTTACTCTCTCAGGGATACAAGGGGT
ACCACTTTCTCGGACTGTTCGCTGCACTTGCATTTCAATATCTAACCAACCTGTAAATCCGCGGA
GCCTGGAAAAATTGGAGATTATACCTGCTTCTCAATTCTGCCCTCGGGTGGAAATCATCGCCAC TABLE 2-continued Exemplary effector molecule sequences

```
TATGAAGAAGAAGGGCGAGAAAAGGTGTCTGAATCCAGAGTCAAAGGCAATCAAAAACCTGCT
GAAAGCGGTGTCAAAGGAACGGTCCAAGAGATCACCCtaG

CXCL11-CXCL10(Mouse)(SEQ ID NO: 88)
ATGAACAGGAAAGTAACAGCCATTGCATTGGCTGCCATCATCTGGGCCACCGCAGCACAGGGT
TTTCTGATGTTTAAGCAAGGGCGCTGTCTCTGTATAGGCCCAGGCATGAAGGCCGTGAAGATGG
CAGAGATTGAGAAGGCATCTGTGATTTATCCTTCTAACGGGTGCGATAAAGTCGAAGTTATTGT
GACAATGAAGGCACACAAACGCCAACGGTGTTTGGACCCACGATCTAAACAGGCAAGATTGAT
TATGCAAGCCATCGAGAAAAAGAACTTTCTCCGAAGGCAAAATATGATCCCTTTGGCTCGGACA
GTGCGGTGTAACTGTATTCACATCGACGATGGGCCAGTACGGATGAGAGCAATAGGAAAGCTC
GAAATCATACCCGCCTCATTGTCTTGTCCCAGGGTGGAAATAATCGCCACTATGAAAAAGAACG
ATGAACAGAGGTGTCTCAACCCAGAGAGTAAGACTATCAAGAACCTTATGAAGGCATTCAGTC
AGAAGAGGTCAAAGCGAGCACCAtaG XCL1(Human)(SEQ ID NO: 89)
ATGAGACTTCTCATATTGGCGCTTCTCGGGATATGTTCTCTTACGGCATACATAGTTGAGGGGGT
GGGATCTGAGGTTAGCGATAAACGAACTTGTGTTAGTCTTACAACACAGAGGCTTCCAGTCTCC
AGGATAAAAACATATACGATAACTGAGGGATCTCTCAGAGCGGTCATCTTCATAACGAAGAGG
GGCCTGAAGGTCTGTGCTGACCCACAAGCGACTTGGGTAAGGGACGTTGTGCGGAGCATGGAC
AGGAAGAGCAATACTCGCAACAACATGATCCAAACCAAACCTACGGGCACCCAACAGTCAACC
AATACTGCGGTAACATTGACGGGGtaG XCL1(Mouse)(SEQ ID NO: 90)
ATGCGCCTCCTTCTGCTGACTTTTCTGGGTGTATGTTGCCTGACACCCTGGGTCGTAGAAGGAGT
AGGAACCGAGGTTCTGGAAGAGTCCTCATGTGTAAACTTGCAGACACAACGACTCCCCGTCCAA
AAAATCAAGACCTATATAATCTGGGAGGGGGCAATGCGGGCCGTCATTTTCGTGACTAAACGA
GGTCTCAAAATCTGCGCCGACCCCGAGGCTAAGTGGGTGAAGGCAGCCATTAAGACCGTGGAT
GGGAGAGCCAGCACCAGAAAGAACATGGCCGAAACAGTACCTACTGGCGCACAGCGGTCAACC
TCAACTGCTATAACCTTGACAGGAtaG m_sCD40L #1(SEQ ID NO: 91)
ATGGAGACTGACACTCTGCTTCTGTGGGTGTTGCTGCTGTGGGTGCCTGGCAGTACAGGCGATA
TGCAACGAGGTGACGAGGACCCTCAAATCGCCGCCCATGTAGTCTCTGAAGCTAATAGCAACG
CTGCATCCGTCTTGCAGTGGGCAAAGAAAGGCTACTATACTATGAAGTCCAACTTGGTAATGCT
TGAAAACGGCAAGCAGTTGACTGTCAAGAGAGAGGGACTTTATTACGTCTATACCCAAGTCAC
ATTCTGTAGCAATCGAGAACCCTCCTCACAGAGGCCTTTTATAGTGGGACTCTGGCTTAAACCA
AGTAGCGGCTCTGAGCGCATACTGTTGAAAGCCGCAAACACACACAGCTCTTCCCAACTCTGCG
AGCAGCAATCCGTGCATCTCGGTGGAGTATTTGAGCTTCAAGCCGGTGCCTCAGTGTTTGTGAA
CGTCACTGAGGCCTCCCAGGTCATACATCGAGTTGGGTTCAGCTCCTTCGGCTTGCTCAAGCTCtaG m_sCD40L #2(SEQ ID NO: 92)
ATGGAAACTGATACATTGCTGCTCTGGGTTTTGCTGCTCTGGGTGCCTGGGAGTACAGGCGACA
TGAGGAGGCAGTTCGAGGATCTCGTTAAGGATATTACCCTTAATAAGGAGGAGAAGAAAGAAA
ACTCTTTTGAGATGCAACGAGGGGACGAAGATCCTCAGATCGCTGCTCACGTGGTCTCTGAAGC
TAACAGCAACGCCGCTTCTGTCCTCCAGTGGGCCAAGAAAGGTTATTACACCATGAAATCAAAC
CTTGTAATGCTTGAAAACGGGAAACAGCTTACAGTGAAGAGGGAAGGTCTTTACTACGTCTATA
CCCAGGTAACCTTCTGCTCAAACAGAGAACCATCAAGCCAGAGGCCATTCATAGTGGGGCTCTG
GCTCAAACCTTCCAGTGGCAGCGAGAGAATCTTGTTGAAAGCTGCTAATACACATAGTAGTAGC
CAGCTTTGCGAGCAACAGTCAGTCCACCTCGGGGGGGGTGTTTGAGTTGCAAGCAGGGGCCTCAG
TATTCGTGAATGTCACTGAGGCTTCCCAGGTAATTCACAGGGTAGGCTTTAGTTCATTCGGTTTG
CTGAAGCTTtaG m_sCD40L #3(SEQ ID NO: 93)
ATGCGAAGAATGCAGCTTCTGCTCCTTATTGCTCTGAGTCTCGCCCTTGTCACCAACTCCGGGGA
CAGAATGAAACAAATCGAGGACAAAATTGAAGAAATACTGAGTAAAAATATATCACATCGAAAA
CGAAATTGCACGCATTAAGAAATTGATTGGCGAACGCACCAGTGGCGGCTCTGGTGGCACCGG
AGGTTCAGGCGGGACCGGGGGCTCTGACAAAGTCGAAGAGGAGGTTAACCTTCATGAGGACTT
TGTGTTCATCAAGAAGCTGAAACGGTGCAATAAAGGAGAAGGTTCTTTGAGCCTCCTTAATTGC
GAAGAGATGCGACGACAGTTCGAGGATCTGGTTAAGGACATTACACTTAATAAGGAAGAGAAA
AAGGAGAACTCTTTCGAAATGCAGCGCGGCGATGAAGATCCCCAGATAGCCGCCCATGTCGTCT
CTGAGGCCAACTCTAACGCAGCATCCGTCCTCCAGTGGGCTAAGAAAGGATATTATACTATGAA
AAGCAATTTGGTCATGCTCGAAAACGGTAAACAGCTCACTGTTAAGAGAGAAGGCCTCTATTAC
GTATATACTCAAGTAACTTTCTGTTCTAATAGGGAACCCTCCTCTCAAAGACCTTTTATCGTAGG
ACTCTGGTTGAAACCAAGTAGCGGTAGTGAAAGGATTCTGCTCAAAGCAGCTAATACTCACTCC
AGCAGTCAACTGTGCGAACAACAAAGCGTTCACCTCGGGGGCGTCTTTGAACTTCAGGCAGGTG
CCAGTGTTTTCGTCAACGTAACAGAAGCATCCCAGGTAATTCATCGAGTAGGGTTTTCTAGCTTT
GGTTTGCTGAAGCTGtaG anti-CD40_FGK4.5(SEQ ID NO: 94)
ATGGAAACTGATCGCCTGTTGCTCTGGGTACTTCTTCTGTGGGTGCCTGGGTCCACTGGTGACAC
TGTACTTACACAATCACCCGCTTTGGCCGTTTCTCCTGGTGAACGGGTCACAATTAGTTGCCGAG
CTTCCGATTCTGTATCTACTCTTATGCATTGGTATCAACAAAAACCTGGTCAGCAGCCAAATTG
CTCATTTATCTTGCTAGTCACTTGGAGTCCGGCGTACCTGCTCTTATTAGTGGTAGTGGGTCTGG
CACAGATTTCACTTTGACCATAGATCCCGTGGAGGCCGATGACACTGCAACCTACTATTGCCAG
CAATCCTGGAACGACCCTTGGACTTTCGGCGGCGGCACCAAGCTGGAACTCAAGCGAGCAGAT
GCTGCCCCAACCGTTAGTATATTCCCACCCTCAACCGAACAACTCGCCACAGGAGGCGCTAGTG
TCGTGTGTCTTATGAACAATTTCTATCCACGAGACATTAGCGTCAAGTGGAAAATTGATGGGAC
AGAAAAGGCGAGATGGAGTTTTGGATTCAGTAACAGACCAGGATTCAAAGGATTCTACCTATAG
```

TABLE 2-continued

Exemplary effector molecule sequences

```
CATGAGCTCCACCTTGAGCCTGACCAAAGCTGATTATGAATCTCATAACCTGTATACTTGTGAA
GTGGTGCATAAGACTTCTAGCTCACCAGTGGTTAAATCTTTTAACCGCAACGAATGTCGGCGCA
AGAGGGGTTCCGGAGAGGGAAGGGGTAGTCTGCTCACCTGCGGCGATGTTGAAGAAAATCCTG
GTCCCATGGACATTCGGCTCTCTTTGGTATTCCTGGTACTTTTTATAAAGGGGGTGCAATGTGAA
GTCCAGCTCGTGGAAAGCGGTGGGGGCCTGGTTCAGCCCGGTCGCAGCCTTAAACTTAGTTGCG
CAGCATCCGGATTTACATTTTCTGACTATAACATGGCCTGGGTTCGACAGGCACCCAAAAAAGG
GCTGGAGTGGGTCGCAACTATCATATACGATGGTTCCCGGACATACTATAGAGATTCAGTGAAG
GGGCGCTTTACAATAAGCAGGGACAATGCTAAGTCTACCTTGTATCTTCAGATGGACTCCCTGA
GGAGCGAAGATACAGCAACATATTATTGTGCTACAAACCGCTGGTTGCTGCTTCATTATTTCGA
CTACTGGGGTCAGGGCGTCATGGTAACTGTATCAAGCGCCGAGACCCACAGCCCCTTCTGTATAT
CCATTGGCACCAGGTACTGCTCTGAAATCCAACTCAATGGTAACCCTTGGATGTCTGGTTAAGG
GTTATTTTCCCGAGCCCGTCACAGTTACTTGGAACTCTGGGGCCCTTTCTAGCGGAGTCCATACC
TTTCCCGCCGTTTTGCAGAGTGGTCTGTACACCCTTACCTCAAGCGTCACAGTTCCATCTAGCAC
ATGGAGCTCCCAGGCAGTAACTTGTAATGTGGCCCATCCAGCCTCCTCAACTAAGGTAGATAAA
AAGATCGTTCCCAGAGAATGCAATCCATGTGGATGCACCGGGTCTGAGGTCAGCAGTGTGTTCA
TTTTCCCACCCAAGACTAAAGATGTATTGACTATTACTCTTACACCCAAAGTAACCTGCGTGGTG
GTTGATATTAGTCAAATGATCCCGAGGTACGGTTCTCTTGGTTTATCGACGACGTCGAAGTAC
ATACAGCTCAGACACACGCTCCCGAGAAACAAAGCAATTCCACTCTTAGGAGCGTGTCCGAGTT
GCCAATCGTACATAGGGATTGGCTTAATGGCAAGACCTTTAAGTGTAAGGTCAATTCAGGGGCA
TTCCCCGCACCAATAGAGAAGAGTATAAGCAAACCCGAGGGGACACCCAGAGGTCCACAGGTC
TATACAATGGCTCCCCCCAAGGAAGAGATGACCCAAAGTCAAGTCTCAATTACATGTATGGTGA
AGGGCTTTTATCCACCCGACATATACACTGAGTGGAAGATGAATGGACAGCCCCAAGAGAATT
ATAAAAACACTCCCCCTACCATGGACACCGACGGGTCCTATTTTCTTTATAGTAAATTGAACGT
GAAAAAGGAGACCTGGCAACAAGGCAACACTTTCACCTGCTCCGTTCTTCACGAGGGCCTGCAT
AATCATCATACCGAAAAGTCTCTCAGTCATTCTCCAGGTAAGtaG

CD40L_2(Human)(SEQ ID NO: 95)
ATGGAAACAGATACGTTGCTGTTGTGGGTACTTCTCCTTTGGGTCCCTGGCAGCACAGGGGACG
AGAATAGTTTCGAAATGCAGAAGGGCGACCAGAACCCACAGATCGCGGCTCACGTTATATCAG
AAGCAAGTAGTAAGACCACTTCCGTACTTCAGTGGGCTGAAAAAGGATATTACACCATGTCCAA
CAATCTCGTGACACTGGAGAACGGTAAACAACTTACGGTGAAACGACAGGGCCTCTATTACATC
TACGCTCAGGTGACATTCTGCTCAAATAGGGGAGGCTTCTAGTCAAGCGCCCTTCATCGCCAGCC
TGTGCCTCAAATCTCCCGGCCGGTTCGAACGAATCCTGTTGCGAGCGGCCAATACCCATAGCTC
AGCTAAACCTTGCGGCCAGCAGAGTATTCATCTTGGTGGTGTGTTTGAACTTCAGCCGGGAGCA
TCTGTGTTCGTCAACGTAACGGACCCTAGCCAAGTGTCTCATGGGACAGGTTTTACATCCTTCGG
ACTCCTCAAGTTGtaG Flt3L(Human)(SEQ ID NO: 96)
ATGACAGTTCTCGCGCCAGCTTGGAGTCCCACCACCACATACTTGCTTTTGCTTCTGCTTCTGTCCTCT
GGCCTGAGTGGGCACCCAAGATTGTTCCTTTCAACATTCCCCAATTAGTTCTGATTTTGCAGTGAA
GATTAGAGAGCTCTCAGACTATCTGCTGCAAGATTATCCTGTCACAGTCGCTTCAAACCTGCAA
GACGAAGAGCTCTGCGGTGCCTTGTGGCGGTTGGTCTTGGCTCAAAGATGGATGGAGAGACTG
AAAACCGTAGCAGGCAGCAAGATGCAGGGTCTCCTGGAAAGGGTGAACACGGAAATCCATTTT
GTGACCAAGTGCGCGTTCCAGCCCCCACCGAGTTGTCTCCGGTTTGTTCAAACGAATATATCCC
GGTTGCTCCAGGAAACCTCAGAACAACTGGTGGCTTTGAAACCCTGGATCACAAGACAAAACTT
TAGTCGGTGCCTCGAACTCCAGTGCCAACCAGATTCTTCTACACTTCCCCCCCCCGTGGTCCCCGC
GCCCGTTGGAAGCAACGGCCCCAtaG TGFb TRAP(Human)(SEQ ID NO: 97)
ATGGCCTGGAGTCCTCTGTTTCTGACTCTTATAACTCACTGTGCCGGCAGTTGGGCTATACCCCC
TCATGTACAGAAGTCTGTAAACAACGACATGATTGTAACCGACAATAATGGCGCAGTGAAATTC
CCACAACTGTGTAAGTTCTGTGATGTACGGTTTAGTACATGCGACAATCAAAAAAGCTGTATGT
CTAACTGCTCTATTACATCCATATGTGAAAAACCTCAGGAGGTGTGTGTTGCCGTTTGGCGAAA
AAATGATGAGAATATCACACTGGAGACAGTATGTCATGACCCTAAACTGCCATACCATGATTTC
ATACTGGAGGACGCCGCCAGTCCTAAGTGCATTATGAAAGAGAAAAAGAAACCCGGTGAAACA
TTCTTTATGTGCTCTTGTAGCTCTGACGAGTGTAACGACAACATTATATTCAGCGAGGAGTACA
ATACAAGCAACCCCGATATACCCACCTCACGTACAAAAAAGTGTCAACAACGATATGATTGTTAC
CGACAATAACGGAGCTGTTAAGTTTCCTCAGTTGTGCAAGTTCTGCGATGTACGATTCTCTACCT
GCGACAACCAAAAGTCATGTATGTCTAACTGTTCCATAACCTCCATCTGCGAGAAGCCCCAGGA
AGTCTGCGTCGCCGTGTGGCGGAAAAACGACGAGAATATCACTCTTGAAACCGTTTGTCATGAT
CCTAAACTGCCCTATCACGACTTTATTCTGGAAGATGCTGCTTTCCCCTAAGTGTATCATGAAAGA
AAAGAAGAAACCTGGGGAGACATTCTTTATGTGTTCATGCTCCTCCGATGAGTGTAACGACAAT
ATCATCTTCTCTGAGGAATACAACACTTCTAACCCTGATTaG Fresolimumab(Human)(SEQ ID NO: 98)
ATGGCCTGGTCCCCTCTTTTTCTGACCCTCATCACACACTGTGCAGGCTCATGGGCTGAGACCGT
CTTGACCCAGTCCCCAGGAACTTTGTCTCTGTCTCCTGGTGAAAGAGCTACCCTTAGTTGTCGAG
CCTCTCAGTCCCTTGGTTCTAGCTATCTCGCTTGGTACCAGCAAAAGCCAGGCCAGGCCCCACG
ACTGCTGATCTACGGAGCATCTTCACGGGCTCCCGGCATTCCCGATCGATTTTCCGGATCTGGTA
GTGGTACAGATTTCACACTGACCATATCTCGCCTGGAGCCCGAGGACTTTGCTGTTTATTATTGT
CAGCAGTACGCCGATTCTCCTATCACTTTTGGACAGGGAACCCGCCTGGAGATTAAGCGCACAG
TAGCAGCTCCATCCGTCTTTATCTTTCCACCATCAGATGAACAGCTCAAGAGTGGGACCGCAAG
TGTAGTATGCCTGCTGAACAATTTTTACCCTAGAGAGGCCAAAGTGCAGTGGAAGGTGGATAAC
GCCCTCCAGAGTGGCAATAGTCAAGAAAGTGTTACTGAGCAAGATAGTAAGGACTCTACATAC
TCTTTGAGTTCTACTTTGACCCTGTCAAAAGCAGATTATGAAAACATAAGGTGTATGCATGTG
AAGTTACACACCAAGGGTTGTCCTCTCCAGTTACAAAATCTTTTAATAGAGGAGAGTGCCGCCG
CAAACGCGGTAGTGGAGAAGGTCGAGGCTCACTCTTGACCTGTGGCGACGTGGAAGAAATCC
CGGTCCTATGGATTGGACTTGGAGGGTATTTTGTCTTTTGGCAGTAACACCTGGAGCTCACCCCC
```

TABLE 2-continued

Exemplary effector molecule sequences

```
AAGTACAGCTCGTCCAATCTGGTGCCGAGGTTAAAAAGCCTGGAAGTTCAGTGAAGGTCTCTTG
CAAGGCATCTGGATACACCTTTTCATCTAACGTCATATCCTGGGTACGGCAAGCCCCAGGACAG
GGACTTGAGTGGATGGGAGGGGTCATCCCCATCGTGGACATTGCTAATTACGCTCAGCGATTCA
AAGGGGGGTTACTATAACTGCCGACGAGTCTACCTCAACTACCTACATGGAGTTGTCCTCTCT
CCGCTCCGAGGACACTGCTGTATATTACTGTGCCAGCACTCTCGGGTTGGTGTTGGATGCCATG
GACTATTGGGGACAAGGAACCCTGGTGACAGTTAGCTCCGCAAGCACTAAAGGCCCTTCTGTTT
TTCCCTTGGCACCTTGTAGTAGGTCTACCTCTGAGTCTACAGCAGCACTTGGATGCTTGGTTAAG
GACTATTTTCCCGAGCCAGTTACAGTCTCTTGGAACAGTGGTGCCCTCACAAGTGGGGTTCATA
CCTTCCCCGCAGTCCTCCAGAGTAGTGGCCTTTACAGCCTCTCATCAGTTGTGACTGTTCCTAGT
TCATCACTCGGTACTAAGACATATACATGTAACGTAGACCACAAGCCAAGCAACACAAAAGTA
GACAAACGAGTCGAATCTAAGTATGGACCCCCTTGTCCCTCCTGTCCTGCTCCCGAGTTCCTTGG
GGGCCCTTCCGTGTTCTTGTTTCCTCCCAAGCCCAAGGATACCCTCATGATCTCACGAACCCCAG
AGGTAACATGTGTGGTTGTTGACGTAAGTCAGGAAGATCCCGAAGTGCAATTTAATTGGTACGT
GGATGGCGTCGAAGTCCATAACGCTAAAACAAAACCCCGAGAGGAACAATTCAATTCCACATA
TCGGGTGGTGAGTGTATTGACCGTTCTTCACCAAGATTGGCTGAACGGCAAGGAGTATAAGTGT
AAAGTAAGCAACAAAGGTCTGCCAAGTAGCATAGAAAAAACAATATCTAAAGCTAAGGGCCAA
CCAAGGGAACCACAAGTATATACATTGCCCCCCTCTCAGGAAGAGATGACAAAGAATCAAGTT
AGCCTGACCTGTTTGGTAAAGGGGTTCTATCCCTCAGATATAGCAGTCGAGTGGGAATCTAACG
GCCAGCCCGAGAATAATTATAAAACAACCCCCCCTGTGTTGGACTCAGACGGCAGCTTCTTTCT
CTATTCACGGCTCACTGTTGATAAGTCCCGATGGCAGGAGGGGAATGTTTTCAGCTGTAGCGTG
ATGCACGAAGCTCTCCACAACCACTATACACAGAAAAGTTTGTCTTTGTCCCTTGGAAAAtaG
```

TGFb neutralizing peptide(Human)(SEQ ID NO: 99)
```
ATGAGTACATCCTTTCCAGAGCTGGATCTGGAGAATTTTGAGTATGACGACAGTGCCGAAGCCT
GCTACCTCGGGGACATAGTCGCATTCGGGACAATCTTTTTGTCTGTATTTTACGCCCTGGTGTTT
ACATTTGGCCTGGTTGGAAATCTGTTGGTCGTACTCGCTCTCACCAATTCCCGAAAACCCAAAA
GTATAACAGACATATACCTGTTGAATCTGGCACTGAGTGACCTTTTGTTCGTCGCCCACCCTTCCT
TTTTGGACACACTACCTTATCAGTCACGAGGGGCTTCATAATGCTATGTGCAAGCTCACTACTGC
CTTCTTCTTTATCGGATTCTTCGGGGGTATCTTTTTTATCACAGTTATTAGCATTGACCGATACCT
TGCCATAGTGCTCGCAGCCAACTCAATGAACAACCGCACCGTGCAGCATGGAGTGACTATTTCC
TTGGGTGTGTGGGCCGCTGCTATACTTGTCGCCAGCCCTCAATTCATGTTTACCAAAAGGAAAG
ACAATGAGTGCCTCGGAGATTACCCTGAGGTGTTGCAAGAAATGTGGCCTGTACTTCGAAATAG
CGAAGTGAATATACTCGGCTTTGCTCTTCCTCTGCTCATCATGTCATTCTGTTATTTTCGAATAAT
CCAAACATTGTTCAGCTGTAAGAACCGAAAGAAAGCCCGCGCCGTACGCCTGATTCTGCTCGTT
GTGTTCGCCTTTTTTCTGTTTTGGACTCCTTACAACATAATGATATTCCTGGAGACTCTCAAATTC
TATAACTTTTTTCCCTCCTGTGATATGAAAAGGGACCTTAGATTGGCTCTCAGTGTCACTGAAAC
AGTAGCCTTTAGCCATTGTTGTCTCAACCCTTTCATATATGCATTTGCAGGGGAAAAGTTCCGGC
GGTATCTCGGACATTTGTATCGGAAGTGCTTGGCCGTGTTGTGTGGTCATCCTGTCCATACCGGA
TTCTCTCCTGAGAGTCAACGGAGCCGCCAAGATTCAATCCTGTCCAGTTTCACTCACTATACTTC
AGAGGGGGATGGCAGCCTTCTGCTC
```

Kyneurinase #1(SEQ ID NO: 100)
```
ATGGAGACCGACACTTTGTTGCTGTGGGTACTTTTGTTGTGGGTCCCAGGATCTACCGGGGATA
TGGAACCCTCTCCTCTTGAACTGCCAGTAGACGCCGTGCGCCGCATTGCAGCCGAGTTGAATTG
CGATCCAACAGATGAACGCGTTGCCCTGAGGCTCGACGAAGAGGATAAATTGTCACATTTCAG
GAACTGCTTTTACATTCCAAAGATGAGGGATCTTCCATCCATAGATCTTAGCCTCGTGTCCGAG
GATGACGATGCCATATATTTTCTTGGGAACAGTCTTGGGTTGCAGCCAAAAATGGTACGGACAT
ATCTCGAAGAGGAGCTGGACAAATGGGCTAAAATGGGTGCTTACGGCCACGACGTGGGAAAAC
GCCCCTGGATAGTTGGCGACGAATCTATCGTGAGTCTTATGAAAGATATAGTTGGAGCACATGA
GAAAGAAATTGCACTGATGAATGCCCTTACTATCAATCTGCATCTCCTCTTGCTTTCATTCTTTA
AGCCCACTCCTAAACGCCACAAAATACTTTTGGAAGCAAAAGCCTTTCCAAGCGACCACTACGC
TATTGAGTCACAAATACAACTCCATGGACTTGATGTGGAAAAGTCTATGCGGATGGTAAAACCA
CGCGAAGGCGAGGAGACCCTTCGAATGGAGGACATACTTGAGGTCATCGAAGAAGAAGGAGAT
AGTATAGCAGTTATCCTTTTCAGCGGGCTGCACTTCTACACAGGTCAACTCTTTAACATTCCAGC
TATTACTAAGGCAGGCCACGCTAAAGGATGCTTCGTGGGCTTTGACCTTGCACACGCAGTAGGA
AACGTAGAGCTCCGCTTGCACGATTGGGGCGTTGATTTCGCCTGCTGGTGTTCATATAAGTATCT
TAACTCAGGAGCTGGTGGGTTGGCAGGCGCATTCGTACACGAGAAACACGCTCATACCGTAAA
GCCTGCACTGGTAGGGTGGTTCGGACACGATCTCTCTACCCGCTTCAATATGGATAATAAACTC
CAGCTTATACCTGGCGCCAATGGATTCAGGATCTCAAATCCTCCTATTTTGCTCGTTTGCAGTTT
GCACGCATCTCTTGAGGTGTTCCAGCAGGCTACCATGACTGCACTCCGCCGGAAGTCAATCCTT
TTGACCGGATACTTGGAGTATATGCTGAAACATTATCACTCAAAAGATAACACTGAGAATAAGG
GCCCCATAGTAAACATTATCACTCCATCTCGGGCTGAAGAGCGCGGCTGCCAACTCACATTGAC
TTTTTCCATTCCCAAGAAGTCAGTGTTCAAAGAGTTGGAGAAACGGGGGGTTGTATGTGATAAG
CGGGAGCCAGATGGAATCCGCGTTGCCCCAGTCCCCCTCTATAATTCTTTTCACGATGTATACA
AGTTTATTAGACTGCTGACAAGTATCTTGGACTCATCTGAGCGATCTtaG
```

Kyneurinase #2(SEQ ID NO: 101)
```
ATGGAACCCTCTCCTCTTGAACTGCCAGTAGACGCCGTGCGCCGCATTGCAGCCGAGTTGAATT
GCGATCCAACAGATGAACGCGTTGCCCTGAGGCTCGACGAAGAGGATAAATTGTCACATTTCA
GGAACTGCTTTTACATTCCAAAGATGAGGGATCTTCCATCCATAGATCTTAGCCTCGTGTCCGA
GGATGACGATGCCATATATTTTCTTGGGAACAGTCTTGGGTTGCAGCCAAAAATGGTACGGACA
TATCTCGAAGAGGAGCTGGACAAATGGGCTAAAATGGGTGCTTACGGCCACGACGTGGGAAAA
CGCCCCTGGATAGTTGGCGACGAATCTATCGTGAGTCTTATGAAAGATATAGTTGGAGCACATG
AGAAAGAAATTGCACTGATGAATGCCCTTACTATCAATCTGCATCTCCTCTTGCTTTCATTCTTT
AAGCCCACTCCTAAACGCCACAAAATACTTTTGGAAGCAAAAGCCTTTCCAAGCGACCACTACG
CTATTGAGTCACAAATACAACTCCATGGACTTGATGTGGAAAAGTCTATGCGGATGGTAAAACC
ACGCGAAGGCGAGGAGACCCTTCGAATGGAGGACATACTTGAGGTCATCGAAGAAGAAGGAG
ATAGTATAGCAGTTATCCTTTTCAGCGGGCTGCACTTCTACACAGGTCAACTCTTTAACATTCCA
```

TABLE 2-continued

Exemplary effector molecule sequences

GCTATTACTAAGGCAGGCCACGCTAAAGGATGCTTCGTGGGCTTTGACCTTGCACACGCAGTAG
GAAACGTAGAGCTCCGCTTGCACGATTGGGGCGTTGATTTCGCCTGCTGGTGTTCATATAAGTA
TCTTAACTCAGGAGCTGGTGGGTTGGCAGGCGCATTCGTACACGAGAAACACGCTCATACCGTA
AAGCCTGCACTGGTAGGGTGGTTCGGACACGATCTCTCTACCCGCTTCAATATGGATAATAAAC
TCCAGCTTATACCTGGCGCCAATGGATTCAGGATCTCAAATCCTCCTATTTTGCTCGTTTGCAGT
TTGCACGCATCTCTTGAGGTGTTCCAGCAGGCTACCATGACTGCACTCCGCCGGAAGTCAATCC
TTTTGACCGGATACTTGGAGTATATGCTGAAACATTATCACTCAAAAGATAACACTGAGAATAA
GGGCCCCATAGTAAACATTATCACTCATCTCGGGCTGAAGAGCGCGGCTGCCAACTCACATTG
ACTTTTTCCATTCCCAAGAAGTCAGTGTTCAAAGAGTTGGAGAAACGGGGGGTTGTATGTGATA
AGCGGGAGCCAGATGGAATCCGCGTTGCCCCAGTCCCCCTCTATAATTCTTTTCACGATGTATA
CAAGTTTATTAGACTGCTGACAAGTATCTTGGACTCATCTGAGCGATCTtaG

VEGF(SEQ ID NO: 102)
ATGAATTTCTTGCTGAGCTGGGTGCATTGGACACTCGCATTGTTGCTGTACTTGCACCATGCCAA
GTGGTCCCAGGCTGCACCCACTACTGAGGGCGAGCAAAAGTCTCATGAGGTGATTAAATTTATG
GACGTTTACCAACGATCATACTGTCGGCCAATCGAAACCCTCGTAGATATATTCCAGGAGTACC
CAGACGAGATCGAATACATTTTCAAGCCCTCATGTGTCCCATTGATGCGATGTGCTGGGTGCTG
TAACGACGAAGCACTTGAATGTGTCCCCACCTCCGAGAGTAACATCACAATGCAAATAATGAG
AATCAAGCCCCACCAATCCCAACATATCGGTGAAATGTCATTCCTTCAGCATTCCCGCTGCGAG
TGCCGGCCTAAGAAGGACCGCACCAAACCAGAGAACCATTGTGAACCCTGTTCTGAGAGACGG
AAGCACTTGTTCGTACAGGACCCTCAAACATGCAAGTGCAGCTGTAAGAATACCGACTCACGGT
GTAAAGCTAGGCAACTGGAGCTTAATGAAAGGACCTGCCGATGCGATAAACCCAGGAGGtaa GM-CSF(SEQ ID NO: 103)
ATGTGGTTGCAGAATTTGCTCTTCCTGGGGATTGTGGTCTACAGCCTCTCCGCACCTACCCGCTC
TCCTATCACAGTTACAAGACCCTGGAAACATGTGGAGGCCATTAAAGAAGCATTGAATTTGTTG
GACGATATGCCCGTCACCCTGAATGAAGAAGTAGAAGTTGTTTCTAATGAGTTCAGCTTTAAAA
AATTGACCTGTGTGCAGACACGGCTTAAAATTTTTGAACAGGGACTTAGAGGAAACTTTACTAA
GCTGAAGGGGGCACTTAACATGACAGCTTCTTATTATCAGACCTATTGTCCTCCAACACCTGAA
ACCGACTGTGAAACACAGGTAACCACTTACGCCGATTTTATTGATTCTTTGAAAACATTCCTCAC
CGATATACCATTTGAGTGTAAGAAGCCAGGCCAAAAGtaG Anti-PD1(SEQ ID NO: 104)
ATGGAAACTGACACACTTCTTCTGTGGGTCTTGCTCCTGTGGGTCCCAGGCTCTACTGGTGACAG
TCCTGATAGGCCATGGAACCCACCTACCTTTAGTCCAGCCTTGCTCGTCGTAACCGAAGGGGAC
AACGCTACATTCACCTGCTCTTTTAGCAATACTTCTGAGAGTTTTCATGTAGTCTGGCATCGGGA
GAGTCCATCCGGACAAACAGATACTTTGGCCGCTTTTCCAGAGGATAGGTCTCAACCTGGGCAA
GACGCAAGGTTTCGAGTCACACAGCTTCCTAACGGGAGAGATTTTCACATGTCTGTAGTTCGGG
CACGCCGAAATGATTCTGGCACATATGTTTGCGGTGTGATCTCACTTGCTCCAAAGATTCAAAT
AAAGGAGAGCCTTCGCGCCGAGTTGCGGGTGACTGAGCGGGAGCCCAAGTCCTGCGACAAAAC
CCATACTTGTCCACCCTGTGGCGGCGGGTCATCCGGTGGCGGGTCTGGGGGGCAACCAAGAGA
GCCACAGGTATATACTCTTCCCCCCAGCAGAGAAGAAATGACAAAAAACCAAGTGTCCCTGAC
ATGTCTGGTTAAAGGATTTTATCCCAGTGACATTGCTGTAGAATGGGAATCCAATGGTCAACCC
GAGAATAACTACAAAACCACTCCTCCAGTATTGGACAGTGACGGTTCCTTCTTCCTCTATTCCAA
ACTTACAGTGGATAAATCCCGCTGGCAGCAAGGGAATGTATTCAGCTGTAGTGTCATGCACGAA
GCTCTTCATAACCATTATACACAGAAATCTCTTTCCCTGAGCCCAGGTAAAtaG Adenosine Deaminase(ADA) #1(Mouse)(SEQ ID NO: 105)
ATGGAGACTGATACACTTTTGCTCTGGGTTTTGCTCTTGTGGGTACCAGGGTCTACTGGAGATGC
ACAAACTCCTGCATTCAACAAGCCTAAGGTAGAGCTTCATGTCCATTTGGACGGAGCCATAAAA
CCTGAAACCATACTCTATTTCGGCAAGAAACGGGGTATAGCACTTCCCGCTGATACCGTGGAAG
AGTTGAGAAATATCATTGGCATGGACAAACCTCTTAGCCTGCCTGGCTTTCTTGCAAAGTTCGA
CTACTATATGCCAGTTATAGCAGGGTGTAGAGAAGCAATAAAGCGAATCGCCTATGAGTTCGTT
GAGATGAAGGCTAAAGAAGGAGTTGTTTACGTGGAAGTCCGGTACTCACCTCATCTGCTTGCTA
ATAGCAAGGTGGACCCAATGCCATGGAATCAAACTGAAGGTGATGTAACCCCTGACGATGTGG
TCGATTTGGTCAATCAAGGTCTCCAAGAAGGCGAGCAGGCTTTCGGCATTAAGGTAAGAAGTAT
ATTGTGCTGTATGCGACATCAACCTTCATGGTCCCTGGAGGTCCTCGAATTGTGCAAAAAGTAC
AATCAAAAAACAGTGGTCGCAATGGATCTCGCTGGAGATGAGACCATAGAAGGTTCCTCTCTTT
TCCCCGGTCATGTCGAAGCATATGAAGGGGCTGTCAAAAATGGTATCCACCGCACCGTCCACGC
AGGGGAAGTAGGGTCCCCAGAAGTAGTCAGGGAAGCCGTTGACATTTTGAAAACAGAAGAGT
CGGGCATGGCTACCATACAATAGAGGACGAAGCCTTGTACAATCGACTTTTGAAAGAAAATAT
GCACTTCGAGGTCTGTCCCTGGAGTTCATATCTCACCGGAGCATGGGACCCCAAAACAACCCAC
GCCGTCGTACGCTTCAAGAATGATAAGGCAAACTACAGTTTGAATACAGATGATCCACTGATAT
TCAAGTCAACACTTGACACTGACTACCAGATGACAAAAAAAGATATGGGTTTCACCGAAGAAG
AGTTCAAGAGATTGAACATTAACGCAGCAAAAGCTCCTTCCTGCCAGAGGAAGAGAAAAAAG
AATTGCTTGAAAGGTTGTATCGAGAATACCAA Adenosine Deaminase(ADA) #2(Mouse)(SEQ ID NO: 106)
ATGGCACAAACTCCAGCTTTTAATAAGCCCAAAGTGGAACTTCATGTTCATCTGGATGGGGCAA
TTAAGCCCGAAACTATATTGTACTTTGGCAAAAAGAGGGGTATTGCCCTGCCAGCAGATACCGT
TGAGGAGCTTCGCAACATCATTGGGATGGACAAGCCCCTCTCTCTGCCAGGTTTTCTCGCTAAA
TTCGATTATTATATGCCTGTTATTGCTGGTTGCCGGGAGGCCATCAAGAGGATAGCCTACGAGT
TTGTTGAGATGAAGGCCAAAGAGGGCGTGGTGTACGTAGAGGTCAGATACTCAGCCCTCACCTGC
TTGCCAACAGCAAGGTGGACCCAATGCCCTGGAACCAAACCGAGGGGGATGTCACTCCCGACG
ACGTTGTAGACCTCGTAAATCAGGGCCTTCAAGAGGGCGAGCAGGCATTTGGCATAAAAGTCC
GGTCTATACTCTGCTGTATGAGGCACCAACCCTCCTGGTCTTTGGAGGTACTTGAGTTGTGTAAG
AAATACAATCAAAAGACTGTAGTCGCCATGGATCTTGCAGGCGATGAAACCATCGAGGGTAGC
TCCTTGTTCCCTGGACATGTTGAAGCCTACGAGGGGGGCCGTAAAAAATGGGATACACAGGACTG TABLE 2-continued Exemplary effector molecule sequences TCCACGCTGGTGAAGTCGGAAGCCCAGAGGTGGTAAGGGAGGCAGTTGACATACTCAAGACAG
AGCGGGTTGGACACGGATACCACACAATTGAGGACGAGGCCCTGTATAACCGCCTCCTCAAAG
AGAACATGCATTTTGAGGTGTGTCCTTGGTCCAGCTACCTGACTGGTGCTTGGGACCCTAAAAC
AACTCACGCCGTGGTCCGGTTCAAGAACGATAAAGCCAATTACTCTTTGAATACCGACGACCCC
CTCATATTCAAATCAACATTGGATACCGACTACCAAATGACCAAAAAGGATATGGGGTTTACTG
AAGAGGAGTTCAAGAGGCTCAACATAAATGCCGCTAAATCCTCCTTTCTCCCCGAGGAAGAAA
AAAAAGAACTCCTTGAGCGGCTGTATAGGGAGTATCAA 4-1BBL #1(Mouse)(SEQ ID NO: 107)
ATGGAAACAGATACACTCTTGCTCTGGGTACTGCTTCTGTGGGTCCCCGGCTCTACTGGGGATG
AAGATGATGTAACTACTACAGAAGAACTCGCTCCCGCTCTTGTCCCCCCACCCAAGGGTACCTG
CGCCGGTTGGATGGCTGGCATCCCAGGACATCCAGGTCACAACGGTACCCCCGGAAGAGATGG
TCGGGATGGAACTCCCGGCGAGAAGGGCGAAAAAGGGGATGCAGGGCTTCTGGGACCTAAAG
GTGAAACAGGGGACGTTGGAATGACTGGTGCAGAAGGGCCTCGCGGCTTTCCTGGCACCCCTG
GGAGGAAAGGAGAGCCCGGAGAGCTCCAGAGAACTGAACCTCGGCCTGCACTCACTATAACTA
CTTCCCCTAATCTTGGGACCCGCGAGAACAACGCCGATCAGGTTACACCTGTAAGCCATATCGG
GTGCCCCAATACTACCCAGCAAGGGAGTCCCGTGTTCGCAAAGCTTTTGGCTAAAAACCAAGCA
TCCCTGTGTAACACTACTCTTAATTGGCATTCACAAGACGGTGCTGGTAGCTCTTATCTTTCTCA
GGGGCTGCGGTACGAAGAAGATAAGAAGGAATTGGTTGTGGATTCTCCAGGACTCTATTATGTC
TTTCTCGAATTGAAGCTCAGTCCCACCTTCACAAACACTGGACACAAAGTCCAGGGCTGGGTAA
GTCTGGTACTCCAAGCAAAGCCCCAGGTTGACGATTTCGACAATTTGGCACTCACCGTAGAGCT
TTTCCCATGCTCCATGGAAAATAAACTTGTTGATCGGTCATGGTCACAGCTCTTGCTGCTTAAGG
CAGGGCATCGCCTCTCAGTGGGTCTGAGAGCTTATTTGCATGGTGCACAAGATGCTTACAGGGA
TTGGGAATTGTCCTACCCAAACACTACAAGTTTCGGGTTGTTCCTTGTCAAACCTGATAACCCAT
GGGAGtaG 4-1BBL #2(Mouse)(SEQ ID NO: 108)
ATGGAAACTGATACACTCCTCCTGTGGGTCCTTCTTTTGTGGGTGCCCGGATCAACCGGCGATG
GCTGGATGGCAGGCATCCCAGGACACCCAGGACACAACGGTACTCCAGGTCGAGACGGTCGGG
ATGGGACTCCTGGGGAGAAAGGCGAGAAAGGGGACGCTGGTTTGCTCGGTCCTAAGGGGGAAA
CCGGGGATGTAGGAATGACAGGGGCTGAAGGGCCTCGGGGATTTCCTGGACACCAGGCAGGA
AGGGTGAACCAGGGGAGGCCCTCCAGCGCACCGAGCCACGGCCAGCTCTGACCATAACAACAA
GTCCAAACCTGGGCACACGCGAAAACAATGCTGACCAGGTGACTCCTGTAAGTCACATCGGAT
GCCCTAACACTACACAACAGGGCTCTCCTGTATTTGCAAAGCTTCTCGCAAAAAATCAAGCATC
ACTTTGTAATACAACCCTGAACTGGCATTCTCAGGACGGAGCAGGGTCCTCTTATTTGTCTCAA
GGGCTCCGCTACGAAGAAGATAAAAAGGAATTGGTTGTTGACAGTCCAGGTTTGTATTATGTGT
TTTTGGAACTTAAGCTGTCACCAACCTTCACTAACACCGGCCACAAGGTCCAAGGCTGGGTTAG
TCTTGTTTTGCAAGCCAAACCTCAAGTGGATGATTTTGACAATCTGGCTTTGACTGTTGAGCTTT
TTCCATGCAGTATGGAGAATAAACTGGTTGATCGGTCATGGTCACAGCTCCTTCTGCTCAAGGC
CGGACATAGGCTGAGTGTGGGACTTCGGGCCTACTTGCACGGCGCCCAGGACGCATACCGAGA
CTGGGAACTCAGCTACCCTAACACAACTTCTTTTGGGTTGTTCCTTGTCAAACCCGATAATCCTT
GGGAAtaG HPGE2 #1(Mouse)(SEQ ID NO: 109)
ATGGAGACTGATACTTTGCTCCTGTGGGTTCTTCTCCTGTGGGTTCCTGGTTCCACAGGGGATAT
GCATGTCAATGGCAAGGTAGCACTCGTGACTGGGGCTGCACAGGGTATCGGGAAAGCTTTTGCC
GAGGCCCTGTTGCTGCATGGCGCCAAGGTCGCTTTGGTAGATTGGAACTTGGAGGCTGGAGTTA
AATGCAAAGCTGCACTCGACGAACAATTTGAGCCTCAAAAAACCCTCTTTGTGCAGTGTGACGT
TGCTGACCAAAAGCAACTCAGGGACACATTCAGGAAGGTCGTAGACCATTTCGGACGCCTCGA
TATACTCGTTAATAATGCCGGGGTAAACAACGAAAAGAACTGGGAACAAACATTGCAAATCAA
CCTGGTAAGTGTCATTAGCGGAACTTATCTGGGTCTTGATTATATGAGCAAGCAGAACGGGGGC
GAGGGCGGGATCATTATCAACATGTCAAGTCTTGCCGGATTGATGCCAGTTGCTCAGCAGCCTG
TTTACTGTGCCAGCAAGCACGGTATTATTGGGTTTACCCGGAGTGCCGCCATGGCCGCAAATCT
TATGAAGAGTGGGGTAAGACTGAATGTTATCTGCCCAGGTTTCGTAGATACCCCAATCCTGGAG
AGCATCGAGAAGGAGGAAAATATGGGACAATACATTGAATATAAAGATCAAATCAAGGCTATG
ATGAAGTTCTACGGGGTTCTGCATCCATCCACAATTGCCAACGGGCTCATTAATCTGATTGAGG
ACGACGCCTTGAACGGAGCTATAATGAAAATCACAGCTTCCAAAGGCATTCACTTCCAAGATTA
TGATATATCACCCTTGCTTGTCAAGGCTCCTCTGACAAGT HPGE2 #2(Mouse)(SEQ ID NO: 110)
ATGCATGTCAATGGCAAGGTAGCACTCGTGACTGGGGCTGCACAGGGTATCGGGAAAGCTTTTG
CCGAGGCCCTGTTGCTGCATGGCGCCAAGGTCGCTTTGGTAGATTGGAACTTGGAGGCTGGAGT
TAAATGCAAAGCTGCACTCGACGAACAATTTGAGCCTCAAAAAACCCTCTTTGTGCAGTGTGAC
GTTGCTGACCAAAAGCAACTCAGGGACACATTCAGGAAGGTCGTAGACCATTTCGGACGCCTC
GATATACTCGTTAATAATGCCGGGGTAAACAACGAAAAGAACTGGGAACAAACATTGCAAATC
AACCTGGTAAGTGTCATTAGCGGAACTTATCTGGGTCTTGATTATATGAGCAAGCAGAACGGGG
GCGAGGGCGGGATCATTATCAACATGTCAAGTCTTGCCGGATTGATGCCAGTTGCTCAGCAGCC
TGTTTACTGTGCCAGCAAGCACGGTATTATTGGGTTTACCCGGAGTGCCGCCATGGCCGCAAAT
CTTATGAAGAGTGGGGTAAGACTGAATGTTATCTGCCCAGGTTTCGTAGATACCCCAATCCTGG
AGAGCATCGAGAAGGAGGAAAATATGGGACAATACATTGAATATAAAGATCAAATCAAGGCTA
TGATGAAGTTCTACGGGGTTCTGCATCCATCCACAATTGCCAACGGGCTCATTAATCTGATTGA
GGACGACGCCTTGAACGGAGCTATAATGAAAATCACAGCTTCCAAAGGCATTCACTTCCAAGAT
TATGATATATCACCCTTGCTTGTCAAGGCTCCTCTGACAAGT Human IL-15 Polypeptide Sequence(SEQ ID NO: 199)
MVLGTIDLCSCFSAGLPKTEANWVNVISDLKKIEDLIQSMHIDATLYTESDVHPSCKVTAMKCFLLE
LQVISLESGDASIHDTVENLIILANNSLSSNGNVTESGCKECEELEEKNIKEFLQSFVHIVQMFINTS TABLE 2-continued Exemplary effector molecule sequences Human IL-15Rα Polypeptide Sequence(SEQ ID NO: 200)
MAPRRARGCRTLGLPALLLLLLLRPPATRGITCPPPMSVEHADIWVKSYSLYSRERYICNSGFKRKA
GTSSLTECVLNKATNVAHWTTPSLKCIRDPALVHQRPAPPSTVTTAGVTPQPESLSPSGKEPAASSPS
SNNTAATTAAIVPGSQLMPSKSPSTGTTEISSHESSHGTPSQTTAKNWELTASASHQPPGVYPQGHSD
TTVAISTSTVLLCGLSAVSLLACYLKSRQTPPLASVEMEAMEALPVTWGTSSRDEDLENCSHHL Human IL-15Rα sushi domain Polypeptide Sequence(SEQ ID NO: 201)
ITCPPPMSVEHADIWVKSYSLYSRERYICNSGFKRKAGTSSLTECVLNKATNVAHWTTPSLKCIR Human IL-15/IL-15Rα sushi domain Polypeptide Sequence(SEQ ID NO: 202)
MDWTWILFLVAAATRVHSNWVNVISDLKKIEDLIQSMHIDATLYTESDVHPSCKVTAMKCFLLELQ
VISLESGDASIHDTVENLIILANNSLSSNGNVTESGCKECEELEEKNIKEFLQSFVHIVQMFINTSSGGS
GGGGSGGGSGGGGSLQITCPPPMSVEHADIWVKSYSLYSRERYICNSGFKRKAGTSSLTECVLNKAT
NVAHWTTPSLKCIR IL-12(IL-12p70)Polypeptide Sequence(SEQ ID NO: 203)
MCHQQLVISWFSLVFLASPLVAIWELKKDVYVVELDWYPDAPGEMVVLTCDTPEEDGITWTLDQSS
EVLGSGKTLTIQVKEFGDAGQYTCHKGGEVLSHSLLLLHKKEDGIWSTDILKDQKEPKNKTFLRCEA
KNYSGRFTCWWLTTISTDLTFSVKSSRGSSDPQGVTCGAATLSAERVRGDNKEYEYSVECQEDSAC
PAAEESLPIEVMVDAVHKLKYENYTSSFFIRDIIKPDPPKNLQLKPLKNSRQVEVSWEYPDTWSTPHS
YFSLTFCVQVQGKSKREKKDRVFTDKTSATVICRKNASISVRAQDRYYSSSWSEWASVPCSGGGSG
GGSGGGSGGGSRNLPVATPDPGMFPCLHHSQNLLRAVSNMLQKARQTLEFYPCTSEEIDHEDITKD
KTSTVEACLPLELTKNESCLNSRETSFITNGSCLASRKTSFMMALCLSSIYEDLKMYQVEFKTMNAK
LLMDPKRQIFLDQNMLAVIDELMQALNFNSETVPQKSSLEEPDFYKTKIKLCILLHAFRIRAVTIDRV
MSYLNAS

Secretion Signals and Signal-Anchors

The one or more effector molecules of the chimeric proteins provided for herein can be secretable effector molecules having a secretion signal peptide (also referred to as a signal peptide or signal sequence) at the chimeric protein's N-terminus (e.g., an effector molecule's N-terminus for S-C-MT) that direct newly synthesized proteins destined for secretion or membrane localization (also referred to as membrane insertion) to the proper protein processing pathways. For chimeric proteins having the formula MT-C-S, a membrane tethering domain generally has a signal-anchor sequence (e.g., signal-anchor sequences of a Type II transmembrane protein) that direct newly synthesized proteins destined for membrane localization to the proper protein processing pathways. For chimeric proteins having the formula S-C-MT, a membrane tethering domain having a reverse signal-anchor sequence (e.g., signal-anchor sequences of certain Type III transmembrane proteins) can be used, generally without a separate secretion signal peptide, that direct newly synthesized proteins destined for membrane localization to the proper protein processing pathways.

In general, for all membrane-cleavable chimeric proteins described herein, the one or more effector molecules are secretable effector molecules (referred to as "S" in the formula S-C-MT or MT-C-S). In embodiments with two or more chimeric proteins, each chimeric protein can comprise a secretion signal. In embodiments with two or more chimeric proteins, each chimeric protein can comprise a secretion signal such that each effector molecule is capable of secretion from an engineered cell following cleavage of the protease cleavage site.

The secretion signal peptide operably associated with an effector molecule can be a native secretion signal peptide (e.g., the secretion signal peptide generally endogenously associated with the given effector molecule). The secretion signal peptide operably associated with an effector molecule can be a non-native secretion signal peptide native secretion signal peptide. Non-native secretion signal peptides can promote improved expression and function, such as maintained secretion, in particular environments, such as tumor microenvironments. Non-limiting examples of non-native secretion signal peptide are shown in Table 3.

TABLE 3

Exemplary Signal Secretion Peptides

| Name | Protein SEQUENCE | Source (Uniprot) | DNA SEQUENCE |
|---|---|---|---|
| IL-12 | MCHQQLVISWFSL VFLASPLVA (SEQ ID NO: 112) | P29460 | ATGTGTCACCAGCAGCTCGTTATAT CCTGGTTTAGTTTGGTGTTTCTGCT TCACCCCTGGTGGCA (SEQ ID NO: 31) |
| IL-12 (Codon Optimized) | MCHQQLVISWFSL VFLASPLVA (SEQ ID NO: 112) | — | ATGTGCCATCAGCAACTCGTCATCT CCTGGTTCTCCCTTGTGTTCCTCGCT TCCCCTCTGGTCGCC (SEQ ID NO: 32) |
| IL-2 (Optimized) | MQLLSCIALILALV (SEQ ID NO: 113) | — | ATGCAACTGCTGTCATGTATCGCAC TCATCCTGGCGCTGGTA (SEQ ID NO: 33) |

TABLE 3-continued

| Name | Protein SEQUENCE | Source (Uniprot) | DNA SEQUENCE |
|---|---|---|---|
| IL-2 (Native) | MYRMQLLSCIALSL ALVTNS (SEQ ID NO: 114) | P60568 | ATGTATCGGATGCAACTTTTGAGCT GCATCGCATTGTCTCTGGCGCTGGT GACAAATTCC (SEQ ID NO: 34) |
| Trypsinogen-2 | MNLLLILTFVAAAV A (SEQ ID NO: 115) | P07478 | ATGAATCTCTTGCTCATACTTACGT TTGTCGCTGCTGCCGTTGCG (SEQ ID NO: 35) |
| Gaussia Luciferase | MGVKVLFALICIAV AEA (SEQ ID NO: 116) | | ATGGGCGTGAAGGTCTTGTTTGCCC TTATCTGCATAGCTGTTGCGGAGGC G (SEQ ID NO: 36) |
| CD5 | MPMGSLQPLATLY LLGMLVASCLG (SEQ ID NO: 117) | P06127 | ATGCCGATGGGGAGCCTTCAACCTT TGGCAACGCTTTATCTTCTGGGGAT GTTGGTTGCTAGTTGCCTTGGG (SEQ ID NO: 37) |
| IgKVII (mouse) | METDTLLLWVLLL WVPGSTGD (SEQ ID NO: 118) | | ATGGAAACTGACACGTTGTTGCTGT GGGTATTGCTCTTGTGGGTCCCAGG ATCTACGGGCGAC (SEQ ID NO: 38) |
| IgKVII (human) | MDMRVPAQLLGLL LLWLRGARC (SEQ ID NO: 119) | P01597 | ATGGATATGAGGGTTCCCGCCCAGC TTTTGGGGCTGCTTTTGTTGTGGCTT CGAGGGGCTCGGTGT (SEQ ID NO: 39) |
| VSV-G | MKCLLYLAFLFIGV NC (SEQ ID NO: 120) | | ATGAAGTGTCTGTTGTACCTGGCGT TTCTGTTCATTGGTGTAAACTGT (SEQ ID NO: 40) |
| Prolactin | MNIKGSPWKGSLL LLLVSNLLLCQSVA P (SEQ ID NO: 121) | P01236 | ATGAATATCAAAGGAAGTCCGTGG AAGGGTAGTCTCCTGCTGCTCCTCG TATCTAACCTTCTCCTTTGTCAATCC GTGGCACCC (SEQ ID NO: 41) |
| Serum albumin preproprotein | MKWVTFISLLFLFS SAYS (SEQ ID NO: 122) | P02768 | ATGAAATGGGTAACATTCATATCAC TTCTCTTTCTGTTCAGCTCTGCGTAT TCT (SEQ ID NO: 42) |
| Azurocidin preproprotein | MTRLTVLALLAGL LASSRA (SEQ ID NO: 123) | 20160 | ATGACAAGGCTTACTGTTTTGGCTC TCCTCGCTGGACTCTTGGCTTCCTC CCGAGCA (SEQ ID NO: 43) |
| Osteonectin (BM40) | MRAWIFFLLCLAG RALA (SEQ ID NO: 124) | P09486 | ATGAGGGCTTGGATTTTTTTTCTGCT CTGCCTTGCCGGTCGAGCCCTGGCG (SEQ ID NO: 44) |
| CD33 | MPLLLLLPLLWAG ALA (SEQ ID NO: 125) | P20138 | ATGCCTCTTCTGCTTTTGCTTCCTCT TTTGTGGGCAGGTGCCCTCGCA (SEQ ID NO: 45) |
| IL-6 | MNSFSTSAFGPVAF SLGLLLVLPAAFPA P (SEQ ID NO: 126) | P05231 | ATGAACTCTTTCTCAACCTCTGCGT TTGGTCCGGTCGCTTTCTCCCTTGG GCTCCTGCTTGTCTTGCCAGCAGCG TTTCCTGCGCCA (SEQ ID NO: 46) |
| IL-8 | MTSKLAVALLAAF LISAALC (SEQ ID NO: 127) | P10145 | ATGACAAGTAAACTGGCGGTAGCC TTGCTCGCGGCCTTTTTGATTTCCGC AGCCCTTTGT (SEQ ID NO: 47) |
| CCL2 | MKVSAALLCLLLIA ATFIPQGLA (SEQ ID NO: 128) | P13500 | ATGAAGGTAAGTGCAGCGTTGCTTT GCCTTCTCCTCATTGCAGCGACCTT TATTCCTCAAGGGCTGGCC (SEQ ID NO: 48) |
| TIMP2 | MGAAARTLRLALG LLLLATLLRPADA (SEQ ID NO: 129) | P16035 | ATGGGAGCGGCAGCTAGAACACTT CGACTTGCCCTTGGGCTCTTGCTCC TTGCAACCCTCCTTAGACCTGCCGA CGCA (SEQ ID NO: 49) |
| VEGFB | MSPLLRRLLLAALL QLAPAQA (SEQ ID NO: 130) | P49765 | ATGTCACCGTTGTTGCGGAGATTGC TGTTGGCCGCACTTTTGCAACTGGC TCCTGCTCAAGCC (SEQ ID NO: 50) |

TABLE 3-continued

Exemplary Signal Secretion Peptides

| Name | Protein SEQUENCE | Source (Uniprot) | DNA SEQUENCE |
| --- | --- | --- | --- |
| Osteoprotegerin | MNNLLCCALVFLDI SIKWTTQ (SEQ ID NO: 131) | O00300 | ATGAATAACCTGCTCTGTTGTGCGC TCGTGTTCCTGGACATTTCTATAAA ATGGACAACGCAA (SEQ ID NO: 51) |
| Serpin E1 | MQMSPALTCLVLG LALVFGEGSA (SEQ ID NO: 132) | P05121 | ATGCAAATGTCTCCTGCCCTTACCT GTCTCGTACTTGGTCTTGCGCTCGT ATTTGGAGAGGGATCAGCC (SEQ ID NO: 52) |
| GROalpha | MARAALSAAPSNP RLLRVALLLLLLVA AGRRAAG (SEQ ID NO: 133) | P09341 | ATGGCAAGGGCTGCACTCAGTGCT GCCCCGTCTAATCCCAGATTGCTTC GAGTTGCATTGCTTCTTCTGTTGCTG GTTGCAGCTGGTAGGAGAGCAGCG GGT (SEQ ID NO: 53) |
| CXCL12 | MNAKVVVVLVLV LTALCLSDG (SEQ ID NO: 134) | P48061 | ATGAATGCAAAAGTCGTGGTCGTG CTGGTTTTGGTTCTGACGGCGTTGT GTCTTAGTGATGGG (SEQ ID NO: 54) |
| IL-21 (Codon Optimized) | MERIVICLMVIFLG TLVHKSSS (SEQ ID NO: 135) | Q9HBE4 | ATGGAACGCATTGTGATCTGCCTGA TGGTCATCTTCCTGGGCACCTTAGT GCACAAGTCGAGCAGC (SEQ ID NO: 55) |
| CD8 | MALPVTALLLPLAL LLHAARP (SEQ ID NO: 136) | – | ATGGCCTTACCAGTGACCGCCTTGC TCCTGCCGCTGGCCTTGCTGCTCCA CGCCGCCAGGCCG (SEQ ID NO: 139) |
| CD8 (Codon Optimized) | MALPVTALLLPLAL LLHAARP (SEQ ID NO: 137) | | ATGGCGCTCCCGGTGACAGCACTTC TCTTGCCTCTTGCCCTGCTGTTGCAT GCCGCGCGCCCA (SEQ ID NO: 140) |
| GMCSF | MLLVTSLLLCELPH PAFLLIP (SEQ ID NO: 138) | – | ATGTTGCTCGTGACATCCCTCTTGC TTTGTGAGTTGCCTCATCCCGCATT CCTGCTCATCCCA (SEQ ID NO: 141) |
| NKG2D | PFFFCCFIAVAMGI RFIIMVA (SEQ ID NO: 192) | | CCCTTCTTCTTCTGTTGCTTTATCGC CGTGGCCATGGGCATCCGCTTCATC ATTATGGTGGCC (SEQ ID NO: 193) |

Protease Cleavage Site

In certain embodiments, the chimeric proteins provided for herein (e.g., in general, for all membrane-cleavable chimeric proteins described herein) contain a protease cleavage site (e.g., referred to as "C" in the formula S-C-MT or MT-C-S for membrane-cleavable chimeric proteins described herein). In general, the protease cleavage site can be any amino acid sequence motif capable of being cleaved by a protease. Examples of protease cleavage sites include, but are not limited to, a Type 1 transmembrane protease cleavage site, a Type II transmembrane protease cleavage site, a GPI anchored protease cleavage site, an ADAM8 protease cleavage site, an ADAM9 protease cleavage site, an ADAM10 protease cleavage site, an ADAM12 protease cleavage site, an ADAM15 protease cleavage site, an ADAM17 protease cleavage site, an ADAM19 protease cleavage site, an ADAM20 protease cleavage site, an ADAM21 protease cleavage site, an ADAM28 protease cleavage site, an ADAM30 protease cleavage site, an ADAM33 protease cleavage site, a BACE1 protease cleavage site, a BACE2 protease cleavage site, a SIP protease cleavage site, an MT1-MMP protease cleavage site, an MT3-MMP protease cleavage site, an MT5-MMP protease cleavage site, a furin protease cleavage site, a PCSK7 protease cleavage site, a matriptase protease cleavage site, a matriptase-2 protease cleavage site, an MMP9 protease cleavage site, or an NS3 protease cleavage site.

One example of a protease cleavage site is a hepatitis C virus (HCV) nonstructural protein 3 (NS3) protease cleavage site, including, but not limited to, a NS3/NS4A, a NS4A/NS4B, a NS4B/NS5A, or a NS5A/NS5B cleavage site. For a description of NS3 protease and representative sequences of its cleavage sites for various strains of HCV, see, e.g., Hepatitis C Viruses: Genomes and Molecular Biology (S. L. Tan ed., Taylor & Francis, 2006), Chapter 6, pp. 163-206; herein incorporated by reference in its entirety. For example, the sequences of HCV NS4A/4B protease cleavage site; HCV NS5A/5B protease cleavage site; C-terminal degron with NS4A/4B protease cleavage site; N-terminal degron with HCV NS5A/5B protease cleavage site are provided. Representative NS3 sequences are listed in the National Center for Biotechnology Information (NCBI) database. See, for example, NCBI entries: Accession Nos. YP_001491553, YP_001469631, YP_001469632, NP_803144, NP_671491, YP_001469634, YP_001469630, YP_001469633, ADA68311, ADA68307, AFP99000, AFP98987, ADA68322, AFP99033, ADA68330, AFP99056, AFP99041, CBF60982, CBF60817, AHH29575, AIZ00747, AIZ00744, AB136969, ABN05226, KF516075, KF516074, KF516056, AB826684, AB826683, JX171009, JX171008, JX171000, EU847455, EF154714, GU085487, JX171065, JX171063; all of which sequences (as entered by the date of filing of this application) are herein incorporated by reference.

Another example of a protease cleavage site is an ADAM17-specific protease (also referred to as Tumor Necrosis Factor-α Converting Enzyme [TACE]) cleavage site. An ADAM17-specific protease cleavage site can be an endogenous sequence of a substrate naturally cleaved by ADAM17. An ADAM17-specific protease cleavage site can be an engineered sequence capable of being cleaved by ADAM17. An engineered ADAM17-specific protease cleavage site can be an engineered for specific desired properties including, but not limited to, optimal expression of the chimeric proteins, specificity for ADAM17, rate-of-cleavage by ADAM17, ratio of secreted and membrane-bound chimeric protein levels, and cleavage in different cell states. A protease cleavage site can be selected for specific cleavage by ADAM17. For example, certain protease cleavage sites capable of being cleaved by ADAM17 are also capable of cleavage by additional ADAM family proteases, such as ADAM10. Accordingly, an ADAM17-specific protease cleavage site can be selected and/or engineered such that cleavage by other proteases, such as ADAM10, is reduced or eliminated. A protease cleavage site can be selected for rate-of-cleavage by ADAM17. For example, it can be desirable to select a protease cleavage site demonstrating a specific rate-of-cleavage by ADAM17, such as reduced cleavage kinetics relative to an endogenous sequence of a substrate naturally cleaved by ADAM17. In such cases, in general, a specific rate-of-cleavage can be selected to regulate the rate of processing of the chimeric protein, which in turn regulates the rate of release/secretion of the payload effector molecule. Accordingly, an ADAM17-specific protease cleavage site can be selected and/or engineered such that the sequence demonstrates a desired rate-of-cleavage by ADAM17. A protease cleavage site can be selected for both specific cleavage by ADAM17 and rate-of-cleavage by ADAM17. Exemplary ADAM17-specific protease cleavage sites, including those demonstrating particular specificity and rate-of-cleavage kinetics, are shown in Table 4A below with reference to the site of cleavage (P5-P1: N-terminal; P1'-P5': C-terminal). Further details of ADAM17 and ADAM10, including expression and protease cleavage sites, are described in Sharma, et al. (J Immunol Oct. 15, 2017, 199 (8) 2865-2872), Pham et al. (Anticancer Res. 2017 October; 37(10):5507-5513), Caescu et al. (Biochem J. 2009 Oct. 23; 424(1): 79-88), and Tucher et al. (J. Proteome Res. 2014, 13, 4, 2205-2214), each herein incorporated by reference for purposes.

TABLE 4A

Various ADAM17 Protease Cleavage Site Sequences

| P5 | P4 | P3 | P2 | P1 | P1' | P2' | P3' | P4' | P5' | FULL SEQ | SEQ ID NO |
|----|----|----|----|----|-----|-----|-----|-----|-----|----------|-----------|
| P | R | A | E | A | V | K | G | G | | PRAEAVKGG | 179 |
| P | R | A | E | A | L | K | G | G | | PRAEALKGG | 180 |
| P | R | A | E | Y | S | K | G | G | | PRAEYSKGG | 181 |
| P | R | A | E | P | I | K | G | G | | PRAEPIKGG | 182 |
| P | R | A | E | A | Y | K | G | G | | PRAEAYKGG | 183 |
| P | R | A | E | S | S | K | G | G | | PRAESSKGG | 184 |
| P | R | A | E | F | T | K | G | G | | PRAEFTKGG | 185 |
| D | E | P | H | Y | S | Q | R | R | | DEPHYSQRR | 187 |

TABLE 4A-continued

Various ADAM17 Protease Cleavage Site Sequences

| P5 | P4 | P3 | P2 | P1 | P1' | P2' | P3' | P4' | P5' | FULL SEQ | SEQ ID NO |
|----|----|----|----|----|-----|-----|-----|-----|-----|----------|-----------|
| P | P | L | G | P | I | F | N | P | G | PPLGPIFNPG | 188 |
| P | L | A | Q | A | Y | R | S | S | | PLAQAYRSS | 189 |
| T | P | I | D | S | S | F | N | P | D | TPIDSSFNPD | 190 |
| V | T | P | E | P | I | F | S | L | I | VTPEPIFSLI | 191 |

In some embodiments, the protease cleavage site comprises a first region having the amino acid sequence of PRAE (SEQ ID NO: 176). In some embodiments, the protease cleavage site comprises a second region having the amino acid sequence of KGG (SEQ ID NO: 177). In some embodiments, the first region is located N-terminal to the second region. In some embodiments, the protease cleavage site comprises the amino acid sequence of PRAEX$_1$X$_2$KGG (SEQ ID NO: 219), wherein X$_1$ is A, Y, P, S, or F, and wherein X$_2$ is V, L, S, I, Y, T, or A. In some embodiments, the protease cleavage site comprises the amino acid sequence of PRAEX$_1$X$_2$KGG (SEQ ID NO: 178), wherein X$_1$ is A, Y, P, S, or F, and wherein X$_2$ is V, L, S, I, Y, or T. In some embodiments, the protease cleavage site comprises the amino acid sequence of PRAEAVKGG (SEQ ID NO: 179). In some embodiments, the protease cleavage site comprises the amino acid sequence of PRAEALKGG (SEQ ID NO: 180). In some embodiments, the protease cleavage site comprises the amino acid sequence of PRAEYSKGG (SEQ ID NO: 181). In some embodiments, the protease cleavage site comprises the amino acid sequence of PRAE-PIKGG (SEQ ID NO: 182). In some embodiments, the protease cleavage site comprises the amino acid sequence of PRAEAYKGG (SEQ ID NO: 183). In some embodiments, the protease cleavage site comprises the amino acid sequence of PRAESSKGG (SEQ ID NO: 184). In some embodiments, the protease cleavage site comprises the amino acid sequence of PRAEFTKGG (SEQ ID NO: 185). In some embodiments, the protease cleavage site comprises the amino acid sequence of PRAEAAKGG (SEQ ID NO: 186).

In some embodiments, the protease cleavage site comprises the amino acid sequence of DEPHYSQRR (SEQ ID NO: 187). In some embodiments, the protease cleavage site comprises the amino acid sequence of PPLGPIFNPG (SEQ ID NO: 188). In some embodiments, the protease cleavage site comprises the amino acid sequence of PLAQAYRSS (SEQ ID NO: 189). In some embodiments, the protease cleavage site comprises the amino acid sequence of TPIDSSFNPD (SEQ ID NO: 190). In some embodiments, the protease cleavage site comprises the amino acid sequence of VTPEPIFSLI (SEQ ID NO: 191). The protease cleavage sites of SEQ ID NOs: 187, 189, and 191 are cleavable by ADAM17.

In some embodiments, the protease cleavage site comprises the amino acid sequence of ITQGLAVSTISSFF (SEQ ID NO: 198), which is a cleavage site that is native to CD16 and is cleavable by ADAM17.

The protease cleavage site can be C-terminal of the secretable effector molecule. The protease cleavage site can be N-terminal of the secretable effector molecule. In general, for all membrane-cleavable chimeric proteins described herein, the protease cleavage site is either: (1) C-terminal of the secretable effector molecule and N-terminal of the cell membrane tethering domain (in other words, the protease cleavage site is in between the secretable effector molecule and the cell membrane tethering domain); or (2) N-terminal of the secretable effector molecule and C-terminal of the cell membrane tethering domain (also between the secretable effector molecule and the cell membrane tethering domain with domain orientation inverted). The protease cleavage site can be connected to the secretable effector molecule by a polypeptide linker, i.e., a polypeptide sequence not generally considered to be part of the effector molecule or protease cleavage site. The protease cleavage site can be connected to the cell membrane tethering domain by a polypeptide linker, i.e., a polypeptide sequence not generally considered to be part of the cell membrane tethering domain or protease cleavage site. A polypeptide linker can be any amino acid sequence that connects a first polypeptide sequence and a second polypeptide sequence. A polypeptide linker can be a flexible linker (e.g., a Gly-Ser-Gly sequence). Examples of polypeptide linkers include, but are not limited to, GSG linkers (e.g., [GS]4GG [SEQ ID NO: 220]), A(EAAAK)₃A (SEQ ID NO: 221), and Whitlow linkers (e.g., a "KEGS" (SEQ ID NO: 227) linker such as the amino acid sequence KESGSVSSEQLAQFRSLD (SEQ ID NO: 222), an eGK linker such as the amino acid sequence EGKSSGSGSESKST (SEQ ID NO: 223), and linkers described in more detail in Issued U.S. Pat. No. 5,990,275 herein incorporated by reference). Additional exemplary polypeptide linkers include SEQ ID NO: 194, SEQ ID NO: 195, SEQ ID NO: 196, and SEQ ID NO: 197. Other polypeptide linkers may be selected based on desired properties (e.g., length, flexibility, amino acid composition etc.) and are known to those skilled in the art.

In the Membrane-Cleavable system, following expression and localization of the chimeric protein into the cell membrane, the protease cleavage site directs cleavage of the chimeric protein such that the effector molecule is released ("secreted") into the extracellular space of a cell.

In general, a protease that cleaves the protease cleavage site is a protease specific for that specific protease cleavage site. For example, in the case of a disintegrin and metalloproteinase ("ADAM") family protease, the protease that cleaves a specific ADAM protease cleavage site is generally limited to the ADAM protease(s) that specifically recognize the specific ADAM protease cleavage site motif. A protease cleavage site can be selected and/or engineered such that cleavage by undesired proteases is reduced or eliminated. Proteases can be membrane-bound or membrane-associated. Proteases can be secreted, e.g., secreted in a specific cellular environment, such as a tumor microenvironment ("TME").

A protease that cleaves the protease cleavage site of the chimeric protein can be expressed in the same cell that expresses the chimeric protein. A protease that cleaves the protease cleavage site of the chimeric protein can be endogenous to a cell expressing the chimeric protein. In other words, a cell engineered to express the chimeric protein can endogenously express the protease specific for the protease cleavage site present in the chimeric protein. Endogenous expression of the protease refers to both expression under generally homeostatic conditions (e.g., a cell generally considered to be healthy), and also to differential expression under non-homeostatic conditions (e.g., upregulated expression in a tumor cell). The protease cleavage site can be selected based on the known proteases endogenously expressed by a desired cell population. In such cases, in general, the cleavage of the protease cleavage site (and thus release/secretion of a payload) can be restricted to only those cells of interest due to the cell-restricted protease needing to come in contact with the protease cleavage site of chimeric protein expressed in the same cell. For example, and without wishing to be bound by theory, ADAM17 is believed to be restricted in its endogenous expression to NK cell and T cells. Thus, selection of an ADAM17-specific protease cleavage site may restrict the cleavage of the protease cleavage site to NK cell and T cells co-expressing the chimeric protein. In other examples, a protease cleavage site can be selected for a specific tumor-associated protease known to be expressed in a particular tumor population of interest (e.g., in a specific tumor cell engineered to express the chimeric protein). Protease and/or expression databases can be used to select an appropriate protease cleavage site, such as selecting a protease cleavage site cleaved by a tumor-associated proteases through consulting Oncomine (www.oncomine.org), the European Bioinformatic Institute (www.ebi.ac.uk) in particular (www.ebi.ac.uk/gxa), PMAP (www.proteolysis.org), ExPASy Peptide Cutter (ca.expasy-.org/tools/peptide cutter) and PMAP.Cut DB (cutdb.burn-ham.org), each of which is incorporated by reference for all purposes.

A protease that cleaves the protease cleavage site of the chimeric protein can be heterologous to a cell expressing the chimeric protein. For example, a cell engineered to express the chimeric protein can also be engineered to express a protease not generally expressed by the cell that is specific for the protease cleavage site present in the chimeric protein. A cell engineered to express both the chimeric protein and the protease can be engineered to express each from separate engineered nucleic acids or from a multicistronic systems (multicistronic and multi-promoter systems are described in greater detail in the Section herein titled "Multicistronic and Multiple Promoter Systems"). Heterologous proteases and their corresponding protease cleavage site can be selected as described above with reference to endogenous proteases.

A protease that cleaves the protease cleavage site of the chimeric protein can be expressed on a separate distinct cell than the cell that expresses the chimeric protein. For example, the protease can be generally expressed in a specific cellular environment, such as a tumor microenvironment. In such cases, in general, the cleavage of the protease cleavage site can be restricted to only those cellular environments of interest (e.g., a tumor microenvironment) due to the environment-restricted protease needing to come in contact with the protease cleavage site. In embodiments having membrane-cleavable chimeric proteins, in general, the secretion of the effector molecule can be restricted to only those cellular environments of interest (e.g., a tumor microenvironment) due to the environment-restricted protease needing to come in contact with the protease cleavage site. A protease that cleaves the protease cleavage site of the chimeric protein can be endogenous to the separate distinct cell. A protease that cleaves the protease cleavage site of the chimeric protein can be heterologous to the separate distinct cell. For example, the separate distinct cell can be engineered to express a protease not generally expressed by the separate distinct cell.

Proteases include, but are not limited to, a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, and an MMP9 protease. A protease can be an NS3 protease. A protease can be an ADAM17 protease.

Proteases can be tumor associated proteases, such as, a cathepsin, a cysteine protease, an aspartyl protease, a serine protease, or a metalloprotease. Specific examples of tumor associated proteases include Cathepsin B, Cathepsin L, Cathepsin S, Cathepsin D, Cathepsin E, Cathepsin A, Cathepsin G, Thrombin, Plasmin, Urokinase, Tissue Plasminogen Activator, Metalloproteinase 1 (MMP1), MMP2, MMP3, MMP4, MMP7, MMP8, MMP9, MMP10, MMP11, MMP12, MMP13, MMP14, MMP15, MMP16, MMP17, MMP20, MMP21, MMP23, MMP24, MMP25, MMP26, MMP28, ADAM, ADAMTS, CD10 (CALLA), or prostate specific antigen. Proteases can also include, but are not limited to, proteases listed in Table 4B below. Exemplary cognate protease cleavage sites for certain proteases are also listed in Table 4B.

TABLE 4B

| Exemplary Proteases with Cognate Cleavage Sites and Inhibitors | | |
| --- | --- | --- |
| Protease (UniProt Accession No.) | Cognate cleavage site | Protease inhibitors |
| HCV NS4A/4B | DEMEECSQHL (SEQ ID NO: 142) EDVVPCSMG (SEQ ID NO: 143) | Simeprevir, Danoprevir, Asunaprevir, Ciluprevir, Boceprevir, Sovaprevir, Paritaprevir, Telaprevir, Grazoprevir |
| HCV NS5A/5B | DEMEECSQHL (SEQ ID NO: 142) EDVVPCSMG (SEQ ID NO: 143) | Simeprevir, Danoprevir, Asunaprevir, Ciluprevir, Boceprevir, Sovaprevir, Paritaprevir, Telaprevir, Grazoprevir |
| HCV NS3 | DEMEECSQHL (SEQ ID NO: 142) EDVVPCSMG (SEQ ID NO: 143) | Simeprevir, Danoprevir, Asunaprevir, Ciluprevir, Boceprevir, Sovaprevir, Paritaprevir, Telaprevir, Grazoprevir |
| HCV NS2-3 | DEMEECSQHL (SEQ ID NO: 142) EDVVPCSMG (SEQ ID NO: 143) | Simeprevir, Danoprevir, Asunaprevir, Ciluprevir, Boceprevir, Sovaprevir, Paritaprevir, Telaprevir, Grazoprevir |
| HIV-1 protease (SEQ ID NO: 144) | | Amprenavir, Atazanavir, Darunavir, Fosamprenavir, Indinavir, Lopinavir, Nelfinavir, Ritonavir, Saquinavir, Tipranavir |
| Signal peptidase (P67812, P15367, P00804, P0803) | preference of eukaryotic signal peptidase for cleavage after residue 20 (Xaa$^{20\downarrow}$) of pre(Δpro)apoA-II: Ala, Cys > Gly > Ser, Thr > Pro > Asn, Val, Ile, Leu, Tyr, His, Arg, Asp. | |
| proprotein convertases cleaving at hydrophobic residues (e.g., Leu, Phe, Val, or Met) (Q16549, Q8NBP7, Q92824, P29120, Q6UW60, P29122, Q9QXV0) | (R/K)-X-(hydrophobic)-X↓, where X is any amino acid | |
| proprotein convertases cleaving at small amino acid residues such as Ala or Thr (Q16549, Q8NBP7, Q92824, P29120, Q6UW60, P29122) | (K/R)-(X)n-(K/R)↓, where n is 0, 2, 4 or 6 and X is any amino acid | |
| proopiomelanocortin converting enzyme (PCE) (Q9UO77615, O776133) | Cleavage at paired basic residues in certain prohormones, either between them, or on the carboxyl side | |

TABLE 4B-continued

Exemplary Proteases with Cognate Cleavage Sites and Inhibitors

| Protease (UniProt Accession No.) | Cognate cleavage site | Protease inhibitors |
| --- | --- | --- |
| chromaffin granule aspartic protease (CGAP) | tends to cleave dipeptide bonds that have hydrophobic residues as well as a beta-methylene group | |
| prohormone thiol protease (cathepsin L1) (P07154, P07711, P06797, P25975, Q28944) | | |
| carboxypeptidases (e.g., carboxypeptidase E/H, carboxypeptidase D and carboxypeptidase Z) (Q9M099, P15169, Q04609, P08819, P08818, O77564, P70627, O35409, P07519, Q8VZU3, P22792, P15087, P16870, Q9JHH6, Q96IY4, Q7L8A9) | cleaves a peptide bond at the carboxy-terminal (C-terminal) end of a protein or peptide | |
| aminopeptidases (e.g., arginine aminopeptidase, lysine aminopeptidase, aminopeptidase B) | cleaves a peptide bond at the amino-terminal (N-terminal) end of a protein or peptide | |
| prolyl endopeptidase (Q12884, P48147, P97321, Q4J6C6) | Hydrolysis of Pro-\|-Xaa >> Ala-\|-Xaa in oligopeptides. Release of an N-terminal dipeptide, Xaa-Yaa-\|-Zaa-, from a polypeptide, preferentially when Yaa is Pro, provided Zaa is neither Pro nor hydroxyproline | |
| aminopeptidase N (P97449, P15144, P15145, P15684) | Release of an N-terminal amino acid, Xaa-\|-Yaa- from a peptide, amide or arylamide. Xaa is preferably Ala, but may be most amino acids including Pro (slow action). When a terminal hydrophobic residue is followed by a prolyl residue, the two may be released as an intact Xaa-Pro dipeptide | |
| insulin degrading enzyme (P14735, P35559, Q9JHR7, P22817, Q24K02) | Degradation of insulin, glucagon and other polypeptides. No action on proteins. Cleaves multiple short polypeptides that vary considerably in sequence | |
| Calpain (O08529, P17655, Q07009, Q27971, P20807, P07384, O35350, O14815, P04632, Q9Y6Q1, O15484, Q9HC96, A6NHC0, Q9UMQ6) | No specific amino acid sequence is uniquely recognized by calpains. Amongst protein substrates, tertiary structure elements rather than primary amino acid sequences appear to be responsible for directing cleavage to a specific substrate. Amongst peptide and small-molecule substrates, the most consistently reported specificity is for small, hydrophobic amino acids (e.g., leucine, valine and isoleucine) at the P2 position, and large hydrophobic amino acids (e.g., phenylalanine and tyrosine) at the P1 position. One fluorogenic calpain substrate is (EDANS)-Glu-Pro-Leu-Phe═Ala-Glu-Arg-Lys-(DABCYL), | |

TABLE 4B-continued

Exemplary Proteases with Cognate Cleavage Sites and Inhibitors

| Protease (UniProt Accession No.) | Cognate cleavage site | Protease inhibitors |
|---|---|---|
| | (EDANSEPLFAERKDABCYL (SEQ ID NO: 145)) with cleavage occurring at the Phe═Ala bond. | |
| caspase 1 (P29466, P29452) | Strict requirement for an Asp residue at position P1 and has a preferred cleavage sequence of Tyr-Val-Ala-Asp-\|- (YVAD; SEQ ID NO: 146). | |
| caspase 2 (P42575, P29594) | Strict requirement for an Asp residue at P1, with 316-asp being essential for proteolytic activity and has a preferred cleavage sequence of Val-Asp-Val-Ala-Asp-\|- (VDVAD; SEQ ID NO: 147). | |
| caspase 3 (P42574, P70677) | Strict requirement for an Asp residue at positions P1 and P4. It has a preferred cleavage sequence of Asp-Xaa-Xaa-Asp-\|- with a hydrophobic amino-acid residue at P2 and a hydrophilic amino-acid residue at P3, although Val or Ala are also accepted at this position. | |
| caspase 4 (P70343, P49662) | Strict requirement for Asp at the P1 position. It has a preferred cleavage sequence of Tyr-Val-Ala-Asp-\|- (YVAD; SEQ ID NO: 146) but also cleaves at Asp-Glu-Val-Asp-\|-(DEVD; SEQ ID NO: 148). | |
| caspase 5 (P51878) | Strict requirement for Asp at the P1 position. It has a preferred cleavage sequence of Tyr-Val-Ala-Asp-\|-(YVAD; SEQ ID NO: 146) but also cleaves at Asp-Glu-Val-Asp-\|- - \|-(DEVD; SEQ ID NO: 148). | |
| caspase 6 (P55212) | Strict requirement for Asp at position P1 and has a preferred cleavage sequence of Val-Glu-His-Asp-\|-(VEHD; SEQ ID NO: 149). | |
| caspase 7 (P97864, P55210) | Strict requirement for an Asp residue at position P1 and has a preferred cleavage sequence of Asp-Glu-Val-Asp-\|- (DEVD; SEQ ID NO: 148). | |
| caspase 8 (Q8IRY7, O89110, Q14790) | Strict requirement for Asp at position P1 and has a preferred cleavage sequence of (Leu/Asp/Val)-Glu-Thr-Asp-\|-(Gly/Ser/Ala). | |
| caspase 9 (P55211, Q8C3Q9, Q5IS54) | Strict requirement for an Asp residue at position P1 and with a marked preference for His at position P2. It has a preferred cleavage sequence of Leu-Gly-His-Asp-\|-Xaa (LGHD; SEQ ID NO: 150). | |
| caspase 10 (Q92851) | Strict requirement for Asp at position P1 and has a preferred cleavage sequence of Leu-Gln-Thr-Asp-\|-Gly (LQTDG; SEQ ID NO: 151). | |

TABLE 4B-continued

Exemplary Proteases with Cognate Cleavage Sites and Inhibitors

| Protease (UniProt Accession No.) | Cognate cleavage site | Protease inhibitors |
| --- | --- | --- |
| puromycin sensitive aminopeptidase (P55786, Q11011) | Release of an N-terminal amino acid, preferentially alanine, from a wide range of peptides, amides and arylamides. | |
| angiotensin converting enzyme (ACE) (P12821, P09470, Q9BYF1) SEQ ID NO: 156 | Release of a C-terminal dipeptide, oligopeptide-\|-Xaa-Yaa, when Xaa is not Pro, and Yaa is neither Asp nor Glu. | Benazepril (Lotensin), Captopril, Enalapril (Vasotec), Fosinopril, Lisinopril (Prinivil, Zestril), Moexipril, Perindopril (Aceon), Quinapril (Accupril), Ramipril (Altace), Trandolapril (Mavik), Zofenopril |
| pyroglutamyl peptidase II (Q9NXJ5) | Release of the N-terminal pyroglutamyl group from pGlu--His-Xaa tripeptides and pGlu--His-Xaa-Gly tetrapeptides | |
| dipeptidyl peptidase IV (P27487, P14740, P28843) | Release of an N-terminal dipeptide, Xaa-Yaa-\|-Zaa-, from a polypeptide, preferentially when Yaa is Pro, provided Zaa is neither Pro nor hydroxyproline | |
| N-arginine dibasic convertase (O43847, Q8BHG1) | Hydrolysis of polypeptides, preferably at -Xaa-\|-Arg-Lys-, and less commonly at -Arg-\|-Arg-Xaa-, in which Xaa is not Arg or Lys | |
| endopeptidase 24.15 (thimet oligopeptidase) (P52888, P24155) | Preferential cleavage of bonds with hydrophobic residues at P1, P2 and P3' and a small residue at P1' in substrates of 5 to 15 residues | |
| endopeptidase 24.16 (neurolysin) (Q9BYT8, Q91YP2) | Preferential cleavage in neurotensin: 10-Pro-\|-Tyr-11 | |
| amyloid precursor protein secretase alpha (P05067, P12023, Q9Y5Z0, P56817) | Endopeptidase of broad specificity. | |
| amyloid precursor protein secretase beta (P05067, P12023, Q9Y5Z0, P56817) | Broad endopeptidase specificity. Cleaves Glu-Val-Asn-Leu-\|-Asp-Ala-Glu-Phe (EVNLDAEF; SEQ ID NO: 152) in the Swedish variant of Alzheimer's amyloid precursor protein | |
| amyloid precursor protein secretase gamma (P05067, P12023, Q9Y5Z0, P56817) | intramembrane cleavage of integral membrane proteins | |
| MMP 1 (P03956, Q9EPL5uy) | Cleavage of the triple helix of collagen at about three-quarters of the length of the molecule from the N-terminus, at 775-Gly-\|-Ile-776 in the alpha-1(I) chain. Cleaves synthetic substrates and alpha-macroglobulins at bonds where P1' is a hydrophobic residue. | SB-3CT p-OH SB-3CT O-phosphate SB-3CT RXP470.1 |
| MMP 2 (P08253, P33434) | Cleavage of gelatin type I and collagen types IV, V, VII, X. Cleaves the collagen-like sequence Pro-Gln-Gly-\|-Ile-Ala-Gly-Gln (PQGIAGQ; SEQ ID NO: 153). | SB-3CT p-OH SB-3CT O-phosphate SB-3CT RXP470.1 |

TABLE 4B-continued

Exemplary Proteases with Cognate Cleavage Sites and Inhibitors

| Protease (UniProt Accession No.) | Cognate cleavage site | Protease inhibitors |
|---|---|---|
| MMP 3 (P08254, P28862) | Preferential cleavage where P1', P2' and P3' are hydrophobic residues. | SB-3CT p-OH SB-3CT O-phosphate SB-3CT RXP470.1 |
| MMP 7 (P09237, Q10738) | Cleavage of 14-Ala-\|-Leu-15 and 16-Tyr-\|-Leu-17 in B chain of insulin. No action on collagen types I, II, IV, V. Cleaves gelatin chain alpha-2(I) > alpha-1(I). | SB-3CT p-OH SB-3CT O-phosphate SB-3CT RXP470.1 |
| MMP 8 (P22894, O70138) | Can degrade fibrillar type I, II, and III collagens. Cleavage of interstitial collagens in the triple helical domain. Unlike EC 3.4.24.7, this enzyme cleaves type III collagen more slowly than type I. | SB-3CT p-OH SB-3CT O-phosphate SB-3CT RXP470.1 |
| MMP 9 (P14780, P41245) | Cleavage of gelatin types I and V and collagen types IV and V. Cleaves KiSS1 at a Gly-\|-Leu bond. Cleaves type IV and type V collagen into large C-terminal three quarter fragments and shorter N-terminal one quarter fragments. Degrades fibronectin but not laminin or Pz-peptide. | SB-3CT p-OH SB-3CT O-phosphate SB-3CT RXP470.1 |
| MMP 10 (P09238, O55123) | Can degrade fibronectin, gelatins of type I, III, IV, and V; weakly collagens III, IV, and V. | SB-3CT p-OH SB-3CT O-phosphate SB-3CT RXP470.1 |
| MMP 11 (P24347, Q02853) | A(A/Q)(N/A)↓(L/Y)(T/V/M/R)(R/K) G(G/A)E↓LR(SEQ ID NO: 225) ↓ denotes the cleavage site | SB-3CT p-OH SB-3CT O-phosphate SB-3CT RXP470.1 |
| MMP 12 (P39900, P34960) | Hydrolysis of soluble and insoluble elastin. Specific cleavages are also produced at 14-Ala-\|-Leu-15 and 16-Tyr-\|-Leu-17 in the B chain of insulin Has significant elastolytic activity. Can accept large and small amino acids at the P1' site, but has a preference for leucine. Aromatic or hydrophobic residues are preferred at the P1 site, with small hydrophobic residues (preferably alanine) occupying P3 | SB-3CT p-OH SB-3CT O-phosphate SB-3CT RXP470.1 |
| MMP 13 (P45452, P33435) | Cleaves triple helical collagens, including type I, type II and type III collagen, but has the highest activity with soluble type II collagen. Can also degrade collagen type IV, type XIV and type X | SB-3CT p-OH SB-3CT O-phosphate SB-3CT RXP470.1 |
| MMP 14 (P50281, P53690) | Activates progelatinase A by cleavage of the propeptide at 37-Asn-\|-Leu-38. Other bonds hydrolyzed include 35-Gly-\|-Ile-36 in the propeptide of collagenase 3, and 341-Asn-\|-Phe-342, 441-Asp-\|-Leu-442 and 354-Gln-\|-Thr-355 in the aggrecan interglobular domain. | SB-3CT p-OH SB-3CT O-phosphate SB-3CT RXP470.1 |
| urokinase plasminogen activator (uPA) (P00749, P06869) | Specific cleavage of Arg-\|-Val bond in plasminogen to form plasmin. | Plasminogen activator inhibitors (PAI) |

TABLE 4B-continued

Exemplary Proteases with Cognate Cleavage Sites and Inhibitors

| Protease (UniProt Accession No.) | Cognate cleavage site | Protease inhibitors |
|---|---|---|
| tissue plasminogen activator (tPA) (P00750, P11214) | Specific cleavage of Arg-\|-Val bond in plasminogen to form plasmin. | Plasminogen activator inhibitors (PAI) |
| tissue plasminogen activator (tPA) (P00750, P11214) | Specific cleavage of Arg-\|-Val bond in plasminogen to form plasmin. | Plasminogen activator inhibitors (PAI) |
| Plasmin (P00747, P20918) | Preferential cleavage: Lys-\|-Xaa > Arg-\|-Xaa, higher selectivity than trypsin. Converts fibrin into soluble products. | α-2-antiplasmin (AP) |
| Thrombin (P00734, P19221) | Cleaves bonds after Arg and Lys Converts fibrinogen to fibrin and activates factors V, VII, VIII, XIII, and, in complex with thrombomodulin, protein C. | |
| BMP-1 (procollagen C-peptidase) (P13497, P98063) | Cleavage of the C-terminal propeptide at Ala-\|-Asp in type I and II procollagens and at Arg-\|-Asp in type III. | |
| ADAM (Q9POK1, Q9UKQ2, Q9JLN6, O14672, Q13444, P78536, Q13443, O43184, P78325, Q9UKF5, Q9BZ11, Q9H2U9, Q99965, O75077, Q9H013, O43506) | | SB-3CT p-OH SB-3CT O-phosphate SB-3CT RXP470.1 |
| granzyme A (P12544, P11032) | Preferential cleavage: - Arg-\|-Xaa-, -Lys-\|-Xaa- >> -Phe-\|-Xaa- in small molecule substrates. | |
| granzyme B (P10144, P04187) | Preference for bulky and aromatic residues at the P1 position and acidic residues at the P3' and P4' sites. | |
| granzyme M (P51124, Q03238) | Cleaves peptide substrates after methionine, leucine, and norleucine. | |
| tobacco Etch virus (TEV) protease (P04517, P0CK09) | E-Xaa-Xaa-Y -Xaa-Q-(G/S), with cleavage occurring between Q and G/S. The most common sequence is ENLYFQS (SEQ ID NO: 154) | |
| chymotrypsin-like serine protease (P08217, Q9UNI1, Q91X79, P08861, P09093, P08218) | | *Thermobifida fusca* Thermopin *Pyrobaculum aerophilum* Aeropin *Thermococcus kodakaraensis* Tk-serpin *Alteromonas* sp. Marinostatin *Streptomyces misionensis* SMTI *Streptomyces* sp. chymostatin |
| alphavirus proteases (P08411, P03317, P13886, Q8JUX6, Q86924, Q4QXJ8, Q8QL53, P27282, Q5XXP4) | | |
| chymotrypsin-like cysteine proteases | | *Thermobifida fusca* Thermopin |

TABLE 4B-continued

Exemplary Proteases with Cognate Cleavage Sites and Inhibitors

| Protease (UniProt Accession No.) | Cognate cleavage site | Protease inhibitors |
|---|---|---|
| (Q86TL0, Q14790, Q99538, O15553) | | *Pyrobaculum aerophilum* Aeropin *Thermococcus kodakaraensis* Tk-serpin *Alteromonas* sp. Marinostatin *Streptomyces misionensis* SMTI *Streptomyces* sp. chymostatin |
| papain-like cysteine proteases (P25774, P53634, Q96K76) | | |
| picornavirus leader proteases (P03305, P03311, P13899) | | |
| HIV proteases (P04585, P03367, P04584, P03369, P12497, P03366, P04587) | | |
| Herpesvirus proteases (P10220, Q2HRB6, O40922, Q69527) | | |
| adenovirus proteases (P03252, P24937, Q83906, P68985, P09569, P11825, P10381) | | |
| *Streptomyces griseus* protease A (SGPA) (P00776) | | |
| *Streptomyces griseus* protease B (SGPB) (P00777) | | |
| alpha-lytic protease (P85142, P00778) | | |
| serine proteases (P48740, P98064, Q9UL52, P05981, O60235) | | |
| cysteine proteases (Q86TL0, Q14790, Q8WYNO, Q96DT6, P55211) | | |
| aspartic proteases (Q9Y5Z0, P56817, Q00663, Q53RT3, P0CY27) | | |
| threonine proteases (Q9UI38, Q16512, Q9H6P5, Q8IWU2) | | |
| Mast cell (MC) chymase (CMA1) (NM_001836) | Abz -HPFHL(SEQ ID NO: 155)-Lys(Dnp)-NH2(SEQ ID NO: 226) | BAY 1142524 SUN13834 |
| Rat mast cell protease-1, -2, -3, -4, -5 (NM_017145, NM_172044, NM_001170466, NM_019321, NM_013092) | Abz-HPFHL(SEQ ID NO: 155)-Lys(Dnp)-NH2(SEQ ID NO: 226) | TY-51469 |
| Rat vascular chymase (RVCH) (O70500) | Abz-HPFHL(SEQ ID NO: 155)-Lys(Dnp)-NH2(SEQ ID NO: 226) | |

TABLE 4B-continued

| Exemplary Proteases with Cognate Cleavage Sites and Inhibitors | | |
| --- | --- | --- |
| Protease (UniProt Accession No.) | Cognate cleavage site | Protease inhibitors |
| DENV NS3pro (NS2B/NS3) SEQ ID NOs: 157, 158, 159, 160 | A strong preference for basic amino acid residues (Arg/Lys) at the P1 positions was observed, whereas the preferences for the P2-4 sites were in the order of Arg > Thr > Gln/Asn/Lys for P2, Lys > Arg > Asn for P3, and Nle > Leu > Lys > Xaa for P4. The prime site substrate specificity was for small and polar amino acids in P1 and P3. | Anthraquinone BP13944 ZINC04321905 MB21 Policresulen SK-12 NSC135618 Biliverdin |

A protease can be any of the following human proteases (MEROPS peptidase database number provided in parentheses; Rawlings N. D., Morton F. R., Kok, C. Y., Kong, J. & Barrett A. J. (2008) MEROPS: the peptidase database. Nucleic Acids Res. 36 Database issue, D320-325; herein incorporated by reference for all purposes): pepsin A (MER000885), gastricsin (MER000894), memapsin-2 (MER005870), renin (MER000917), cathepsin D (MER000911), cathepsin E (MER000944), memapsin-1 (MER005534), napsin A (MER004981), Memname-AA034 peptidase (MER014038), pepsin A4 (MER037290), pepsin A5 (*Homo sapiens*) (MER037291), hCG1733572 (*Homo sapiens*)-type putative peptidase (MER107386), napsin B pseudogene (MER004982), CYMP g.p. (*Homo sapiens*) (MER002929), subfamily A1A unassigned peptidases (MER181559), mouse mammary tumor virus retropepsin (MER048030), rabbit endogenous retrovirus endopeptidase (MER043650), S71-related human endogenous retropepsin (MER001812), RTVL-H-type putative peptidase (MER047117), RTVL-H-type putative peptidase (MER047133), RTVL-H-type putative peptidase (MER047160), RTVL-H-type putative peptidase (MER047206), RTVL-H-type putative peptidase (MER047253), RTVL-H-type putative peptidase (MER047260), RTVL-H-type putative peptidase (MER047291), RTVL-H-type putative peptidase (MER047418), RTVL-H-type putative peptidase (MER047440), RTVL-H-type putative peptidase (MER047479), RTVL-H-type putative peptidase (MER047559), RTVL-H-type putative peptidase (MER047583), RTVL-H-type putative peptidase (MER015446), human endogenous retrovirus retropepsin homologue 1 (MER015479), human endogenous retrovirus retropepsin homologue 2 (MER015481), endogenous retrovirus retropepsin pseudogene 1 (*Homo sapiens* chromosome 14) (MER029977), endogenous retrovirus retropepsin pseudogene 2 (*Homo sapiens* chromosome 8) (MER029665), endogenous retrovirus retropepsin pseudogene 3 (*Homo sapiens* chromosome 17) (MER002660), endogenous retrovirus retropepsin pseudogene 3 (*Homo sapiens* chromosome 17) (MER030286), endogenous retrovirus retropepsin pseudogene 3 (*Homo sapiens* chromosome 17) (MER047144), endogenous retrovirus retropepsin pseudogene 5 (*Homo sapiens* chromosome 12) (MER029664), endogenous retrovirus retropepsin pseudogene 6 (*Homo sapiens* chromosome 7) (MER002094), endogenous retrovirus retropepsin pseudogene 7 (*Homo sapiens* chromosome 6) (MER029776), endogenous retrovirus retropepsin pseudogene 8 (*Homo sapiens* chromosome Y) (MER030291), endogenous retrovirus retropepsin pseudogene 9 (*Homo sapiens* chromosome 19) (MER029680), endogenous retrovirus retropepsin pseudogene 10 (*Homo sapiens* chromosome 12) (MER002848), endogenous retrovirus retropepsin pseudogene 11 (*Homo sapiens* chromosome 17) (MER004378), endogenous retrovirus retropepsin pseudogene 12 (*Homo sapiens* chromosome 11) (MER003344), endogenous retrovirus retropepsin pseudogene 13 (*Homo sapiens* chromosome 2 and similar) (MER029779), endogenous retrovirus retropepsin pseudogene 14 (*Homo sapiens* chromosome 2) (MER029778), endogenous retrovirus retropepsin pseudogene 15 (*Homo sapiens* chromosome 4) (MER047158), endogenous retrovirus retropepsin pseudogene 15 (*Homo sapiens* chromosome 4) (MER047332), endogenous retrovirus retropepsin pseudogene 15 (*Homo sapiens* chromosome 4) (MER003182), endogenous retrovirus retropepsin pseudogene 16 (MER047165), endogenous retrovirus retropepsin pseudogene 16 (MER047178), endogenous retrovirus retropepsin pseudogene 16 (MER047200), endogenous retrovirus retropepsin pseudogene 16 (MER047315), endogenous retrovirus retropepsin pseudogene 16 (MER047405), endogenous retrovirus retropepsin pseudogene 16 (MER030292), endogenous retrovirus retropepsin pseudogene 17 (*Homo sapiens* chromosome 8) (MER005305), endogenous retrovirus retropepsin pseudogene 18 (*Homo sapiens* chromosome 4) (MER030288), endogenous retrovirus retropepsin pseudogene 19 (*Homo sapiens* chromosome 16) (MER001740), endogenous retrovirus retropepsin pseudogene 21 (*Homo sapiens*) (MER047222), endogenous retrovirus retropepsin pseudogene 21 (*Homo sapiens*) (MER047454), endogenous retrovirus retropepsin pseudogene 21 (*Homo sapiens*) (MER047477), endogenous retrovirus retropepsin pseudogene 21 (*Homo sapiens*) (MER004403), endogenous retrovirus retropepsin pseudogene 22 (*Homo sapiens* chromosome X) (MER030287), subfamily A2A non-peptidase homologues (MER047046), subfamily A2A non-peptidase homologues (MER047052), subfamily A2A non-peptidase homologues (MER047076), subfamily A2A non-peptidase homologues (MER047080), subfamily A2A non-peptidase homologues (MER047088), subfamily A2A non-peptidase homologues (MER047089), subfamily A2A non-peptidase homologues (MER047091), subfamily A2A non-peptidase homologues (MER047092), subfamily A2A non-peptidase homologues (MER047093), subfamily A2A non-peptidase homologues (MER047094), subfamily A2A non-peptidase homologues (MER047097), subfamily A2A non-peptidase homologues (MER047099), subfamily A2A non-peptidase homologues MER047101), subfamily A2A non-peptidase homologues (MER047102),
subfamily A2A non-peptidase homologues (MER047107),
subfamily A2A non-peptidase homologues (MER047108),
subfamily A2A non-peptidase homologues (MER047109),
subfamily A2A non-peptidase homologues (MER047110),
subfamily A2A non-peptidase homologues MER047111),
subfamily A2A non-peptidase homologues (MER047114),
subfamily A2A non-peptidase homologues (MER047118),
subfamily A2A non-peptidase homologues (MER047121),
subfamily A2A non-peptidase homologues (MER047122),
subfamily A2A non-peptidase homologues (MER047126),
subfamily A2A non-peptidase homologues (MER047129),
subfamily A2A non-peptidase homologues (MER047130),
subfamily A2A non-peptidase homologues (MER047134),
subfamily A2A non-peptidase homologues (MER047135),
subfamily A2A non-peptidase homologues (MER047137),
subfamily A2A non-peptidase homologues (MER047140),
subfamily A2A non-peptidase homologues (MER047141),
subfamily A2A non-peptidase homologues (MER047142),
subfamily A2A non-peptidase homologues (MER047148),
subfamily A2A non-peptidase homologues (MER047149),
subfamily A2A non-peptidase homologues (MER047151),
subfamily A2A non-peptidase homologues (MER047154),
subfamily A2A non-peptidase homologues (MER047155),
subfamily A2A non-peptidase homologues (MER047156),
subfamily A2A non-peptidase homologues (MER047157),
subfamily A2A non-peptidase homologues (MER047159),
subfamily A2A non-peptidase homologues (MER047161),
subfamily A2A non-peptidase homologues (MER047163),
subfamily A2A non-peptidase homologues (MER047166),
subfamily A2A non-peptidase homologues (MER047171),
subfamily A2A non-peptidase homologues (MER047173),
subfamily A2A non-peptidase homologues (MER047174),
subfamily A2A non-peptidase homologues (MER047179),
subfamily A2A non-peptidase homologues (MER047183),
subfamily A2A non-peptidase homologues (MER047186),
subfamily A2A non-peptidase homologues (MER047190),
subfamily A2A non-peptidase homologues (MER047191),
subfamily A2A non-peptidase homologues (MER047196),
subfamily A2A non-peptidase homologues (MER047198),
subfamily A2A non-peptidase homologues (MER047199),
subfamily A2A non-peptidase homologues (MER047201),
subfamily A2A non-peptidase homologues (MER047202),
subfamily A2A non-peptidase homologues (MER047203),
subfamily A2A non-peptidase homologues (MER047204),
subfamily A2A non-peptidase homologues (MER047205),
subfamily A2A non-peptidase homologues (MER047207),
subfamily A2A non-peptidase homologues (MER047208),
subfamily A2A non-peptidase homologues (MER047210),
subfamily A2A non-peptidase homologues (MER047211),
subfamily A2A non-peptidase homologues (MER047212),
subfamily A2A non-peptidase homologues (MER047213),
subfamily A2A non-peptidase homologues (MER047215),
subfamily A2A non-peptidase homologues (MER047216),
subfamily A2A non-peptidase homologues (MER047218),
subfamily A2A non-peptidase homologues (MER047219),
subfamily A2A non-peptidase homologues (MER047221),
subfamily A2A non-peptidase homologues (MER047224),
subfamily A2A non-peptidase homologues (MER047225),
subfamily A2A non-peptidase homologues (MER047226),
subfamily A2A non-peptidase homologues (MER047227),
subfamily A2A non-peptidase homologues (MER047230),
subfamily A2A non-peptidase homologues (MER047232),
subfamily A2A non-peptidase homologues (MER047233),
subfamily A2A non-peptidase homologues (MER047234),
subfamily A2A non-peptidase homologues (MER047236),
subfamily A2A non-peptidase homologues (MER047238), subfamily A2A non-peptidase homologues (MER047239),
subfamily A2A non-peptidase homologues (MER047240),
subfamily A2A non-peptidase homologues (MER047242),
subfamily A2A non-peptidase homologues (MER047243),
subfamily A2A non-peptidase homologues (MER047249),
subfamily A2A non-peptidase homologues (MER047251),
subfamily A2A non-peptidase homologues (MER047252),
subfamily A2A non-peptidase homologues (MER047254),
subfamily A2A non-peptidase homologues (MER047255),
subfamily A2A non-peptidase homologues (MER047263),
subfamily A2A non-peptidase homologues (MER047265),
subfamily A2A non-peptidase homologues (MER047266),
subfamily A2A non-peptidase homologues (MER047267),
subfamily A2A non-peptidase homologues (MER047268),
subfamily A2A non-peptidase homologues (MER047269),
subfamily A2A non-peptidase homologues (MER047272),
subfamily A2A non-peptidase homologues (MER047273),
subfamily A2A non-peptidase homologues (MER047274),
subfamily A2A non-peptidase homologues (MER047275),
subfamily A2A non-peptidase homologues (MER047276),
subfamily A2A non-peptidase homologues (MER047279),
subfamily A2A non-peptidase homologues (MER047280),
subfamily A2A non-peptidase homologues (MER047281),
subfamily A2A non-peptidase homologues (MER047282),
subfamily A2A non-peptidase homologues (MER047284),
subfamily A2A non-peptidase homologues (MER047285),
subfamily A2A non-peptidase homologues (MER047289),
subfamily A2A non-peptidase homologues (MER047290),
subfamily A2A non-peptidase homologues (MER047294),
subfamily A2A non-peptidase homologues (MER047295),
subfamily A2A non-peptidase homologues (MER047298),
subfamily A2A non-peptidase homologues (MER047300),
subfamily A2A non-peptidase homologues (MER047302),
subfamily A2A non-peptidase homologues (MER047304),
subfamily A2A non-peptidase homologues (MER047305),
subfamily A2A non-peptidase homologues (MER047306),
subfamily A2A non-peptidase homologues (MER047307),
subfamily A2A non-peptidase homologues (MER047310),
subfamily A2A non-peptidase homologues (MER047311),
subfamily A2A non-peptidase homologues (MER047314),
subfamily A2A non-peptidase homologues (MER047318),
subfamily A2A non-peptidase homologues (MER047320),
subfamily A2A non-peptidase homologues (MER047321),
subfamily A2A non-peptidase homologues (MER047322),
subfamily A2A non-peptidase homologues (MER047326),
subfamily A2A non-peptidase homologues (MER047327),
subfamily A2A non-peptidase homologues (MER047330),
subfamily A2A non-peptidase homologues (MER047333),
subfamily A2A non-peptidase homologues (MER047362),
subfamily A2A non-peptidase homologues (MER047366),
subfamily A2A non-peptidase homologues (MER047369),
subfamily A2A non-peptidase homologues (MER047370),
subfamily A2A non-peptidase homologues (MER047371),
subfamily A2A non-peptidase homologues (MER047375),
subfamily A2A non-peptidase homologues (MER047376),
subfamily A2A non-peptidase homologues (MER047381),
subfamily A2A non-peptidase homologues (MER047383),
subfamily A2A non-peptidase homologues (MER047384),
subfamily A2A non-peptidase homologues (MER047385),
subfamily A2A non-peptidase homologues (MER047388),
subfamily A2A non-peptidase homologues (MER047389),
subfamily A2A non-peptidase homologues (MER047391),
subfamily A2A non-peptidase homologues (MER047394),
subfamily A2A non-peptidase homologues (MER047396),
subfamily A2A non-peptidase homologues (MER047400),
subfamily A2A non-peptidase homologues (MER047401),
subfamily A2A non-peptidase homologues (MER047403), subfamily A2A non-peptidase homologues (MER047406), subfamily A2A non-peptidase homologues (MER047407), subfamily A2A non-peptidase homologues (MER047410), subfamily A2A non-peptidase homologues (MER047411), subfamily A2A non-peptidase homologues (MER047413), subfamily A2A non-peptidase homologues (MER047414), subfamily A2A non-peptidase homologues (MER047416), subfamily A2A non-peptidase homologues (MER047417), subfamily A2A non-peptidase homologues (MER047420), subfamily A2A non-peptidase homologues (MER047423), subfamily A2A non-peptidase homologues (MER047424), subfamily A2A non-peptidase homologues (MER047428), subfamily A2A non-peptidase homologues (MER047429), subfamily A2A non-peptidase homologues (MER047431), subfamily A2A non-peptidase homologues (MER047434), subfamily A2A non-peptidase homologues (MER047439), subfamily A2A non-peptidase homologues (MER047442), subfamily A2A non-peptidase homologues (MER047445), subfamily A2A non-peptidase homologues (MER047449), subfamily A2A non-peptidase homologues (MER047450), subfamily A2A non-peptidase homologues (MER047452), subfamily A2A non-peptidase homologues (MER047455), subfamily A2A non-peptidase homologues (MER047457), subfamily A2A non-peptidase homologues (MER047458), subfamily A2A non-peptidase homologues (MER047459), subfamily A2A non-peptidase homologues (MER047463), subfamily A2A non-peptidase homologues (MER047468), subfamily A2A non-peptidase homologues (MER047469), subfamily A2A non-peptidase homologues (MER047470), subfamily A2A non-peptidase homologues (MER047476), subfamily A2A non-peptidase homologues (MER047478), subfamily A2A non-peptidase homologues (MER047483), subfamily A2A non-peptidase homologues (MER047488), subfamily A2A non-peptidase homologues (MER047489), subfamily A2A non-peptidase homologues (MER047490), subfamily A2A non-peptidase homologues (MER047493), subfamily A2A non-peptidase homologues (MER047494), subfamily A2A non-peptidase homologues (MER047495), subfamily A2A non-peptidase homologues (MER047496), subfamily A2A non-peptidase homologues (MER047497), subfamily A2A non-peptidase homologues (MER047499), subfamily A2A non-peptidase homologues (MER047502), subfamily A2A non-peptidase homologues (MER047504), subfamily A2A non-peptidase homologues (MER047511), subfamily A2A non-peptidase homologues (MER047513), subfamily A2A non-peptidase homologues (MER047514), subfamily A2A non-peptidase homologues (MER047515), subfamily A2A non-peptidase homologues (MER047516), subfamily A2A non-peptidase homologues (MER047520), subfamily A2A non-peptidase homologues (MER047533), subfamily A2A non-peptidase homologues (MER047537), subfamily A2A non-peptidase homologues (MER047569), subfamily A2A non-peptidase homologues (MER047570), subfamily A2A non-peptidase homologues (MER047584), subfamily A2A non-peptidase homologues (MER047603), subfamily A2A non-peptidase homologues (MER047604), subfamily A2A non-peptidase homologues (MER047606), subfamily A2A non-peptidase homologues (MER047609), subfamily A2A non-peptidase homologues (MER047616), subfamily A2A non-peptidase homologues (MER047619), subfamily A2A non-peptidase homologues (MER047648), subfamily A2A non-peptidase homologues (MER047649), subfamily A2A non-peptidase homologues (MER047662), subfamily A2A non-peptidase homologues (MER048004), subfamily A2A non-peptidase homologues (MER048018), subfamily A2A non-peptidase homologues (MER048019), subfamily A2A non-peptidase homologues (MER048023), subfamily A2A non-peptidase homologues (MER048037), subfamily A2A unassigned peptidases (MER047164), subfamily A2A unassigned peptidases (MER047231), subfamily A2A unassigned peptidases (MER047386), skin aspartic protease (MER057097), presenilin 1 (MER005221), presenilin 2 (MER005223), impas 1 peptidase (MER019701), impas 1 peptidase (MER184722), impas 4 peptidase (MER019715), impas 2 peptidase (MER019708), impas 5 peptidase (MER019712), impas 3 peptidase (MER019711), possible family A22 pseudogene (*Homo sapiens* chromosome 18) (MER029974), possible family A22 pseudogene (*Homo sapiens* chromosome 11) (MER023159), cathepsin V (MER004437), cathepsin X (MER004508), cathepsin F (MER004980), cathepsin L (MER000622), cathepsin S (MER000633), cathepsin O (MER001690), cathepsin K (MER000644), cathepsin W (MER003756), cathepsin H (MER000629), cathepsin B (MER000686), dipeptidyl-peptidase I (MER001937), bleomycin hydrolase (animal) (MER002481), tubulointerstitial nephritis antigen (MER016137), tubulointerstitial nephritis antigen-related protein (MER021799), cathepsin L-like pseudogene 1 (*Homo sapiens*) (MER002789), cathepsin B-like pseudogene (chromosome 4, *Homo sapiens*) (MER029469), cathepsin B-like pseudogene (chromosome 1, *Homo sapiens*) (MER029457), CTSLL2 g.p. (*Homo sapiens*) (MER005210), CTSLL3 g.p. (*Homo sapiens*) (MER005209), calpain-1 (MER000770), calpain-2 (MER000964), calpain-3 (MER001446), calpain-9 (MER004042), calpain-8 (MER021474), calpain-15 (MER004745), calpain-5 (MER002939), calpain-11 (MER005844), calpain-12 (MER029889), calpain-10 (MER013510), calpain-13 (MER020139), calpain-14 (MER029744), Mername-AA253 peptidase (MER005537), calpamodulin (MER000718), hypothetical protein 940251 (MER003201), ubiquitinyl hydrolase-L1 (MER000832), ubiquitinyl hydrolase-L3 (MER000836), ubiquitinyl hydrolase-BAP1 (MER003989), ubiquitinyl hydrolase-UCH37 (MER005539), ubiquitin-specific peptidase 5 (MER002066), ubiquitin-specific peptidase 6 (MER000863), ubiquitin-specific peptidase 4 (MER001795), ubiquitin-specific peptidase 8 (MER001884), ubiquitin-specific peptidase 13 (MER002627), ubiquitin-specific peptidase 2 (MER004834), ubiquitin-specific peptidase 11 (MER002693), ubiquitin-specific peptidase 14 (MER002667), ubiquitin-specific peptidase 7 (MER002896), ubiquitin-specific peptidase 9X (MER005877), ubiquitin-specific peptidase 10 (MER004439), ubiquitin-specific peptidase 1 (MER004978), ubiquitin-specific peptidase 12 (MER005454), ubiquitin-specific peptidase 16 (MER005493), ubiquitin-specific peptidase 15 (MER005427), ubiquitin-specific peptidase 17 (MER002900), ubiquitin-specific peptidase 19 (MER005428), ubiquitin-specific peptidase 20 (MER005494), ubiquitin-specific peptidase 3 (MER005513), ubiquitin-specific peptidase 9Y (MER004314), ubiquitin-specific peptidase 18 (MER005641), ubiquitin-specific peptidase 21 (MER006258), ubiquitin-specific peptidase 22 (MER012130), ubiquitin-specific peptidase 33 (MER014335), ubiquitin-specific peptidase 29 (MER012093), ubiquitin-specific peptidase 25 (MER011115), ubiquitin-specific peptidase 36 (MER014033), ubiquitin-specific peptidase 32 (MER014290), ubiquitin-specific peptidase 26 (*Homo sapiens*-type) (MER014292), ubiquitin-specific peptidase 24

(MER005706), ubiquitin-specific peptidase 42 (MER011852), ubiquitin-specific peptidase 46 (MER014629), ubiquitin-specific peptidase 37 (MER014633), ubiquitin-specific peptidase 28 (MER014634), ubiquitin-specific peptidase 47 (MER014636), ubiquitin-specific peptidase 38 (MER014637), ubiquitin-specific peptidase 44 (MER014638), ubiquitin-specific peptidase 50 (MER030315), ubiquitin-specific peptidase 35 (MER014646), ubiquitin-specific peptidase 30 (MER014649), Mername-AA091 peptidase (MER014743), ubiquitin-specific peptidase 45 (MER030314), ubiquitin-specific peptidase 51 (MER014769), ubiquitin-specific peptidase 34 (MER014780), ubiquitin-specific peptidase 48 (MER064620), ubiquitin-specific peptidase 40 (MER015483), ubiquitin-specific peptidase 41 (MER045268), ubiquitin-specific peptidase 31 (MER015493), Mername-AA129 peptidase (MER016485), ubiquitin-specific peptidase 49 (MER016486), Mername-AA187 peptidase (MER052579), USP17-like peptidase (MER030192), ubiquitin-specific peptidase 54 (MER028714), ubiquitin-specific peptidase 53 (MER027329), ubiquitin-specific endopeptidase 39 [misleading] (MER064621), Mername-AA090 non-peptidase homologue (MER014739), ubiquitin-specific peptidase 43 [misleading] (MER030140), ubiquitin-specific peptidase 52 [misleading] (MER030317), NEK2 pseudogene (MER014736), C19 pseudogene (Homo sapiens: chromosome 5) (MER029972), Mername-AA088 peptidase (MER014750), autophagin-2 (MER013564), autophagin-1 (MER013561), autophagin-3 (MER014316), autophagin-4 (MER064622), Cezanne deubiquitinylating peptidase (MER029042), Cezanne-2 peptidase (MER029044), tumor necrosis factor alpha-induced protein 3 (MER029050), trabid peptidase (MER029052), VCIP135 deubiquitinating peptidase (MER152304), otubain-1 (MER029056), otubain-2 (MER029061), CylD protein (MER030104), UfSP1 peptidase (MER042724), UfSP2 peptidase (MER060306), DUBA deubiquitinylating enzyme (MER086098), KIAA0459 (Homo sapiens)-like protein (MER122467), Otud1 protein (MER125457), glycosyltransferase 28 domain containing 1, isoform CRA_c (Homo sapiens)-like (MER123606), hin1L g.p. (Homo sapiens) (MER139816), ataxin-3 (MER099998), ATXN3L putative peptidase (MER115261), Josephin domain containing 1 (Homo sapiens) (MER125334), Josephin domain containing 2 (Homo sapiens) (MER124068), YOD1 peptidase (MER116559), legumain (plant alpha form) (MER044591), legumain (MER001800), glycosylphosphatidylinositol:protein transamidase (MER002479), legumain pseudogene (Homo sapiens) (MER029741), family C13 unassigned peptidases (MER175813), caspase-1 (MER000850), caspase-3 (MER000853), caspase-7 (MER002705), caspase-6 (MER002708), caspase-2 (MER001644), caspase-4 (MER001938), caspase-5 (MER002240), caspase-8 (MER002849), caspase-9 (MER002707), caspase-10 (MER002579), caspase-14 (MER012083), paracaspase (MER019325), Mername-AA143 peptidase (MER021304), Mername-AA186 peptidase (MER020516), putative caspase (Homo sapiens) (MER021463), FLIP protein (MER003026), Mername-AA142 protein (MER021316), caspase-12 pseudogene (Homo sapiens) (MER019698), Mername-AA093 caspase pseudogene (MER014766), subfamily C14A non-peptidase homologues (MER185329), subfamily C14A non-peptidase homologues (MER179956), separase (Homo sapiens-type) (MER011775), separase-like pseudogene (MER014797), SENP1 peptidase (MER011012), SENP3 peptidase (MER011019), SENP6 peptidase (MER011109), SENP2 peptidase (MER012183), SENP5 peptidase (MER014032), SENP7 peptidase (MER014095), SENP8 peptidase (MER016161), SENP4 peptidase (MER005557), pyroglutamyl-peptidase I (chordate) (MER011032), Mername-AA073 peptidase (MER029978), Sonic hedgehog protein (MER002539), Indian hedgehog protein (MER002538), Desert hedgehog protein (MER012170), dipeptidyl-peptidase III (MER004252), Mername-AA164 protein (MER020410), LOC138971 g.p. (Homo sapiens) (MER020074), Atp23 peptidase (MER060642), prenyl peptidase 1 (MER004246), aminopeptidase N (MER000997), aminopeptidase A (MER001012), leukotriene A4 hydrolase (MER001013), pyroglutamyl-peptidase II (MER012221), cytosol alanyl aminopeptidase (MER002746), cystinyl aminopeptidase (MER002060), aminopeptidase B (MER001494), aminopeptidase PILS (MER005331), arginyl aminopeptidase-like 1 (MER012271), leukocyte-derived arginine aminopeptidase (MER002968), aminopeptidase Q (MER052595), aminopeptidase O (MER019730), Tata binding protein associated factor (MER026493), angiotensin-converting enzyme peptidase unit 1 (MER004967), angiotensin-converting enzyme peptidase unit 2 (MER001019), angiotensin-converting enzyme-2 (MER011061), Mername-AA153 protein (MER020514), thimet oligopeptidase (MER001737), neurolysin (MER010991), mitochondrial intermediate peptidase (MER003665), Mername-AA154 protein (MER021317), leishmanolysin-2 (MER014492), leishmanolysin-3 (MER180031), matrix metallopeptidase-1 (MER001063), matrix metallopeptidase-8 (MER001084), matrix metallopeptidase-2 (MER001080), matrix metallopeptidase-9 (MER001085), matrix metallopeptidase-3 (MER001068), matrix metallopeptidase-10 (Homo sapiens-type) (MER001072), matrix metallopeptidase-11 (MER001075), matrix metallopeptidase-7 (MER001092), matrix metallopeptidase-12 (MER001089), matrix metallopeptidase-13 (MER001411), membrane-type matrix metallopeptidase-1 (MER001077), membrane-type matrix metallopeptidase-2 (MER002383), membrane-type matrix metallopeptidase-3 (MER002384), membrane-type matrix metallopeptidase-4 (MER002595), matrix metallopeptidase-20 (MER003021), matrix metallopeptidase-19 (MER002076), matrix metallopeptidase-23B (MER004766), membrane-type matrix metallopeptidase-5 (MER005638), membrane-type matrix metallopeptidase-6 (MER012071), matrix metallopeptidase-21 (MER006101), matrix metallopeptidase-22 (MER014098), matrix metallopeptidase-26 (MER012072), matrix metallopeptidase-28 (MER013587), matrix metallopeptidase-23A (MER037217), macrophage elastase homologue (chromosome 8, Homo sapiens) (MER030035), Mername-AA156 protein (MER021309), matrix metallopeptidase-like 1 (MER045280), subfamily M10A non-peptidase homologues (MER175912), subfamily M10A non-peptidase homologues (MER187997), subfamily M10A non-peptidase homologues (MER187998), subfamily M10A non-peptidase homologues (MER180000), meprin alpha subunit (MER001111), meprin beta subunit (MER005213), procollagen C-peptidase (MER001113), mammalian tolloid-like 1 protein (MER005124), mammalian-type tolloid-like 2 protein (MER005866), ADAMTS9 peptidase (MER012092), ADAMTS14 peptidase (MER016700), ADAMTS15 peptidase (MER017029), ADAMTS16 peptidase (MER015689), ADAMTS17 peptidase (MER016302), ADAMTS18 peptidase (MER016090), ADAMTS19 peptidase (MER015663), ADAM8 peptidase (MER003902), ADAM9 peptidase (MER001140), ADAM10 peptidase (MER002382), ADAM12 peptidase (MER005107), ADAM19 peptidase (MER012241), ADAM15 peptidase (MER002386), ADAM17 peptidase (MER003094), ADAM20 peptidase (MER004725), ADAMDEC1 peptidase (MER000743), ADAMTS3 peptidase (MER005100), ADAMTS4 peptidase (MER005101), ADAMTS1 peptidase (MER005546), ADAM28 peptidase (*Homo sapiens*-type) (MER005495), ADAMTS5 peptidase (MER005548), ADAMTS8 peptidase (MER005545), ADAMTS6 peptidase (MER005893), ADAMTS7 peptidase (MER005894), ADAM30 peptidase (MER006268), ADAM21 peptidase (*Homo sapiens*-type) (MER004726), ADAMTS10 peptidase (MER014331), ADAMTS12 peptidase (MER014337), ADAMTS13 peptidase (MER015450), ADAM33 peptidase (MER015143), ovastacin (MER029996), ADAMTS20 peptidase (*Homo sapiens*-type) (MER026906), procollagen I N-peptidase (MER004985), ADAM2 protein (MER003090), ADAM6 protein (MER047044), ADAM7 protein (MER005109), ADAM18 protein (MER012230), ADAM32 protein (MER026938), non-peptidase homologue (*Homo sapiens* chromosome 4) (MER029973), family M12 non-peptidase homologue (*Homo sapiens* chromosome 16) (MER047654), family M12 non-peptidase homologue (*Homo sapiens* chromosome 15) (MER047250), ADAM3B protein (*Homo sapiens*-type) (MER005199), ADAM11 protein (MER001146), ADAM22 protein (MER005102), ADAM23 protein (MER005103), ADAM29 protein (MER006267), protein similar to ADAM21 peptidase preproprotein (*Homo sapiens*) (MER026944), Mername-AA225 peptidase homologue (*Homo sapiens*) (MER047474), putative ADAM pseudogene (chromosome 4, *Homo sapiens*) (MER029975), ADAM3A g.p. (*Homo sapiens*) (MER005200), ADAM1 g.p. (*Homo sapiens*) (MER003912), subfamily M12B non-peptidase homologues (MER188210), subfamily M12B non-peptidase homologues (MER188211), subfamily M12B non-peptidase homologues (MER188212), subfamily M12B non-peptidase homologues (MER188220), neprilysin (MER001050), endothelin-converting enzyme 1 (MER001057), endothelin-converting enzyme 2 (MER004776), DINE peptidase (MER005197), neprilysin-2 (MER013406), Kell blood-group protein (MER001054), PHEX peptidase (MER002062), i-AAA peptidase (MER001246), i-AAA peptidase (MER005755), paraplegin (MER004454), Afg3-like protein 2 (MER005496), Afg3-like protein 1A (MER014306), pappalysin-1 (MER002217), pappalysin-2 (MER014521), farnesylated-protein converting enzyme 1 (MER002646), metalloprotease-related protein-1 (MER030873), aminopeptidase AMZ2 (MER011907), aminopeptidase AMZ1 (MER058242), carboxypeptidase A1 (MER001190), carboxypeptidase A2 (MER001608), carboxypeptidase B (MER001194), carboxypeptidase N (MER001198), carboxypeptidase E (MER001199), carboxypeptidase M (MER001205), carboxypeptidase U (MER001193), carboxypeptidase A3 (MER001187), metallocarboxypeptidase D peptidase unit 1 (MER003781), metallocarboxypeptidase Z (MER003428), metallocarboxypeptidase D peptidase unit 2 (MER004963), carboxypeptidase A4 (MER013421), carboxypeptidase A6 (MER013456), carboxypeptidase A5 (MER017121), metallocarboxypeptidase O (MER016044), cytosolic carboxypeptidase-like protein 5 (MER033174), cytosolic carboxypeptidase 3 (MER033176), cytosolic carboxypeptidase 6 (MER033178), cytosolic carboxypeptidase 1 (MER033179), cytosolic carboxypeptidase 2 (MER037713), metallocarboxypeptidase D non-peptidase unit (MER004964), adipocyte-enhancer binding protein 1

(MER003889), carboxypeptidase-like protein X1 (MER013404), carboxypeptidase-like protein X2 (MER078764), cytosolic carboxypeptidase (MER026952), family M14 non-peptidase homologues (MER199530), insulysin (MER001214), mitochondrial processing peptidase beta-subunit (MER004497), nardilysin (MER003883), eupitrilysin (MER004877), mitochondrial processing peptidase non-peptidase alpha subunit (MER001413), ubiquinol-cytochrome c reductase core protein I (MER003543), ubiquinol-cytochrome c reductase core protein II (MER003544), ubiquinol-cytochrome c reductase core protein domain 2 (MER043998), insulysin unit 2 (MER046821), nardilysin unit 2 (MER046874), insulysin unit 3 (MER078753), mitochondrial processing peptidase subunit alpha unit 2 (MER124489), nardilysin unit 3 (MER142856), LOC133083 g.p. (*Homo sapiens*) (MER021876), subfamily M16B non-peptidase homologues (MER188757), leucyl aminopeptidase (animal) (MER003100), Mername-AA040 peptidase (MER003919), leucyl aminopeptidase-1 (*Caenorhabditis*-type) (MER013416), methionyl aminopeptidase 1 (MER001342), methionyl aminopeptidase 2 (MER001728), aminopeptidase P2 (MER004498), Xaa-Pro dipeptidase (eukaryote) (MER001248), aminopeptidase P1 (MER004321), mitochondrial intermediate cleaving peptidase 55 kDa (MER013463), mitochondrial methionyl aminopeptidase (MER014055), Mername-AA020 peptidase homologue (MER010972), proliferation-association protein 1 (MER005497), chromatin-specific transcription elongation factor 140 kDa subunit (MER026495), proliferation-associated protein 1-like (*Homo sapiens* chromosome X) (MER029983), Mername-AA226 peptidase homologue (*Homo sapiens*) (MER056262), Mername-AA227 peptidase homologue (*Homo sapiens*) (MER047299), subfamily M24A non-peptidase homologues (MER179893), aspartyl aminopeptidase (MER003373), Gly-Xaa carboxypeptidase (MER033182), carnosine dipeptidase II (MER014551), carnosine dipeptidase I (MER015142), Mername-AA161 protein (MER021873), aminoacylase (MER001271), glutamate carboxypeptidase II (MER002104), NAALADASE L peptidase (MER005239), glutamate carboxypeptidase III (MER005238), plasma glutamate carboxypeptidase (MER005244), Mername-AA103 peptidase (MER015091), Fxna peptidase (MER029965), transferrin receptor protein (MER002105), transferrin receptor 2 protein (MER005152), glutaminyl cyclise (MER015095), glutamate carboxypeptidase II (*Homo sapiens*)-type non-peptidase homologue (MER026971), nicalin (MER044627), membrane dipeptidase (MER001260), membrane-bound dipeptidase-2 (MER013499), membrane-bound dipeptidase-3 (MER013496), dihydro-orotase (MER005767), dihydropyrimidinase (MER033266), dihydropyrimidinase related protein-1 (MER030143), dihydropyrimidinase related protein-2 (MER030155), dihydropyrimidinase related protein-3 (MER030151), dihydropyrimidinase related protein-4 (MER030149), dihydropyrimidinase related protein-5 (MER030136), hypothetical protein like 5730457F11RIK (MER033184), 1300019j08rik protein (MER033186)), guanine aminohydrolase (MER037714), Kael putative peptidase (MER001577), OSGEPLI-like protein (MER013498), S2P peptidase (MER004458), subfamily M23B non-peptidase homologues (MER199845), subfamily M23B non-peptidase homologues (MER199846), subfamily M23B non-peptidase homologues (MER199847), subfamily M23B non-peptidase homologues (MER137320), subfamily M23B non-peptidase homologues (MER201557), subfamily M23B non-peptidase homologues (MER199417), subfamily M23B non-peptidase homologues (MER199418), subfamily M23B non-peptidase homologues (MER199419), subfamily M23B non-peptidase homologues (MER199420), subfamily M23B non-peptidase homologues (MER175932), subfamily M23B non-peptidase homologues (MER199665), Pohl peptidase (MER020382), Jab1/MPN domain metalloenzyme (MER022057), Mername-AA165 peptidase (MER021865), Brcc36 isopeptidase (MER021890), histone H2A deubiquitinase MYSM1 (MER021887), AMSH deubiquitinating peptidase (MER030146), putative peptidase (*Homo sapiens* chromosome 2) (MER029970), Mername-AA168 protein (MER021886), COP9 signalosome subunit 6 (MER030137), 26S proteasome non-ATPase regulatory subunit 7 (MER030134), eukaryotic translation initiation factor 3 subunit 5 (MER030133), IFP38 peptidase homologue (MER030132), subfamily M67A non-peptidase homologues (MER191181), subfamily M67A unassigned peptidases (MER191144), granzyme B (*Homo sapiens*-type) (MER000168), testisin (MER005212), tryptase beta (MER000136), kallikrein-related peptidase 5 (MER005544), corin (MER005881), kallikrein-related peptidase 12 (MER006038), DESC1 peptidase (MER006298), tryptase gamma 1 (MER011036), kallikrein-related peptidase 14 (MER011038), hyaluronan-binding peptidase (MER003612), transmembrane peptidase, serine 4 (MER011104), intestinal serine peptidase (rodent) (MER016130), adrenal secretory serine peptidase (MER003734), tryptase delta 1 (*Homo sapiens*) (MER005948), matriptase-3 (MER029902), marapsin (MER006119), tryptase-6 (MER006118), ovochymase-1 domain 1 (MER099182), transmembrane peptidase, serine 3 (MER005926), kallikrein-related peptidase 15 (MER000064), Mername-AA031 peptidase (MER014054), TMPRSS13 peptidase (MER014226), Mername-AA038 peptidase (MER062848), Mername-AA204 peptidase (MER029980), cationic trypsin (*Homo sapiens*-type) (MER000020), elastase-2 (MER000118), mannan-binding lectin-associated serine peptidase-3 (MER031968), cathepsin G (MER000082), myeloblastin (MER000170), granzyme A (MER001379), granzyme M (MER001541), chymase (*Homo sapiens*-type) (MER000123), tryptase alpha (MER000135), granzyme K (MER001936), granzyme H (MER000166), chymotrypsin B (MER000001), elastase-1 (MER003733), pancreatic endopeptidase E (MER000149), pancreatic elastase II (MER000146), enteropeptidase (MER002068), chymotrypsin C (MER000761), prostasin (MER002460), kallikrein 1 (MER000093), kallikrein-related peptidase 2 (MER000094), kallikrein-related peptidase 3 (MER000115), mesotrypsin (MER000022), complement component C1r-like peptidase (MER016352), complement factor D (MER000130), complement component activated C1r (MER000238), complement component activated C1s (MER000239), complement component C2a (MER000231), complement factor B (MER000229), mannan-binding lectin-associated serine peptidase 1 (MER000244), complement factor I (MER000228), pancreatic endopeptidase E form B (MER000150), pancreatic elastase IIB (MER000147), coagulation factor XIIa (MER000187), plasma kallikrein (MER000203) coagulation factor Xia (MER000210), coagulation factor IXa (MER000216), coagulation factor VIIa (MER000215), coagulation factor Xa (MER000212), thrombin (MER000188), protein C (activated) (MER000222), acrosin (MER000078), hepsin (MER000156), hepatocyte growth factor activator (MER000186), mannan-binding lectin-associated serine peptidase 2 (MER002758), u-plasminogen activator (MER000195), t-plasminogen activator (MER000192), plasmin (MER000175), kallikrein-related peptidase 6 (MER002580), neurotrypsin (MER004171), kallikrein-related peptidase 8 (MER005400), kallikrein-related peptidase 10 (MER003645), epitheliasin (MER003736), kallikrein-related peptidase 4 (MER005266), prosemin (MER004214), chymopasin (MER001503), kallikrein-related peptidase 11 (MER004861), kallikrein-related peptidase 11 (MER216142), trypsin-2 type A (MER000021), HtrA1 peptidase (*Homo sapiens*-type) (MER002577), HtrA2 peptidase (MER208413), HtrA2 peptidase (MER004093), HtrA3 peptidase (MER014795), HtrA4 peptidase (MER016351), Tysnd1 peptidase (MER050461), TMPRSS12 peptidase (MER017085), HAT-like putative peptidase 2 (MER021884), trypsin C (MER021898), kallikrein-related peptidase 7 (MER002001), matriptase (MER003735), kallikrein-related peptidase 13 (MER005269), kallikrein-related peptidase 9 (MER005270), matriptase-2 (MER005278), umbilical vein peptidase (MER005421), LCLP peptidase (MER001900), spinesin (MER014385), marapsin-2 (MER021929), complement factor D-like putative peptidase (MER056164), ovochymase-2 (MER022410), HAT-like 4 peptidase (MER044589), ovochymase 1 domain 1 (MER022412), epidermis-specific SP-like putative peptidase (MER029900), testis serine peptidase 5 (MER029901), Mername-AA258 peptidase (MER000285), polyserase-IA unit 1 (MER030879), polyserase-IA unit 2 (MER030880), testis serine peptidase 2 (human-type) (MER033187), hypothetical acrosin-like peptidase (*Homo sapiens*) (MER033253), HAT-like 5 peptidase (MER028215), polyserase-3 unit 1 (MER061763), polyserase-3 unit 2 (MER061748), peptidase similar to tryptophan/serine protease (MER056263), polyserase-2 unit 1 (MER061777), Mername-AA123 peptidase (MER021930), HAT-like 2 peptidase (MER099184), hCG2041452-like protein (MER099172), hCG22067 (*Homo sapiens*) (MER099169), brain-rescue-factor-1 (*Homo sapiens*) (MER098873), hCG2041108 (*Homo sapiens*) (MER099173), polyserase-2 unit 2 (MER061760), polyserase-2 unit 3 (MER065694), Mername-AA201 (peptidase homologue) MER099175, secreted trypsin-like serine peptidase homologue (MER030000), polyserase-1A unit 3 (MER029880), azurocidin (MER000119), haptoglobin-1 (MER000233), haptoglobin-related protein (MER000235), macrophage-stimulating protein (MER001546), hepatocyte growth factor (MER000185), protein Z (MER000227), TESP1 protein (MER047214), LOC136242 protein (MER016132), plasma kallikrein-like protein 4 (MER016346), PRSS35 protein (MER016350), DKFZp586H2123-like protein (MER066474), apolipoprotein (MER000183), psi-KLK1 pseudogene (*Homo sapiens*) (MER033287), tryptase pseudogene I (MER015077), tryptase pseudogene II (MER015078), tryptase pseudogene III (MER015079), subfamily S1A unassigned peptidases (MER216982), subfamily S1A unassigned peptidases (MER216148), amidophosphoribosyltransferase precursor (MER003314), glutamine-fructose-6-phosphate transaminase 1 (MER003322), glutamine:fructose-6-phosphate amidotransferase (MER012158), Mername-AA144 protein (MER021319), asparagine synthetase (MER033254), family C44 non-peptidase homologues (MER159286), family C44 unassigned peptidases (MER185625) family C44 unassigned peptidases (MER185626), secernin 1 (MER045376), secernin 2 (MER064573), secernin 3 (MER064582), acid ceramidase precursor (MER100794), N-acylethanolamine acid amidase precursor (MER141667), proteasome catalytic subunit 1 (MER000556), proteasome catalytic subunit 2 (MER002625), proteasome catalytic subunit 3

(MER002149), proteasome catalytic subunit 1i (MER000552), proteasome catalytic subunit 2i (MER001515), proteasome catalytic subunit 3i (MER000555), proteasome catalytic subunit 5t (MER026203), protein serine kinase c17 (MER026497), proteasome subunit alpha 6 (MER000557), proteasome subunit alpha 2 (MER000550), proteasome subunit alpha 4 (MER000554), proteasome subunit alpha 7 (MER033250), proteasome subunit alpha 5 (MER000558), proteasome subunit alpha 1 (MER000549), proteasome subunit alpha 3 (MER000553), proteasome subunit XAPC7 (MER004372), proteasome subunit beta 3 (MER001710), proteasome subunit beta 2 (MER002676), proteasome subunit beta 1 (MER000551), proteasome subunit beta 4 (MER001711), Mername-AA230 peptidase homologue (*Homo sapiens*) (MER047329), Mername-AA231 pseudogene (*Homo sapiens*) (MER047172), Mername-AA232 pseudogene (*Homo sapiens*) (MER047316), glycosylasparaginase precursor (MER003299), isoaspartyl dipeptidase (threonine type) (MER031622), taspase-1 (MER016969), gamma-glutamyl-transferase 5 (mammalian-type) (MER001977), gamma-glutamyltransferase 1 (mammalian-type) (MER001629), gamma-glutamyltransferase 2 (*Homo sapiens*) (MER001976), gamma-glutamyltransferase-like protein 4 (MER002721), gamma-glutamyltransferase-like protein 3 (MER016970), similar to gamma-glutamyltransferase 1 precursor (*Homo sapiens*) (MER026204), similar to gamma-glutamyltransferase 1 precursor (*Homo sapiens*) (MER026205), Mername-AA211 putative peptidase (MER026207), gamma-glutamyltransferase 6 (MER159283), gamma-glutamyl transpeptidase homologue (chromosome 2, *Homo sapiens*) (MER037241), polycystin-1 (MER126824), KIAA1879 protein (MER159329), polycystic kidney disease 1-like 3 (MER172554), gamma-glutamyl hydrolase (MER002963), guanine 5"-monophosphate synthetase (MER043387), carbamoyl-phosphate synthase (*Homo sapiens*-type) (MER078640), dihydro-orotase (N-terminal unit) (*Homo sapiens*-type) (MER060647), DJ-1 putative peptidase (MER003390), Mername-AA100 putative peptidase (MER014802), Mername-AA101 non-peptidase homologue (MER014803), KIAA0361 protein (*Homo sapiens*-type) (MER042827), F1134283 protein (*Homo sapiens*) (MER044553), non-peptidase homologue chromosome 21 open reading frame 33 (*Homo sapiens*) (MER160094), family C56 non-peptidase homologues (MER177016), family C56 non-peptidase homologues (MER176613), family C56 non-peptidase homologues (MER176918), EGF-like module containing mucin-like hormone receptor-like 2 (MER037230), CD97 antigen (human type) (MER037286), EGF-like module containing mucin-like hormone receptor-like 3 (MER037288), EGF-like module containing mucin-like hormone receptor-like 1 (MER037278), EGF-like module containing mucin-like hormone receptor-like 4 (MER037294), cadherin EGF LAG seven-pass G-type receptor 2 precursor (*Homo sapiens*) (MER045397), Gpr64 (*Mus musculus*)-type protein (MER123205), GPR56 (*Homo sapiens*)-type protein (MER122057), latrophilin 2 (MER122199), latrophilin-1 (MER126380), latrophilin 3 (MER124612), protocadherin Flamingo 2 (MER124239), ETL protein (MER126267), G protein-coupled receptor 112 (MER126114), seven transmembrane helix receptor (MER125448), Gpr114 protein (MER159320), GPR126 vascular inducible G protein-coupled receptor (MER140015), GPR125 (*Homo sapiens*)-type protein (MER159279), GPR116 (*Homo sapiens*)-type G-protein coupled receptor (MER159280), GPR128 (*Homo sapiens*)-type G-protein coupled receptor (MER162015), GPR133 (*Homo sapiens*)-type protein (MER159334), GPR110 G-protein coupled receptor (MER159277), GPR97 protein (MER159322), KPG_006 protein (MER161773), KPG_008 protein (MER161835), KPG_009 protein (MER159335), unassigned homologue (MER166269), GPR113 protein (MER159352), brain-specific angiogenesis inhibitor 2 (MER159746), PIDD auto-processing protein unit 1 (MER020001), PIDD auto-processing protein unit 2 (MER063690), MUC1 self-cleaving mucin (MER074260), dystroglycan (MER054741), proprotein convertase 9 (MER022416), site-1 peptidase (MER001948), furin (MER000375), proprotein convertase 1 (MER000376), proprotein convertase 2 (MER000377), proprotein convertase 4 (MER028255), PACE4 proprotein convertase (MER000383), proprotein convertase 5 (MER002578), proprotein convertase 7 (MER002984), tripeptidyl-peptidase II (MER000355), subfamily S8A non-peptidase homologues (MER201339), subfamily S8A non-peptidase homologues (MER191613), subfamily S8A unassigned peptidases (MER191611), subfamily S8A unassigned peptidases (MER191612), subfamily S8A unassigned peptidases (MER191614), tripeptidyl-peptidase I (MER003575), prolyl oligopeptidase (MER000393), dipeptidyl-peptidase IV (eukaryote) (MER000401), acylaminoacyl-peptidase (MER000408), fibroblast activation protein alpha subunit (MER000399), PREPL A protein (MER004227), dipeptidyl-peptidase 8 (MER013484), dipeptidyl-peptidase 9 (MER004923), FLJ1 putative peptidase (MER017240), Mername-AA194 putative peptidase (MER017353), Mername-AA195 putative peptidase (MER017367), Mername-AA196 putative peptidase (MER017368), Mername-AA197 putative peptidase (MER017371), C14orf29 protein (MER033244), hypothetical protein (MER033245), hypothetical esterase/lipase/thioesterase (MER047309), protein bat5 (MER037840), hypothetical protein flj40219 (MER033212), hypothetical protein flj37464 (MER033240), hypothetical protein flj33678 (MER033241), dipeptidylpeptidase homologue DPP6 (MER000403), dipeptidylpeptidase homologue DPP10 (MER005988), protein similar to *Mus musculus* chromosome 20 open reading frame 135 (MER037845), kynurenine formamidase (MER046020), thyroglobulin precursor (MER011604), acetylcholinesterase (MER033188), cholinesterase (MER033198), carboxylesterase D1 (MER033213), liver carboxylesterase (MER033220), carboxylesterase 3 (MER033224), carboxylesterase 2 (MER033226), bile salt-dependent lipase (MER033227), carboxylesterase-related protein (MER033231), neuroligin 3 (MER033232), neuroligin 4, X-linked (MER033235), neuroligin 4, Y-linked (MER033236), esterase D (MER043126), arylacetamide deacetylase (MER033237), KIAA1363-like protein (MER033242), hormone-sensitive lipase (MER033274), neuroligin 1 (MER033280), neuroligin 2 (MER033283), family S9 non-peptidase homologues (MER212939), family S9 non-peptidase homologues (MER211490), subfamily S9C unassigned peptidases (MER192341), family S9 unassigned peptidases (MER209181), family S9 unassigned peptidases (MER200434), family S9 unassigned peptidases (MER209507), family S9 unassigned peptidases (MER209142), serine carboxypeptidase A (MER000430), vitellogenic carboxypeptidase-like protein (MER005492), RISC peptidase (MER010960), family S15 unassigned peptidases (MER199442), family S15 unassigned peptidases (MER200437), family S15 unassigned peptidases (MER212825), lysosomal Pro-Xaa carboxypeptidase (MER000446), dipeptidyl-peptidase II (MER004952), thymus-specific serine peptidase (MER005538), epoxide hydrolase-like putative peptidase (MER031614), Loc328574-like protein (MER033246), abhydrolase domain-containing protein 4 (MER031616), epoxide hydrolase (MER000432), mesoderm specific transcript protein (MER199890), mesoderm specific transcript protein (MER017123), cytosolic epoxide hydrolase (MER029997), cytosolic epoxide hydrolase (MER213866), similar to hypothetical protein FLJ22408 (MER031608), CGI-58 putative peptidase (MER030163), Williams-Beuren syndrome critical region protein 21 epoxide hydrolase (MER031610), epoxide hydrolase (MER031612), hypothetical protein 922408 (epoxide hydrolase) (MER031617), monoglyceride lipase (MER033247), hypothetical protein (MER033249), valacyclovir hydrolase (MER033259), Ccg1-interacting factor b (MER210738), glycosylasparaginase precursor (MER003299), isoaspartyl dipeptidase (threonine type) (MER031622). taspase-1 (MER016969), gamma-glutamyltransferase 5 (mammalian-type) (MER001977), gamma-glutamyltransferase 1 (mammalian-type) (MER001629), gamma-glutamyltransferase 2 (*Homo sapiens*) (MER001976), gamma-glutamyltransferase-like protein 4 (MER002721). gamma-glutamyltransferase-like protein 3 (MER016970). similar to gamma-glutamyltransferase 1 precursor (*Homo sapiens*) (MER026204). similar to gamma-glutamyltransferase 1 precursor (*Homo sapiens*) (MER026205). Mername-AA211 putative peptidase (MER026207). gamma-glutamyltransferase 6 (MER159283). gamma-glutamyl transpeptidase homologue (chromosome 2, *Homo sapiens*) (MER037241). polycystin-1 (MER126824), KIAA1879 protein (MER159329). polycystic kidney disease 1-like 3 (MER172554). gamma-glutamyl hydrolase (MER002963). guanine 5"-monophosphate synthetase (MER043387). carbamoyl-phosphate synthase (*Homo sapiens*-type) (MER078640). dihydro-orotase (N-terminal unit) (*Homo sapiens*-type) (MER060647). DJ-1 putative peptidase (MER003390). Mername-AA100 putative peptidase (MER014802). Mername-AA101 non-peptidase homologue (MER014803). KIAA0361 protein (*Homo sapiens*-type) (MER042827). F1134283 protein (*Homo sapiens*) (MER044553). non-peptidase homologue chromosome 21 open reading frame 33 (*Homo sapiens*) (MER160094). family C56 non-peptidase homologues (MER177016), family C56 non-peptidase homologues (MER176613). family C56 non-peptidase homologues (MER176918). EGF-like module containing mucin-like hormone receptor-like 2 (MER037230). CD97 antigen (human type) (MER037286). EGF-like module containing mucin-like hormone receptor-like 3 (MER037288). EGF-like module containing mucin-like hormone receptor-like 1 (MER037278). EGF-like module containing mucin-like hormone receptor-like 4 (MER037294). cadherin EGF LAG seven-pass G-type receptor 2 precursor (*Homo sapiens*) (MER045397), Gpr64 (*Mus musculus*)-type protein (MER123205). GPR56 (*Homo sapiens*)-type protein (MER122057). latrophilin 2 (MER122199). latrophilin-1 (MER126380). latrophilin 3 (MER124612). protocadherin Flamingo 2 (MER124239). ETL protein (MER126267). G protein-coupled receptor 112 (MER126114). seven transmembrane helix receptor (MER125448). Gpr114 protein (MER159320). GPR126 vascular inducible G protein-coupled receptor (MER140015). GPR125 (*Homo sapiens*)-type protein (MER159279). GPR116 (*Homo sapiens*)-type G-protein coupled receptor (MER159280). GPR128 (*Homo sapiens*)-type G-protein coupled receptor (MER162015). GPR133 (*Homo sapiens*)-type protein (MER159334) GPR110 G-protein coupled receptor (MER159277), GPR97 protein (MER159322), KPG_006 protein (MER161773) KPG_008 protein (MER161835), KPG_009 protein (MER159335), unassigned homologue (MER166269), GPR113 protein (MER159352), brain-specific angiogenesis inhibitor 2 (MER159746), PIDD auto-processing protein unit 1 (MER020001), PIDD auto-processing protein unit 2 (MER063690), MUC1 self-cleaving mucin (MER074260), dystroglycan (MER054741), proprotein convertase 9 (MER022416), site-1 peptidase (MER001948), furin (MER000375), proprotein convertase 1 (MER000376), proprotein convertase 2 (MER000377), proprotein convertase 4 (MER028255), PACE4 proprotein convertase (MER000383), proprotein convertase 5 (MER002578), proprotein convertase 7 (MER002984), tripeptidyl-peptidase II (MER000355), subfamily S8A non-peptidase homologues (MER201339), subfamily S8A non-peptidase homologues (MER191613), subfamily S8A unassigned peptidases (MER191611), subfamily S8A unassigned peptidases (MER191612), subfamily S8A unassigned peptidases (MER191614), tripeptidyl-peptidase I (MER003575), prolyl oligopeptidase (MER000393), dipeptidyl-peptidase IV (eukaryote) (MER000401), acylaminoacyl-peptidase (MER000408), fibroblast activation protein alpha subunit (MER000399), PREPL A protein (MER004227), dipeptidyl-peptidase 8 (MER013484), dipeptidyl-peptidase 9 (MER004923), FLJ1 putative peptidase (MER017240), Mername-AA194 putative peptidase (MER017353), Mername-AA195 putative peptidase (MER017367), Mername-AA196 putative peptidase (MER017368), Mername-AA197 putative peptidase (MER017371), C14orf29 protein (MER033244), hypothetical protein (MER033245), hypothetical esterase/lipase/thioesterase (MER047309), protein bat5 (MER037840), hypothetical protein flj40219 (MER033212), hypothetical protein flj37464 (MER033240), hypothetical protein flj33678 (MER033241), dipeptidylpeptidase homologue DPP6 (MER000403), dipeptidylpeptidase homologue DPP10 (MER005988), protein similar to *Mus musculus* chromosome 20 open reading frame 135 (MER037845), kynurenine formamidase (MER046020), thyroglobulin precursor (MER011604), acetylcholinesterase (MER033188), cholinesterase (MER033198), carboxylesterase D1 (MER033213), liver carboxylesterase (MER033220), carboxylesterase 3 (MER033224), carboxylesterase 2 (MER033226), bile salt-dependent lipase (MER033227), carboxylesterase-related protein (MER033231), neuroligin 3 (MER033232), neuroligin 4, X-linked (MER033235), neuroligin 4, Y-linked (MER033236), esterase D (MER043126), arylacetamide deacetylase (MER033237), KIAA1363-like protein (MER033242), hormone-sensitive lipase (MER033274), neuroligin 1 (MER033280), neuroligin 2 (MER033283), family S9 non-peptidase homologues (MER212939), family S9 non-peptidase homologues (MER211490), subfamily S9C unassigned peptidases (MER192341), family S9 unassigned peptidases (MER209181), family S9 unassigned peptidases (MER200434), family S9 unassigned peptidases (MER209507), family S9 unassigned peptidases (MER209142), serine carboxypeptidase A (MER000430), vitellogenic carboxypeptidase-like protein (MER005492), RISC peptidase (MER010960), family S15 unassigned peptidases (MER199442), family S15 unassigned peptidases (MER200437), family S15 unassigned peptidases (MER212825), lysosomal Pro-Xaa carboxypeptidase (MER000446), dipeptidyl-peptidase II (MER004952), thymus-specific serine peptidase (MER005538), epoxide hydrolase-like putative peptidase (MER031614), Loc328574-like protein (MER033246), abhydrolase domain-containing protein 4 (MER031616), epoxide hydrolase (MER000432), mesoderm specific transcript protein (MER199890), mesoderm specific transcript protein (MER017123), cytosolic epoxide hydrolase (MER029997), cytosolic epoxide hydrolase (MER213866), similar to hypothetical protein FLJ22408 (MER031608), CGI-58 putative peptidase (MER030163), Williams-Beuren syndrome critical region protein 21 epoxide hydrolase (MER031610), epoxide hydrolase (MER031612), hypothetical protein flj22408 (epoxide hydrolase) (MER031617), monoglyceride lipase (MER033247), hypothetical protein (MER033249), valacyclovir hydrolase (MER033259), Ccg1-interacting factor b (MER210738).

Protease enzymatic activity can be regulated. For example, certain proteases can be inactivated by the presence or absence of a specific agent (e.g., that binds to the protease, such as specific small molecule inhibitors). Such proteases can be referred to as a "repressible protease." Exemplary inhibitors for certain proteases are listed in Table 4B. For example, an NS3 protease can be repressed by a protease inhibitor including, but not limited to, simeprevir, danoprevir, asunaprevir, ciluprevir, boceprevir, sovaprevir, paritaprevir, telaprevir, grazoprevir, glecaprevir, and voxilaprevir. In another example, protease activity can be regulated through regulating expression of the protease itself, such as engineering a cell to express a protease using an inducible promoter system (e.g., Tet On/Off systems) or cell-specific promoters (promoters that can be used to express a heterologous protease are described in more detail in the Section herein titled "Promoters"). A protease can also contain a degron, such as any of the degrons described herein, and can be regulated using any of the degron systems described herein.

Protease enzymatic activity can also be regulated through selection of a specific protease cleavage site. For example, a protease cleavage site can be selected and/or engineered such that the sequence demonstrates a desired rate-of-cleavage by a desired protease, such as reduced cleavage kinetics relative to an endogenous sequence of a substrate naturally cleaved by the desired protease. As another example, a protease cleavage site can be selected and/or engineered such that the sequence demonstrates a desired rate-of-cleavage in a cell-state specific manner. For example, various cell states (e.g., following cellular signaling, such as immune cell activation) can influence the expression and/or localization of certain proteases. As an illustrative example, ADAM17 protein levels and localization is known to be influenced by signaling, such as through Protein kinase C (PKC) signaling pathways (e.g., activation by the PKC activator Phorbol-12-myristat-13-acetat [PMA]). Accordingly, a protease cleavage site can be selected and/or engineered such that cleavage of the protease cleavage site and subsequent release of an effector molecule is increased or decreased, as desired, depending on the protease properties (e.g., expression and/or localization) in a specific cell state. As another example, a protease cleavage site (particularly in combination with a specific membrane tethering domain) can be selected and/or engineered for optimal protein expression of the chimeric protein.

Cell Membrane Tethering Domain

The membrane-cleavable chimeric proteins provided for herein contain a cell-membrane tethering domain (referred to as "MT" in the formula S-C-MT or MT-C-S). In general, the cell-membrane tethering domain can be any amino acid sequence motif capable of directing the chimeric protein to be localized to (e.g., inserted into), or otherwise associated with, the cell membrane of the cell expressing the chimeric protein. The cell-membrane tethering domain can be a transmembrane-intracellular domain. The cell-membrane tethering domain can be a transmembrane domain. The cell-membrane tethering domain can be an integral membrane protein domain (e.g., a transmembrane domain). The cell-membrane tethering domain can be derived from a Type I, Type II, or Type III transmembrane protein. The cell-membrane tethering domain can include post-translational modification tag, or motif capable of post-translational modification to modify the chimeric protein to include a post-translational modification tag, where the post-translational modification tag allows association with a cell membrane. Examples of post-translational modification tags include, but are not limited to, lipid-anchor domains (e.g., a GPI lipid-anchor, a myristoylation tag, or palmitoylation tag). Examples of cell-membrane tethering domains include, but are not limited to, a transmembrane-intracellular domain and/or transmembrane domain derived from PDGFR-beta, CD8, CD28, CD3zeta-chain, CD4, 4-1BB, OX40, ICOS, CTLA-4, PD-1, LAG-3, 2B4, LNGFR, NKG2D, EpoR, TNFR2, B7-1, or BTLA. The cell membrane tethering domain can be a cell surface receptor or a cell membrane-bound portion thereof.

In some embodiments, the cell-membrane tethering domain comprises a transmembrane domain derived from a B-71 polypeptide. In some embodiments, the transmembrane domain comprises the sequence LLPSWAITLISVN-GIFVICCLTYCFAPRCRERRRNERLRRESVRPV (SEQ ID NO: 204)

In some embodiments, the cell-membrane tethering domain comprises a transmembrane domain derived from a CD8 polypeptide. Any suitable CD8 polypeptide may be used. Exemplary CD8 polypeptides include, without limitation, NCBI Reference Nos. NP_001139345 and AAA92533.1. Examples of CD8 transmembrane domains include IYIWAPLAGTCGVLLLSLVIT (SEQ ID NO:205), IYIWAPLAGTCGVLLLSLVITLYCNHR (SEQ ID NO:206), and IYIWAPLAGTCGVLLLSLVITLYCNHRN (SEQ ID NO:207). In some embodiments, the transmembrane domain comprises the sequence IYIWAPLAGTCGVLLLSLVIT (SEQ ID NO:205). In some embodiments, the transmembrane domain comprises the sequence IYIWAPLAGTCGVLLLSLVITLYCNHR (SEQ ID NO:206). In some embodiments, the transmembrane domain comprises the sequence IYIWAPLAGTCGVLLLSLVITLYCNHRN (SEQ ID NO:_207). In some embodiments, the cell-membrane tethering domain comprises a hinge and transmembrane domain derived from CD8. In some embodiments, the CD8 hinge comprises the sequence

```
                              (SEQ ID NO: 208)
   TTTPAPRPPTPAPTIALQPLSLRPEACRPAAGGAVHTRGLDFACD.
```

In some embodiments, the CD8 hinge comprises the sequence

```
                              (SEQ ID NO: 209)
   AAAFVPVFLPAKPTTTPAPRPPTPAPTIASQPLSLRPEACRP

AAGGAVHTRGLDFACDIYIWAPLAGTCGVLLLSLVITLYCNH

RN.
```

In general, for all membrane-cleavable chimeric proteins described herein, the cell membrane tethering domain is either: (1) C-terminal of the protease cleavage site and N-terminal of any intracellular domain, if present (in other words, the cell membrane tethering domain is in between the protease cleavage site and, if present, an intracellular domain); or (2) N-terminal of the protease cleavage site and C-terminal of any intracellular domain, if present (also between the protease cleavage site and, if present, an intracellular domain with domain orientation inverted). In embodiments featuring a degron associated with the chimeric protein, the degron domain is the terminal cytoplasmic-oriented domain, specifically relative to the cell membrane tethering (in other words, the cell membrane tethering domain is in between the protease cleavage site and the degron). The cell membrane tethering domain can be connected to the protease cleavage site by a polypeptide linker, i.e., a polypeptide sequence not generally considered to be part of cell membrane tethering domain or protease cleavage site. The cell membrane tethering domain can be connected to an intracellular domain, if present, by a polypeptide linker, i.e., a polypeptide sequence not generally considered to be part of the cell membrane tethering domain or the intracellular domain. The cell membrane tethering domain can be connected to the degron, if present, by a polypeptide linker, i.e., a polypeptide sequence not generally considered to be part of the cell membrane tethering domain or degron. A polypeptide linker can be any amino acid sequence that connects a first polypeptide sequence and a second polypeptide sequence. A polypeptide linker can be a flexible linker (e.g., a Gly-Ser-Gly sequence). Examples of polypeptide linkers include, but are not limited to, GSG linkers (e.g., [GS]$_4$GG [SEQ ID NO: 220]), A(EAAAK)$_3$A (SEQ ID NO: 221), and Whitlow linkers (e.g., a "KEGS" (SEQ ID NO: 227) linker such as the amino acid sequence KESGSVSSE-QLAQFRSLD (SEQ ID NO: 222), an eGK linker such as the amino acid sequence EGKSSGSGSESKST (SEQ ID NO:223), and linkers described in more detail in Issued U.S. Pat. No. 5,990,275 herein incorporated by reference). Additional polypeptide linkers include SEQ ID NO: 194, SEQ ID NO: 195, SEQ ID NO: 196, and SEQ ID NO: 197. Other polypeptide linkers may be selected based on desired properties (e.g., length, flexibility, amino acid composition etc.) and are known to those skilled in the art.

In general, the cell-membrane tethering domain is oriented such that the secreted effector molecule and the protease cleavage site are extracellularly exposed following insertion into, or association with, the cell membrane, such that the protease cleavage site is capable of being cleaved by its respective protease and releasing ("secreting") the effector molecule into the extracellular space.

Degron Systems and Domains

In some embodiments, any of the proteins described herein can include a degron domain including, but not limited to, a protease, a transcription factor, a promoter or constituent of a promoter system (e.g., an ACP), and/or any of the membrane-cleavable chimeric protein described herein. In general, the degron domain can be any amino acid sequence motif capable of directing regulated degradation, such as regulated degradation through a ubiquitin-mediated pathway. In the presence of an immunomodulatory drug (IMiD), the degron domain directs ubiquitin-mediated degradation of a degron-fusion protein.

The degron domain can be a cereblon (CRBN) polypeptide substrate domain capable of binding CRBN in response to an immunomodulatory drug (IMiD) including, but not limited to, IKZF1, IKZF3, CK1a, ZFP91, GSPT1, MEIS2, GSS E4F1, ZN276, ZN517, ZN582, ZN653, ZN654, ZN692, ZN787, and ZN827, or a fragment thereof that is capable of drug-inducible binding of CRBN. The CRBN polypeptide substrate domain can be a chimeric fusion product of native CRBN polypeptide sequences, such as a IKZF3/ZFP91/IKZF3 chimeric fusion product having the amino acid sequence of FNVLMVHKRSHTGERPLQCE-ICGFTCRQKGNLLRHIKLHTGEKPFKCHLCNY-ACQRR DAL (SEQ ID NO: 175). Degron domains, and in particular CRBN degron systems, are described in more detail in International Application Pub. No. WO2019/089592A1, herein incorporated by reference for all purposes. Other examples of degron domains include, but are not limited to HCV NS4 degron, PEST (two copies of residues 277-307 of human IκBα; SEQ ID NO: 161), GRR (residues 352-408 of human p105; SEQ ID NO: 162), DRR (residues 210-295 of yeast Cdc34; SEQ ID NO: 163), SNS (tandem repeat of SP2 and NB (SP2-NB-SP2 of influenza A or influenza B; e.g., SEQ ID NO: 164), RPB (four copies of residues 1688-1702 of yeast RPB; SEQ ID NO: 165), SPmix (tandem repeat of SP1 and SP2 (SP2-SP1-SP2-SP1-SP2 of influenza A virus M2 protein; SEQ ID NO: 166), NS2 (three copies of residues 79-93 of influenza A virus NS protein; SEQ ID NO: 167), ODC (residues 106-142 of ornithine decarboxylase; SEQ ID NO: 168), Nek2A, mouse ODC (residues 422-461; SEQ ID NO: 169), mouse ODC_DA (residues 422-461 of mODC including D433A and D434A point mutations), an APC/C degron, a COP1 E3 ligase binding degron motif, a CRL4-Cdt2 binding PIP degron, an actinfilin-binding degron, a KEAP1 binding degron, a KLHL2 and KLHL3 binding degron, an MDM2 binding motif, an N-degron, a hydroxyproline modification in hypoxia signaling, a phytohormone-dependent SCF-LRR-binding degron, an SCF ubiquitin ligase binding phosphodegron, a phytohormone-dependent SCF-LRR-binding degron, a DSGxxS phospho-dependent degron, an Siah binding motif, an SPOP SBC docking motif, or a PCNA binding PIP box.

Regulated degradation can be drug-inducible. Drugs capable of mediating/regulating degradation can be small-molecule compounds. Drugs capable of mediating/regulating degradation can include an "immunomodulatory drug" (IMiD). In general, as used herein, IMiDs refer to a class of small-molecule immunomodulatory drugs containing an imide group. Cereblon (CRBN) is known target of IMiDs and binding of an IMiD to CRBN or a CRBN polypeptide substrate domain alters the substrate specificity of the CRBN E3 ubiquitin ligase complex leading to degradation of proteins having a CRBN polypeptide substrate domain (e.g., any of secretable effector molecules or other proteins of interest described herein). For degron domains having a CRBN polypeptide substrate domain, examples of imide-containing IMiDs include, but are not limited to, a thalidomide, a lenalidomide, or a pomalidomide. The IMiD can be an FDA-approved drug.

Chimeric proteins described herein can contain a degron domain (e.g., referred to as "D" in the formula S-C-MT-D or D-MT-C-S for membrane-cleavable chimeric proteins described herein). In the absence of an IMiD, degron/ubiquitin-mediated degradation of the chimeric protein does not occur. Following expression and localization of the chimeric protein into the cell membrane, the protease cleavage site directs cleavage of the chimeric protein such that the effector molecule is released ("secreted") into the extracellular space. In the presence of an immunomodulatory drug (IMiD), the degron domain directs ubiquitin-mediated degradation of the chimeric protein such that secretion of the effector molecule is reduced or eliminated. In general, for membrane-cleavable chimeric proteins fused to a degron domain, the degron domain is the terminal cytoplasmic-oriented domain, specifically relative to the cell membrane tethering domain, e.g., the most C-terminal domain in the formula S-C-MT-D or the most N-terminal domain in the formula D-MT-C-S. The degron domain can be connected to the cell membrane tethering domain by a polypeptide linker, i.e., a polypeptide sequence not generally considered to be part of the cell membrane tethering domain or the degron domain. A polypeptide linker can be any amino acid sequence that connects a first polypeptide sequence and a second polypeptide sequence. A polypeptide linker can be a flexible linker (e.g., a Gly-Ser-Gly sequence). Examples of polypeptide linkers include, but are not limited to, GSG linkers (e.g., [GS]$_4$GG [SEQ ID NO: 220]), A(EAAAK)$_3$A (SEQ ID NO: 221), and Whitlow linkers (e.g., a "KEGS" (SEQ ID NO: 227) linker such as the amino acid sequence KESGSVSSEQLAQFRSLD (SEQ ID NO: 222), an eGK linker such as the amino acid sequence EGKSSGSGS-ESKST (SEQ ID NO: 223), and linkers described in more detail in Issued U.S. Pat. No. 5,990,275 herein incorporated by reference). Additional polypeptide linkers include SEQ ID NO: 194, SEQ ID NO: 195, SEQ ID NO: 196, and SEQ ID NO: 197. Other polypeptide linkers may be selected based on desired properties (e.g., length, flexibility, amino acid composition etc.) and are known to those skilled in the art. In general, the degron is oriented in relation to the cell membrane tethering domain such that the degron is exposed to the cytosol following localization to the cell membrane such that the degron domain is capable of mediating degradation (e.g., exposure to the cytosol and cytosol) and is capable of mediating ubiquitin-mediated degradation.

For degron-fusion proteins, the degron domain can be N-terminal or C-terminal of the protein of interest, e.g., the effector molecule. The degron domain can be connected to the protein of interest by a polypeptide linker, i.e., a polypeptide sequence not generally considered to be part of the protein of interest or the degron domain. A polypeptide linker can be any amino acid sequence that connects a first polypeptide sequence and a second polypeptide sequence. A polypeptide linker can be a flexible linker (e.g., a Gly-Ser-Gly sequence). Examples of polypeptide linkers include, but are not limited to, GSG linkers (e.g., [GS]$_4$GG [SEQ ID NO: 220]), A(EAAAK)$_3$A (SEQ ID NO: 221), and Whitlow linkers (e.g., a "KEGS" (SEQ ID NO: 227) linker such as the amino acid sequence KESGSVSSEQLAQFRSLD (SEQ ID NO: 222), an eGK linker such as the amino acid sequence EGKSSGSGSESKST (SEQ ID NO:223), and linkers described in more detail in Issued U.S. Pat. No. 5,990,275 herein incorporated by reference). Additional polypeptide linkers include SEQ ID NO: 194, SEQ ID NO: 195, SEQ ID NO: 196, and SEQ ID NO: 197. Other polypeptide linkers may be selected based on desired properties (e.g., length, flexibility, amino acid composition etc.) and are known to those skilled in the art. A polypeptide linker can be cleavable, e.g., any of the protease cleavage sites described herein.

Homing Molecules

A "tumor microenvironment" is the cellular environment in which a tumor exists, including surrounding blood vessels, immune cells, fibroblasts, bone marrow-derived inflammatory cells, lymphocytes, signaling molecules and the extracellular matrix (ECM) (see, e.g., Pattabiraman, D. R. & Weinberg, R. A. *Nature Reviews Drug Discovery* 13, 497-512 (2014); Balkwill, F. R. et al. *J Cell Sci* 125, 5591-5596, 2012; and Li, H. et al. *J Cell Biochem* 101(4), 805-15, 2007).

In some embodiments, engineered nucleic acids are configured to produce at least one homing molecule. For example, in membrane-cleavable chimeric proteins described herein containing a secreted effector molecule, the secreted effector molecule can be a homing molecule. "Homing," refers to active navigation (migration) of a cell to a target site (e.g., a cell, tissue (e.g., tumor), or organ). A "homing molecule" refers to a molecule that directs cells to a target site. In some embodiments, a homing molecule functions to recognize and/or initiate interaction of an engineered cell to a target site. Non-limiting examples of homing molecules include CXCR1, CCR9, CXCR2, CXCR3, CXCR4, CCR2, CCR4, FPR2, VEGFR, IL6R, CXCR1, CSCR7, and PDGFR.

In some embodiments, a homing molecule is a chemokine receptor (cell surface molecule that binds to a chemokine). Chemokines are small cytokines or signaling proteins secreted by cells that can induce directed chemotaxis in cells. Chemokines can be classified into four main subfamilies: CXC, CC, CX3C and XC, all of which exert biological effects by binding selectively to chemokine receptors located on the surface of target cells. In some embodiments, engineered nucleic acids are configured to produce CXCR4, a chemokine receptor which allows engineered cells to home along a chemokine gradient towards a stromal cell-derived factor 1 (also known as SDF1, C-X-C motif chemokine 12, and CXCL12)-expressing cell, tissue, or tumor. Non-limiting examples of chemokine receptors that may be encoded by the engineered nucleic acids of the present disclosure include: CXC chemokine receptors (e.g., CXCR1, CXCR2, CXCR3, CXCR4, CXCR5, CXCR6, and CXCR7), CC chemokine receptors (CCR1, CCR2, CCR3, CCR4, CCR5, CCR6, CCR7, CCR8, CCR9, CCR10, and CCR11), CX3C chemokine receptors (e.g., CX3CR1, which binds to CX3CL1), and XC chemokine receptors (e.g., XCR1). In some embodiments, a chemokine receptor is a G protein-linked transmembrane receptor, or a member of the tumor necrosis factor (TNF) receptor superfamily (including but not limited to TNFRSF1A, TNFRSF1B). In some embodiments, engineered nucleic acids are configured to produce CXCL8, CXCL9, and/or CXCL10 (promote T-cell recruitment), CCL3 and/or CXCL5, CCL21 (Th1 recruitment and polarization).

In some embodiments, engineered nucleic acids are configured to produce G-protein coupled receptors (GPCRs) that detect N-formylated-containing oligopeptides (including but not limited to FPR2 and FPRL1).

In some embodiments, engineered nucleic acids are configured to produce receptors that detect interleukins (including but not limited to IL6R).

In some embodiments, engineered nucleic acids are configured to produce receptors that detect growth factors secreted from other cells, tissues, or tumors (including but not limited to FGFR, PDGFR, EGFR, and receptors of the VEGF family, including but not limited to VEGF-C and VEGF-D).

In some embodiments, a homing molecule is an integrin. Integrins are transmembrane receptors that facilitate cell-extracellular matrix (ECM) adhesion. Integrins are obligate heterodimers having two subunits: α (alpha) and β (beta). The a subunit of an integrin may be, without limitation: ITGA1, ITGA2, ITGA3, ITGA4, ITGA5, ITGA6, IGTA7, ITGA8, ITGA9, IGTA10, IGTA11, ITGAD, ITGAE, ITGAL, ITGAM, ITGAV, ITGA2B, ITGAX. The β subunit of an integrin may be, without limitation: ITGB1, ITGB2, ITGB3, ITGB4, ITGB5, ITGB6, ITGB7, and ITGB8. Engineered nucleic acids can be configured to produce any combination of the integrin α and β subunits.

In some embodiments, a homing molecule is a matrix metalloproteinase (MMP). MMPs are enzymes that cleave components of the basement membrane underlying the endothelial cell wall. Non-limiting examples of MMPs include MMP-2, MMP-9, and MMP. In some embodiments, engineered nucleic acids are configured to produce an inhibitor of a molecule (e.g., protein) that inhibits MMPs. For example, engineered nucleic acids can be configured to express an inhibitor (e.g., an RNAi molecule) of membrane type 1 MMP (MT1-MMP) or TIMP metallopeptidase inhibitor 1 (TIMP-1).

In some embodiments, a homing molecule is a ligand that binds to selectin (e.g., hematopoietic cell E-/L-selectin ligand (HCELL), Dykstran et al., Stem Cells. 2016 October; 34(10):2501-2511) on the endothelium of a target tissue, for example.

The term "homing molecule" also encompasses transcription factors that regulate the production of molecules that improve/enhance homing of cells.

In some embodiments, a homing molecule includes an antibody, such as anti-integrin alpha4,beta7 or anti-MAd-CAM.

Engineered Nucleic Acids

Provided herein are engineered nucleic acids encoding at least one chimeric protein of the present disclosure, such as such as the membrane-cleavable chimeric proteins having the formula S-C-MT or MT-C-S described herein. Provided herein are engineered nucleic acids encoding two or more chimeric proteins.

In certain embodiments described herein, the engineered nucleic acids encode an expression cassette containing a promoter and an exogenous polynucleotide sequence encoding a membrane-cleavable chimeric protein, oriented from N-terminal to C-terminal, having the formula: S-C-MT or MT-C-S. S refers to a secretable effector molecule. C refers to a protease cleavage site. MT refers to a cell membrane tethering domain. The promoter is operably linked to the exogenous polynucleotide sequence and S-C-MT or MT-C-S is configured to be expressed as a single polypeptide.

In certain embodiments described herein, the engineered nucleic acids encode an expression cassette containing a promoter and an exogenous polynucleotide sequence encoding a membrane-cleavable chimeric protein having a protein of interest (e.g., any of the effector molecules described herein). The promoter is operably linked to the exogenous polynucleotide sequence and the membrane-cleavable chimeric protein is configured to be expressed as a single polypeptide.

An "engineered nucleic acid" is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a murine nucleotide sequence, a bacterial nucleotide sequence, a human nucleotide sequence, and/or a viral nucleotide sequence. The term "engineered nucleic acids" includes recombinant nucleic acids and synthetic nucleic acids. A "recombinant nucleic acid" refers to a molecule that is constructed by joining nucleic acid molecules and, in some embodiments, can replicate in a live cell. A "synthetic nucleic acid" refers to a molecule that is amplified or chemically, or by other means, synthesized. Synthetic nucleic acids include those that are chemically modified, or otherwise modified, but can base pair with naturally-occurring nucleic acid molecules.

Modifications include, but are not limited to, one or more modified internucleotide linkages and non-natural nucleic acids. Modifications are described in further detail in U.S. Pat. No. 6,673,611 and U.S. Application Publication 2004/0019001 and, each of which is incorporated by reference in their entirety. Modified internucleotide linkages can be a phosphorodithioate or phosphorothioate linkage. Non-natural nucleic acids can be a locked nucleic acid (LNA), a peptide nucleic acid (PNA), glycol nucleic acid (GNA), a phosphorodiamidate morpholino oligomer (PMO or "morpholino"), and threose nucleic acid (TNA). Non-natural nucleic acids are described in further detail in International Application WO 1998/039352, U.S. Application Pub. No. 2013/0156849, and U.S. Pat. Nos. 6,670,461; 5,539,082; 5,185,444, each herein incorporated by reference in their entirety. Recombinant nucleic acids and synthetic nucleic acids also include those molecules that result from the replication of either of the foregoing. Engineered nucleic acid of the present disclosure may be encoded by a single molecule (e.g., included in the same plasmid or other vector) or by multiple different molecules (e.g., multiple different independently-replicating molecules). Engineered nucleic acids can be an isolated nucleic acid. Isolated nucleic acids include, but are not limited to a cDNA polynucleotide, an RNA polynucleotide, an RNAi oligonucleotide (e.g., siR-NAs, miRNAs, antisense oligonucleotides, shRNAs, etc.), an mRNA polynucleotide, a circular plasmid, a linear DNA fragment, a vector, a minicircle, a ssDNA, a bacterial artificial chromosome (BAC), and yeast artificial chromosome (YAC), and an oligonucleotide.

Engineered nucleic acid of the present disclosure may be produced using standard molecular biology methods (see, e.g., Green and Sambrook, Molecular Cloning, A Laboratory Manual, 2012, Cold Spring Harbor Press). In some embodiments, engineered nucleic acid constructs are produced using GIBSON ASSEMBLY® Cloning (see, e.g., Gibson, D. G. et al. Nature Methods, 343-345, 2009; and Gibson, D. G. et al. Nature Methods, 901-903, 2010, each of which is incorporated by reference herein). GIBSON ASSEMBLY® typically uses three enzymatic activities in a single-tube reaction: 5' exonuclease, the 'Y extension activity of a DNA polymerase and DNA ligase activity. The 5' exonuclease activity chews back the 5'-end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. In some embodiments, engineered nucleic acid constructs are produced using IN-FUSION® cloning (Clontech).

Promoters

In general, in all embodiments described herein, the engineered nucleic acids encoding the one or more membrane-cleavable chimeric proteins encode an expression cassette containing a promoter. In some embodiments, an engineered nucleic acid (e.g., an engineered nucleic acid comprising an expression cassette) comprises a promoter operably linked to a nucleotide sequence (e.g., an exogenous polynucleotide sequence) encoding at least 2 distinct proteins. For example, the engineered nucleic acid may comprise a promoter operably linked to a nucleotide sequence encoding at least 3, at least 4, at least 5, at least 6, at least 7, at least 8, at least 8, at least 9, or at least 10 distinct proteins. In some embodiments, an engineered nucleic acid comprises a promoter operably linked to a nucleotide sequence encoding 1, 2, 3, 4, 5, 6, 7, 8, 9, 10, or more distinct proteins. In some embodiments, an engineered nucleic acid (e.g., an engineered nucleic acid comprising an expression cassette) comprises a promoter operably linked to a nucleotide sequence (e.g., an exogenous polynucleotide sequence) encoding at least 2 membrane-cleavable chimeric proteins. For example, the engineered nucleic acid may comprise a promoter operably linked to a nucleotide sequence encoding at least 3, at least 4, at least 5, at least 6, at least 7, at least 8, at least 8, at least 9, or at least 10 membrane-cleavable chimeric proteins. In some embodiments, an engineered nucleic acid comprises a promoter operably linked to a nucleotide sequence encoding 1, 2, 3, 4, 5, 6, 7, 8, 9, 10, or more membrane-cleavable chimeric proteins.

A "promoter" refers to a control region of a nucleic acid sequence at which initiation and rate of transcription of the remainder of a nucleic acid sequence are controlled. A promoter may also contain sub-regions at which regulatory proteins and molecules may bind, such as RNA polymerase and other transcription factors. Promoters may be constitutive, inducible, repressible, tissue-specific or any combination thereof. A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous." In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see, e.g., U.S. Pat. Nos. 4,683,202 and 5,928,906).

Promoters of an engineered nucleic acid may be "inducible promoters," which refer to promoters that are characterized by regulating (e.g., initiating or activating) transcriptional activity when in the presence of, influenced by or contacted by a signal. The signal may be endogenous or a normally exogenous condition (e.g., light), compound (e.g., chemical or non-chemical compound) or protein (e.g., cytokine) that contacts an inducible promoter in such a way as to be active in regulating transcriptional activity from the inducible promoter. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

A promoter is "responsive to" or "modulated by" a local tumor state (e.g., inflammation or hypoxia) or signal if in the presence of that state or signal, transcription from the promoter is activated, deactivated, increased, or decreased. In some embodiments, the promoter comprises a response element. A "response element" is a short sequence of DNA within a promoter region that binds specific molecules (e.g., transcription factors) that modulate (regulate) gene expression from the promoter. Response elements that may be used in accordance with the present disclosure include, without limitation, a phloretin-adjustable control element (PEACE), a zinc-finger DNA-binding domain (DBD), an interferon-gamma-activated sequence (GAS) (Decker, T. et al. *J Interferon Cytokine Res.* 1997 March; 17(3):121-34, incorporated herein by reference), an interferon-stimulated response element (ISRE) (Han, K. J. et al. *J Biol Chem.* 2004 Apr. 9; 279(15):15652-61, incorporated herein by reference), a NF-kappaB response element (Wang, V. et al. Cell Reports. 2012; 2(4): 824-839, incorporated herein by reference), and a STAT3 response element (Zhang, D. et al. *J of Biol Chem.* 1996; 271: 9503-9509, incorporated herein by reference). Other response elements are encompassed herein. Response elements can also contain tandem repeats (e.g., consecutive repeats of the same nucleotide sequence encoding the response element) to generally increase sensitivity of the response element to its cognate binding molecule. Tandem repeats can be labeled 2×, 3×, 4×, 5×, etc. to denote the number of repeats present.

Non-limiting examples of responsive promoters (also referred to as "inducible promoters") (e.g., TGF-beta responsive promoters) are listed in Table 5A, which shows the design of the promoter and transcription factor, as well as the effect of the inducer molecule towards the transcription factor (TF) and transgene transcription (T) is shown (B, binding; D, dissociation; n.d., not determined) (A, activation; DA, deactivation; DR, derepression) (see Homer, M. & Weber, W. *FEBS Letters* 586 (2012) 20784-2096m, and references cited therein). Non-limiting examples of components of inducible promoters include those presented in Table 5B.

TABLE 5A

| | | | | Response to inducer | |
| | Promoter and | Transcription | | | |
| System | operator | factor (TF) | Inducer molecule | TF | T |
|---|---|---|---|---|---|
| Transcriptional activator-responsive promoters | | | | | |
| AIR | PAIR (OalcA-PhCMVmin) | AlcR | Acetaldehyde | n.d. | A |
| ART | PART (OARG-PhCMVmin) | ArgR-VP16 | l-Arginine | B | A |

TABLE 5A-continued

Examples of Responsive Promoters

| System | Promoter and operator | Transcription factor (TF) | Inducer molecule | Response to inducer TF | T |
|---|---|---|---|---|---|
| BIT | PBIT3 (OBirA3-PhCMVmin) | BIT (BirA-VP16) | Biotin | B | A |
| Cumate - activator | PCR5 (OCuO6-PhCMVmin) | cTA (CymR-VP16) | Cumate | D | DA |
| Cumate - reverse activator | PCR5 (OCuO6-PhCMVmin) | rcTA (rCymR-VP16) | Cumate | B | A |
| E-OFF | PETR (OETR-PhCMVmin) | ET (E-VP16) | Erythromycin | D | DA |
| NICE-OFF | PNIC (ONIC-PhCMVmin) | NT (HdnoR-VP16) | 6-Hydroxy-nicotine | D | DA |
| PEACE | PTtgR1 (OTtgR-PhCMVmin) | TtgA1 (TtgR-VP16) | Phloretin | D | DA |
| PIP-OFF | PPIR (OPIR-Phsp70min) | PIT (PIP-VP16) | Pristinamycin I | D | DA |
| QuoRex | PSCA (OscbR-PhCMVmin)PSPA (OpapRI-PhCMVmin) | SCA (ScbR-VP16) | SCB1 | D | DA |
| Redox | PROP (OROP-PhCMVmin) | REDOX (REX-VP16) | NADH | D | DA |
| TET-OFF | PhCMV*-1 (OtetO7-PhCMVmin) | tTA (TetR-VP16) | Tetracycline | D | DA |
| TET-ON | PhCMV*-1 (OtetO7-PhCMVmin) | rtTA (rTetR-VP16) | Doxycycline | B | A |
| TIGR | PCTA (OrheO-PhCMVmin) | CTA (RheA-VP16) | Heat | D | DA |
| TraR | O7x(tra box)-PhCMVmin | p65-TraR | 3-Oxo-C8-HSL | B | A |
| VAC-OFF | P1VanO2 (OVanO2-PhCMVmin) | VanA1 (VanR-VP16) | Vanillic acid | D | DA |
| Transcriptional repressor-responsive promoters | | | | | |
| Cumate - repressor | PCuO (PCMV5-OCuO) | CymR | Cumate | D | DR |
| E-ON | PETRON8 (PSV40-OETR8) | E-KRAB | Erythromycin | D | DR |
| NICE-ON | PNIC (PSV40-ONIC8) | NS (HdnoR-KRAB) | 6-Hydroxy-nicotine | D | DR |
| PIP-ON | PPIRON (PSV40-OPIR3) | PIT3 (PIP-KRAB) | Pristinamycin I | D | DR |
| Q-ON | PSCAON8 (PSV40-OscbR8) | SCS (ScbR-KRAB) | SCB1 | D | DR |
| TET-ON repressor-based | OtetO-PHPRT | tTS-H4 (TetR-HDAC4) | Doxycycline | D | DR |
| T-REX | PTetO (PhCMV-OtetO2) | TetR | Tetracycline | D | DR |
| UREX | PUREX8 (PSV40-OhucO8) | mUTS (KRAB-HucR) | Uric acid | D | DR |
| VAC-ON | PVanON8 (PhCMV-OVanO8) | VanA4 (VanR-KRAB) | Vanillic acid | D | DR |
| Hybrid promoters | | | | | |
| QuoRexPIP-ON(NOT IF gate) | OscbR8-OPIR3-PhCMVmin | SCAPIT3 | SCB1Pristinamycin I | DD | DADR |
| QuoRexE-ON(NOT IF gate) | OscbR-OETR8-PhCMVmin | SCAE-KRAB | SCB1Erythromycin | DD | DADR |
| TET-OFFE-ON(NOT IF gate) | OtetO7-OETR8-PhCMVmin | tTAE-KRAB | TetracyclineErythromycin | DD | DADR |
| TET-OFFPIP-ONE-ON | OtetO7-OPIR3-OETR8-PhCMVmin | tTAPIT3E-KRAB | TetracyclinePristinamycin IErythromycin | DDD | DADRDR |

TABLE 5B

Exemplary Components of Inducible Promoters

| Name | DNA SEQUENCE |
| --- | --- |
| minimal promoter; minP | AGAGGGTATATAATGGAAGCTCGACTTCCAG (SEQ ID NO: 1) |
| NFKB response element protein promoter; 5x NFkB-RE | GGGAATTTCCGGGGACTTTCCGGGAATTTCCGGGGACTTTCCGGGAAT TTCC (SEQ ID NO: 2) |
| CREB response element protein promoter; 4x CRE | CACCAGACAGTGACGTCAGCTGCCAGATCCCATGGCCGTCATACTGTG ACGTCTTTCAGACACCCCATTGACGTCAATGGGAGAA (SEQ ID NO: 3) |
| NFAT response element protein promoter; 3x NFAT binding sites | GGAGGAAAAACTGTTTCATACAGAAGGCGTGGAGGAAAAACTGTTTC ATACAGAAGGCGTGGAGGAAAAACTGTTTCATACAGAAGGCGT (SEQ ID NO: 4) |
| SRF response element protein promoter; 5x SRE | AGGATGTCCATATTAGGACATCTAGGATGTCCATATTAGGACATCTAG GATGTCCATATTAGGACATCTAGGATGTCCATATTAGGACATCTAGGA TGTCCATATTAGGACATCT (SEQ ID NO: 5) |
| SRF response element protein promoter 2; 5x SRF-RE | AGTATGTCCATATTAGGACATCTACCATGTCCATATTAGGACATCTAC TATGTCCATATTAGGACATCTTGTATGTCCATATTAGGACATCTAAAA TGTCCATATTAGGACATCT (SEQ ID NO: 6) |
| AP1 response element protein promoter; 6x AP1-RE | TGAGTCAGTGACTCAGTGAGTCAGTGACTCAGTGAGTCAGTGACTCA G (SEQ ID NO: 7) |
| TCF-LEF response element promoter; 8x TCF-LEF-RE | AGATCAAAGGGTTTAAGATCAAAGGGCTTAAGATCAAAGGGTATAAG ATCAAAGGGCCTAAGATCAAAGGGACTAAGATCAAAGGGTTTAAGAT CAAAGGGCTTAAGATCAAAGGGCCTA (SEQ ID NO: 8) |
| SBEx4 | GTCTAGACGTCTAGACGTCTAGACGTCTAGAC (SEQ ID NO: 9) |
| SMAD2/3-CAGACA x4 | CAGACACAGACACAGACACAGACA (SEQ ID NO: 10) |
| STAT3 binding site | Ggatccggtactcgagatctgcgatctaagtaagcttggcattccg gtactgttggtaaagccac (SEQ ID NO: 11) |
| minCMV | taggcgtgtacggtgggaggcctatataagcagagctcgtttagtg aaccgtcagatcgcctgga (SEQ ID NO: 170) |
| YB_TATA | TCTAGAGGGTATATAATGGGGGCCA (SEQ ID NO: 171) |
| minTK | Ttcgcatattaaggtgacgcgtgtggcctcgaacaccgagcgaccc tgcagcgacccgcttaa (SEQ ID NO: 172) |

Non-limiting examples of promoters include the cytomegalovirus (CMV) promoter, the elongation factor 1-alpha (EF1a) promoter, the elongation factor (EFS) promoter, the MND promoter (a synthetic promoter that contains the U3 region of a modified MoMuLV LTR with myeloproliferative sarcoma virus enhancer), the phosphoglycerate kinase (PGK) promoter, the spleen focus-forming virus (SFFV) promoter, the simian virus 40 (SV40) promoter, and the ubiquitin C (UbC) promoter (see Table 5C).

TABLE 5C

Exemplary Constitutive Promoters

| Name | DNA SEQUENCE |
| --- | --- |
| CMV | GTTGACATTGATTATTGACTAGTTATTAATAGTAA TCAATTACGGGGTCATTAGTTCATAGCCCATATAT GGAGTTCCGCGTTACATAACTTACGGTAAATGGCC CGCCTGGCTGACCGCCCAACGACCCCCGCCCATTG ACGTCAATAATGACGTATGTTCCCATAGTAACGCC AATAGGGACTTTCCATTGACGTCAATGGGTGGAGT ATTTACGGTAAACTGCCCACTTGGCAGTACATCAA GTGTATCATATGCCAAGTACGCCCCCTATTGACGT CAATGACGGTAAATGGCCCGCCTGGCATTATGCCC AGTACATGACCTTATGGGACTTTCCTACTTGGCAG TACATCTACGTATTAGTCATCGCTATTACCATGGT |

TABLE 5C-continued

Exemplary Constitutive Promoters

| Name | DNA SEQUENCE |
| --- | --- |
|  | GATGCGGTTTTGGCAGTACATCAATGGGCGTGGAT AGCGGTTTGACTCACGGGGATTTCCAAGTCTCCAC CCCATTGACGTCAATGGGAGTTTGTTTTGGCACCA AAATCAACGGGACTTTCCAAAATGTCGTAACAACT CCGCCCCATTGACGCAAATGGGCGGTAGGCGTGTA CGGTGGGAGGTCTATATAAGCAGAGCTC (SEQ ID NO: 12) |
| EF1a | GGCTCCGGTGCCCGTCAGTGGGCAGAGCGCACATC GCCCACAGTCCCCGAGAAGTTGGGGGGAGGGGTCG GCAATTGAACCGGTGCCTAGAGAAGGTGGCGCGGG GTAAACTGGGAAAGTGATGCCGTGTACTGGCTCCG CCTTTTTCCCGAGGGTGGGGGAGAACCGTATATAA GTGCAGTAGTCGCCGTGAACGTTCTTTTTCGCAAC GGGTTTGCCGCCAGAACACAGGTAAGTGCCGTGTG TGGTTCCCGCGGGCCTGGCCTCTTTACGGGTTATG GCCCTTGCGTGCCTTGAATTACTTCCACCTGGCTG CAGTACGTGATTCTTGATCCCGAGCTTCGGGTTGG AAGTGGGTGGGAGAGTTCGAGGCCTTGCGCTTAAG GAGCCCCTTCGCCTCGTGCTTGAGTTGAGGCCTGG CCTGGGCGCTGGGGCCGCCGCGTGCGAATCTGGTG GCACCTTCGCGCCTGTCTCGCTGCTTTCGATAAGT CTCTAGCCATTTAAAATTTTTGATGACCTGCTGCG |

TABLE 5C-continued

Exemplary Constitutive Promoters

| Name | DNA SEQUENCE |
|------|--------------|
| | ACGCTTTTTTTCTGGCAAGATAGTCTTGTAAATGC |
| | GGGCCAAGATCTGCACACTGGTATTTCGGTTTTTG |
| | GGGCCGCGGGCGGCGACGGGGCCCGTGCGTCCCAG |
| | CGCACATGTTCGGCGAGGCGGGGCCTGCGAGCGCG |
| | ACCACCGAGAATCGGACGGGGGTAGTCTCAAGCTG |
| | GCCGGCCTGCTCTGGTGCCTGTCCTCGCGCCGCCG |
| | TGTATCGCCCCGCCCCGGGCGGCAAGGCTGGCCCG |
| | GTCGGCACCAGTTGCGTGAGCGGAAAGATGGCCGC |
| | TTCCCGGTCCTGCTGCAGGGAGCTCAAAATGGAGG |
| | ACGCGGCGCTCGGGAGAGCGGGCGGGTGAGTCACC |
| | CACACAAAGGAAAAGGGCCTTTCCGTCCTCAGCCG |
| | TCGCTTCATGTGACTCCACGGAGTACCGGGCGCCG |
| | TCCAGGCACCTCGATTAGTTCTCGAGCTTTTGGAG |
| | TACGTCGTCTTTAGGTTGGGGGGAGGGGTTTTATG |
| | CGATGGAGTTTCCCCACACTGAGTGGGTGGAGACT |
| | GAAGTTAGGCCAGCTTGGCACTTGATGTAATTCTC |
| | CTTGGAATTTGCCCTTTTTGAGTTTGGATCTTGGT |
| | TCATTCTCAAGCCTCAGACAGTGGTTCAAAGTTTT |
| | TTTCTTCCATTTCAGGTGTCGTGA |
| | (SEQ ID NO: 13) |
| EFS | GGATCTGCGATCGCTCCGGTGCCCGTCAGTGGGCA |
| | GAGCGCACATCGCCCACAGTCCCCGAGAAGTTGGG |
| | GGGAGGGGTCGGCAATTGAACCGGTGCCTAGAGAA |
| | GGTGGCGCGGGGTAAACTGGGAAAGTGATGTCGTG |
| | TACTGGCTCCGCCTTTTTCCCGAGGGTGGGGGAGA |
| | ACCGTATATAAGTGCAGTAGTCGCCGTGAACGTTC |
| | TTTTTCGCAACGGGTTTGCCGCCAGAACACAGCTG |
| | AAGCTTCGAGGGGCTCGCATCTCTCCTTCACGCGC |
| | CCGCCGCCCTACCTGAGGCCGCCATCCACGCCGGT |
| | TGAGTCGCGTTCTGCCGCCTCCCGCCTGTGGTGCC |
| | TCCTGAACTGCGTCCGCCGTCTAGGTAAGTTTAAA |
| | GCTCAGGTCGAGACCGGGCCTTTGTCCGGCGCTCC |
| | CTTGGAGCCTACCTAGACTCAGCCGGCTCTCCACG |
| | CTTTGCCTGACCCTGCTTGCTCAACTCTACGTCTT |
| | TGTTTCGTTTTCTGTTCTGCGCCGTTACAGATCCA |
| | AGCTGTGACCGGCGCCTAC |
| | (SEQ ID NO: 14) |
| MND | TTTATTTAGTCTCCAGAAAAAGGGGGGAATGAAAG |
| | ACCCCACCTGTAGGTTTGGCAAGCTAGGATCAAGG |
| | TTAGGAACAGAGAGACAGCAGAATATGGGCCAAAC |
| | AGGATATCTGTGGTAAGCAGTTCCTGCCCCGGCTC |
| | AGGGGCCAAGAACAGTTGGAACAGCAGAATATGGGC |
| | CAAACAGGATATCTGTGGTAAGCAGTTCCTGCCCC |
| | GGCTCAGGGCCAAGAACAGATGGTCCCCAGATGCG |
| | GTCCCGCCCTCAGCAGTTTCTAGAGAACCATCAGA |
| | TGTTTCCAGGGTGCCCCAAGGACCTGAAATGACCC |
| | TGTGCCTTATTTGAACTAACCAATCAGTTCGCTTC |
| | TCGCTTCTGTTCGCGCGCTTCTGCTCCCCGAGCTC |
| | AATAAAAGAGCCCA |
| | (SEQ |
| | ID NO: 15) |
| PGK | GGGGTTGGGGTTGCGCCTTTTCCAAGGCAGCCCTG |
| | GGTTTGCGCAGGGACGCGGCTGCTCTGGGCGTGGT |
| | TCCGGGAAACGCAGCGGCGCCGACCCTGGGTCTCG |
| | CACATTCTTCACGTCCGTTCGCAGCGTCACCCGGA |
| | TCTTCGCCGCTACCCTTGTGGGCCCCCCGGCGACG |
| | CTTCCTGCTCCGCCCCTAAGTCGGGAAGGTTCCTT |
| | GCGGTTCGCGGCGTGCCGGACGTGACAAACGGAAG |
| | CCGCACGTCTCACTAGTACCCTCGCAGACGGACAG |
| | CGCCAGGGAGCAATGGCAGCGCGCCGACCGCGATG |
| | GGCTGTGGCCAATAGCGGCTGCTCAGCGGGGCGCG |
| | CCGAGAGCAGCGGCCGGGAAGGGGCGGTGCGGGAG |
| | GCGGGGTGTGGGCGGTAGTGTGGGCCCTGTTCCT |
| | GCCCGCGCGGTGTTCCGCATTCTGCAAGCCTCCGG |
| | AGCGCACGTCGGCAGTCGGCTCCCTCGTTGACCGA |
| | ATCACCGACCTCTCTCCCCAG |
| | (SEQ ID NO: 16) |
| SFFV | GTAACGCCATTTTGCAAGGCATGGAAAAATACCAA |
| | ACCAAGAATAGAGAAGTTCAGATCAAGGGCGGGTA |
| | CATGAAAATAGCTAACGTTGGGCCAAACAGGATAT |
| | CTGCGGTGAGCAGTTTCGGCCCCGGCCCGGGGCCA |
| | AGAACAGATGGTCACCGCAGTTTCGGCCCCGGCCC |

TABLE 5C-continued

Exemplary Constitutive Promoters

| Name | DNA SEQUENCE |
|------|--------------|
| | GAGGCCAAGAACAGATGGTCCCCAGATATGGCCCA |
| | ACCCTCAGCAGTTTCTTAAGACCCATCAGATGTTT |
| | CCAGGCTCCCCCAAGGACCTGAAATGACCCTGCGC |
| | CTTATTTGAATTAACCAATCAGCCTGCTTCTCGCT |
| | TCTGTTCGCGCGCTTCTGCTTCCCGAGCTCTATAA |
| | AAGAGCTCACAACCCCTCACTCGGCGCGCCAGTCC |
| | TCCGACAGACTGAGTCGCCCGGG |
| | (SEQ ID NO: 17) |
| SV40 | CTGTGGAATGTGTGTCAGTTAGGGTGTGGAAAGTC |
| | CCCAGGCTCCCCAGCAGGCAGAAGTATGCAAAGCA |
| | TGCATCTCAATTAGTCAGCAACCAGGTGTGGAAAG |
| | TCCCCAGGCTCCCCAGCAGGCAGAAGTATGCAAAG |
| | CATGCATCTCAATTAGTCAGCAACCATAGTCCCGC |
| | CCCTAACTCCGCCCATCCCGCCCCTAACTCCGCCC |
| | AGTTCCGCCCATTCTCCGCCCCATGGCTGACTAAT |
| | TTTTTTATTTATGCAGAGGCCGAGGCCGCCTCTG |
| | CCTCTGAGCTATTCCAGAAGTAGTGAGGAGGCTTT |
| | TTTGGAGGCCTAGGCTTTTGCAAAAAGCT |
| | (SEQ ID |
| | NO: 18) |
| UbC | GCGCCGGGTTTTGGCGCCTCCCGCGGGCGCCCCCC |
| | TCCTCACGGCGAGCGCTGCCACGTCAGACGAAGGG |
| | CGCAGGAGCGTTCCTGATCCTTCCGCCCGGACGCT |
| | CAGGACAGCGGCCCGCTGCTCATAAGACTCGGCCT |
| | TAGAACCCCAGTATCAGCAGAAGGACATTTTAGGA |
| | CGGGACTTGGGTGACTCTAGGGCACTGGTTTTCTT |
| | TCCAGAGAGCGGAACAGGCGAGGAAAAGTAGTCCC |
| | TTCTCGGCGATTCTGCGGAGGGATCTCCGTGGGGC |
| | GGTGAACGCCGATGATTATATAAGGACGCGCCGGG |
| | TGTGGCACAGCTAGTTCCGTCGCAGCCGGGATTTG |
| | GGTCGCGGTTCTTGTTTGTGGATCGCTGTGATCGT |
| | CACTTGGTGAGTTGCGGGCTGCTGGGCTGGCCGGG |
| | GCTTTCGTGGCCGCCGGGCCGCTCGGTGGGACGGA |
| | AGCGTGTGGAGAGACCGCCAAGGGCTGTAGTCTGG |
| | GTCCGCGAGCAAGGTTGCCCTGAACTGGGGGTTGG |
| | GGGGAGCGCACAAAATGGCGGCTGTTCCCGAGTCT |
| | TGAATGGAAGACGCTTGTAAGGCGGGCTGTGAGGT |
| | CGTTGAAACAAGGTGGGGGGCATGGTGGGCGGCAA |
| | GAACCCAAGGTCTTGAGGCCTTCGCTAATGCGGGA |
| | AAGCTCTTATTCGGGTGACTGGGGAGTGGGGCACCA |
| | TCTGGGGACCCTGACGTGAAGTTTGTCACTGACTG |
| | GAGAACTCGGGTTTGTCGTCTGGTTGCGGGGGCGG |
| | CAGTTATGCGGTGCCGTTGGGCAGTGCACCCGTAC |
| | CTTTGGGAGCGCGCGCCTCGTCGTGTCGTGACGTC |
| | ACCCGTTCTGTTGGCTTATAATGCAGGGTGGGGCC |
| | ACCTGCCGGTAGGTGTGCGGTAGGCTTTTCTCCGT |
| | CGCAGGACGCAGGGTTCGGGCCTAGGGTAGGCTCT |
| | CCTGAATCGACAGGCGCCGGACCTCTGGTGAGGGG |
| | AGGGATAAGTGAGGCGTCAGTTTCTTTGGTCGGTT |
| | TTATGTACCTATCTTCTTAAGTAGCTGAAGCTCCG |
| | GTTTTGAACTATGCGCTCGGGGTTGGCGAGTGTGT |
| | TTTGTGAAGTTTTTTAGGCACCTTTTGAAATGTAA |
| | TCATTTGGGTCAATATGTAATTTTCAGTGTTAGAC |
| | TAGTAAAGCTTCTGCAGGTCGACTCTAGAAAATTG |
| | TCCGCTAAATTCTGGCCGTTTTTGGCTTTTTTGTT |
| | AGAC |
| | (SEQ ID NO: 19) |
| hEF1aV1 | GGCTCCGGTGCCCGTCAGTGGGCAGAGCGCACATC |
| | GCCCACAGTCCCCGAGAAGTTGGGGGGGAGGGGTCG |
| | GCAATTGAACCGGTGCCTAGAGAAGGTGGCGCGGG |
| | GTAAACTGGGAAAGTGATGTCGTGTACTGGCTCCG |
| | CCTTTTTCCCGAGGGTGGGGGAGAACCGTATATAA |
| | GTGCAGTAGTCGCCGTGAACGTTCTTTTTTCGCAAC |
| | GGGTTTGCCGCCAGAACACAGGTAAGTGCCGTGTG |
| | TGGTTCCCGCGGGCCTGGCCTCTTTACGGGTTATG |
| | GCCCTTGCGTGCCTTGAATTACTTCCACCTGGCTG |
| | CAGTACGTGATTCTTGATCCCGAGCTTCGGGTTGG |
| | AAGTGGGTGGGAGAGTTCGAGGCCTTGCGCTTAAG |
| | GAGCCCCTTCGCCTCGTGCTTGAGTTGAGGCCTGG |
| | CCTGGGCGCTGGGGCCGCCGCGTGCGAATCTGGTG |
| | GCACCTTCGCGCCTGTCTCGCTGCTTTCGATAAGT |
| | CTCTAGCCATTTAAAATTTTTGATGACCTGCTGCG |
| | ACGCTTTTTTTCTGGCAAGATAGTCTTGTAAATGC |

TABLE 5C-continued

Exemplary Constitutive Promoters

| Name | DNA SEQUENCE |
|------|--------------|
| | GGGCCAAGATCTGCACACTGGTATTTCGGTTTTTG |
| | GGGCCGCGGGCGGCGACGGGGCCCGTGCGTCCCAG |
| | CGCACATGTTCGGCGAGGCGGGGCCTGCGAGCGCG |
| | GCCACCGAGAATCGGACGGGGGTAGTCTCAAGCTG |
| | GCCGGCCTGCTCTGGTGCCTGGTCTCGCGCCGCCG |
| | TGTATCGCCCCGCCCTGGGCGGCAAGGCTGGCCCG |
| | GTCGGCACCAGTTGCGTGAGCGGAAAGATGGCCGC |
| | TTCCCGGCCCTGCTGCAGGGAGCTCAAAATGGAGG |
| | ACGCGGCGCTCGGGAGAGCGGGCGGGTGAGTCACC |
| | CACACAAAGGAAAAGGGCCTTTCCGTCCTCAGCCG |
| | TCGCTTCATGTGACTCCACGGAGTACCGGGCGCCG |
| | TCCAGGCACCTCGATTAGTTCTCGAGCTTTTGGAG |
| | TACGTCGTCTTTAGGTTGGGGGGAGGGGTTTTATG |
| | CGATGGAGTTTCCCCACACTGAGTGGGTGGAGACT |
| | GAAGTTAGGCCAGCTTGGCACTTGATGTAATTCTC |
| | CTTGGAATTTGCCCTTTTTGAGTTTGGATCTTGGT |
| | TCATTCTCAAGCCTCAGACAGTGGTTCAAAGTTTT |
| | TTTCTTCCATTTCAGGTGTCGTGA |
| | (SEQ ID NO: 20) |
| hCAGG | ACTAGTTATTAATAGTAATCAATTACGGGGTCATT |
| | AGTTCATAGCCCATATATGGAGTTCCGCGTTACAT |
| | AACTTACGGTAAATGGCCCGCCTGGCTGACCGCCC |
| | AACGACCCCCGCCCATTGACGTCAATAATGACGTA |
| | TGTTCCCATAGTAACGCCAATAGGGACTTTCCATT |
| | GACGTCAATGGGTGGAGTATTTACGGTAAACTGCC |
| | CACTTGGCAGTACATCAAGTGTATCATATGCCAAG |
| | TACGCCCCCTATTGACGTCAATGACGGTAAATGGC |
| | CCGCCTGGCATTATGCCCAGTACATGACCTTATGG |
| | GACTTTCCTACTTGGCAGTACATCTACGTATTAGT |
| | CATCGCTATTACCATGGTCGAGGTGAGCCCCACGT |
| | TCTGCTTCACTCTCCCCATCTCCCCCCCCTCCCCA |
| | CCCCCAATTTTGTATTTATTTATTTTTTAATTATT |
| | TTGTGCAGCGATGGGGGCGGGGGGGGGGGGGGGGG |
| | GCGCGCCAGGCGGGGCGGGGCGGGGCGAGGGGGGG |
| | GGCGGGGCGAGGCGGAGAGGTGCGGCGGCAGCCAA |
| | TCAGAGCGGCGCGCTCCGAAAGTTTCCTTTTATGG |
| | CGAGGCGGCGGCGGCGGCGGCCCTATAAAAAGCGA |
| | AGCGCGCGGCGGGCGGGGGAGTCGCTGCGACGCTGC |
| | CTTCGCCCCGTGCCCCGCTCCGCCGCCGCCTCGCG |
| | CCGCCCGCCCCGGCTCTGACTGACCGCGTTACTCC |
| | CACAGGTGAGCGGGCGGGACGGCCCTTCTCCTCCG |
| | GGCTGTAATTAGCGCTTGGTTTAATGACGGCTTGT |
| | TTCTTTTCTGTGGCTGCGTGAAAGCCTTGAGGGGC |
| | TCCGGGAGGGCCCTTTGTGCGGGGGGAGCGGCTCG |
| | GGGGGTGCGTGCGTGTGTGTGTGCGTGGGGAGCGC |
| | CGCGTGCGGCTCCGCGCTGCCCGGCGGCTGTGAGC |
| | GCTGCGGGCGCGGCGCGGGGCTTTGTGCGCTCCGC |
| | AGTGTGCGCGAGGGGAGCGCGGCCGGGGGCGGTGC |
| | CCCGCGGTGCGGGGGGCTGCGAGGGGAACAAAG |
| | GCTGCGTGCGGGGTGTGTGCGTGGGGGGGTGAGCA |
| | GGGGGTGTGGGCGCGTCGGTCGGGCTGCAACCCCC |
| | CCTGCACCCCCCTCCCCGAGTTGCTGAGCACGGCC |
| | CGGCTTCGGGTGCGGGGCTCCGTACGGGGCGTGGC |
| | GCGGGGCTCGCCGTGCCGGGCGGGGGTGGCGGCA |
| | GGTGGGGGTGCCGGGCGGGGCGGGGCCGCCTCGGG |
| | CCGGGGAGGGCTCGGGGAGGGGCGCGGCGGCCCC |
| | CGGAGCGCCGGCGGCTGTCGAGGCGCGGCGAGCCG |
| | CAGCCATTGCCTTTTATGGTAATCGTGCGAGAGGG |
| | CGCAGGGACTTCCTTTGTCCCAAATCTGTGCGGAG |
| | CCGAAATCTGGGAGGCGCCGCCGCACCCCCTCTAG |
| | CGGGCGCGGGCGAAGCGGTGCGGCGCCGGCAGGA |
| | AGGAAATGGGCGGGGAGGGGCCTTCGTGCGTCGCCG |
| | CGCCGCCGTCCCCTTCTCCCCTCTCCAGCCTCGGGG |
| | CTGTCCGCGGGGGGACGGCTGCCTTCGGGGGGGGAC |
| | GGGGCAGGGCGGGGTTCGGCTTCTGGCGTGTGACC |
| | GGCGGCTCTAGAGCCTCTGCTAACCATGTTCATGC |
| | CTTCTTCTTTTTCCTACAGCTCCTGGGCAACGTGC |
| | TGGTTATTGTGCTGTCTCATCATTTTGGCAAAGAA |
| | TTC |
| | (SEQ ID NO: 21) |
| hEF1aV2 | Gggcagagcgcacatcgcccacagtccccgagaag |
| | ttggggggagggggtcggcaattgaaccggtgccta |
| | gagaaggtggcgcggggtaaactgggaaagtgatg |
| | tcgtgtactggctccgcctttttcccgagggggggg |

TABLE 5C-continued

Exemplary Constitutive Promoters

| Name | DNA SEQUENCE |
|------|--------------|
| | gagaaccgtatataagtgcagtagtcgccgtgaac |
| | gttcttttttcgcaacgggtttgccgccagaacaca |
| | g |
| | (SEQ ID NO: 22) |
| hACTb | CCACTAGTTCCATGTCCTTATATGGACTCATCTTT |
| | GCCTATTGCGACACACACTCAATGAACACCTACTA |
| | CGCGCTGCAAAGAGCCCCGCAGGCCTGAGGTGCCC |
| | CCACCTCACCACTCTTCCTATTTTTGTGTAAAAAT |
| | CCAGCTTCTTGTCACCACCTCCAAGGAGGGGGAGG |
| | AGGAGGAAGGCAGGTTCCTCTAGGCTGAGCCGAAT |
| | GCCCCTCTGTGGTCCCACGCCACTGATCGCTGCAT |
| | GCCCACCACCTGGGTACACACAGTCTGTGATTCCC |
| | GGAGCAGAACGGGACCCTGCCCACCCGGTCTTGTGT |
| | GCTACTCAGTGGACAGACCCAAGGCAAGAAAGGGT |
| | GACAAGGACAGGGTCTTCCCAGGCTGGCTTTGAGT |
| | TCCTAGCACCGCCCCGCCCCCAATCCTCTGTGGCA |
| | CATGGAGTCTTGGTCCCCAGAGTCCCCCAGCGGCC |
| | TCCAGATGGTCTGGGAGGGCAGTTCAGCTGTGGCT |
| | GCGCATAGCAGACATACAACGGACGGTGGGCCCAG |
| | ACCCAGGCTGTGTAGACCCAGCCCCCCCGCCCCGC |
| | AGTGCCTAGGTCACCCACTAACGCCCCCAGGCCTGG |
| | TCTTGGCTGGGCGTGACTGTTACCCTCAAAAGCAG |
| | GCAGCTCCAGGGTAAAAGGTGCCCTGCCCTGTAGA |
| | GCCCACCTTCCTTCCCAGGGCTGCGGCTGGGTAGG |
| | TTTGTAGCCTTCATCACGGGCCACCTCCAGCCACT |
| | GGACCGCTGGCCCCTGCCCTGTCCTGGGGAGTGTG |
| | GTCCTGCGACTTCTAAGTGGCCGCAAGCCACCTGA |
| | CTCCCCCAACACCACACTCTACCTCTCAAGCCCAG |
| | GTCTCTCCCTAGTGACCCACCCAGCACATTTAGCT |
| | AGCTGAGCCCCACAGCCAGAGGTCCTCAGGCCCTG |
| | CTTTTCAGGGCAGTTGCTCTGAAGTCGGCAAGGGGG |
| | AGTGACTGCCTGGCCACTCCATGCCCTCCAAGAGC |
| | TCCTTCTGCAGGAGCGTACAGAACCCAGGGCCCTG |
| | GCACCCGTGCAGACCCTGGCCCACCCCACCTGGGC |
| | GCTCAGTGCCCAAGAGATGTCCACACCTAGGATGT |
| | CCCGCGGTGGGTGGGGGGCCCGAGAGACGGGCAGG |
| | CCGGGGGCAGGCCTGGCCATGCGGGGCCGAACCGG |
| | GCACTGCCCAGCGTGGGGCGCGGGGGCCCACGGCGC |
| | GCGCCCCAGCCCCCGGGCCCAGCACCCCAAGGCG |
| | GCCAACGCCAAAACTCTCCCTCCTCCTCTTCCTCA |
| | ATCTCGCTCTGCCTCTTTTTTTTTTTCGCAAAAGG |
| | AGGGGAGAGGGGGTAAAAAAAATGCTGCACTGTGCG |
| | GCGAAGCCGGTGAGTGAGCGGCGCGGGGCCAATCA |
| | GCGTGCGCCGTTCCGAAAGTTGCCTTTTATGGCTC |
| | GAGCGGCCGCGGCGGCGCCCTATAAAACCCAGCGG |
| | CGCGACGCGCCACCACCGCCGAGACCGCGTCCGCC |
| | CCGCGAGCACAGAGCCTCGCCTTTGCCGATCCGCC |
| | GCCCGTCCACACCCGCCGCCAGgtaagcccggcca |
| | gccgaccggggcaggcggctcacggcccggccgca |
| | ggcggccgcgcgccccttcgcccgtgcagagccgcc |
| | gtctgggccgcagcggggggcgcatgggggggggaa |
| | ccggaccgcgctgggggcgcggggagaagcccctg |
| | ggcctccggagatgggggacaccccacgccagttc |
| | ggaggcgcgaggccgcgctcgggaggcgcgctccg |
| | ggggtgccgctctcggggcggggggcaaccggcggg |
| | gtctttgtctgagccgggctcttgccaatggggat |
| | cgcaggggggcgcggcggagccccgccaggcccg |
| | gtggggggctggggcgccattgcgcgtgcgcgctgg |
| | tcctttgggcgctaactgcgtgcgcgctgggaatt |
| | ggcgctaattgcgcgtgcgcgctgggactcaaggc |
| | gctaactgcgcgtgcgttctggggcccggggtgcc |
| | gcggcctgggctggggcgaaggcgggctcggccgg |
| | aaggggtggggtcgccgcggctcccgggcgcttgc |
| | gcgcacttcctgcccgagccgctcggccgcccgagg |
| | gtgtggccgctgcgtgcgcgcgcgcgaccccggcg |
| | ctgtttgaaccgggcggaggcggggctggcgccg |
| | gttgggagggggttggggcctggcttcctgccgcg |
| | cgccgcggggcgcctccgaccagtgtttgccttt |
| | tatggtaataacgcggccggccggcttccttttgt |
| | ccccaatctgggcgcgccgccggcgcccctggcgg |
| | cctaaggactcggcgcgccggaagtggccaggggg |
| | gggcgacctcggctcacagcgcgcccggctat |
| | (SEQ ID NO: 23) |

TABLE 5C-continued

Exemplary Constitutive Promoters

| Name | DNA SEQUENCE |
|---|---|
| heIF4A1 | GTTGATTTCCTTCATCCCTGGCACACGTCCAGGCA<br>GTGTCGAATCCATCTCTGCTACAGGGGAAAACAAA<br>TAACATTTGAGTCCAGTGGAGACCGGGAGCAGAAG<br>TAAAGGGAAGTGATAACCCCCAGAGCCCGGAAGCC<br>TCTGGAGGCTGAGACCTCGCCCCCCTTGCGTGATA<br>GGGCCTACGGAGCCACATGACCAAGGCACTGTCGC<br>CTCCGCACGTGTGAGAGTGCAGGGCCCCAAGATGG<br>CTGCCAGGCCTCGAGGCCTGACTCTTCTATGTCAC<br>TTCCGTACCGGCGAGAAAGGCGGGCCCTCCAGCCA<br>ATGAGGCTGCGGGGGGGGCCTTCACCTTGATAGGC<br>ACTCGAGTTATCCAATGGTGCCTGCGGGCCGGAGC<br>GACTAGGAACTAACGTCATGCCGAGTTGCTGAGCG<br>CCGGCAGGCGGGGCCGGGGCGGCCAAACCAATGCG<br>ATGGCCGGGGCGGAGTCGGGCGCTCTATAAGTTGT<br>CGATAGGCGGGCACTCCGCCCTAGTTTCTAAGGAC<br>CATG<br>(SEQ ID NO: 24) |
| hGAPDH | AGTTCCCCAACTTTCCCGCCTCTCAGCCTTT<br>GAAAGAAAGAAAGGGGAGGGGGGCAGCCGTGC<br>AGTCGCGAGCGGTGCTGGGCTCCGGCTCCAATTC<br>CCCATCTCAGTCGCTCCCAAAGTCCTTCTGTTTCA<br>TCCAAGCGTGTAAGGGTCCCCGTCCTTGACTCCCT<br>AGTGTCCTGCTGCCCACAGTCCAGTCCTGGGAACC<br>AGCACCGATCACCTCCCATCGGGCCAATCTCAGTC<br>CCTTCCCCCCTACGTCGGGGCCCACACGCTCGGTG<br>CGTGCCCAGTTGAACCAGGCGGCTGCGGAAAAAAA<br>AAAGCGGGGAGAAAGTAGGGCCCGGCTACTAGCGG<br>TTTTACGGGCGCACGTAGCTCAGGCCTTCAAGACCT<br>TGGGCTGGGACTGGCTGAGCCTGGCGGGAGGCGGG<br>GTCCGAGTCACCGCCTGCCGCCGCGCCCCGGTTT<br>CTATAAATTGAGCCCGCAGCCTCCCGCTTCGCTCT<br>CTGCTCCTCCTGTTCGACAGTCAGCCGCATCTTCT<br>TTTGCGTCGCCAGgtgaagacgggcggagagaaac<br>ccgggaggctagggacggcctgaaggcggcagggg<br>cgggcgcaggccggatgtgttcgcgccgctgcggg<br>gtgggcccgggcggcctccgcattgcagggggcggg<br>cggaggacgtgatgcggcgcgggctgggcatggag<br>gcctggtggggagagggagggagagcgtgggtgtc<br>ggccgggggccactaggcgctcactgttctctccct<br>ccgcgcagCCGAGCCACATCGCTGAGACAC<br>(SEQ ID NO: 25) |
| hGRP78 | AGTGCCGGTTACCAGCGGAAATGCCTCGGGGTCAGA<br>AGTCGCAGGAGAGATAGACAGCTGCTGAACCAATG<br>GGACCAGCGGATGGGGCGGATGTTATCTACCATTG<br>GTGAACGTTAGAAACGAATAGCAGCCAATGAATCA<br>GCTGGGGGGGCGGAGCAGTGACGTTTATTGCGGAG<br>GGGGCCGCTTCGAATCGGCGGCGCCAGCTTGGTG<br>GCCTGGGCCAATGAACGGCCTCCAACGAGCAGGGC<br>CTTCACCAATCGGCGGCCTCCACGACGGGGCTGGG<br>GGAGGGTATATAAGCCGAGTAGGCGACGGTGAGGT<br>CGACGCCGGCCAAGACAGCACAGACAGATTGACCT<br>ATTGGGGTGTTTCGCGAGTGTGAGAGGGAAGCGCC<br>GCGGCCTGTATTTCTAGACCTGCCCTTCGCCTGGT<br>TCGTGGCGCCTTGTGACCCCGGGCCCCTGCCGCCT<br>GCAAGTCGGAAATTGCGCTGTGCTCCTGTGCTACG<br>GCCTGTGGCTGGACTGCCTGCTGCTGCCCAACTGG<br>CTGGCAC<br>(SEQ ID NO: 26) |
| hGRP94 | TAGTTTCATCACCACCGCCACCCCCCCGCCCCCCC<br>GCCATCTGAAAGGGTTCTAGGGGATTTGCAACCTC<br>TCTCGTGTGTTTCTTCTTTCCGAGAAGCGCCGCCA<br>CACGAGAAAGCTGGCCGCGAAAGTCGTGCTGGAAT<br>CACTTCCAACGAAACCCCAGGCATAGATGGGAAAG<br>GGTGAAGAACACGTTGCCATGGCTACCGTTTCCCC<br>GGTCACGGAATAAACGCTCTCTAGGATCCGGAAGT<br>AGTTCCGCCGCGACCTCTCTAAAAGGATGGATGTG<br>TTCTCTGCTTACATTCATTGGACGTTTTCCCTTAG<br>AGGCCAAGGCCGCCCAGGCAAAGGGGCGGTCCCAC<br>GCGTGAGGGGCCCGCGGAGCCATTTGATTGGAGAA<br>AAGCTGCAAACCCTGACCAATCGGAAGGAGCCACG<br>CTTCGGGCATCGGTCACCGCACCTGGACAGCTCCG<br>ATTGGTGGACTTCCGCCCCCCCCTCACGAATCCTCA |

TABLE 5C-continued

Exemplary Constitutive Promoters

| Name | DNA SEQUENCE |
|---|---|
| | TTGGGTGCCGTGGGTGCGTGGTGCGGCGCGATTGG<br>TGGGTTCATGTTTCCCGTCCCCCGCCCGCGAGAAG<br>TGGGGGGTGAAAAGCGGCCCGACCTGCTTGGGGTGT<br>AGTGGGCGGACCGCGCGGCTGGAGGTGTGAGGATC<br>CGAACCCAGGGGTGGGGGGTGGAGGCGGCTCCTGC<br>GATCGAAGGGGACTTGAGACTCACCGGCCGCACGT<br>C<br>(SEQ ID NO: 27) |
| hHSP70 | GGGCCGCCCACTCCCCCTTCCTCTCAGGGTCCCTG<br>TCCCCTCCAGTGAATCCCAGAAGACTCTGGAGAGT<br>TCTGAGCAGGGGGCGGCACTCTGGCCTCTGATTGG<br>TCCAAGGAAGGCTGGGGGCAGGACGGGAGGCGAA<br>AACCCTGGAATATTCCCGACCTGGCAGCCTCATCG<br>AGCTCGGTGATTGGCTCAGAAGGGAAAAGGCGGGT<br>CTCCGTGACGACTTATAAAAGCCCAGGGGCAAGCG<br>GTCCGGATAACGGCTAGCCTGAGGAGCTGCTGCGA<br>CAGTCCACTACCTTTTTCGAGAGTGACTCCCGTTG<br>TCCCAAGGCTTCCCAGAGCGAACCTGTGCGGCTGC<br>AGGCACCGGCGCGTCGAGTTTCCGGCGTCCGGAAG<br>GACCGAGCTCTTCTCGCGGATCCAGTGTTCCGTTT<br>CCAGCCCCCAATCTCAGAGCGGAGCCGACAGAGAG<br>CAGGGAACCC<br>(SEQ ID NO: 28) |
| hKINb | GCCCCACCCCCGTCCGCGTTACAACCGGGAGGCCC<br>GCTGGGTCCTGCACCGTCACCCTCCTCCCTGTGAC<br>CGCCCACCTGATACCCAAACAACTTTCTCGCCCCT<br>CCAGTCCCCAGCTCGCCGAGCGCTTGCGGGGAGCC<br>ACCCAGCCTCAGTTTCCCCAGCCCCGGGCGGGGCG<br>AGGGGCGATGACGTCATGCCGGCGCGCGGCATTGT<br>GGGGCGGGCGAGGCGGGGCGCGGGGGGGAGCAAC<br>ACTGAGACGCCATTTTCGGCGGCGGGAGCGGCGCA<br>GGCGGCCGAGCGGGACTGGCTGGGTCGGCTGGGCT<br>GCTGGTGCGAGGAGCCGCGGGGCGTGTGCTCGGCGG<br>CCAAGGGGACAGCGCGTGGGTGGCCGAGGATGCTG<br>CGGGGCGGTAGCTCCGGCGCCCCTCGCTGGTGACT<br>GCTGCGCCGTGCCTCACACAGCCGAGGCGGGCTCG<br>GCGCACAGTCGCTGCTCCGCGCTCGCGCCCGGCGG<br>CGCTCCAGGTGCTGACAGCGCGAGAGAGCGCGGCC<br>TCAGGAGCAACAC<br>(SEQ ID NO: 29) |
| hUBIb | TTCCAGAGCTTTCGAGGAAGGTTTCTTCAACTCAA<br>ATTCATCCGCCTGATAATTTTCTTTATATTTTCCTA<br>AAGAAGGAAGAGAAGCGCATAGAGGAGAAGGGAAA<br>TAATTTTTTAGGAGCCTTTCTTACGGCTATGAGGA<br>ATTTGGGGCTCAGTTGAAAAGCCTAAACTGCCTCT<br>CGGGGAGGTTGGGCGCGGCGAACTACTTTCAGCGGC<br>GCACGGAGACGGCGTCTACGTGAGGGGGTGATAAGT<br>GACGCAACACTCGTTGCATAAATTTGCGCTCCGCC<br>AGCCCGGAGCATTTAGGGGCGGTTGGCTTTGTTGG<br>GTGAGCTTGTTTGTGTCCCTGTGGGTGGACGTGGT<br>TGGTGATTGGCAGGATCCTGGTATCCGCTAACAGg<br>tactggcccacagccgtaaagacctgcgggggcgt<br>gagagggggggaatgggtgaggtcaagctggaggct<br>tcttggggttgggtgggccgctgaggggagggggag<br>ggcgaggtgacgcgacacccggccttttctgggaga<br>gtgggccttgttgacctaaggggggcgagggcagt<br>tggcacgcgcacgcgccgacagaaactaacagaca<br>ttaaccaacagcgattccgtcgcgtttacttggga<br>ggaaggcggaaaagaggtagtttgtgtggcttctg<br>gaaaccctaaatttggaatcccagtatgagaatgg<br>tgtcccttcttgtgtttcaatgggatttttacttc<br>gcgagtcttgtgggtttggtttttgttttcagtttg<br>cctaacaccgtgcttaggtttgaggcagattggag<br>ttcggtcgggagtgtttgaatatccggaacagtta<br>gtgggggaaagctgtggacgcttggtaagagagcgc<br>tctggattttccgctgttgacgttgaaaccttgaa<br>tgacgaatttcgtattaagtgacttagccttgtaa<br>aattgaggggaggcttgcggaatattaacgtattt<br>aaggcattttgaaggaatagttgctaattttgaag<br>aatattaggtgtaaaagcaagaaatacaatgatcc<br>tgaggtgacacgcttatgtttttacttttaaactag<br>GTCACC<br>(SEQ ID NO: 30) |

TABLE 5C-continued

Exemplary Constitutive Promoters

| Name | DNA SEQUENCE |
| --- | --- |
| CAG | gacattgattattgactagttattaatagtaatca attacggggtcattagttcatagcccatatatgga gttccgcgttacataacttacggtaaatggcccgc ctggctgaccgcccaacgaccccgcccattgacg tcaataatgacgtatgttcccatagtaacgccaat agggactttccattgacgtcaatgggtggagtatt tacggtaaactgcccacttggcagtacatcaagtg tatcatatgccaagtacgcccctattgacgtcaa tgacggtaaatggcccgcctggcattatgcccagt acatgaccttatgggactttcctacttggcagtac atctacgtattagtcatcgctattaccatggtcga ggtgagccccacgttctgcttcactctccccatct cccccccctccccacccccaattttgtatttattt attttttaattattttgtgcagcgatgggggggg ggggggggggggcgcgcgccaggcggggggggggg gcgaggggggggggggcgaggcggagaggtgcggc ggcagccaatcagagcggcgcgctccgaaagtttc cttttatggcgaggcggcggcggcggcggcggccctat aaaaagcgaagcgcgcggcgggcg (SEQ ID NO: 173) |
| HLP | Tgtttgctgcttgcaatgtttgcccattttagggt ggacacaggacgctgtggtttctgagccagggggc gactcagatcccagccagtggacttagcccctgtt tgctcctccgataactggggtgaccttggttaata ttcaccagcagcctcccccgttgcccctctggatc cactgcttaaatacggacgaggacagggccctgtc tcctcagcttcaggcaccaccactgacctgggaca gtgaat (SEQ ID NO: 174) |

The promoter can be a tissue-specific promoter. In general, a tissue-specific promoter directs transcription of a nucleic acid, (e.g., the engineered nucleic acids encoding the chimeric proteins, such as membrane-cleavable chimeric proteins having the formula S-C-MT or MT-C-S such that expression is limited to a specific cell type, organelle, or tissue. Tissue-specific promoters include, but are not limited to, albumin (liver specific, Pinkert et al., (1987)), lymphoid specific promoters (Calame and Eaton, 1988), particular promoters of T-cell receptors (Winoto and Baltimore, (1989)) and immunoglobulins; Banerji et al., (1983); Queen and Baltimore, 1983), neuron specific promoters (e.g. the neurofilament promoter; Byrne and Ruddle, 1989), pancreas specific promoters (Edlund et al., (1985)) or mammary gland specific promoters (milk whey promoter, U.S. Pat. No. 4,873,316 and European Application Publication No. 264, 166) as well as developmentally regulated promoters such as the murine hox promoters (Kessel and Gruss, Science 249: 374-379 (1990)) or the α-fetoprotein promoter (Campes and Tilghman, Genes Dev. 3:537-546 (1989)), the contents of each of which are fully incorporated by reference herein. The promoter can be constitutive in the respective specific cell type, organelle, or tissue. Tissue-specific promoters and/or regulatory elements can also include promoters from the liver fatty acid binding (FAB) protein gene, specific for colon epithelial cells; the insulin gene, specific for pancreatic cells; the transphyretin, .alpha.1-antitrypsin, plasminogen activator inhibitor type 1 (PAI-I), apolipoprotein A1 and LDL receptor genes, specific for liver cells; the myelin basic protein (MBP) gene, specific for oligodendrocytes; the glial fibrillary acidic protein (GFAP) gene, specific for glial cells; OPSIN, specific for targeting to the eye; and the neural-specific enolase (NSE) promoter that is specific for nerve cells. Examples of tissue-specific promoters include, but are not limited to, the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol L 7-alpha hydrolyase (CYP-7) promoter, beta-galactosidase alpha-2,6 sialylkansferase promoter, insulin-like growth factor binding protein (IGFBP-I) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human H+/K+-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include, but are not limited to, the uteroglobin promoter. Exemplary tissue-specific expression elements for adrenal cells include, but are not limited to, cholesterol side-chain cleavage (SCC) promoter. Exemplary tissue-specific expression elements for the general nervous system include, but are not limited to, gamma-gamman enolase (neuron-specific enolase, NSE) promoter. Exemplary tissue-specific expression elements for the brain include, but are not limited to, the neurofilament heavy chain (NF—H) promoter. Exemplary tissue-specific expression elements for lymphocytes include, but are not limited to, the human CGL-1/granzyme B promoter, the terminal deoxy transferase (TdT), lambda 5, VpreB, and lck (lymphocyte specific tyrosine protein kinase p561ck) promoter, the humans CD2 promoter and its 3'-transcriptional enhancer, and the human NK and T cell specific activation (NKG5) promoter. Exemplary tissue-specific expression elements for the colon include, but are not limited to, pp60c-src tyrosine kinase promoter, organ-specific neoantigens (OSNs) promoter, and colon specific antigen-P promoter. Tissue-specific expression elements for breast cells are for example, but are not limited to, the human alpha-lactalbumin promoter. Exemplary tissue-specific expression elements for the lung include, but are not limited to, the cystic fibrosis transmembrane conductance regulator (CFTR) gene promoter.

In some embodiments, a promoter of the present disclosure is modulated by signals within a tumor microenvironment. A tumor microenvironment is considered to modulate a promoter if, in the presence of the tumor microenvironment, the activity of the promoter is increased or decreased by at least 10%, relative to activity of the promoter in the absence of the tumor microenvironment. In some embodiments, the activity of the promoter is increased or decreased by at least 20%, at least 30%, at least 40%, at least 50%, at least 60%, at least 70%, at least 80%, at least 90%, at least 100%, relative to activity of the promoter in the absence of the tumor microenvironment. For example, the activity of the promoter is increased or decreased by 10-20%, 10-30%, 10-40%, 10-50%, 10-60%, 10-70%, 10-80%, 10-90%, 10-100%, 10-200%, 20-30%, 20-40%, 20-50%, 20-60%, 20-70%, 20-80%, 20-90%, 20-100%, 20-200%, 50-60%, 50-70%, 50-80%, 50-90%, 50-100%, or 50-200%, relative to activity of the promoter in the absence of the tumor microenvironment.

In some embodiments, the activity of the promoter is increased or decreased by at least 2 fold (e.g., 2, 3, 4, 5, 10, 25, 20, 25, 50, or 100 fold), relative to activity of the promoter in the absence of the tumor microenvironment. For example, the activity of the promoter is increased or decreased by at least 3 fold, at least 5 fold, at least 10 fold, at least 20 fold, at least 50 fold, or at least 100 fold, relative to activity of the promoter in the absence of the tumor microenvironment. In some embodiments, the activity of the promoter is increased or decreased by 2-10, 2-20, 2-30, 2-40, 2-50, 2-60, 2-70, 2-80, 2-90, or 2-100 fold, relative to activity of the promoter in the absence of the tumor microenvironment.

In some embodiments, a promoter of the present disclosure is activated under a hypoxic condition. A "hypoxic condition" is a condition where the body or a region of the body is deprived of adequate oxygen supply at the tissue level. Hypoxic conditions can cause inflammation (e.g., the level of inflammatory cytokines increase under hypoxic conditions). In some embodiments, the promoter that is activated under hypoxic condition is operably linked to a nucleotide encoding a chimeric proteins that decreases the expression of activity of inflammatory cytokines, thus reducing the inflammation caused by the hypoxic condition. In some embodiments, the promoter that is activated under hypoxic conditions comprises a hypoxia responsive element (HRE). A "hypoxia responsive element (HRE)" is a response element that responds to hypoxia-inducible factor (HIF). The HRE, in some embodiments, comprises a consensus motif NCGTG (where N is either A or G).

Activation-Conditional Control Polypeptide (ACP) Promoter Systems

In some embodiments, a synthetic promoter is a promoter system including an activation-conditional control polypeptide- (ACP-) binding domain sequence and a promoter sequence. Such a system is also referred to herein as an "ACP-responsive promoter." In general, an ACP promoter system includes a first expression cassette encoding an activation-conditional control polypeptide (ACP) and a second expression cassette encoding an ACP-responsive promoter operably linked to an exogenous polynucleotide sequence, such as the exogenous polynucleotide sequence encoding the membrane-cleavable chimeric proteins described herein or any other protein of interest (e.g., a protease). In some embodiments, the first expression cassette and second expression cassette are each encoded by a separate engineered nucleic acid. In other embodiments, the first expression cassette and the second expression cassette are encoded by the same engineered nucleic acid. The ACP-responsive promoter can be operably linked to a nucleotide sequence encoding a single protein of interest or multiple proteins of interest.

The promoters of the ACP promoter system, e.g., either a promoter driving expression of the ACP or the promoter sequence of the ACP-responsive promoter, can include any of the promoter sequences described herein (see "Promoters" above). The ACP-responsive promoter can be derived from minP, NFkB response element, CREB response element, NFAT response element, SRF response element 1, SRF response element 2, AP1 response element, TCF-LEF response element promoter fusion, Hypoxia responsive element, SMAD binding element, STAT3 binding site, minCMV, YB_TATA, minTK, inducer molecule responsive promoters, and tandem repeats thereof. In some embodiments, the ACP-responsive promoter includes a minimal promoter.

In some embodiments, the ACP-binding domain includes one or more zinc finger binding sites. In some embodiments, the ACP-responsive promoter includes a minimal promoter and the ACP-binding domain includes one or more zinc finger binding sites. The ACP-binding domain can include 1, 2, 3, 4, 5, 6, 7, 8, 9, 10 or more zinc finger binding sites. In some embodiments, the transcription factor is a zinc-finger-containing transcription factor. In some embodiments, the zinc-finger-containing transcription factor is a synthetic transcription factor. In some embodiments, the ACP-binding domain includes one or more zinc finger binding sites and the ACP has a DNA-binding zinc finger protein domain (ZF protein domain). In some embodiments, the ACP has a DNA-binding zinc finger protein domain (ZF protein domain) and an effector domain. In some embodiments, the ACP-binding domain includes one or more zinc finger binding sites and the ACP has a DNA-binding zinc finger protein domain (ZF protein domain) and an effector domain. In some embodiments, the ZF protein domain is modular in design and is composed of zinc finger arrays (ZFA). A zinc finger array comprises multiple zinc finger protein motifs that are linked together. Each zinc finger motif binds to a different nucleic acid motif. This results in a ZFA with specificity to any desired nucleic acid sequence, e.g., a ZFA with desired specificity to an ACP-binding domain having a specific zinc finger binding site composition and/or configuration. The ZF motifs can be directly adjacent to each other, or separated by a flexible linker sequence. In some embodiments, a ZFA is an array, string, or chain of ZF motifs arranged in tandem. A ZFA can have 1, 2, 3, 4, 5, 6, 7, 8, 9, 10, 11, 12, 13, 14, or 15 zinc finger motifs. The ZFA can have from 1-10, 1-15, 1-2, 1-3, 1-4, 1-5, 1-6, 1-7, 1-8, 1-9, 2-3, 2-4, 2-5, 2-6, 2-7, 2-8, 2-9, 2-10, 3-4, 3-5 3-6, 3-7, 3-8, 3-9, 3-10, 4-5, 4-6, 4-7, 4-8, 4-9, 4-10, 5-6, 5-7, 5-8, 5-9, 5-10, or 5-15 zinc finger motifs. The ZF protein domain can have 1, 2, 3, 4, 5, 6, 7, 8, 9, 10, 11, 12, 13, 14, 15, or more ZFAs. The ZF domain can have from 1-10, 1-15, 1-2, 1-3, 1-4, 1-5, 1-6, 1-7, 1-8, 1-9, 2-3, 2-4, 2-5, 2-6, 2-7, 2-8, 2-9, 2-10, 3-4, 3-5 3-6, 3-7, 3-8, 3-9, 3-10, 4-5, 4-6, 4-7, 4-8, 4-9, 4-10, 5-6, 5-7, 5-8, 5-9, 5-10, or 5-15 ZFAs. In some embodiments, the ZF protein domain comprises one to ten ZFA(s). In some embodiments, the ZF protein domain comprises at least one ZFA. In some embodiments, the ZF protein domain comprises at least two ZFAs. In some embodiments, the ZF protein domain comprises at least three ZFAs. In some embodiments, the ZF protein domain comprises at least four ZFAs. In some embodiments, the ZF protein domain comprises at least five ZFAs. In some embodiments, the ZF protein domain comprises at least ten ZFAs.

In some embodiments, the ACP is a transcriptional modulator. In some embodiments, the ACP is a transcriptional repressor. In some embodiments, the ACP is a transcriptional activator. In some embodiments, the ACP is a transcription factor. In some embodiments, the ACP comprises a DNA-binding domain and a transcriptional effector domain. In some embodiments, the DNA-binding domain comprises a tetracycline (or derivative thereof) repressor (TetR) domain. In some embodiments, the ACP is an antigen recognizing receptor of the present disclosure.

The ACP can also further include an effector domain, such as a transcriptional effector domain. For instance, a transcriptional effector domain can be the effector or activator domain of a transcription factor. Transcription factor activation domains are also known as transactivation domains, and act as scaffold domains for proteins such as transcription coregulators that act to activate or repress transcription of genes. Any suitable transcriptional effector domains can be used in the ACP including, but not limited to, a Herpes Simplex Virus Protein 16 (VP16) activation domain; an activation domain consisting of four tandem copies of VP16, a VP64 activation domain; a p65 activation domain of NFκB; an Epstein-Barr virus R transactivator (Rta) activation domain; a tripartite activator comprising the VP64, the p65, and the Rta activation domains, the tripartite activator is known as a VPR activation domain; a histone acetyltransferase (HAT) core domain of the human E1A-associated protein p300, known as a p300 HAT core activation domain; a Krüppel associated box (KRAB) repression domain; a Repressor Element Silencing Transcription Factor (REST) repression domain; a WRPW (SEQ ID NO: 224) motif of the hairy-related basic helix-loop-helix repressor proteins, the motif is known as a WRPW (SEQ ID NO: 224) repression domain; a DNA (cytosine-5)-methyltransferase 3B (DNMT3B) repression domain; and an HP1 alpha chromoshadow repression domain, or any combination thereof.

In some embodiments, the effector domain is s transcription effector domain selected from: a Herpes Simplex Virus Protein 16 (VP16) activation domain; an activation domain consisting of four tandem copies of VP16, a VP64 activation domain; a p65 activation domain of NFκB; an Epstein-Barr virus R transactivator (Rta) activation domain; a tripartite activator comprising the VP64, the p65, and the Rta activation domains, the tripartite activator is known as a VPR activation domain; a histone acetyltransferase (HAT) core domain of the human E1A-associated protein p300, known as a p300 HAT core activation domain; a Krüppel associated box (KRAB) repression domain; a Repressor Element Silencing Transcription Factor (REST) repression domain; a WRPW (SEQ ID NO: 224) motif of the hairy-related basic helix-loop-helix repressor proteins, the motif is known as a WRPW (SEQ ID NO: 224) repression domain; a DNA (cytosine-5)-methyltransferase 3B (DNMT3B) repression domain; and an HP1 alpha chromoshadow repression domain.

In some embodiments, the ACP is a small molecule (e.g., drug) inducible polypeptide. For example, in some embodiments, the ACP may be induced by tetracycline (or derivative thereof), and comprises a TetR domain and a VP16 effector domain. In some embodiments, the ACP includes an estrogen receptor variant, such as ERT2, and may be regulated by tamoxifen, or a metabolite thereof (such as 4-hydroxy-tamoxifen [4-OHT], N-desmethyltamoxifen, tamoxifen-N-oxide, or endoxifen), through tamoxifen-controlled nuclear localization.

In some embodiments, the ACP is a small molecule (e.g., drug) inducible polypeptide that includes a repressible protease and one or more cognate cleavage sites of the repressible protease. In some embodiments, a repressible protease is active (cleaves a cognate cleavage site) in the absence of the specific agent and is inactive (does not cleave a cognate cleavage site) in the presence of the specific agent. In some embodiments, the specific agent is a protease inhibitor. In some embodiments, the protease inhibitor specifically inhibits a given repressible protease of the present disclosure. The repressible protease can be any of the proteases described herein that is capable of inactivation by the presence or absence of a specific agent (see "Protease Cleavage Site" above for exemplary repressible proteases, cognate cleavage sites, and protease inhibitors).

In some embodiments, the ACP has a degron domain (see "Degron Systems and Domains" above for exemplary degron sequences). The degron domain can be in any order or position relative to the individual domains of the ACP. For example, the degron domain can be N-terminal of the repressible protease, C-terminal of the repressible protease, N-terminal of the ZF protein domain, C-terminal of the ZF protein domain, N-terminal of the effector domain, or C-terminal of the effector domain.

Multicistronic and Multiple Promoter Systems

In some embodiments, engineered nucleic acids (e.g., an engineered nucleic acid comprising an expression cassette) are configured to produce multiple chimeric proteins. For example, nucleic acids may be configured to produce 2-20 different chimeric proteins. In some embodiments, nucleic acids are configured to produce 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, or 19-20 chimeric proteins. In some embodiments, nucleic acids are configured to produce 1, 2, 3, 4, 5, 6, 7, 8, 9, 10, 11, 12, 13, 14, 15, 16, 17, 18, 19, or 20 chimeric proteins.

In some embodiments, engineered nucleic acids can be multicistronic, i.e., more than one separate polypeptide (e.g., multiple chimeric proteins) can be produced from a single mRNA transcript. Engineered nucleic acids can be multicistronic through the use of various linkers, e.g., a polynucleotide sequence encoding a first chimeric proteins can be linked to a nucleotide sequence encoding a second chimeric protein, such as in a first gene:linker:second gene 5' to 3' orientation. A linker can encode a 2A ribosome skipping element, such as T2A. Other 2A ribosome skipping elements include, but are not limited to, E2A, P2A, and F2A. 2A ribosome skipping elements allow production of separate polypeptides encoded by the first and second genes are produced during translation. A linker can encode a cleavable linker polypeptide sequence, such as a Furin cleavage site or a TEV cleavage site, wherein following expression the cleavable linker polypeptide is cleaved such that separate polypeptides encoded by the first and second genes are produced. A cleavable linker can include a polypeptide sequence, such as such a flexible linker (e.g., a Gly-Ser-Gly sequence), that further promotes cleavage.

A linker can encode an Internal Ribosome Entry Site (IRES), such that separate polypeptides encoded by the first and second genes are produced during translation. A linker can encode a splice acceptor, such as a viral splice acceptor.

A linker can be a combination of linkers, such as a Furin-2A linker that can produce separate polypeptides through 2A ribosome skipping followed by further cleavage of the Furin site to allow for complete removal of 2A residues. In some embodiments, a combination of linkers can include a Furin sequence, a flexible linker, and 2A linker.

Accordingly, in some embodiments, the linker is a Furin-Gly-Ser-Gly-2A fusion polypeptide. In some embodiments, a linker of the present disclosure is a Furin-Gly-Ser-Gly-T2A fusion polypeptide.

In general, a multicistronic system can use any number or combination of linkers, to express any number of genes or portions thereof (e.g., an engineered nucleic acid can encode a first, a second, and a third chimeric protein, each separated by linkers such that separate polypeptides encoded by the first, second, and third chimeric proteins are produced).

Engineered nucleic acids can use multiple promoters to express genes from multiple ORFs, i.e., more than one separate mRNA transcript can be produced from a single engineered nucleic acid. For example, a first promoter can be operably linked to a polynucleotide sequence encoding a first chimeric protein, and a second promoter can be operably linked to a polynucleotide sequence encoding a second chimeric protein. In general, any number of promoters can be used to express any number of chimeric proteins. In some embodiments, at least one of the ORFs expressed from the multiple promoters can be multicistronic.

"Linkers," as used herein can refer to polypeptides that link a first polypeptide sequence and a second polypeptide sequence, the multicistronic linkers described above, or the additional promoters that are operably linked to additional ORFs described above.

Engineered Cells

Provided herein are engineered cells, and methods of producing the engineered cells, that produce membrane-cleavable chimeric proteins. In general, engineered cells of the present disclosure may be engineered to express the chimeric proteins provided for herein, such as the membrane-cleavable chimeric proteins having the formula S-C-MT or MT-C-S described herein. These cells are referred to herein as "engineered cells." These cells, which typically contain engineered nucleic acid, do not occur in nature. In some embodiments, the cells are engineered to include a nucleic acid comprising a promoter operably linked to a nucleotide sequence encoding a chimeric protein, for example, a membrane-cleavable chimeric protein. An engineered cell can comprise an engineered nucleic acid integrated into the cell's genome. An engineered cell can comprise an engineered nucleic acid capable of expression without integrating into the cell's genome, for example, engineered with a transient expression system such as a plasmid or mRNA.

The present disclosure also encompasses additivity and synergy between a chimeric protein(s) and the engineered cell from which they are produced. In some embodiments, cells are engineered to produce at least two (e.g., 2, 3, 4, 5, 6, 7, 8, 9, 10 or more) chimeric proteins, for example ate least two membrane-cleavable chimeric proteins. In other embodiments, cells are engineered to produce at least one chimeric proteins having an effector molecule that is not natively produced by the cells. Such an effector molecule may, for example, complement the function of effector molecules natively produced by the cells.

In some embodiments, cells are engineered to express membrane-tethered anti-CD3 and/or anti-CD28 agonist extracellular domains.

In some embodiments, a cell (e.g., an immune cell or a stem cell) is engineered to produce multiple chimeric proteins. For example, cells may be engineered to produce 2-20 different chimeric proteins, such as 2-20 different membrane-cleavable chimeric proteins. In some embodiments, cells engineered to produce 2-20, 2-19, 2-18, 2-17, 2-16, 2-15, 2-14, 2-13, 2-12, 2-11, 2-10, 2-9, 2-8, 2-7, 2-6, 2-5, 2-4, 2-3, 3-20, 3-19, 3-18, 3-17, 3-16, 3-15, 3-14, 3-13, 3-12, 3-11, 3-10, 3-9, 3-8, 3-7, 3-6, 3-5, 3-4, 4-20, 4-19, 4-18, 4-17, 4-16, 4-15, 4-14, 4-13, 4-12, 4-11, 4-10, 4-9, 4-8, 4-7, 4-6, 4-5, 5-20, 5-19, 5-18, 5-17, 5-16, 5-15, 5-14, 5-13, 5-12, 5-11, 5-10, 5-9, 5-8, 5-7, 5-6, 6-20, 6-19, 6-18, 6-17, 6-16, 6-15, 6-14, 6-13, 6-12, 6-11, 6-10, 6-9, 6-8, 6-7, 7-20, 7-19, 7-18, 7-17, 7-16, 7-15, 7-14, 7-13, 7-12, 7-11, 7-10, 7-9, 7-8, 8-20, 8-19, 8-18, 8-17, 8-16, 8-15, 8-14, 8-13, 8-12, 8-11, 8-10, 8-9, 9-20, 9-19, 9-18, 9-17, 9-16, 9-15, 9-14, 9-13, 9-12, 9-11, 9-10, 10-20, 10-19, 10-18, 10-17, 10-16, 10-15, 10-14, 10-13, 10-12, 10-11, 11-20, 11-19, 11-18, 11-17, 11-16, 11-15, 11-14, 11-13, 11-12, 12-20, 12-19, 12-18, 12-17, 12-16, 12-15, 12-14, 12-13, 13-20, 13-19, 13-18, 13-17, 13-16, 13-15, 13-14, 14-20, 14-19, 14-18, 14-17, 14-16, 14-15, 15-20, 15-19, 15-18, 15-17, 15-16, 16-20, 16-19, 16-18, 16-17, 17-20, 17-19, 17-18, 18-20, 18-19, or 19-20 chimeric proteins. In some embodiments, cells are engineered to produce 1, 2, 3, 4, 5, 6, 7, 8, 9, 10, 11, 12, 13, 14, 15, 16, 17, 18, 19, or 20 chimeric proteins.

In some embodiments, engineered cells comprise one or more engineered nucleic acids encoding a promoter operably linked to a nucleotide sequence encoding a chimeric protein. In some embodiments, cells are engineered to include a plurality of engineered nucleic acids, e.g., at least two engineered nucleic acids, each encoding a promoter operably linked to a nucleotide sequence encoding at least one (e.g., 1, 2 or 3) chimeric protein. For example, cells may be engineered to comprise at least 2, at least 3, at least 4, at least 5, at least 6, at least 7, at least 8, at least 8, at least 9, or at least 10, engineered nucleic acids, each encoding a promoter operably linked to a nucleotide sequence encoding at least one (e.g., 1, 2 or 3) chimeric protein. In some embodiments, the cells are engineered to comprise 2, 3, 4, 5, 6, 7, 8, 9, 10, or more engineered nucleic acids, each encoding a promoter operably linked to a nucleotide sequence encoding at least one (e.g., 1, 2 or 3) chimeric protein. Engineered cells can comprise an engineered nucleic acid encoding at least one of the linkers described above, such as polypeptides that link a first polypeptide sequence and a second polypeptide sequence, one or more multicistronic linker described above, one or more additional promoters operably linked to additional ORFs, or a combination thereof.

In some embodiments, a cell (e.g., an immune cell or a stem cell) is engineered to express a protease. In some embodiments, a cell is engineered to express a protease heterologous to a cell. In some embodiments, a cell is engineered to express a protease heterologous to a cell expressing a chimeric protein, such as a heterologous protease that cleaves the protease cleavage site of a membrane-cleavable chimeric protein. In some embodiments, engineered cells comprise one or more engineered nucleic acids encoding a promoter operably linked to a nucleotide sequence encoding a protease, such as a heterologous protease. Protease and protease cleavage sites are described in greater detail in the Section herein titled "Protease Cleavage site."

In some embodiments, a cell (e.g., an immune cell or a stem cell) is engineered to produce at least one homing molecule. "Homing," refers to active navigation (migration) of a cell to a target site (e.g., a cell, tissue (e.g., tumor), or organ). A "homing molecule" refers to a molecule that directs cells to a target site. In some embodiments, a homing molecule functions to recognize and/or initiate interaction of an engineered cell to a target site. Non-limiting examples of homing molecules include CXCR1, CCR9, CXCR2, CXCR3, CXCR4, CCR2, CCR4, FPR2, VEGFR, IL6R, CXCR1, CSCR7, and PDGFR.

In some embodiments, a homing molecule is a chemokine receptor (cell surface molecule that binds to a chemokine). Non-limiting examples of chemokine receptors that may be produced by the engineered cells of the present disclosure include: CXC chemokine receptors (e.g., CXCR1, CXCR2, CXCR3, CXCR4, CXCR5, CXCR6, and CXCR7), CC chemokine receptors (CCR1, CCR2, CCR3, CCR4, CCR5, CCR6, CCR7, CCR8, CCR9, CCR10, and CCR11), CX3C chemokine receptors (e.g., CX3CR1, which binds to CX3CL1), and XC chemokine receptors (e.g., XCR1). In some embodiments, a chemokine receptor is a G protein-linked transmembrane receptor, or a member of the tumor necrosis factor (TNF) receptor superfamily (including but not limited to TNFRSF1A, TNFRSF1B). In some embodiments, cells are engineered to produce CXCL8, CXCL9, and/or CXCL10 (promote T-cell recruitment), CCL3 and/or CXCL5, CCL21 (Th1 recruitment and polarization). In some embodiments, cells are engineered to produce CXCR4.

In some embodiments, a cell (e.g., an immune cell or a stem cell) is engineered to produce G-protein coupled receptors (GPCRs) that detect N-formylated-containing oligopeptides (including but not limited to FPR2 and FPRL1).

In some embodiments, a cell (e.g., an immune cell or a stem cell) is engineered to produce receptors that detect interleukins (including but not limited to IL6R).

In some embodiments, a cell (e.g., an immune cell or a stem cell) is engineered to produce receptors that detect growth factors secreted from other cells, tissues, or tumors (including but not limited to FGFR, PDGFR, EGFR, and receptors of the VEGF family, including but not limited to VEGF-C and VEGF-D).

In some embodiments, a cell (e.g., an immune cell or a stem cell) is engineered to produce one or more integrins. Cells of the present disclosure may be engineered to produce any combination of integrin α and β subunits. The a subunit of an integrin may be, without limitation: ITGA1, ITGA2, ITGA3, ITGA4, ITGA5, ITGA6, IGTA7, ITGA8, ITGA9, IGTA10, IGTA11, ITGAD, ITGAE, ITGAL, ITGAM, ITGAV, ITGA2B, ITGAX. The β subunit of an integrin may be, without limitation: ITGB1, ITGB2, ITGB3, ITGB4, ITGB5, ITGB6, ITGB7, and ITGB8.

In some embodiments, a cell (e.g., an immune cell or a stem cell) is engineered to produce one or more matrix metalloproteinases (MMP). Non-limiting examples of MMPs include MMP-2, MMP-9, and MMP. In some embodiments, cells are engineered to produce an inhibitor of a molecule (e.g., protein) that inhibits MMPs. For example, cells may be engineered to express an inhibitor (e.g., an RNAi molecule) of membrane type 1 MMP (MT1-MMP) or TIMP metallopeptidase inhibitor 1 (TIMP-1).

In some embodiments, a cell (e.g., an immune cell or a stem cell) is engineered to produce a ligand that binds to selectin (e.g., hematopoietic cell E-/L-selectin ligand (HCELL), Dykstran et al., Stem Cells. 2016 October; 34(10):2501-2511) on the endothelium of a target tissue, for example.

The term "homing molecule" also encompasses transcription factors that regulate the production of molecules that improve/enhance homing of cells.

Also provided herein are engineered cells that are engineered to produce multiple chimeric proteins, at least two of which include effector molecules that modulate different tumor-mediated immunosuppressive mechanisms. In some embodiments, at least one (e.g., 1, 2, 3, 4, 5, or more)

chimeric protein includes an effector molecule that stimulates at least one immunostimulatory mechanism in the tumor microenvironment, or inhibits at least one immunosuppressive mechanism in the tumor microenvironment. In some embodiments, at least one (e.g., 1, 2, 3, 4, 5, or more) chimeric protein includes an effector molecule that inhibits at least one immunosuppressive mechanism in the tumor microenvironment, and at least one chimeric protein (e.g., 1, 2, 3, 4, 5, or more) inhibits at least one immunosuppressive mechanism in the tumor microenvironment. In yet other embodiments, at least two (e.g., 2, 3, 4, 5, or more) chimeric proteins includes an effector molecule that stimulate at least one immunostimulatory mechanism in the tumor microenvironment. In still other embodiments, at least two (e.g., 1, 2, 3, 4, 5, or more) chimeric proteins includes an effector molecule that inhibit at least one immunosuppressive mechanism in the tumor microenvironment.

In some embodiments, a cell (e.g., an immune cell or a stem cell) is engineered to produce at least one chimeric protein including an effector molecule that stimulates T cell signaling, activity and/or recruitment. In some embodiments, a cell is engineered to produce at least one chimeric protein that includes an effector molecule that stimulates antigen presentation and/or processing. In some embodiments, a cell is engineered to produce at least one chimeric protein that includes an effector molecule that stimulates natural killer cell-mediated cytotoxic signaling, activity and/or recruitment. In some embodiments, a cell is engineered to produce at least one chimeric protein that includes an effector molecule that stimulates dendritic cell differentiation and/or maturation. In some embodiments, a cell is engineered to produce at least one chimeric protein that includes an effector molecule that stimulates immune cell recruitment. In some embodiments, a cell is engineered to produce at least one chimeric protein includes an effector molecule that that stimulates M1 macrophage signaling, activity and/or recruitment. In some embodiments, a cell is engineered to produce at least one chimeric protein that includes an effector molecule that stimulates Th1 polarization. In some embodiments, a cell is engineered to produce at least one chimeric protein that includes an effector molecule that stimulates stroma degradation. In some embodiments, a cell is engineered to produce at least one chimeric protein that includes an effector molecule that stimulates immunostimulatory metabolite production. In some embodiments, a cell is engineered to produce at least one chimeric protein that includes an effector molecule that stimulates Type I interferon signaling. In some embodiments, a cell is engineered to produce at least one chimeric protein that includes an effector molecule that inhibits negative costimulatory signaling. In some embodiments, a cell is engineered to produce at least one chimeric protein that includes an effector molecule that inhibits pro-apoptotic signaling (e.g., via TRAIL) of anti-tumor immune cells. In some embodiments, a cell is engineered to produce at least one chimeric protein that includes an effector molecule that inhibits T regulatory (T$_{reg}$) cell signaling, activity and/or recruitment. In some embodiments, a cell is engineered to produce at least one chimeric protein that includes an effector molecule that inhibits tumor checkpoint molecules. In some embodiments, a cell is engineered to produce at least one chimeric protein that includes an effector molecule that activates stimulator of interferon genes (STING) signaling. In some embodiments, a cell is engineered to produce at least one chimeric protein that includes an effector molecule that inhibits myeloid-derived suppressor cell signaling, activity and/or recruitment. In some embodiments, a cell is engineered to produce at least one chimeric protein that includes an effector molecule that degrades immunosuppressive factors/metabolites. In some embodiments, a cell is engineered to produce at least one chimeric protein that includes an effector molecule that inhibits vascular endothelial growth factor signaling. In some embodiments, a cell is engineered to produce at least one chimeric protein that includes an effector molecule that directly kills tumor cells (e.g., granzyme, perforin, oncolytic viruses, cytolytic peptides and enzymes, anti-tumor antibodies, e.g., that trigger ADCC).

In some embodiments, at least one chimeric protein including an effector molecule that: stimulates T cell signaling, activity and/or recruitment, stimulates antigen presentation and/or processing, stimulates natural killer cell-mediated cytotoxic signaling, activity and/or recruitment, stimulates dendritic cell differentiation and/or maturation, stimulates immune cell recruitment, stimulates macrophage signaling, stimulates stroma degradation, stimulates immunostimulatory metabolite production, or stimulates Type I interferon signaling; and at least one chimeric protein including an effector molecule that inhibits negative costimulatory signaling, inhibits pro-apoptotic signaling of anti-tumor immune cells, inhibits T regulatory (Treg) cell signaling, activity and/or recruitment, inhibits tumor checkpoint molecules, activates stimulator of interferon genes (STING) signaling, inhibits myeloid-derived suppressor cell signaling, activity and/or recruitment, degrades immunosuppressive factors/metabolites, inhibits vascular endothelial growth factor signaling, or directly kills tumor cells.

In some embodiments, a cell (e.g., an immune cell or a stem cell) is engineered to produce at least one chimeric protein including an effector molecule selected from IL-12, IFN-β, IFN-γ, IL-2, IL-15, IL-7, IL-36γ, IL-18, IL-1β, OX40-ligand, and CD40L; and/or at least a checkpoint inhibitor. Illustrative immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GAL9, LAG3, TIM3, B7H3, B7H4, VISTA, KIR, 2B4 (belongs to the CD2 family of molecules and is expressed on all NK, γδ T, and memory CD8+ (αβ) T cells), CD160 (also referred to as BY55), and CGEN-15049. Immune checkpoint inhibitors include antibodies, or antigen binding fragments thereof, or other binding proteins, that bind to and block or inhibit the activity of one or more of CTLA-4, PDL1, PDL2, PD1, B7-H3, B7-H4, BTLA, HVEM, TIM3, GAL9, LAG3, TIM3, B7H3, B7H4, VISTA, KIR, 2B4, CD160, and CGEN-15049. Exemplary checkpoint inhibitors include, but are not limited to, anti-PD-1 antibodies, anti-PD-L1 antibodies, anti-PD-L2 antibodies, anti-CTLA-4 antibodies, anti-LAG-3 antibodies, anti-TIM-3 antibodies, anti-TIGIT antibodies, anti-VISTA antibodies, anti-KIR antibodies, anti-B7-H3 antibodies, anti-B7-H4 antibodies, anti-HVEM antibodies, anti-BTLA antibodies, anti-GAL9 antibodies, anti-A2AR antibodies, anti-phosphatidylserine antibodies, anti-CD27 antibodies, anti-TNFa antibodies, anti-TREM1 antibodies, and anti-TREM2 antibodies. Illustrative immune checkpoint inhibitors include pembrolizumab (anti-PD-1; MK-3475/Keytruda®—Merck), nivolumab (anti-PD-1; Opdivo®—BMS), pidilizumab (anti-PD-1 antibody; CT-011—Teva/CureTech), AMP224 (anti-PD-1; NCI), avelumab (anti-PD-L1; Bavencio®—Pfizer), durvalumab (anti-PD-L1; MEDI4736/Imfinzi®-Medimmune/AstraZeneca), atezolizumab (anti-PD-L1; Tecentriq®—Roche/Genentech), BMS-936559 (anti-PD-L1—BMS), tremelimumab (anti-CTLA-4; Medimmune/AstraZeneca), ipilimumab (anti-CTLA-4; Yervoy®—BMS), lirilumab (anti-KIR; BMS), monalizumab (anti-NKG2A; Innate Pharma/AstraZeneca).

In some embodiments, a cell (e.g., an immune cell or a stem cell) is engineered to produce at least one chimeric protein including an effector molecule selected from IL-12, IFN-β, IFN-γ, IL-2, IL-15, IL-7, IL-36γ, IL-18, IL-1β, OX40-ligand, and CD40L; and/or at least one checkpoint inhibitor selected from anti-PD-1 antibodies, anti-PD-L1 antibodies, anti-CTLA-4 antibodies, and anti-IL-35 antibodies; and/or at least one chimeric protein including an effector molecule selected from MIP1α (CCL3), MIP1β (CCL5), and CCL21; and/or at least one chimeric protein including an effector molecule selected from CpG oligodeoxynucleotides; and/or at least one chimeric protein including an effector molecule selected from microbial peptides.

In some embodiments, a cell (e.g., an immune cell or a stem cell) is engineered to produce IFN-β and at least one chimeric protein including an effector molecule selected from cytokines, antibodies, chemokines, nucleotides, peptides, enzymes, and stimulators of interferon genes (STINGs). In some embodiments, a cell is engineered to produce IFN-β and at least one cytokine or receptor/ligand (e.g., IL-12, IFN-γ, IL-2, IL-15, IL-7, IL-36γ, IL-18, IL-1β, OX40-ligand, and/or CD40L).

In some embodiments, a cell (e.g., an immune cell or a stem cell) is engineered to produce at least one membrane-cleavable chimeric protein where the secretable effector molecule (e.g., "S" in the formula S-C-MT or MT-C-S) is a cytokine, a chemokine, a homing molecule, a growth factor, a co-activation molecule, a tumor microenvironment modifier, a ligand, an antibody, a peptide, or an enzyme. In some embodiments, a cell is engineered to produce at least one membrane-cleavable chimeric protein where the secretable effector molecule is a cytokine. In some embodiments, a cell is engineered to produce at least one membrane-cleavable chimeric protein where the secretable effector molecule is a chemokine. In some embodiments, a cell is engineered to produce at least one membrane-cleavable chimeric protein where the secretable effector molecule is a homing molecule. In some embodiments, a cell is engineered to produce at least one membrane-cleavable chimeric protein where the secretable effector molecule is a growth factor. In some embodiments, a cell is engineered to produce at least one membrane-cleavable chimeric protein where the secretable effector molecule is a co-activation molecule. In some embodiments, a cell is engineered to produce at least one membrane-cleavable chimeric protein where the secretable effector molecule is a tumor microenvironment modifier. In some embodiments, a cell is engineered to produce at least one membrane-cleavable chimeric protein where the secretable effector molecule is a ligand. In some embodiments, a cell is engineered to produce at least one membrane-cleavable chimeric protein where the secretable effector molecule is an antibody. In some embodiments, a cell is engineered to produce at least one membrane-cleavable chimeric protein where the secretable effector molecule is a peptide. In some embodiments, a cell is engineered to produce at least one membrane-cleavable chimeric protein where the secretable effector molecule is an enzyme.

In some embodiments, a cell is engineered to produce at least one membrane-cleavable chimeric protein where the secretable effector molecule (e.g., "S" in the formula S-C-MT or MT-C-S) is IL-1-beta, IL-2, IL-4, IL-6, IL-7, IL-10, IL-12, an IL-12p70 fusion protein, IL-15, IL17A, IL18, IL21, IL22, Type I interferons, Interferon-gamma, or TNF-alpha. In some embodiments, a cell is engineered to produce at least one membrane-cleavable chimeric protein where the secretable effector molecule is CCL21a, CXCL10, CXCL11, CXCL13, a CXCL10-CXCL11 fusion protein, CCL19, CXCL9, or XCL1. In some embodiments, a cell is engineered to produce at least one membrane-cleavable chimeric protein where the secretable effector molecule is anti-integrin alpha4,beta7, anti-MAdCAM, SDF1, or MMP-2. In some embodiments, a cell is engineered to produce at least one membrane-cleavable chimeric protein where the secretable effector molecule is 4-1BBL or CD40L. In some embodiments, a cell is engineered to produce at least one membrane-cleavable chimeric protein where the secretable effector molecule is adenosine deaminase, a TGFbeta inhibitor, an immune checkpoint inhibitor, a VEGF inhibitor, or HPGE2. In some embodiments, a cell is engineered to produce at least one membrane-cleavable chimeric protein where the secretable effector molecule is an anti-TGFbeta peptide, an anti-TGFbeta antibody, a TGFb-TRAP, or combinations thereof. In some embodiments, a cell is engineered to produce at least one membrane-cleavable chimeric protein where the secretable effector molecule is an anti-VEGF antibody, an anti-VEGF peptide, or a combination thereof. In some embodiments, a cell is engineered to produce at least one membrane-cleavable chimeric protein where the secretable effector molecule is an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, or an anti-TREM2 antibody.

In some embodiments, a cell is engineered to produce at least one membrane-cleavable chimeric protein where the secretable effector molecule (e.g., "S" in the formula S C-MT or MT-C-S) comprises IL-15. In some embodiments, a cell is engineered to produce at least one membrane-cleavable chimeric protein where the secretable effector molecule is a fusion of IL-15 and the sushi domain of IL-15Ra. In some embodiments, a cell is engineered to produce at least one membrane-cleavable chimeric protein where the secretable effector consists of IL-15. In some embodiments, a cell is engineered to produce at least one membrane-cleavable chimeric protein where the secretable effector molecule is IL-15 and the cell is further engineered to produce one or more additional effector molecules. In some embodiments, a cell is engineered to produce at least one membrane-cleavable chimeric protein where the secretable effector molecule is IL-15 and the cell is further engineered to produce one or more additional secretable effector molecules. In some embodiments, a cell is engineered to produce at least one membrane-cleavable chimeric protein where the secretable effector molecule is IL-15 and the cell is further engineered to produce a cytokine, a chemokine, a homing molecule, a growth factor, a co-activation molecule, a tumor microenvironment modifier, a ligand, an antibody, a polynucleotide, a peptide, or an enzyme. In some embodiments, a cell is engineered to produce at least one membrane-cleavable chimeric protein where the secretable effector molecule is IL-15 and the cell is further engineered to produce IL-12, IFN-γ, IL-2, IL-7, IL-36γ, IL-18, IL-1β, OX40-ligand, or CD40L. In some embodiments, a cell is engineered to produce at least one membrane-cleavable chimeric protein where the secretable effector molecule is IL-15 and the cell is further engineered to produce IL-12. In some embodiments, a cell is engineered to produce at least one membrane-cleavable chimeric protein where the secretable effector molecule is IL-15 and the cell is further engineered to produce IFN-γ. In some embodiments, a cell is engineered to produce at least one membrane-cleavable chimeric protein where the secretable effector molecule is IL-15 and the cell is further engineered to produce IL-2. In some embodiments, a cell is engineered to produce at least one membrane-cleavable chimeric protein where the secretable effector molecule is IL-15 and the cell is further engineered to produce IL-7. In some embodiments, a cell is engineered to produce at least one membrane-cleavable chimeric protein where the secretable effector molecule is IL-15 and the cell is further engineered to produce IL-36γ. In some embodiments, a cell is engineered to produce at least one membrane-cleavable chimeric protein where the secretable effector molecule is IL-15 and the cell is further engineered to produce IL-18. In some embodiments, a cell is engineered to produce at least one membrane-cleavable chimeric protein where the secretable effector molecule is IL-15 and the cell is further engineered to produce IL-1β. In some embodiments, a cell is engineered to produce at least one membrane-cleavable chimeric protein where the secretable effector molecule is IL-15 and the cell is further engineered to produce OX40-ligand. In some embodiments, a cell is engineered to produce at least one membrane-cleavable chimeric protein where the secretable effector molecule is IL-15 and the cell is further engineered to produce CD40L.

In some embodiments, a cell is engineered to produce at least one membrane-cleavable chimeric protein and the cell is further engineered to produce one or more additional membrane-cleavable chimeric proteins.

In some embodiments, a cell is engineered to produce at least one membrane-cleavable chimeric protein where the secretable effector molecule (e.g., "S" in the formula S-C-MT or MT-C-S) is IL-15 and the cell is further engineered to produce one or more additional membrane-cleavable chimeric proteins. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is produce a cytokine, a chemokine, a homing molecule, a growth factor, a co-activation molecule, a tumor microenvironment modifier, a ligand, an antibody, a polynucleotide, a peptide, or an enzyme. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IL-12, IFN-γ, IL-2, IL-7, IL-36γ, IL-18, IL-1β, OX40-ligand, or CD40L. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IL-12. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IFN-γ. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IL-2. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IL-7. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IL-36γ. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IL-18. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is IL-1β. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is OX40-ligand. In some embodiments, a cell is engineered to produce at least one membrane-cleavable chimeric protein where the secretable effector molecule is IL-15 and the cell is further engineered an additional membrane-cleavable chimeric protein where the additional secretable effector molecule is CD40L.

A cell can also be further engineered to express additional proteins in addition to the chimeric proteins (e.g., the membrane-cleavable chimeric proteins having the formula S-C-MT or MT-C-S described herein), proteins of interest, or effector molecules described herein. A cell can be further engineered to express one or more antigen recognizing receptors. Examples of antigens that may be targeted by one or more antigen recognizing receptors include, but are not limited to, 5T4, ADAM9, AFP, AXL, B7-H3, B7-H4, B7-H6, BCMA, C4.4, CA6, Cadherin 3, Cadherin 6, CCR4, CD19, CD20, CD22, CD123, CD133, CD138, CD142, CD166, CD25, CD30, CD33, CD352, CD37, CD38, CD44, CD56, CD66e, CD70, CD71, CD74, CD79b, CD80, CEA, CEACAM5, Claudin18.2, cMet, CSPG4, CTLA, DLK1, DLL3, DR5, EGFR, ENPP3, EpCAM, EphA2, Ephrin A4, ETBR, FGFR2, FGFR3, FLT3, FRalpha, FRb, GCC, GD2, GFRa4, gpA33, GPC2, GPC3, gpNBM, GPRC5, HER2, IL-13R, IL-13Ra, IL-13Ra2, IL-8, IL-15, IL1RAP, Integrin aV, KIT, L1CAM, LAMP1, Lewis Y, LeY, LIV-1, LRRC, LY6E, MCSP, Mesothelin, MUC1, MUC16, MUC1C, NaPi2B, Nectin 4, NKG2D, NOTCH3, NY ESO 1, Ovarin, P-cadherin, pan-Erb2, PSCA, PSMA, PTK7, ROR1, S Aures, SCT, SLAMF7, SLITRK6, SSTR2, STEAP1, Survivin, TDGF1, TIM1, TROP2, and WT1.

An antigen recognizing receptor can include an antigen-binding domain, such as an antibody, an antigen-binding fragment of an antibody, a F(ab) fragment, a F(ab') fragment, a single chain variable fragment (scFv), or a single-domain antibody (sdAb). An antigen recognizing receptors can include an scFv. An scFv can include a heavy chain variable domain (VH) and a light chain variable domain (VL), which can be separated by a peptide linker. For example, an scFv can include the structure VH-L-VL or VL-L-VH, wherein VH is the heavy chain variable domain, L is the peptide linker, and VL is the light chain variable domain.

An antigen recognizing receptor can be a chimeric antigen receptor (CAR). A CAR can have one or more intracellular signaling domains, such as a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, a MyD88 intracellular signaling domain, fragments thereof, combinations thereof, or combinations of fragments thereof. A CAR can have a transmembrane domain, such as a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, a BTLA transmembrane domain, fragments thereof, combinations thereof, or combinations of fragments thereof. A CAR can have a spacer region between the antigen-binding domain and the transmembrane domain.

An antigen recognizing receptor can be a T cell receptor (TCR).

Engineered Cell Types

Also provided herein are engineered cells. Cells can be engineered to comprise any of the engineered nucleic acids described herein (e.g., any of the engineered nucleic acids encoding the membrane-cleavable chimeric proteins described herein). Cells can be engineered to possess any of the features of any of the engineered cells described herein. In a particular aspect, provided herein are cells engineered to produce one or more chimeric proteins, where the one or more chimeric proteins are the membrane-cleavable chimeric proteins having the formula S-C-MT or MT-C-S described herein. In a particular aspect, provided herein are cells engineered to produce two or more chimeric proteins. In a particular aspect, provided herein are cells engineered to produce two or more of the chimeric proteins described herein, where each chimeric protein is a different protein of interest or effector molecule. In a particular aspect, provided herein are cells engineered to produce any of the chimeric proteins described herein and engineered to separately produce a different effector molecule or protein of interest (e.g., a homing molecule, antigen receptor, etc.).

The engineered cells can be an immune cell, including but not limited to, a T cell, a CD8+ T cell, a CD4+ T cell, a gamma-delta (γδ) T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, or a dendritic cell. The engineered cells can be a T cell. The engineered cells can be an NK cell.

The engineered cells can be a stem cell, including but not limited to, a human embryonic stem cell (ESC), an ESC-derived cell, a pluripotent stem cell, a mesenchymal stromal cell (MSC), an induced pluripotent stem cell (iPSC), or an iPSC-derived cell.

The engineered cells can be tumor-derived cells. Examples of tumor cells include, but are not limited to, a bladder tumor cell, a brain tumor cell, a breast tumor cell, a cervical tumor cell, a colorectal tumor cell, an esophageal tumor cell, a glioma cell, a kidney tumor cell, a liver tumor cell, a lung tumor cell, a melanoma cell, an ovarian tumor cell, a pancreatic tumor cell, a prostate tumor cell, a skin tumor cell, a thyroid tumor cell, and a uterine tumor cell.

A cell can be engineered to produce the chimeric proteins using methods known to those skilled in the art. For example, cells can be transduced to engineer the tumor. In an embodiment, the cell is transduced using a virus.

In a particular embodiment, the cell is transduced using an oncolytic virus. Examples of oncolytic viruses include, but are not limited to, an oncolytic herpes simplex virus, an oncolytic adenovirus, an oncolytic measles virus, an oncolytic influenza virus, an oncolytic Indiana vesiculovirus, an oncolytic Newcastle disease virus, an oncolytic vaccinia virus, an oncolytic poliovirus, an oncolytic myxoma virus, an oncolytic reovirus, an oncolytic mumps virus, an oncolytic Maraba virus, an oncolytic rabies virus, an oncolytic rotavirus, an oncolytic hepatitis virus, an oncolytic rubella virus, an oncolytic dengue virus, an oncolytic chikungunya virus, an oncolytic respiratory syncytial virus, an oncolytic lymphocytic choriomeningitis virus, an oncolytic morbillivirus, an oncolytic lentivirus, an oncolytic replicating retrovirus, an oncolytic rhabdovirus, an oncolytic Seneca Valley virus, an oncolytic sindbis virus, and any variant or derivative thereof.

The virus, including any of the oncolytic viruses described herein, can be a recombinant virus that encodes one more transgenes encoding one or more chimeric proteins, such as any of the engineered nucleic acids described herein. The virus, including any of the oncolytic viruses described herein, can be a recombinant virus that encodes one more transgenes encoding one or more of the two or more chimeric proteins, such as any of the engineered nucleic acids described herein.

Also provided herein are engineered erythrocytes. Erythrocytes can be engineered to comprise any of the engineered nucleic acids described herein. Erythrocytes can be engineered to possess any of the features of any of the engineered cells described herein. In a particular aspect, provided herein are erythrocytes engineered to produce one or more of the chimeric proteins described herein. In a particular aspect, provided herein are erythrocytes engineered to produce two or more of the chimeric proteins described herein.

Also provided herein are engineered platelet cells. Platelet cells can be engineered to comprise any of the engineered nucleic acids described herein. Platelet cells can be engineered to possess any of the features of any of the engineered cells described herein. In a particular aspect, provided herein are platelet cells engineered to produce one or more of the chimeric proteins described herein. In a particular aspect, provided herein are platelet cells engineered to produce two or more of the chimeric proteins described herein.

Also provided herein are engineered bacterial cells. Bacterial cells can be engineered to comprise any of the engineered nucleic acids described herein. Bacterial cells can be engineered to possess any of the features of any of the engineered cells described herein. In a particular aspect, provided herein are bacterial cells engineered to produce two or more of the chimeric proteins described herein. Bacterial cells can be engineered to produce one or more mammalian-derived chimeric proteins. Bacterial cells can be engineered to produce two or more mammalian-derived chimeric proteins. Examples of bacterial cells include, but are not limited to, *Clostridium beijerinckii, Clostridium sporogenes, Clostridium novyi, Escherichia coli, Pseudomonas aeruginosa, Listeria monocytogenes, Salmonella typhimurium*, and *Salmonella choleraesuis*.

An engineered cell can be a human cell. An engineered cell can be a human primary cell. An engineered primary cell can be a tumor infiltrating primary cell. An engineered primary cell can be a primary T cell. An engineered primary cell can be a hematopoietic stem cell (HSC). An engineered primary cell can be a natural killer (NK) cell. An engineered primary cell can be any somatic cell. An engineered primary cell can be a MSC. Human cells (e.g., immune cells) can be engineered to comprise any of the engineered nucleic acids described herein. Human cells (e.g., immune cells) can be engineered to possess any of the features of any of the engineered cells described herein. In a particular aspect, provided herein are human cells (e.g., immune cells) engineered to produce one or more of the chimeric proteins described herein. In a particular aspect, provided herein are human cells (e.g., immune cells) engineered to produce two or more of the chimeric proteins described herein.

An engineered cell can be isolated from a subject (autologous), such as a subject known or suspected to have cancer. Cell isolation methods are known to those skilled in the art and include, but are not limited to, sorting techniques based on cell-surface marker expression, such as FACS sorting, positive isolation techniques, and negative isolation, magnetic isolation, and combinations thereof. An engineered cell can be allogenic with reference to the subject being administered a treatment. Allogenic modified cells can be HLA-matched to the subject being administered a treatment. An engineered cell can be a cultured cell, such as an ex vivo cultured cell. An engineered cell can be an ex vivo cultured cell, such as a primary cell isolated from a subject. A cultured cell can be cultured with one or more cytokines.

Also provided herein are methods that include culturing the engineered cells of the present disclosure. Methods of culturing the engineered cells described herein are known. One skilled in the art will recognize that culturing conditions will depend on the particular engineered cell of interest. One skilled in the art will recognize that culturing conditions will depend on the specific downstream use of the engineered cell, for example, specific culturing conditions for subsequent administration of the engineered cell to a subject.

Methods of Engineering Cells

Also provided herein are compositions and methods for engineering cells to produce one or more proteins of interest or effector molecules (e.g., the membrane-cleavable chimeric proteins having the formula S-C-MT or MT-C-S described herein).

In general, cells are engineered to produce proteins of interest or effector molecules through introduction (i.e., delivery) of polynucleotides encoding the one or more proteins of interest or effector molecules, e.g., the chimeric proteins described herein including the protein of interest or effector molecule, into the cell's cytosol and/or nucleus. For example, the polynucleotides encoding the one or more chimeric proteins can be any of the engineered nucleic acids encoding the membrane-cleavable chimeric proteins having the formula S-C-MT or MT-C-S described herein. Delivery methods include, but are not limited to, viral-mediated delivery, lipid-mediated transfection, nanoparticle delivery, electroporation, sonication, and cell membrane deformation by physical means. One skilled in the art will appreciate the choice of delivery method can depend on the specific cell type to be engineered.

Viral-Mediated Delivery

Viral vector-based delivery platforms can be used to engineer cells. In general, a viral vector-based delivery platform engineers a cell through introducing (i.e., delivering) into a host cell. For example, a viral vector-based delivery platform can engineer a cell through introducing any of the engineered nucleic acids described herein (e.g., any of the exogenous polynucleotide sequences encoding the chimeric proteins described herein, such as the membrane-cleavable chimeric proteins having the formula S-C-MT or MT-C-S described herein, and/or any of the expression cassettes described herein containing a promoter and an exogenous polynucleotide sequence encoding the chimeric proteins, oriented from N-terminal to C-terminal). A viral vector-based delivery platform can be a nucleic acid, and as such, an engineered nucleic acid can also encompass an engineered virally-derived nucleic acid. Such engineered virally-derived nucleic acids can also be referred to as recombinant viruses or engineered viruses.

A viral vector-based delivery platform can encode more than one engineered nucleic acid, gene, or transgene within the same nucleic acid. For example, an engineered virally-derived nucleic acid, e.g., a recombinant virus or an engineered virus, can encode one or more transgenes, including, but not limited to, any of the engineered nucleic acids described herein that encode one or more of the chimeric proteins described herein. The one or more transgenes encoding the one or more chimeric proteins can be configured to express the one or more chimeric proteins and/or other protein of interest. A viral vector-based delivery platform can encode one or more genes in addition to the one or more transgenes (e.g., transgenes encoding the one or more chimeric proteins and/or other protein of interest), such as viral genes needed for viral infectivity and/or viral production (e.g., capsid proteins, envelope proteins, viral polymerases, viral transcriptases, etc.), referred to as cis-acting elements or genes.

A viral vector-based delivery platform can comprise more than one viral vector, such as separate viral vectors encoding the engineered nucleic acids, genes, or transgenes described herein, and referred to as trans-acting elements or genes. For example, a helper-dependent viral vector-based delivery platform can provide additional genes needed for viral infectivity and/or viral production on one or more additional separate vectors in addition to the vector encoding the one or more chimeric proteins and/or other protein of interest. One viral vector can deliver more than one engineered nucleic acids, such as one vector that delivers engineered nucleic acids that are configured to produce two or more chimeric proteins and/or other protein of interest. More than one viral vector can deliver more than one engineered nucleic acids, such as more than one vector that delivers one or more engineered nucleic acid configured to produce one or more chimeric proteins and/or other protein of interest. The number of viral vectors used can depend on the packaging capacity of the above mentioned viral vector-based vaccine platforms, and one skilled in the art can select the appropriate number of viral vectors.

In general, any of the viral vector-based systems can be used for the in vitro production of molecules, such as the chimeric proteins, effector molecules, and/or other protein of interest described herein, or used in vivo and ex vivo gene therapy procedures, e.g., for in vivo delivery of the engineered nucleic acids encoding one or more chimeric proteins and/or other protein of interest. The selection of an appropriate viral vector-based system will depend on a variety of factors, such as cargo/payload size, immunogenicity of the viral system, target cell of interest, gene expression strength and timing, and other factors appreciated by one skilled in the art.

Viral vector-based delivery platforms can be RNA-based viruses or DNA-based viruses. Exemplary viral vector-based delivery platforms include, but are not limited to, a herpes simplex virus, a adenovirus, a measles virus, an influenza virus, a Indiana vesiculovirus, a Newcastle disease virus, a vaccinia virus, a poliovirus, a myxoma virus, a reovirus, a mumps virus, a Maraba virus, a rabies virus, a rotavirus, a hepatitis virus, a rubella virus, a dengue virus, a chikungunya virus, a respiratory syncytial virus, a lymphocytic choriomeningitis virus, a morbillivirus, a lentivirus, a replicating retrovirus, a rhabdovirus, a Seneca Valley virus, a sindbis virus, and any variant or derivative thereof. Other exemplary viral vector-based delivery platforms are described in the art, such as vaccinia, fowlpox, self-replicating alphavirus, marabavirus, adenovirus (See, e.g., Tatsis et al., Adenoviruses, *Molecular Therapy* (2004) 10, 616-629), or lentivirus, including but not limited to second, third or hybrid second/third generation lentivirus and recombinant lentivirus of any generation designed to target specific cell types or receptors (See, e.g., Hu et al., Immunization Delivered by Lentiviral Vectors for Cancer and Infectious Diseases, *Immunol Rev.* (2011) 239(1): 45-61, Sakuman et al., Lentiviral vectors: basic to translational, *Biochem J.* (2012) 443(3):603-18, Cooper et al., Rescue of splicing-mediated intron loss maximizes expression in lentiviral vectors containing the human ubiquitin C promoter, *Nucl. Acids Res.* (2015) 43 (1): 682-690, Zufferey et al., Self-Inactivating Lentivirus Vector for Safe and Efficient In vivo Gene Delivery, *J. Virol.* (1998) 72 (12): 9873-9880).

The sequences may be preceded with one or more sequences targeting a subcellular compartment. Upon introduction (i.e. delivery) into a host cell, infected cells (i.e., an engineered cell) can express the chimeric proteins and/or other protein of interest. Vaccinia vectors and methods useful in immunization protocols are described in, e.g., U.S. Pat. No. 4,722,848. Another vector is BCG (Bacille Calmette Guerin). BCG vectors are described in Stover et al. (Nature 351:456-460 (1991)). A wide variety of other vectors useful for the introduction (i.e., delivery) of engineered nucleic acids, e.g., *Salmonella typhi* vectors, and the like will be apparent to those skilled in the art from the description herein.

The viral vector-based delivery platforms can be a virus that targets a cell, herein referred to as an oncolytic virus. Examples of oncolytic viruses include, but are not limited to, an oncolytic herpes simplex virus, an oncolytic adenovirus, an oncolytic measles virus, an oncolytic influenza virus, an oncolytic Indiana vesiculovirus, an oncolytic Newcastle disease virus, an oncolytic vaccinia virus, an oncolytic poliovirus, an oncolytic myxoma virus, an oncolytic reovirus, an oncolytic mumps virus, an oncolytic Maraba virus, an oncolytic rabies virus, an oncolytic rotavirus, an oncolytic hepatitis virus, an oncolytic rubella virus, an oncolytic dengue virus, an oncolytic chikungunya virus, an oncolytic respiratory syncytial virus, an oncolytic lymphocytic choriomeningitis virus, an oncolytic morbillivirus, an oncolytic lentivirus, an oncolytic replicating retrovirus, an oncolytic rhabdovirus, an oncolytic Seneca Valley virus, an oncolytic sindbis virus, and any variant or derivative thereof. Any of the oncolytic viruses described herein can be a recombinant oncolytic virus comprising one more transgenes (e.g., an engineered nucleic acid) encoding one or more chimeric proteins and/or other protein of interest. The transgenes encoding the one or more chimeric proteins and/or other protein of interest can be configured to express the chimeric proteins and/or other protein of interest.

The viral vector-based delivery platform can be retrovirus-based. In general, retroviral vectors are comprised of cis-acting long terminal repeats with packaging capacity for up to 6-10 kb of foreign sequence. The minimum cis-acting LTRs are sufficient for replication and packaging of the vectors, which are then used to integrate the one or more engineered nucleic acids (e.g., transgenes encoding the one or more chimeric proteins and/or other protein of interest) into the target cell to provide permanent transgene expression. Retroviral-based delivery systems include, but are not limited to, those based upon murine leukemia, virus (MuLV), gibbon ape leukemia virus (GaLV), Simian Immuno deficiency vims (SIV), human immuno deficiency vims (HIV), and combinations thereof (see, e.g., Buchscher et al., J. Virol. 66:2731-2739 (1992); Johann et ah, J. Virol. 66:1635-1640 (1992); Sommnerfelt et al., Virol. 176:58-59 (1990); Wilson et ah, J. Virol. 63:2374-2378 (1989); Miller et al, J, Virol. 65:2220-2224 (1991); PCT/US94/05700). Other retroviral systems include the Phoenix retrovirus system.

The viral vector-based delivery platform can be lentivirus-based. In general, lentiviral vectors are retroviral vectors that are able to transduce or infect non-dividing cells and typically produce high viral titers. Lentiviral-based delivery platforms can be HIV-based, such as ViraPower systems (ThermoFisher) or pLenti systems (Cell Biolabs). Lentiviral-based delivery platforms can be SIV, or FIV-based. Other exemplary lentivirus-based delivery platforms are described in more detail in U.S. Pat. Nos. 7,311,907; 7,262,049; 7,250,299; 7,226,780; 7,220,578; 7,211,247; 7,160,721; 7,078,031; 7,070,993; 7,056,699; 6,955,919, each herein incorporated by reference for all purposes.

The viral vector-based delivery platform can be adenovirus-based. In general, adenoviral based vectors are capable of very high transduction efficiency in many cell types, do not require cell division, achieve high titer and levels of expression, and can be produced in large quantities in a relatively simple system. In general, adenoviruses can be used for transient expression of a transgene within an infected cell since adenoviruses do not typically integrate into a host's genome. Adenovirus-based delivery platforms are described in more detail in Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655, each herein incorporated by reference for all purposes. Other exemplary adenovirus-based delivery platforms are described in more detail in U.S. Pat. Nos. 5,585,362; 6,083,716; 7,371,570; 7,348,178; 7,323,177; 7,319,033; 7,318,919; and 7,306,793 and International Patent Application WO96/13597, each herein incorporated by reference for all purposes.

The viral vector-based delivery platform can be adeno-associated virus (AAV)-based. Adeno-associated virus ("AAV") vectors may be used to transduce cells with engineered nucleic acids (e.g., any of the engineered nucleic acids described herein). AAV systems can be used for the in vitro production of proteins of interest, such as the chimeric proteins described herein and/or effector molecules, or used in vivo and ex vivo gene therapy procedures, e.g., for in vivo delivery of the engineered nucleic acids encoding one or more chimeric proteins and/or other protein of interest (see, e.g., West et al., Virology 160:38-47 (1987); U.S. Pat. Nos. 4,797,368; 5,436,146; 6,632,670; 6,642,051; 7,078,387; 7,314,912; 6,498,244; 7,906,111; US patent publications US 2003-0138772, US 2007/0036760, and US 2009/0197338; Gao, et al., J. Virol, 78(12):6381-6388 (June 2004); Gao, et al, Proc Natl Acad Sci USA, 100(10):6081-6086 (May 13, 2003); and International Patent applications WO 2010/138263 and WO 93/24641; Kotin, Human Gene Therapy 5:793-801 (1994); Muzyczka, J. Clin. Invest. 94:1351 (1994), each herein incorporated by reference for all purposes). Exemplary methods for constructing recombinant AAV vectors are described in more detail in U.S. Pat. No. 5,173,414; Tratschin et ah, Mol. Cell. Biol. 5:3251-3260 (1985); Tratschin, et ah, Mol. Cell, Biol. 4:2072-2081 (1984); Hermonat & Muzyczka, PNAS 81:64666470 (1984); and Samuiski et ah, J. Virol. 63:03822-3828 (1989), each herein incorporated by reference for all purposes. In general, an AAV-based vector comprises a capsid protein having an amino acid sequence corresponding to any one of AAV1, AAV2, AAV3, AAV4, AAV5, AAV6, AAV7, AAV8, AAV9, AAV.Rh10, AAV11 and variants thereof. In particular examples, an AAV-based vector has a capsid protein having an amino acid sequence corresponding to AAV2. In particular examples, an AAV-based vector has a capsid protein having an amino acid sequence corresponding to AAV8.

AAV vectors can be engineered to have any of the exogenous polynucleotide sequences encoding the membrane-cleavable chimeric proteins described herein having the formula: S-C-MT or MT-C-S.

The viral vector-based delivery platform can be a virus-like particle (VLP) platform. In general, VLPs are constructed by producing viral structural proteins and purifying resulting viral particles. Then, following purification, a cargo/payload (e.g., any of the engineered nucleic acids described herein) is encapsulated within the purified particle ex vivo. Accordingly, production of VLPs maintains separation of the nucleic acids encoding viral structural proteins and the nucleic acids encoding the cargo/payload. The viral structural proteins used in VLP production can be produced in a variety of expression systems, including mammalian, yeast, insect, bacterial, or in vivo translation expression systems. The purified viral particles can be denatured and reformed in the presence of the desired cargo to produce VLPs using methods known to those skilled in the art. Production of VLPs are described in more detail in Seow et al. (Mol Ther. 2009 May; 17(5): 767-777), herein incorporated by reference for all purposes.

The viral vector-based delivery platform can be engineered to target (i.e., infect) a range of cells, target a narrow subset of cells, or target a specific cell. In general, the envelope protein chosen for the viral vector-based delivery platform will determine the viral tropism. The virus used in the viral vector-based delivery platform can be pseudotyped to target a specific cell of interest. The viral vector-based delivery platform can be pantropic and infect a range of cells. For example, pantropic viral vector-based delivery platforms can include the VSV-G envelope. The viral vector-based delivery platform can be amphotropic and infect mammalian cells. Accordingly, one skilled in the art can select the appropriate tropism, pseudotype, and/or envelope protein for targeting a desired cell type.

Lipid Structure Delivery Systems

Engineered nucleic acids (e.g., any of the engineered nucleic acids described herein) can be introduced into a cell using a lipid-mediated delivery system. In general, a lipid-mediated delivery system uses a structure composed of an outer lipid membrane enveloping an internal compartment. Examples of lipid-based structures include, but are not limited to, a lipid-based nanoparticle, a liposome, a micelle, an exosome, a vesicle, an extracellular vesicle, a cell, or a tissue. Lipid structure delivery systems can deliver a cargo/payload (e.g., any of the engineered nucleic acids described herein) in vitro, in vivo, or ex vivo.

A lipid-based nanoparticle can include, but is not limited to, a unilamellar liposome, a multilamellar liposome, and a lipid preparation. As used herein, a "liposome" is a generic term encompassing in vitro preparations of lipid vehicles formed by enclosing a desired cargo, e.g., an engineered nucleic acid, such as any of the engineered nucleic acids described herein, within a lipid shell or a lipid aggregate. Liposomes may be characterized as having vesicular structures with a bilayer membrane, generally comprising a phospholipid, and an inner medium that generally comprises an aqueous composition. Liposomes include, but are not limited to, emulsions, foams, micelles, insoluble monolayers, liquid crystals, phospholipid dispersions, lamellar layers and the like. Liposomes can be unilamellar liposomes. Liposomes can be multilamellar liposomes. Liposomes can be multivesicular liposomes. Liposomes can be positively charged, negatively charged, or neutrally charged. In certain embodiments, the liposomes are neutral in charge. Liposomes can be formed from standard vesicle-forming lipids, which generally include neutral and negatively charged phospholipids and a sterol, such as cholesterol. The selection of lipids is generally guided by consideration of a desired purpose, e.g., criteria for in vivo delivery, such as liposome size, acid lability and stability of the liposomes in the blood stream. A variety of methods are available for preparing liposomes, as described in, e.g., Szokan et al., Ann. Rev. Biophys. Bioeng. 9; 467 (1980), U.S. Pat. Nos. 4,235,871, 4,501,728, 4,501,728, 4,837,028, and 5,019,369, each herein incorporated by reference for all purposes.

A multilamellar liposome is generated spontaneously when lipids comprising phospholipids are suspended in an excess of aqueous solution such that multiple lipid layers are separated by an aqueous medium. Water and dissolved solutes are entrapped in closed structures between the lipid bilayers following the lipid components undergoing self-rearrangement. A desired cargo (e.g., a polypeptide, a nucleic acid, a small molecule drug, an engineered nucleic acid, such as any of the engineered nucleic acids described herein, a viral vector, a viral-based delivery system, etc.) can be encapsulated in the aqueous interior of a liposome, attached to a liposome via a linking molecule that is associated with both the liposome and the polypeptide/nucleic acid, interspersed within the lipid bilayer of a liposome, entrapped in a liposome, complexed with a liposome, or otherwise associated with the liposome such that it can be delivered to a target entity. Lipophilic molecules or molecules with lipophilic regions may also dissolve in or associate with the lipid bilayer.

A liposome used according to the present embodiments can be made by different methods, as would be known to one of ordinary skill in the art. Preparations of liposomes are described in further detail in WO 2016/201323, International Applications PCT/US85/01161 and PCT/US89/05040, and U.S. Pat. Nos. 4,728,578, 4,728,575, 4,737,323, 4,533,254, 4,162,282, 4,310,505, and 4,921,706; each herein incorporated by reference for all purposes.

Liposomes can be cationic liposomes. Examples of cationic liposomes are described in more detail in U.S. Pat. Nos. 5,962,016; 5,030,453; 6,680,068, U.S. Application 2004/0208921, and International Patent Applications WO03/015757A1, WO04029213A2, and WO02/100435A1, each hereby incorporated by reference in their entirety.

Lipid-mediated gene delivery methods are described, for instance, in WO 96/18372; WO 93/24640; Mannino & Gould-Fogerite, BioTechniques 6(7): 682-691 (1988); U.S. Pat. No. 5,279,833 Rose U.S. Pat. No. 5,279,833; WO91/06309; and Felgner et al., Proc. Natl. Acad. Sci. USA 84: 7413-7414 (1987), each herein incorporated by reference for all purposes.

Exosomes are small membrane vesicles of endocytic origin that are released into the extracellular environment following fusion of multivesicular bodies with the plasma membrane. The size of exosomes ranges between 30 and 100 nm in diameter. Their surface consists of a lipid bilayer from the donor cell's cell membrane, and they contain cytosol from the cell that produced the exosome, and exhibit membrane proteins from the parental cell on the surface. Exosomes useful for the delivery of nucleic acids are known to those skilled in the art, e.g., the exosomes described in more detail in U.S. Pat. No. 9,889,210, herein incorporated by reference for all purposes.

As used herein, the term "extracellular vesicle" or "EV" refers to a cell-derived vesicle comprising a membrane that encloses an internal space. In general, extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. The cargo can comprise nucleic acids (e.g., any of the engineered nucleic acids described herein), proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and/or cultured cells.

As used herein the term "exosome" refers to a cell-derived small (between 20-300 nm in diameter, more preferably 40-200 nm in diameter) vesicle comprising a membrane that encloses an internal space, and which is generated from the cell by direct plasma membrane budding or by fusion of the late endosome with the plasma membrane. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA, such as any of the engineered nucleic acids described herein), a sugar (e.g., a simple sugar, polysaccharide, or glycan) or other molecules. The exosome can be derived from a producer cell, and isolated from the producer cell based on its size, density, biochemical parameters, or a combination thereof. An exosome is a species of extracellular vesicle. Generally, exosome production/biogenesis does not result in the destruction of the producer cell. Exosomes and preparation of exosomes are described in further detail in WO 2016/201323, which is hereby incorporated by reference in its entirety.

As used herein, the term "nanovesicle" (also referred to as a "microvesicle") refers to a cell-derived small (between 20-250 nm in diameter, more preferably 30-150 nm in diameter) vesicle comprising a membrane that encloses an internal space, and which is generated from the cell by direct or indirect manipulation such that said nanovesicle would not be produced by said producer cell without said manipulation. In general, a nanovesicle is a sub-species of an extracellular vesicle. Appropriate manipulations of the producer cell include but are not limited to serial extrusion, treatment with alkaline solutions, sonication, or combinations thereof. The production of nanovesicles may, in some instances, result in the destruction of said producer cell. Preferably, populations of nanovesicles are substantially free of vesicles that are derived from producer cells by way of direct budding from the plasma membrane or fusion of the late endosome with the plasma membrane. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA, such as any of the engineered nucleic acids described herein), a sugar (e.g., a simple sugar, polysaccharide, or glycan) or other molecules. The nanovesicle, once it is derived from a producer cell according to said manipulation, may be isolated from the producer cell based on its size, density, biochemical parameters, or a combination thereof.

Lipid nanoparticles (LNPs), in general, are synthetic lipid structures that rely on the amphiphilic nature of lipids to form membranes and vesicle like structures (Riley 2017). In general, these vesicles deliver cargo/payloads, such as any of the engineered nucleic acids or viral systems described herein, by absorbing into the membrane of target cells and releasing the cargo into the cytosol. Lipids used in LNP formation can be cationic, anionic, or neutral. The lipids can be synthetic or naturally derived, and in some instances biodegradable. Lipids can include fats, cholesterol, phospholipids, lipid conjugates including, but not limited to, polyethyleneglycol (PEG) conjugates (PEGylated lipids), waxes, oils, glycerides, and fat soluble vitamins. Lipid compositions generally include defined mixtures of materials, such as the cationic, neutral, anionic, and amphipathic lipids. In some instances, specific lipids are included to prevent LNP aggregation, prevent lipid oxidation, or provide functional chemical groups that facilitate attachment of additional moieties. Lipid composition can influence overall LNP size and stability. In an example, the lipid composition comprises dilinoleylmethyl-4-dimethylaminobutyrate (MC3) or MC3-like molecules. MC3 and MC3-like lipid compositions can be formulated to include one or more other lipids, such as a PEG or PEG-conjugated lipid, a sterol, or neutral lipids. In addition, LNPs can be further engineered or functionalized to facilitate targeting of specific cell types. Another consideration in LNP design is the balance between targeting efficiency and cytotoxicity.

Micelles, in general, are spherical synthetic lipid structures that are formed using single-chain lipids, where the single-chain lipid's hydrophilic head forms an outer layer or membrane and the single-chain lipid's hydrophobic tails form the micelle center. Micelles typically refer to lipid structures only containing a lipid mono-layer. Micelles are described in more detail in Quader et al. (Mol Ther. 2017 Jul. 5; 25(7): 1501-1513), herein incorporated by reference for all purposes.

Nucleic-acid vectors, such as expression vectors, exposed directly to serum can have several undesirable consequences, including degradation of the nucleic acid by serum nucleases or off-target stimulation of the immune system by the free nucleic acids. Similarly, viral delivery systems exposed directly to serum can trigger an undesired immune response and/or neutralization of the viral delivery system.

Therefore, encapsulation of an engineered nucleic acid and/or viral delivery system can be used to avoid degradation, while also avoiding potential off-target affects. In certain examples, an engineered nucleic acid and/or viral delivery system is fully encapsulated within the delivery vehicle, such as within the aqueous interior of an LNP. Encapsulation of an engineered nucleic acid and/or viral delivery system within an LNP can be carried out by techniques well-known to those skilled in the art, such as microfluidic mixing and droplet generation carried out on a microfluidic droplet generating device. Such devices include, but are not limited to, standard T-junction devices or flow-focusing devices. In an example, the desired lipid formulation, such as MC3 or MC3-like containing compositions, is provided to the droplet generating device in parallel with an engineered nucleic acid or viral delivery system and any other desired agents, such that the delivery vector and desired agents are fully encapsulated within the interior of the MC3 or MC3-like based LNP. In an example, the droplet generating device can control the size range and size distribution of the LNPs produced. For example, the LNP can have a size ranging from 1 to 1000 nanometers in diameter, e.g., 1, 10, 50, 100, 500, or 1000 nanometers. Following droplet generation, the delivery vehicles encapsulating the cargo/payload (e.g., an engineered nucleic acid and/or viral delivery system) can be further treated or engineered to prepare them for administration.

Nanoparticle Delivery

Nanomaterials can be used to deliver engineered nucleic acids (e.g., any of the engineered nucleic acids described herein). Nanomaterial vehicles, importantly, can be made of non-immunogenic materials and generally avoid eliciting immunity to the delivery vector itself. These materials can include, but are not limited to, lipids (as previously described), inorganic nanomaterials, and other polymeric materials. Nanomaterial particles are described in more detail in Riley et al. (Recent Advances in Nanomaterials for Gene Delivery-A Review. Nanomaterials 2017, 7(5), 94), herein incorporated by reference for all purposes.

Genomic Editing Systems

A genomic editing systems can be used to engineer a host genome to encode an engineered nucleic acid, such as an engineered nucleic acid encoding one or more of the chimeric proteins (e.g., any of the membrane-cleavable chimeric proteins having the formula S-C-MT or MT-C-S described herein). In general, a "genomic editing system" refers to any system for integrating an exogenous gene into a host cell's genome. Genomic editing systems include, but are not limited to, a transposon system, a nuclease genomic editing system, and a viral vector-based delivery platform.

A transposon system can be used to integrate an engineered nucleic acid, such as an engineered nucleic acid encoding one or more of the chimeric proteins (e.g., any of the membrane-cleavable chimeric proteins having the formula S-C-MT or MT-C-S described herein), into a host genome. Transposons generally comprise terminal inverted repeats (TIR) that flank a cargo/payload nucleic acid and a transposase. The transposon system can provide the transposon in cis or in trans with the TIR-flanked cargo. A transposon system can be a retrotransposon system or a DNA transposon system. In general, transposon systems integrate a cargo/payload (e.g., an engineered nucleic acid) randomly into a host genome. Examples of transposon systems include systems using a transposon of the Tc1/mariner transposon superfamily, such as a Sleeping Beauty transposon system, described in more detail in Hudecek et al. (Crit Rev Biochem Mol Biol. 2017 August; 52(4):355-

380), and U.S. Pat. Nos. 6,489,458, 6,613,752 and 7,985,739, each of which is herein incorporated by reference for all purposes. Another example of a transposon system includes a PiggyBac transposon system, described in more detail in U.S. Pat. Nos. 6,218,185 and 6,962,810, each of which is herein incorporated by reference for all purposes.

A nuclease genomic editing system can be used to engineer a host genome to encode an engineered nucleic acid, such as an engineered nucleic acid encoding one or more of the chimeric proteins (e.g., any of the membrane-cleavable chimeric proteins having the formula S-C-MT or MT-C-S described herein). Without wishing to be bound by theory, in general, the nuclease-mediated gene editing systems used to introduce an exogenous gene take advantage of a cell's natural DNA repair mechanisms, particularly homologous recombination (HR) repair pathways. Briefly, following an insult to genomic DNA (typically a double-stranded break), a cell can resolve the insult by using another DNA source that has identical, or substantially identical, sequences at both its 5' and 3' ends as a template during DNA synthesis to repair the lesion. In a natural context, HDR can use the other chromosome present in a cell as a template. In gene editing systems, exogenous polynucleotides are introduced into the cell to be used as a homologous recombination template (HRT or HR template). In general, any additional exogenous sequence not originally found in the chromosome with the lesion that is included between the 5' and 3' complimentary ends within the HRT (e.g., a gene or a portion of a gene) can be incorporated (i.e., "integrated") into the given genomic locus during templated HDR. Thus, a typical HR template for a given genomic locus has a nucleotide sequence identical to a first region of an endogenous genomic target locus, a nucleotide sequence identical to a second region of the endogenous genomic target locus, and a nucleotide sequence encoding a cargo/payload nucleic acid (e.g., any of the engineered nucleic acids described herein, such as any of the engineered nucleic acids encoding one or more chimeric proteins (e.g., any of the membrane-cleavable chimeric proteins having the formula S-C-MT or MT-C-S described herein)).

In some examples, a HR template can be linear. Examples of linear HR templates include, but are not limited to, a linearized plasmid vector, a ssDNA, a synthesized DNA, and a PCR amplified DNA. In particular examples, a HR template can be circular, such as a plasmid. A circular template can include a supercoiled template.

The identical, or substantially identical, sequences found at the 5' and 3' ends of the HR template, with respect to the exogenous sequence to be introduced, are generally referred to as arms (HR arms). HR arms can be identical to regions of the endogenous genomic target locus (i.e., 100% identical). HR arms in some examples can be substantially identical to regions of the endogenous genomic target locus. While substantially identical HR arms can be used, it can be advantageous for HR arms to be identical as the efficiency of the HDR pathway may be impacted by HR arms having less than 100% identity.

Each HR arm, i.e., the 5' and 3' HR arms, can be the same size or different sizes. Each HR arm can each be greater than or equal to 50, 100, 200, 300, 400, or 500 bases in length. Although HR arms can, in general, be of any length, practical considerations, such as the impact of HR arm length and overall template size on overall editing efficiency, can also be taken into account. An HR arms can be identical, or substantially identical to, regions of an endogenous genomic target locus immediately adjacent to a cleavage site. Each HR arms can be identical to, or substantially identical to, regions of an endogenous genomic target locus immediately adjacent to a cleavage site. Each HR arms can be identical, or substantially identical to, regions of an endogenous genomic target locus within a certain distance of a cleavage site, such as 1 base-pair, less than or equal to 10 base-pairs, less than or equal to 50 base-pairs, or less than or equal to 100 base-pairs of each other.

A nuclease genomic editing system can use a variety of nucleases to cut a target genomic locus, including, but not limited to, a Clustered Regularly Interspaced Short Palindromic Repeats (CRISPR) family nuclease or derivative thereof, a Transcription activator-like effector nuclease (TALEN) or derivative thereof, a zinc-finger nuclease (ZFN) or derivative thereof, and a homing endonuclease (HE) or derivative thereof.

A CRISPR-mediated gene editing system can be used to engineer a host genome to encode an engineered nucleic acid, such as an engineered nucleic acid encoding one or more of the chimeric proteins (e.g., any of the degron-fusion chimeric proteins described herein or the membrane-cleavable chimeric proteins having the formula S-C-MT or MT-C-S described herein). CRISPR systems are described in more detail in M. Adli ("The CRISPR tool kit for genome editing and beyond" Nature Communications; volume 9 (2018), Article number: 1911), herein incorporated by reference for all that it teaches. In general, a CRISPR-mediated gene editing system comprises a CRISPR-associated (Cas) nuclease and a RNA(s) that directs cleavage to a particular target sequence. An exemplary CRISPR-mediated gene editing system is the CRISPR/Cas9 systems comprised of a Cas9 nuclease and a RNA(s) that has a CRISPR RNA (crRNA) domain and a trans-activating CRISPR (tracrRNA) domain. The crRNA typically has two RNA domains: a guide RNA sequence (gRNA) that directs specificity through base-pair hybridization to a target sequence ("a defined nucleotide sequence"), e.g., a genomic sequence; and an RNA domain that hybridizes to a tracrRNA. A tracrRNA can interact with and thereby promote recruitment of a nuclease (e.g., Cas9) to a genomic locus. The crRNA and tracrRNA polynucleotides can be separate polynucleotides. The crRNA and tracrRNA polynucleotides can be a single polynucleotide, also referred to as a single guide RNA (sgRNA). While the Cas9 system is illustrated here, other CRISPR systems can be used, such as the Cpf1/Cas12 or Cas13 systems. Nucleases can include derivatives thereof, such as Cas9 functional mutants, e.g., a Cas9 "nickase" mutant that in general mediates cleavage of only a single strand of a defined nucleotide sequence as opposed to a complete double-stranded break typically produced by Cas9 enzymes.

In general, the components of a CRISPR system interact with each other to form a Ribonucleoprotein (RNP) complex to mediate sequence specific cleavage. In some CRISPR systems, each component can be separately produced and used to form the RNP complex. In some CRISPR systems, each component can be separately produced in vitro and contacted (i.e., "complexed") with each other in vitro to form the RNP complex. The in vitro produced RNP can then be introduced (i.e., "delivered") into a cell's cytosol and/or nucleus, e.g., a T cell's cytosol and/or nucleus. The in vitro produced RNP complexes can be delivered to a cell by a variety of means including, but not limited to, electroporation, lipid-mediated transfection, cell membrane deformation by physical means, lipid nanoparticles (LNP), virus like particles (VLP), and sonication. In a particular example, in vitro produced RNP complexes can be delivered to a cell using a Nucleofactor/Nucleofection® electroporation-based delivery system (Lonza®). Other electroporation systems include, but are not limited to, MaxCyte electroporation systems, Miltenyi CliniMACS electroporation systems, Neon electroporation systems, and BTX electroporation systems. CRISPR nucleases, e.g., Cas9, can be produced in vitro (i.e., synthesized and purified) using a variety of protein production techniques known to those skilled in the art. CRISPR system RNAs, e.g., an sgRNA, can be produced in vitro (i.e., synthesized and purified) using a variety of RNA production techniques known to those skilled in the art, such as in vitro transcription or chemical synthesis.

An in vitro produced RNP complex can be complexed at different ratios of nuclease to gRNA. An in vitro produced RNP complex can be also be used at different amounts in a CRISPR-mediated editing system. For example, depending on the number of cells desired to be edited, the total RNP amount added can be adjusted, such as a reduction in the amount of RNP complex added when editing a large number of cells in a reaction.

In some CRISPR systems, each component (e.g., Cas9 and an sgRNA) can be separately encoded by a polynucleotide with each polynucleotide introduced into a cell together or separately. In some CRISPR systems, each component can be encoded by a single polynucleotide (i.e., a multi-promoter or multicistronic vector, see description of exemplary multicistronic systems below) and introduced into a cell. Following expression of each polynucleotide encoded CRISPR component within a cell (e.g., translation of a nuclease and transcription of CRISPR RNAs), an RNP complex can form within the cell and can then direct site-specific cleavage.

Some RNPs can be engineered to have moieties that promote delivery of the RNP into the nucleus. For example, a Cas9 nuclease can have a nuclear localization signal (NLS) domain such that if a Cas9 RNP complex is delivered into a cell's cytosol or following translation of Cas9 and subsequent RNP formation, the NLS can promote further trafficking of a Cas9 RNP into the nucleus.

The engineered cells described herein can be engineered using non-viral methods, e.g., the nuclease and/or CRISPR mediated gene editing systems described herein can be delivered to a cell using non-viral methods. The engineered cells described herein can be engineered using viral methods, e.g., the nuclease and/or CRISPR mediated gene editing systems described herein can be delivered to a cell using viral methods such as adenoviral, retroviral, lentiviral, or any of the other viral-based delivery methods described herein.

In some CRISPR systems, more than one CRISPR composition can be provided such that each separately target the same gene or general genomic locus at more than target nucleotide sequence. For example, two separate CRISPR compositions can be provided to direct cleavage at two different target nucleotide sequences within a certain distance of each other. In some CRISPR systems, more than one CRISPR composition can be provided such that each separately target opposite strands of the same gene or general genomic locus. For example, two separate CRISPR "nickase" compositions can be provided to direct cleavage at the same gene or general genomic locus at opposite strands.

In general, the features of a CRISPR-mediated editing system described herein can apply to other nuclease-based genomic editing systems. TALEN is an engineered site-specific nuclease, which is composed of the DNA-binding domain of TALE (transcription activator-like effectors) and the catalytic domain of restriction endonuclease Fok1. By changing the amino acids present in the highly variable residue region of the monomers of the DNA binding domain, different artificial TALENs can be created to target various nucleotides sequences. The DNA binding domain subsequently directs the nuclease to the target sequences and creates a double-stranded break. TALEN-based systems are described in more detail in U.S. Ser. No. 12/965,590; U.S. Pat. Nos. 8,450,471; 8,440,431; 8,440,432; 10,172,880; and U.S. Ser. No. 13/738,381, all of which are incorporated by reference herein in their entirety. ZFN-based editing systems are described in more detail in U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties for all purposes.

Other Engineering Delivery Systems

Various additional means to introduce engineered nucleic acids (e.g., any of the engineered nucleic acids described herein) into a cell or other target recipient entity, such as any of the lipid structures described herein.

Electroporation can used to deliver polynucleotides to recipient entities. Electroporation is a method of internalizing a cargo/payload into a target cell or entity's interior compartment through applying an electrical field to transiently permeabilize the outer membrane or shell of the target cell or entity. In general, the method involves placing cells or target entities between two electrodes in a solution containing a cargo of interest (e.g., any of the engineered nucleic acids described herein). The lipid membrane of the cells is then disrupted, i.e., permeabilized, by applying a transient set voltage that allows the cargo to enter the interior of the entity, such as the cytoplasm of the cell. In the example of cells, at least some, if not a majority, of the cells remain viable. Cells and other entities can be electroporated in vitro, in vivo, or ex vivo. Electroporation conditions (e.g., number of cells, concentration of cargo, recovery conditions, voltage, time, capacitance, pulse type, pulse length, volume, cuvette length, electroporation solution composition, etc.) vary depending on several factors including, but not limited to, the type of cell or other recipient entity, the cargo to be delivered, the efficiency of internalization desired, and the viability desired. Optimization of such criteria are within the scope of those skilled in the art. A variety devices and protocols can be used for electroporation. Examples include, but are not limited to, Neon® Transfection System, MaxCyte® Flow Electroporation™, Lonza® Nucleofector™ systems, and Bio-Rad® electroporation systems.

Other means for introducing engineered nucleic acids (e.g., any of the engineered nucleic acids described herein) into a cell or other target recipient entity include, but are not limited to, sonication, gene gun, hydrodynamic injection, and cell membrane deformation by physical means.

Compositions and methods for delivering engineered mRNAs in vivo, such as naked plasmids or mRNA, are described in detail in Kowalski et al. (Mol Ther. 2019 Apr. 10; 27(4): 710-728) and Kaczmarek et al. (Genome Med. 2017; 9: 60.), each herein incorporated by reference for all purposes.

Delivery Vehicles

Also provided herein are compositions for delivering a cargo/payload (a "delivery vehicle").

The cargo can comprise nucleic acids (e.g., any of the engineered nucleic acids described herein, such as any of the engineered nucleic acids described herein encoding the chimeric proteins including the membrane-cleavable chimeric proteins having the formula S-C-MT or MT-C-S described herein), as described above. The cargo can comprise proteins, carbohydrates, lipids, small molecules, and/or combinations thereof. The cargo can be any of the chimeric proteins provided for herein (e.g., any of the membrane-cleavable chimeric proteins having the formula S-C-MT or MT-C-S described herein). The cargo can be a combination of the chimeric proteins described herein, e.g., two or more of the chimeric proteins described herein. The cargo can be a combination of the chimeric protein described herein and another cargo of interest, such as another protein, carbohydrate, lipid, small molecule, and/or combination thereof.

The delivery vehicle can comprise any composition suitable for delivering a cargo. The delivery vehicle can comprise any composition suitable for delivering a protein (e.g., any of the chimeric proteins described herein). The delivery vehicle can be any of the lipid structure delivery systems described herein. For example, a delivery vehicle can be a lipid-based structure including, but not limited to, a lipid-based nanoparticle, a liposome, a micelle, an exosome, a vesicle, an extracellular vesicle, a cell, or a tissue. The delivery vehicle can be any of the nanoparticles described herein, such as nanoparticles comprising lipids (as previously described), inorganic nanomaterials, and other polymeric materials.

The delivery vehicle can be capable of delivering the cargo to a cell, such as delivering any of the chimeric proteins described herein to a cell. The delivery vehicle can be capable of delivering the cargo to a cell, such as delivering any of the chimeric proteins described herein to a cell. The delivery vehicle can be configured to target a specific cell, such as configured with a re-directing antibody to target a specific cell. The delivery vehicle can be capable of delivering the cargo to a cell in vivo.

The delivery vehicle can be capable of delivering the cargo to a tissue or tissue environment (e.g., a tumor microenvironment), such as delivering any of the chimeric proteins described herein to a tissue or tissue environment in vivo. Delivering a cargo can include secreting the cargo, such as secreting any of the chimeric proteins described herein. Accordingly, the delivery vehicle can be capable of secreting the cargo, such as secreting any of the chimeric proteins described herein. The delivery vehicle can be capable of secreting the cargo to a tissue or tissue environment (e.g., a tumor microenvironment), such as secreting any of the chimeric proteins described herein into a tissue or tissue environment. The delivery vehicle can be configured to target a specific tissue or tissue environment (e.g., a tumor microenvironment), such as configured with a re-directing antibody to target a specific tissue or tissue environment.

Methods of Treatment

Further provided herein are methods that include delivering, or administering, to a subject (e.g., a human subject) engineered cells as provided herein to produce in vivo at least one protein of interest produced by the engineered cells (e.g., any of the chimeric proteins provided for herein, such as the membrane-cleavable chimeric proteins having the formula S-C-MT or MT-C-S described herein, or the secreted effector molecules provided for herein following protease cleavage of the chimeric protein). Further provided herein are methods that include delivering, or administering, to a subject (e.g., a human subject) engineered cells as provided herein to produce in vivo at least two proteins of interest, e.g., at least two of the chimeric proteins provided for herein, such as the membrane-cleavable chimeric proteins having the formula S-C-MT or MT-C-S described herein, produced by the engineered cells.

Further provided herein are methods that include delivering, or administering, to a subject (e.g., a human subject)

any of the delivery vehicles described herein, such as any of the delivery vehicles described herein comprising any of the proteins of interest described herein, e.g., any of the chimeric proteins provided for herein, such as the membrane-cleavable chimeric proteins having the formula S-C-MT or MT-C-S described herein. Further provided herein are methods that include delivering, or administering, to a subject (e.g., a human subject) any of the delivery vehicles described herein, such as any of the delivery vehicles described herein comprising two or more proteins of, e.g., at least two of the chimeric proteins provided for herein, such as the membrane-cleavable chimeric proteins having the formula S-C-MT or MT-C-S described herein.

In some embodiments, the engineered cells or delivery vehicles are administered via intravenous, intraperitoneal, intratracheal, subcutaneous, intratumoral, oral, anal, intranasal (e.g., packed in a delivery particle), or arterial (e.g., internal carotid artery) routes. Thus, the engineered cells or delivery vehicles may be administered systemically or locally (e.g., to a TME or via intratumoral administration). An engineered cell can be isolated from a subject, such as a subject known or suspected to have cancer. An engineered cell can be allogenic with reference to the subject being administered a treatment. Allogenic modified cells can be HLA-matched to the subject being administered a treatment. Delivery vehicles can be any of the lipid structure delivery systems described herein. Delivery vehicles can be any of the nanoparticles described herein.

Engineered cells or delivery vehicles can be administered alone or in combination with other treatments, either simultaneously or sequentially dependent upon the condition to be treated. For example, engineered cells or delivery vehicles can be administered in combination with one or more IMiDs described herein. FDA-approved IMiDs can be administered in their approved fashion. In another example, engineered cells or delivery vehicles can be administered in combination with a checkpoint inhibitor therapy. Exemplary checkpoint inhibitors include, but are not limited to, anti-PD-1 antibodies, anti-PD-L1 antibodies, anti-PD-L2 antibodies, anti-CTLA-4 antibodies, anti-LAG-3 antibodies, anti-TIM-3 antibodies, anti-TIGIT antibodies, anti-VISTA antibodies, anti-KIR antibodies, anti-B7-H3 antibodies, anti-B7-H4 antibodies, anti-HVEM antibodies, anti-BTLA antibodies, anti-GAL9 antibodies, anti-A2AR antibodies, anti-phosphatidylserine antibodies, anti-CD27 antibodies, anti-TNFa antibodies, anti-TREM1 antibodies, and anti-TREM2 antibodies. Illustrative immune checkpoint inhibitors include pembrolizumab (anti-PD-1; MK-3475/Keytruda®—Merck), nivolumab (anti-PD-1; Opdivo®—BMS), pidilizumab (anti-PD-1 antibody; CT-011—Teva/CureTech), AMP224 (anti-PD-1; NCI), avelumab (anti-PD-L1; Bavencio®—Pfizer), durvalumab (anti-PD-L1; MEDI4736/Imfinzi®-Medimmune/AstraZeneca), atezolizumab (anti-PD-L1; Tecentriq®—Roche/Genentech), BMS-936559 (anti-PD-L1—BMS), tremelimumab (anti-CTLA-4; Medimmune/AstraZeneca), ipilimumab (anti-CTLA-4; Yervoy®—BMS), lirilumab (anti-KIR; BMS), monalizumab (anti-NKG2A; Innate Pharma/AstraZeneca). In other examples, engineered cells or delivery vehicles can be administered in combination with TGFbeta inhibitors, VEGF inhibitors, or HPGE2. In another example, engineered cells or delivery vehicles can be administered in combination with an anti-CD40 antibody.

Some methods comprise selecting a subject (or patient population) having a tumor (or cancer) and treating that subject with engineered cells or delivery vehicles that modulate tumor-mediated immunosuppressive mechanisms.

The engineered cells or delivery vehicles of the present disclosure may be used, in some instances, to treat cancer, such as ovarian cancer. Other cancers are described herein. For example, the engineered cells may be used to treat bladder tumors, brain tumors, breast tumors, cervical tumors, colorectal tumors, esophageal tumors, gliomas, kidney tumors, liver tumors, lung tumors, melanomas, ovarian tumors, pancreatic tumors, prostate tumors, skin tumors, thyroid tumors, and/or uterine tumors. The engineered cells or delivery vehicles of the present disclosure can be used to treat cancers with tumors located in the peritoneal space of a subject.

The methods provided herein also include delivering a preparation of engineered cells or delivery vehicles. A preparation, in some embodiments, is a substantially pure preparation, containing, for example, less than 5% (e.g., less than 4%, 3%, 2%, or 1%) of cells other than engineered cells. A preparation may comprise $1 \times 10^5$ cells/kg to $1 \times 10^7$ cells/kg cells. Preparation of engineered cells or delivery vehicles can include pharmaceutical compositions having one or more pharmaceutically acceptable carriers. For example, preparations of engineered cells or delivery vehicles can include any of the engineered viruses, such as an engineered AAV virus, or any of the engineered viral vectors, such as AAV vector, described herein.

In Vivo Expression

The methods provided herein also include delivering a composition in vivo capable of producing the engineered cells described herein, e.g., capable of delivering any of the engineered nucleic acids described herein to a cell in vivo. Such compositions include any of the viral-mediated delivery platforms, any of the lipid structure delivery systems, any of the nanoparticle delivery systems, any of the genomic editing systems, or any of the other engineering delivery systems described herein capable of engineering a cell in vivo.

The methods provided herein also include delivering a composition in vivo capable of producing any of the proteins of interest described herein, e.g., any of the chimeric proteins provided for herein, such as the membrane-cleavable chimeric proteins having the formula S-C-MT or MT-C-S described herein. The methods provided herein also include delivering a composition in vivo capable of producing two or more of the proteins of interest described herein. Compositions capable of in vivo production of proteins of interest include, but are not limited to, any of the engineered nucleic acids described herein. Compositions capable of in vivo production proteins of interest can be a naked mRNA or a naked plasmid.

ADDITIONAL EMBODIMENTS

1. An engineered nucleic acid comprising an expression cassette comprising a promoter and an exogenous polynucleotide sequence encoding a membrane-cleavable chimeric protein, oriented from N-terminal to C-terminal, having the formula:

S-C-MT or MT-C-S wherein
    S comprises a secretable effector molecule,
    C comprises a protease cleavage site, and
    MT comprises a cell membrane tethering domain,
    wherein the promoter is operably linked to the exogenous polynucleotide sequence, and wherein S-C-MT or MT-C-S is configured to be expressed as a single polypeptide.

2. The engineered nucleic acid of embodiment 1, wherein the promoter is a constitutive promoter.

3. The engineered nucleic acid of embodiment 2, wherein the constitutive promoter is selected from the group consisting of: CAG, HLP, CMV, EFS, SFFV, SV40, MND, PGK, UbC, hEF1aV1, hCAGG, hEF1aV2, hACTb, heIF4A1, hGAPDH, hGRP78, hGRP94, hHSP70, hKINb, and hUBIb.

4. The engineered nucleic acid of any one of embodiments 1-3, wherein the promoter is an inducible promoter.

5. The engineered nucleic acid of embodiment 4, wherein the inducible promoter comprises a response element selected from the group consisting of: an NFkB response element, a CREB response element, an NFAT response element, SRF response element 1, SRF response element 2, an AP1 response element, a TCF-LEF response element promoter fusion, a Hypoxia responsive element, a SMAD binding element, a STAT3 binding site, a inducer molecule responsive element, and tandem repeats thereof.

6. The engineered nucleic acid of any one of embodiments 1-5, wherein the promoter is a synthetic promoter.

7. The engineered nucleic acid of embodiment 6, wherein the synthetic promoter comprises a minimal promoter and at least one regulatory element that is heterologous to the minimal promoter.

8. The engineered nucleic acid of embodiment 7, wherein the at least one regulatory element comprises an activation-conditional control polypeptide- (ACP-) binding domain sequence and a promoter sequence.

9. The engineered nucleic acid of embodiment 8, wherein the ACP-binding domain comprises one or more zinc finger binding sites.

10. The engineered nucleic acid of embodiment 8 or embodiment 9, wherein the synthetic promoter is regulatable by an activation-conditional control polypeptide (ACP) that binds to the ACP-binding domain of the synthetic promoter.

11. The engineered nucleic acid of embodiment 10, wherein the ACP is a transcriptional modulator.

12. The engineered nucleic acid of embodiment 10 or embodiment 11, wherein the ACP is a transcriptional repressor.

13. The engineered nucleic acid of embodiment 10 or embodiment 11, wherein the ACP is a transcriptional activator.

14. The engineered nucleic acid of any one of embodiments 10-13, wherein the ACP further comprises a repressible protease and one or more cognate cleavage sites of the repressible protease.

15. The engineered nucleic acid of any one of embodiments 10-14, wherein the ACP further comprises a hormone-binding domain of estrogen receptor (ERT2 domain).

16. The engineered nucleic acid of any one of embodiments 10-14, wherein the ACP is a transcription factor.

17. The engineered nucleic acid of embodiment 16, wherein the transcription factor is a zinc-finger-containing transcription factor.

18. The engineered nucleic acid of any one of embodiments 10-17, wherein the ACP comprises a DNA-binding zinc finger protein domain (ZF protein domain) and a transcriptional effector domain.

19. The engineered nucleic acid of embodiment 18, wherein the ZF protein domain is modular in design and is composed of zinc finger arrays (ZFA).

20. The engineered nucleic acid of embodiment 19, wherein the ZF protein domain comprises one to ten ZFA.

21. The engineered nucleic acid of any one of embodiments 18-20, wherein the effector domain is selected from the group consisting of: a Herpes Simplex Virus Protein 16 (VP16) activation domain; an activation domain comprising four tandem copies of VP16, a VP64 activation domain; a p65 activation domain of NFκB; an Epstein-Barr virus R transactivator (Rta) activation domain; a tripartite activator comprising the VP64, the p65, and the Rta activation domains (VPR activation domain); a histone acetyltransferase (HAT) core domain of the human E1A-associated protein p300 (p300 HAT core activation domain); a Krüppel associated box (KRAB) repression domain; a Repressor Element Silencing Transcription Factor (REST) repression domain; a WRPW (SEQ ID NO: 224) motif of the hairy-related basic helix-loop-helix repressor proteins, the motif is known as a WRPW (SEQ ID NO: 224) repression domain; a DNA (cytosine-5)-methyltransferase 3B (DNMT3B) repression domain; and an HP1 alpha chromoshadow repression domain.

22. The engineered nucleic acid of any one of embodiments 14-21, wherein the one or more cognate cleavage sites of the repressible protease are localized between the ZF protein domain and the effector domain.

23. The engineered nucleic acid of any one of embodiments 14-22, wherein the repressible protease is hepatitis C virus (HCV) nonstructural protein 3 (NS3).

24. The engineered nucleic acid of embodiment 23, wherein the cognate cleavage site comprises an NS3 protease cleavage site.

25. The engineered nucleic acid of embodiment 24, wherein the NS3 protease cleavage site comprises a NS3/NS4A, a NS4A/NS4B, a NS4B/NS5A, or a NS5A/NS5B junction cleavage site.

26. The engineered nucleic acid of any one of embodiments 23-25, wherein the NS3 protease can be repressed by a protease inhibitor.

27. The engineered nucleic acid of embodiment 26, wherein the protease inhibitor is selected from the group consisting of: simeprevir, danoprevir, asunaprevir, ciluprevir, boceprevir, sovaprevir, paritaprevir, telaprevir, grazoprevir, glecaprevir, and voxiloprevir.

28. The engineered nucleic acid of any one of embodiments 15-27, wherein the ACP is capable of undergoing nuclear localization upon binding of the ERT2 domain to tamoxifen or a metabolite thereof.

29. The engineered nucleic acid of embodiment 28, wherein the tamoxifen metabolite is selected from the group consisting of: 4-hydroxytamoxifen, N-desmethyltamoxifen, tamoxifen-N-oxide, and endoxifen.

30. The engineered nucleic acid of any one of embodiments 10-29, wherein the ACP further comprises a degron domain, and wherein the degron domain is operably linked to the ACP.

31. The engineered nucleic acid of embodiment 30, wherein the degron domain is derived from a degron selected from the group consisting of HCV NS4 degron, PEST (two copies of residues 277-307 of human IκBα), GRR (residues 352-408 of human p105), DRR (residues 210-295 of yeast Cdc34), SNS (tandem repeat of SP2 and NB (SP2-NB-SP2 of influenza A or influenza B), RPB (four copies of residues 1688-1702 of yeast RPB), SPmix (tandem repeat of SP1 and SP2 (SP2-SP1-SP2-SP1-SP2 of influenza A virus M2 protein), NS2 (three copies of residues 79-93 of influenza A virus NS protein), ODC (residues 106-142 of ornithine decarboxylase), Nek2A, mouse ODC (residues 422-461), mouse ODC_DA (residues 422-461 of mODC including D433A and D434A point mutations), an APC/C degron, a COP1 E3 ligase binding degron motif, a CRL4-Cdt2 binding PIP degron, an actinfilin-binding degron, a KEAP1 binding degron, a KLHL2 and KLHL3 binding degron, an MDM2 binding motif, an N-degron, a hydroxyproline modification in hypoxia signaling, a phytohormone-dependent SCF-LRR-binding degron, an SCF ubiquitin ligase binding phosphodegron, a phytohormone-dependent SCF-LRR-binding degron, a DSGxxS phospho-dependent degron, an Siah binding motif, an SPOP SBC docking motif, and a PCNA binding PIP box.

32. The engineered nucleic acid of embodiment 30, wherein the degron domain comprises a cereblon (CRBN) polypeptide substrate domain capable of binding CRBN in response to an immunomodulatory drug (IMiD) thereby promoting ubiquitin pathway-mediated degradation of the ACP.

33. The engineered nucleic acid of embodiment 32, wherein the CRBN polypeptide substrate domain is selected from the group consisting of: IKZF1, IKZF3, CK1a, ZFP91, GSPT1, MEIS2, GSS E4F1, ZN276, ZN517, ZN582, ZN653, ZN654, ZN692, ZN787, and ZN827, or a fragment thereof that is capable of drug-inducible binding of CRBN.

34. The engineered nucleic acid of embodiment 32, wherein the CRBN polypeptide substrate domain is a chimeric fusion product of native CRBN polypeptide sequences.

35. The engineered nucleic acid of embodiment 32, wherein the CRBN polypeptide substrate domain is a IKZF3/ZFP91/IKZF3 chimeric fusion product having the amino acid sequence of

```
                                    (SEQ ID NO: 175)
FNVLMVHKRSHTGERPLQCEICGFTCRQKGNLLRHIK

LHTGEKPFKCHLCNYACQRRDAL.
```

36. The engineered nucleic acid of any one of embodiments 32-35, wherein the IMiD is an FDA-approved drug.

37. The engineered nucleic acid of any one of embodiments 32-36, wherein the IMiD is selected from the group consisting of: thalidomide, lenalidomide, and pomalidomide.

38. The engineered nucleic acid of any one of embodiments 30-37, wherein the degron domain is N-terminal of the repressible protease, C-terminal of the repressible protease, N-terminal of the ZF protein domain, C-terminal of the ZF protein domain, N-terminal of the effector domain, or C-terminal of the effector domain.

39. The engineered nucleic acid of any one of embodiments 1-38, wherein the promoter is a tissue-specific promoter.

40. The engineered nucleic acid of any one of embodiments 1-39, wherein the secretable effector molecule comprises a signal peptide or a signal-anchor sequence.

41. The engineered nucleic acid of embodiment 40, wherein the signal peptide comprises a native signal peptide native to the secretable effector molecule.

42. The engineered nucleic acid of embodiment 40, wherein the signal peptide comprises a non-native signal peptide or the signal-anchor sequence comprises a non-native signal-anchor sequence non-native to the secretable effector molecule.

43. The engineered nucleic acid of embodiment 42, wherein the non-native signal peptide or the non-native signal-anchor sequence is selected from the group consisting of: IL-12, IL-2, optimized IL-2, trypsiongen-2, *Gaussia* luciferase, CD5, human IgKVII, murine IgKVII, VSV-G, prolactin, serum albumin preprotein, azurocidin preprotein, osteonectin, CD33, IL-6, IL-8, CCL2, TIMP2, VEGFB, osteoprotegerin, serpin E1, GROalpha, CXCL12, IL-21, CD8, NKG2D, TNFR2, and GMCSF.

44. The engineered nucleic acid of any one of embodiments 1-43, wherein the secretable effector molecule is selected from a therapeutic class, wherein the therapeutic class is selected from the group consisting of: a cytokine, a chemokine, a homing molecule, a growth factor, a co-activation molecule, a tumor microenvironment modifier, a ligand, an antibody, a peptide, and an enzyme.

45. The engineered nucleic acid of embodiment 44, wherein the cytokine is selected from the group consisting of: IL-1-beta, IL-2, IL-4, IL-6, IL-7, IL-10, IL-12, an IL-12p70 fusion protein, IL-15, IL-17A, IL-18, IL-21, IL-22, Type I interferons, Interferon-gamma, and TNF-alpha.

46. The engineered nucleic acid of any one of embodiments 1-43, wherein the secretable effector molecule comprises IL-15, IL-12, or an IL-12p70 fusion protein.

47. The engineered nucleic acid of any one of embodiments 1-43, wherein the secretable effector molecule comprises IL-15.

48. The engineered nucleic acid of embodiment 47, wherein the secretable effector molecule comprises the amino acid sequence of SEQ ID NO: 199.

49. The engineered nucleic acid of any one of embodiments 1-43, wherein the secretable effector molecule comprises IL-15 and IL-15Rα sushi domain or an IL15/IL-15Rα sushi domain fusion protein.

50. The engineered nucleic acid of embodiment 49, wherein the secretable effector molecule comprises the amino acid sequence of SEQ ID NO: 202.

51. The engineered nucleic acid of any one of embodiments 1-43, wherein the secretable effector molecule comprises IL-12 or an IL-12p70 fusion protein.

52. The engineered nucleic acid of embodiment 51, wherein the secretable effector molecule comprises the amino acid sequence of SEQ ID NO: 203.

53. The engineered nucleic acid of embodiment 44, wherein the chemokine is selected from the group consisting of: CCL21a, CXCL10, CXCL11, CXCL13, a CXCL10-CXCL11 fusion protein, CCL19, CXCL9, and XCL1.

54. The engineered nucleic acid of embodiment 44, wherein the homing molecule is selected from the group consisting of: anti-integrin alpha4,beta7; anti-MAdCAM; SDF1; and MMP-2.

55. The engineered nucleic acid of embodiment 44, wherein the growth factor is selected from the group consisting of: FLT3L and GM-CSF.

56. The engineered nucleic acid of embodiment 44, wherein the co-activation molecule is selected from the group consisting of: 4-1BBL and CD40L.

57. The engineered nucleic acid of embodiment 44, wherein the tumor microenvironment modifier is selected from the group consisting of: adenosine deaminase, a TGFbeta inhibitor, an immune checkpoint inhibitor, a VEGF inhibitor, and HPGE2.

58. The engineered nucleic acid of embodiment 57, wherein the TGFbeta inhibitor is selected from the group consisting of: an anti-TGFbeta peptide, an anti-TGFbeta antibody, a TGFb-TRAP, and a combination thereof.

59. The engineered nucleic acid of embodiment 57, wherein the immune checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody.

60. The engineered nucleic acid of embodiment 57, wherein the VEGF inhibitor comprises an anti-VEGF antibody, an anti-VEGF peptide, or a combination thereof.

61. The engineered nucleic acid of any one of embodiments 1-60, wherein the secretable effector molecule is a human-derived effector molecule.

62. The engineered nucleic acid of any one of embodiments 1-61, wherein the protease cleavage site is cleavable by a protease selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, an MMP9 protease, and an NS3 protease.

63. The engineered nucleic acid of any one of embodiments 1-62, wherein the protease cleavage site is cleavable by an ADAM17 protease.

64. The engineered nucleic acid of any one of embodiments 1-63, wherein the protease cleavage site comprises a first region having the amino acid sequence of PRAE (SEQ ID NO: 176).

65. The engineered nucleic acid of embodiment 64, wherein the protease cleavage site comprises a second region having the amino acid sequence of KGG (SEQ ID NO: 177).

66. The engineered nucleic acid of embodiment 65, wherein the first region is located N-terminal to the second region.

67. The engineered nucleic acid of any one of embodiments 1-66, wherein the protease cleavage site comprises the amino acid sequence of $PRAEX_1X_2KGG$ (SEQ ID NO: 219),
wherein $X_1$ is A, Y, P, S, or F, and
wherein $X_2$ is V, L, S, I, Y, T, or A.

68. The engineered nucleic acid of any one of embodiments 1-66, wherein the protease cleavage site comprises the amino acid sequence of $PRAEX_1X_2KGG$ (SEQ ID NO: 178), wherein X$_1$ is A, Y, P, S, or F, and wherein X$_2$ is V, L, S, I, Y, or T.

69. The engineered nucleic acid of any one of embodiments 1-68, wherein the protease cleavage site comprises the amino acid sequence of PRAEAVKGG (SEQ ID NO: 179).

70. The engineered nucleic acid of any one of embodiments 1-68, wherein the protease cleavage site comprises the amino acid sequence of PRAEALKGG (SEQ ID NO: 180).

71. The engineered nucleic acid of any one of embodiments 1-68, wherein the protease cleavage site comprises the amino acid sequence of PRAEYSKGG (SEQ ID NO: 181).

72. The engineered nucleic acid of any one of embodiments 1-68, wherein the protease cleavage site comprises the amino acid sequence of PRAEPIKGG (SEQ ID NO: 182).

73. The engineered nucleic acid of any one of embodiments 1-68, wherein the protease cleavage site comprises the amino acid sequence of PRAEAYKGG (SEQ ID NO: 183).

74. The engineered nucleic acid of any one of embodiments 1-68, wherein the protease cleavage site comprises the amino acid sequence of PRAESSKGG (SEQ ID NO: 184).

75. The engineered nucleic acid of any one of embodiments 1-68, wherein the protease cleavage site comprises the amino acid sequence of PRAEFTKGG (SEQ ID NO: 185).

76. The engineered nucleic acid of any one of embodiments 1-68, wherein the protease cleavage site comprises the amino acid sequence of PRAEAAKGG (SEQ ID NO: 186).

77. The engineered nucleic acid of any one of embodiments 1-66, wherein the protease cleavage site comprises the amino acid sequence of DEPHYSQRR (SEQ ID NO: 187).

78. The engineered nucleic acid of any one of embodiments 1-66, wherein the protease cleavage site comprises the amino acid sequence of PPLGPIFNPG (SEQ ID NO: 188).

79. The engineered nucleic acid of any one of embodiments 1-66, wherein the protease cleavage site comprises the amino acid sequence of PLAQAYRSS (SEQ ID NO: 189).

80. The engineered nucleic acid of any one of embodiments 1-66, wherein the protease cleavage site comprises the amino acid sequence of TPIDSSFNPD (SEQ ID NO: 190).

81. The engineered nucleic acid of any one of embodiments 1-66, wherein the protease cleavage site comprises the amino acid sequence of VTPEPIFSLI (SEQ ID NO: 191).

82. The engineered nucleic acid of any one of embodiments 1-66, wherein the protease cleavage site comprises the amino acid sequence of ITQGLAVSTISSFF (SEQ ID NO: 198).

83. The engineered nucleic acid of any one of embodiments 1-82, wherein the cell membrane tethering domain comprises a transmembrane-intracellular domain or a transmembrane domain.

84. The engineered nucleic acid of embodiment 83, wherein the transmembrane-intracellular domain and/ or transmembrane domain is derived from PDGFR-beta, CD8, CD28, CD3zeta-chain, CD4, 4-1BB, OX40, ICOS, CTLA-4, PD-1, LAG-3, 2B4, LNGFR, NKG2D, EpoR, TNFR2, B7-1, or BTLA.

85. The engineered nucleic acid of any one of embodiments 1-84, wherein the cell membrane tethering domain comprises a post-translational modification tag, or motif capable of post-translational modification to modify the chimeric protein to include a post-translational modification tag, where the post-translational modification tag is capable of association with a cell membrane.

86. The engineered nucleic acid of embodiment 85, wherein the post-translational modification tag comprises a lipid-anchor domain, optionally wherein the lipid-anchor domain is selected from the group consisting of: a GPI lipid-anchor, a myristoylation tag, and a palmitoylation tag.

87. The engineered nucleic acid of any one of embodiments 1-84, wherein the cell membrane tethering domain comprises a cell surface receptor, or a cell membrane-bound portion thereof.

88. The engineered nucleic acid of any one of embodiments 1-87, wherein when expressed in a cell, the secretable effector molecule is tethered to a cell membrane of the cell.

89. The engineered nucleic acid of embodiment 88, wherein when expressed in a cell expressing a protease capable of cleaving the protease cleavage site, the secretable effector molecule is released from the cell membrane.

90. The engineered nucleic acid of embodiment 89, wherein the protease expressed on the cell membrane is endogenous to the cell.

91. The engineered nucleic acid of embodiment 90, wherein the protease is selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, and an MMP9 protease.

92. The engineered nucleic acid of embodiment 91, wherein the protease is an ADAM17 protease.

93. The engineered nucleic acid of embodiment 89, wherein the protease expressed on the cell membrane is heterologous to the cell.

94. The engineered nucleic acid of embodiment 93, wherein the protease is hepatitis C virus (HCV) non-structural protein 3 (NS3).

95. The engineered nucleic acid of embodiment 94, wherein the protease cleavage site comprises an NS3 protease cleavage site.

96. The engineered nucleic acid of embodiment 95, wherein the NS3 protease cleavage site comprises a NS3/NS4A, a NS4A/NS4B, a NS4B/NS5A, or a NS5A/NS5B junction cleavage site.

97. The engineered nucleic acid of any one of embodiments 89-96, wherein the protease can be repressed by a protease inhibitor.

98. The engineered nucleic acid of embodiment 97, wherein the protease inhibitor is selected from the group consisting of: simeprevir, danoprevir, asunaprevir, ciluprevir, boceprevir, sovaprevir, paritaprevir, telaprevir, grazoprevir, glecaprevir, and voxiloprevir.

99. The engineered nucleic acid of any one of embodiments 89-98, wherein expression and/or localization of the protease is capable of regulation.

100. The engineered nucleic acid of embodiment 99, wherein the expression and/or localization is regulated by a cell state of the cell.

101. The engineered nucleic acid of any one of embodiments 1-100, wherein the engineered nucleic acid is a single-stranded or double-stranded nucleic acid selected from the group consisting of: a DNA, a cDNA, an RNA, an mRNA, and a naked plasmid.

102. An expression vector comprising the engineered nucleic acid of any one of embodiments 1-101.

103. The expression vector of embodiment 102, wherein the expression vector is a viral vector.

104. The expression vector of embodiment 103, wherein the viral vector is a retroviral vector.

105. A membrane-cleavable chimeric protein, oriented from N-terminal to C-terminal, having the formula:

S-C-MT or MT-C-S wherein
    S comprises a secretable effector molecule,
    C comprises a protease cleavage site, and
    MT comprises a cell membrane tethering domain,
    wherein S-C-MT or MT-C-S is configured to be expressed as a single polypeptide.

106. The chimeric protein of embodiment 105, wherein the secretable effector molecule comprises a signal peptide or a signal-anchor sequence.

107. The chimeric protein of embodiment 106, wherein the signal peptide comprises a native signal peptide native to the secretable effector molecule.

108. The chimeric protein of embodiment 106, wherein the signal peptide comprises a non-native signal peptide or the signal-anchor sequence comprises a non-native signal-anchor sequence non-native to the secretable effector molecule.

109. The chimeric protein of embodiment 108, wherein the non-native signal peptide or the non-native signal-anchor sequence is selected from the group consisting of: IL-12, IL-2, optimized IL-2, trypsiongen-2, *Gaussia* luciferase, CD5, human IgKVII, murine IgKVII, VSV-G, prolactin, serum albumin preprotein, azurocidin preprotein, osteonectin, CD33, IL-6, IL-8, CCL2, TIMP2, VEGFB, osteoprotegerin, serpin E1, GROalpha, CXCL12, IL-21, CD8, NKG2D, TNFR2, and GMCSF.

110. The chimeric protein of any one of embodiments 105-109, wherein the secretable effector molecule is selected from a therapeutic class, wherein the therapeutic class is selected from the group consisting of: a cytokine, a chemokine, a homing molecule, a growth factor, a co-activation molecule, a tumor microenvironment modifier, a ligand, an antibody, a peptide, and an enzyme.

111. The chimeric protein of embodiment 110, wherein the cytokine is selected from the group consisting of: IL-1-beta, IL-2, IL-4, IL-6, IL-7, IL-10, IL-12, an IL-12p70 fusion protein, IL-15, IL-17A, IL-18, IL-21, IL-22, Type I interferons, Interferon-gamma, and TNF-alpha.

112. The chimeric protein of any one of embodiments 105-111, wherein the secretable effector molecule comprises IL-15, IL-12, or an IL-12p70 fusion protein.

113. The chimeric protein of embodiment 112, wherein the secretable effector molecule comprises IL-15.

114. The chimeric protein of embodiment 113, wherein the secretable effector molecule comprises the amino acid sequence of SEQ ID NO: 199.

115. The chimeric protein of embodiment 113, wherein the secretable effector molecule comprises IL-15 and IL-15Rα sushi domain or an IL15/IL-15Rα sushi domain fusion protein.

116. The chimeric protein of any one of embodiment 115, wherein the secretable effector molecule comprises the amino acid sequence of SEQ ID NO: 202.

117. The chimeric protein of embodiment 112, wherein the secretable effector molecule comprises IL-12 or an IL-12p70 fusion protein.

118. The chimeric protein of embodiment 117, wherein the secretable effector molecule comprises the amino acid sequence of SEQ ID NO: 203.

119. The chimeric protein of embodiment 110, wherein the chemokine is selected from the group consisting of: CCL21a, CXCL10, CXCL11, CXCL13, a CXCL10-CXCL11 fusion protein, CCL19, CXCL9, and XCL1.

120. The chimeric protein of embodiment 110, wherein the homing molecule is selected from the group consisting of: anti-integrin alpha4,beta7; anti-MAdCAM; SDF1; and MMP-2.

121. The chimeric protein of embodiment 110, wherein the growth factor is selected from the group consisting of: FLT3L and GM-CSF.

122. The chimeric protein of embodiment 110, wherein the co-activation molecule is selected from the group consisting of: 4-1BBL and CD40L.

123. The chimeric protein of embodiment 110, wherein the tumor microenvironment modifier is selected from the group consisting of: adenosine deaminase, a TGF-beta inhibitor, an immune checkpoint inhibitor, a VEGF inhibitor, and HPGE2.

124. The chimeric protein of embodiment 123, wherein the TGF-beta inhibitor is selected from the group consisting of: an anti-TGFbeta peptide, an anti-TGF-beta antibody, a TGFb-TRAP, and a combination thereof.

125. The chimeric protein of embodiment 123, wherein the immune checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody.

126. The chimeric protein of embodiment 123, wherein the VEGF inhibitor comprises an anti-VEGF antibody, an anti-VEGF peptide, or a combination thereof.

127. The chimeric protein of any one of embodiments 105-126, wherein the secretable effector molecule is a human-derived effector molecule.

128. The chimeric protein of any one of embodiments 105-127, wherein the protease cleavage site is cleavable by a protease selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, an MMP9 protease, and an NS3 protease.

129. The chimeric protein of any one of embodiments 105-128, wherein the protease cleavage site is cleavable by an ADAM17 protease.

130. The chimeric protein of any one of embodiments 105-129, wherein the protease cleavage site comprises a first region having the amino acid sequence of PRAE (SEQ ID NO: 176).

131. The chimeric protein of embodiment 130, wherein the protease cleavage site comprises a second region having the amino acid sequence of KGG (SEQ ID NO: 177).

132. The chimeric protein of embodiment 131, wherein the first region is located N-terminal to the second region.

133. The chimeric protein of any one of embodiments 105-132, wherein the protease cleavage site comprises the amino acid sequence of PRAEX$_1$X$_2$KGG (SEQ ID NO: 219),
wherein X$_1$ is A, Y, P, S, or F, and
wherein X$_2$ is V, L, S, I, Y, T, or A.

134. The chimeric protein of any one of embodiments 105-132, wherein the protease cleavage site comprises the amino acid sequence of PRAEX$_1$X$_2$KGG (SEQ ID NO: 178),
wherein X$_1$ is A, Y, P, S, or F, and
wherein X$_2$ is V, L, S, I, Y, or T.

135. The chimeric protein of any one of embodiments 105-134, wherein the protease cleavage site comprises the amino acid sequence of PRAEAVKGG (SEQ ID NO: 179).

136. The chimeric protein of any one of embodiments 105-134, wherein the protease cleavage site comprises the amino acid sequence of PRAEALKGG (SEQ ID NO: 180).

137. The chimeric protein of any one of embodiments 105-134, wherein the protease cleavage site comprises the amino acid sequence of PRAEYSKGG (SEQ ID NO: 181).

138. The chimeric protein of any one of embodiments 105-134, wherein the protease cleavage site comprises the amino acid sequence of PRAEPIKGG (SEQ ID NO: 182).

139. The chimeric protein of any one of embodiments 105-134, wherein the protease cleavage site comprises the amino acid sequence of PRAEAYKGG (SEQ ID NO: 183).

140. The chimeric protein of any one of embodiments 105-134, wherein the protease cleavage site comprises the amino acid sequence of PRAESSKGG (SEQ ID NO: 184).

141. The chimeric protein of any one of embodiments 105-134, wherein the protease cleavage site comprises the amino acid sequence of PRAEFTKGG (SEQ ID NO: 185).

142. The chimeric protein of any one of embodiments 105-134, wherein the protease cleavage site comprises the amino acid sequence of PRAEAAKGG (SEQ ID NO: 186).

143. The chimeric protein of any one of embodiments 105-132, wherein the protease cleavage site comprises the amino acid sequence of DEPHYSQRR (SEQ ID NO: 187).

144. The chimeric protein of any one of embodiments 105-132, wherein the protease cleavage site comprises the amino acid sequence of PPLGPIFNPG (SEQ ID NO: 188).

145. The chimeric protein of any one of embodiments 105-132, wherein the protease cleavage site comprises the amino acid sequence of PLAQAYRSS (SEQ ID NO: 189).

146. The chimeric protein of any one of embodiments 105-132, wherein the protease cleavage site comprises the amino acid sequence of TPIDSSFNPD (SEQ ID NO: 190).

147. The chimeric protein of any one of embodiments 105-132, wherein the protease cleavage site comprises the amino acid sequence of VTPEPIFSLI (SEQ ID NO: 191).

148. The chimeric protein of any one of embodiments 105-132, wherein the protease cleavage site comprises the amino acid sequence of ITQGLAVSTISSFF (SEQ ID NO: 198).

149. The chimeric protein of any one of embodiments 105-148, wherein the cell membrane tethering domain comprises a transmembrane-intracellular domain or a transmembrane domain.

150. The chimeric protein of embodiment 149, wherein the transmembrane-intracellular domain and/or transmembrane domain is derived from PDGFR-beta, CD8, CD28, CD3zeta-chain, CD4, 4-1BB, OX40, ICOS, CTLA-4, PD-1, LAG-3, 2B4, LNGFR, NKG2D, EpoR, TNFR2, B7-1, or BTLA.

151. The chimeric protein of any one of embodiments 105-150, wherein the cell membrane tethering domain comprises a post-translational modification tag, or motif capable of post-translational modification to modify the chimeric protein to include a post-translational modification tag, where the post-translational modification tag is capable of association with a cell membrane.

152. The chimeric protein of embodiment 151, wherein the post-translational modification tag comprises a lipid-anchor domain, optionally wherein the lipid-anchor domain is selected from the group consisting of: a GPI lipid-anchor, a myristoylation tag, and a palmitoylation tag.

153. The chimeric protein of any one of embodiments 105-152, wherein the cell membrane tethering domain comprises a cell surface receptor, or a cell membrane-bound portion thereof.

154. The chimeric protein of any one of embodiments 105-153, wherein when expressed in a cell, the secretable effector molecule is tethered to a cell membrane of the cell.

155. The chimeric protein of embodiment 154, wherein when expressed in a cell expressing a protease capable of cleaving the protease cleavage site, the secretable effector molecule is released from the cell membrane.

156. The chimeric protein of embodiment 155, wherein the protease expressed on the cell membrane is endogenous to the cell.

157. The chimeric protein of embodiment 156, wherein the protease is selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, and an MMP9 protease.

158. The chimeric protein of embodiment 156, wherein the protease is an ADAM17 protease.

159. The chimeric protein of embodiment 155, wherein the protease expressed on the cell membrane is heterologous to the cell.

160. The chimeric protein of embodiment 159, wherein the protease is hepatitis C virus (HCV) nonstructural protein 3 (NS3).

161. The chimeric protein of embodiment 160, wherein the protease cleavage site comprises an NS3 protease cleavage site.

162. The chimeric protein of embodiment 161, wherein the NS3 protease cleavage site comprises a NS3/NS4A, a NS4A/NS4B, a NS4B/NS5A, or a NS5A/NS5B junction cleavage site.

163. The chimeric protein of any one of embodiments 155-162, wherein the protease can be repressed by a protease inhibitor.

164. The chimeric protein of embodiment 163, wherein the protease inhibitor is selected from the group consisting of: simeprevir, danoprevir, asunaprevir, ciluprevir, boceprevir, sovaprevir, paritaprevir, telaprevir, grazoprevir, glecaprevir, and voxiloprevir.

165. The chimeric protein of any one of embodiments 155-164, wherein the protease further comprises a degron.

166. The chimeric protein of any one of embodiments 155-165, wherein expression and/or localization of the protease is capable of regulation.

167. The chimeric protein of embodiment 166, wherein the expression and/or localization is regulated by a cell state of the cell.

168. A composition comprising the engineered nucleic acid of any one of embodiments 1-101, or the expression vector of any one of embodiments 102-104, or the membrane-cleavable chimeric protein of any one of embodiments 105-167 and a pharmaceutically acceptable carrier.

169. An isolated cell comprising the engineered nucleic acid of any one of embodiments 1-101, or the expression vector of any one of embodiments 102-104, or the membrane-cleavable chimeric protein of any one of embodiments 105-167.

170. An isolated cell comprising an engineered nucleic acid, wherein the engineered nucleic acid comprises an expression cassette comprising a promoter and an exogenous polynucleotide sequence encoding a membrane-cleavable chimeric protein, oriented from N-terminal to C-terminal, having the formula:

S-C-MT or MT-C-S wherein
    S comprises a secretable effector molecule,
    C comprises a protease cleavage site, and
    MT comprises a cell membrane tethering domain, wherein the promoter is operably linked to the exogenous polynucleotide sequence, and wherein S-C-MT or MT-C-S is configured to be expressed as a single polypeptide.

171. The isolated cell of embodiment 169 or embodiment 170, wherein the engineered nucleic acid is recombinantly expressed.

172. The isolated cell of any one of embodiments 169-171, wherein the engineered nucleic acid is expressed from a vector or a selected locus from the genome of the cell.

173. An isolated cell comprising a membrane-cleavable chimeric protein, wherein the membrane-cleavable chimeric protein, oriented from N-terminal to C-terminal, has the formula:

S-C-MT or MT-C-S wherein
    S comprises a secretable effector molecule,
    C comprises a protease cleavage site, and
    MT comprises a cell membrane tethering domain,
    and wherein S-C-MT or MT-C-S is configured to be expressed as a single polypeptide.

174. The isolated cell of any one of embodiments 169-173, wherein the cell is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, a mesenchymal stromal cell (MSC), an induced pluripotent stem cell (iPSC), and an iPSC-derived cell.

175. The isolated cell of any one of embodiments 169-173, wherein the cell is a Natural Killer (NK) cell.

176. The isolated cell of any one of embodiments 169-175, wherein the cell is autologous.

177. The isolated cell of any one of embodiments 169-175, wherein the cell is allogeneic.

178. The isolated cell of any one of embodiments 169-173, wherein the cell is a tumor cell selected from the group consisting of: a bladder tumor cell, a brain tumor cell, a breast tumor cell, a cervical tumor cell, a colorectal tumor cell, an esophageal tumor cell, a glioma cell, a kidney tumor cell, a liver tumor cell, a lung tumor cell, a melanoma cell, an ovarian tumor cell, a pancreatic tumor cell, a prostate tumor cell, a skin tumor cell, a thyroid tumor cell, and a uterine tumor cell.

179. The isolated cell of embodiment 178, wherein the cell was engineered via transduction with an oncolytic virus.

180. The isolated cell of any one of embodiments 169-179, wherein the cell further comprises a protease capable of cleaving the protease cleavage site.

181. The isolated cell of embodiment 180, wherein the protease is an endogenous protease.

182. The isolated cell of embodiment 181, wherein the endogenous protease is selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, and an MMP9 protease.

183. The isolated cell of embodiment 181, wherein the endogenous protease is an ADAM17 protease.

184. The isolated cell of embodiment 180, wherein the protease is a heterologous protease.

185. The isolated cell of embodiment 184, wherein the heterologous protease is hepatitis C virus (HCV) non-structural protein 3 (NS3).

186. The isolated cell of any one of embodiments 180-185, wherein the protease is expressed on the cell membrane of the cell.

187. The isolated cell of embodiment 186, wherein the protease is capable of cleaving the protease cleavage site.

188. The isolated cell of embodiment 187, wherein cleavage of the protease cleavage site releases the secretable effector molecule from the cell membrane of the cell.

189. The isolated cell of any one of embodiments 169-188, wherein the protease cleavage site comprises a first region having the amino acid sequence of PRAE (SEQ ID NO: 176).

190. The isolated cell of embodiment 189, wherein the protease cleavage site comprises a second region having the amino acid sequence of KGG (SEQ ID NO: 177).

191. The isolated cell of embodiment 190, wherein the first region is located N-terminal to the second region.

192. The isolated cell of any one of embodiments 169-191, wherein the protease cleavage site comprises the amino acid sequence of PRAEX$_1$X$_2$KGG (SEQ ID NO: 219),
wherein X$_1$ is A, Y, P, S, or F, and
wherein X$_2$ is V, L, S, I, Y, T, or A.

193. The isolated cell of any one of embodiments 169-191, wherein the protease cleavage site comprises the amino acid sequence of PRAEX$_1$X$_2$KGG (SEQ ID NO: 178),
wherein X$_1$ is A, Y, P, S, or F, and
wherein X$_2$ is V, L, S, I, Y, or T.

194. The isolated cell of any one of embodiments 169-193, wherein the protease cleavage site comprises the amino acid sequence of PRAEAVKGG (SEQ ID NO: 179).

195. The isolated cell of any one of embodiments 169-193, wherein the protease cleavage site comprises the amino acid sequence of PRAEALKGG (SEQ ID NO: 180).

196. The isolated cell of any one of embodiments 169-193, wherein the protease cleavage site comprises the amino acid sequence of PRAEYSKGG (SEQ ID NO: 181).

197. The isolated cell of any one of embodiments 169-193, wherein the protease cleavage site comprises the amino acid sequence of PRAEPIKGG (SEQ ID NO: 182).

198. The isolated cell of any one of embodiments 169-193, wherein the protease cleavage site comprises the amino acid sequence of PRAEAYKGG (SEQ ID NO: 183).

199. The isolated cell of any one of embodiments 169-193, wherein the protease cleavage site comprises the amino acid sequence of PRAESSKGG (SEQ ID NO: 184).

200. The isolated cell of any one of embodiments 169-193, wherein the protease cleavage site comprises the amino acid sequence of PRAEFTKGG (SEQ ID NO: 185).

201. The isolated cell of any one of embodiments 169-193, wherein the protease cleavage site comprises the amino acid sequence of PRAEAAKGG (SEQ ID NO: 186).

202. The isolated cell of any one of embodiments 169-191, wherein the protease cleavage site comprises the amino acid sequence of DEPHYSQRR (SEQ ID NO: 187).

203. The isolated cell of any one of embodiments 169-191, wherein the protease cleavage site comprises the amino acid sequence of PPLGPIFNPG (SEQ ID NO: 188).

204. The isolated cell of any one of embodiments 169-191, wherein the protease cleavage site comprises the amino acid sequence of PLAQAYRSS (SEQ ID NO: 189).

205. The isolated cell of any one of embodiments 169-191, wherein the protease cleavage site comprises the amino acid sequence of TPIDSSFNPD (SEQ ID NO: 190).

206. The isolated cell of any one of embodiments 169-191, wherein the protease cleavage site comprises the amino acid sequence of VTPEPIFSLI (SEQ ID NO: 191).

207. The isolated cell of any one of embodiments 169-191, wherein the protease cleavage site comprises the amino acid sequence of ITQGLAVSTISSFF (SEQ ID NO: 198).

208. The isolated cell of any one of embodiments 169-207, wherein the cell further comprises an antigen recognizing receptor.

209. The isolated cell of embodiment 208, wherein the antigen recognizing receptor comprises an antigen-binding domain.

210. The isolated cell of embodiment 209, wherein the antigen-binding domain comprises an antibody, an antigen-binding fragment of an antibody, a F(ab) fragment, a F(ab') fragment, a single chain variable fragment (scFv), or a single-domain antibody (sdAb).

211. The isolated cell of embodiment 209, wherein the antigen-binding domain comprises a single chain variable fragment (scFv).

212. The isolated cell of embodiment 211, wherein the scFv comprises a heavy chain variable domain (VH) and a light chain variable domain (VL).

213. The isolated cell of embodiment 212, wherein the VH and VL are separated by a peptide linker.

214. The isolated cell of embodiment 213, wherein the scFv comprises the structure VH-L-VL or VL-L-VH, wherein VH is the heavy chain variable domain, L is the peptide linker, and VL is the light chain variable domain.

215. The isolated cell of any one of embodiments 208-214, wherein the antigen recognizing receptor is a chimeric antigen receptor (CAR) or T cell receptor (TCR).

216. The isolated cell of any one of embodiments 208-214, wherein the antigen recognizing receptor is a CAR.

217. The isolated cell of embodiment 216, wherein the CAR comprises one or more intracellular signaling domains, and the one or more intracellular signaling domains are selected from the group consisting of: a CD3zeta-chain intracellular signaling domain, a CD97 intracellular signaling domain, a CD11a-CD18 intracellular signaling domain, a CD2 intracellular signaling domain, an ICOS intracellular signaling domain, a CD27 intracellular signaling domain, a CD154 intracellular signaling domain, a CD8 intracellular signaling domain, an OX40 intracellular signaling domain, a 4-1BB intracellular signaling domain, a CD28 intracellular signaling domain, a ZAP40 intracellular signaling domain, a CD30 intracellular signaling domain, a GITR intracellular signaling domain, an HVEM intracellular signaling domain, a DAP10 intracellular signaling domain, a DAP12 intracellular signaling domain, and a MyD88 intracellular signaling domain.

218. The isolated cell of embodiment 216 or embodiment 217, wherein the CAR comprises a transmembrane domain, and the transmembrane domain is selected from the group consisting of: a CD8 transmembrane domain, a CD28 transmembrane domain a CD3zeta-chain transmembrane domain, a CD4 transmembrane domain, a 4-1BB transmembrane domain, an OX40 transmembrane domain, an ICOS transmembrane domain, a CTLA-4 transmembrane domain, a PD-1 transmembrane domain, a LAG-3 transmembrane domain, a 2B4 transmembrane domain, and a BTLA transmembrane domain.

219. The isolated cell of any one of embodiments 216-218, wherein the CAR comprises a spacer region between the antigen-binding domain and the transmembrane domain.

220. A composition comprising the isolated cell of any one of embodiments 169-219, and a pharmaceutically acceptable carrier.

221. A method of treating a subject in need thereof, the method comprising administering a therapeutically effective dose of any of the isolated cells of any one of embodiments 169-219 or the composition of embodiment 220.

222. The method of embodiment 221, wherein the isolated cell is derived from the subject.

223. The method of embodiment 221 or embodiment 222, wherein the isolated cell is allogeneic with reference to the subject.

224. A lipid-based structure comprising the engineered nucleic acid of any one of embodiments 1-101, or the expression vector of any one of embodiments 102-104, or the membrane-cleavable chimeric protein of any one of embodiments 105-167.

225. The lipid-based structure of embodiment 224, wherein the lipid-based structure comprises a extracellular vesicle, a lipid nanoparticle, a micelle, or a liposome.

226. A composition comprising the lipid-based structure of embodiment 224 or embodiment 225, and a pharmaceutically acceptable carrier.

227. A method of treating a subject in need thereof, the method comprising administering a therapeutically effective dose of any of the lipid-based structures of embodiment 224 or embodiment 225, or the composition of embodiment 226.

228. The method of embodiment 227, wherein the administering comprises systemic administration.

229. The method of embodiment 227 or embodiment 228, wherein the lipid-based structure is capable of engineering a cell in the subject.

230. The method of any one of embodiments 227-229, wherein the method further comprises administering a checkpoint inhibitor.

231. The method of embodiment 230, wherein the checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody.

232. The method of any one of embodiments 227-231, wherein the method further comprises administering an anti-CD40 antibody.

233. A nanoparticle comprising the engineered nucleic acid of any one of embodiments 1-101 or the membrane-cleavable chimeric protein of any one of embodiments 105-167.

234. The nanoparticle of embodiment 233, wherein the nanoparticle comprises an inorganic material.

235. A composition comprising the nanoparticle of embodiment 233 or embodiment 234.

236. A method of treating a subject in need thereof, the method comprising administering a therapeutically effective dose of any of the nanoparticles of embodiment 233 or embodiment 234, or the composition of embodiment 235.

237. The method of embodiment 236, wherein the administering comprises systemic administration.

238. The method of embodiment 236 or embodiment 237, wherein the nanoparticle is capable of engineering a cell in the subject.

239. The method of any one of embodiments 236-238, wherein the method further comprises administering a checkpoint inhibitor.

240. A virus engineered to comprise the engineered nucleic acid of any one of embodiments 1-101 or the expression vector of any one of embodiments 102-104.

241. The engineered virus of embodiment 240, wherein the virus is selected from the group consisting of: a lentivirus, a retrovirus, an oncolytic virus, an adenovirus, an adeno-associated virus (AAV), and a virus-like particle (VLP).

242. A composition comprising the engineered virus of embodiment 240 or embodiment 241, and a pharmaceutically acceptable carrier.

243. A method of treating a subject in need thereof, the method comprising administering a therapeutically effective dose of the engineered virus of embodiment 240 or embodiment 241, or the composition of embodiment 242.

244. The method of embodiment 243, wherein the administering comprises systemic administration.

245. The method of embodiment or embodiment 244, wherein the engineered virus infects a cell in the subject and expresses the expression cassette.

246. The method of any one of embodiments 243-245, wherein the method further comprises administering a checkpoint inhibitor.

247. A method of inducing release of a membrane-tethered effector molecule, comprising:
  a) providing a cell, wherein the cell comprises a membrane-bound protease and a membrane-cleavable chimeric protein, oriented from N-terminal to C-terminal, having the formula:

S-C-MT or MT-C-S wherein
  S comprises a secretable effector molecule,
  C comprises a cognate protease cleavage site of the membrane-bound protease, and
  MT comprises a cell membrane tethering domain,
  wherein S-C-MT or MT-C-S is configured to be expressed as a single polypeptide; and
  b) culturing the cell under conditions suitable for expression of the membrane-bound protease and the membrane-cleavable chimeric protein,
    wherein upon expression, the membrane-cleavable chimeric protein is tethered to the cell membrane of the cell, and
    wherein, upon expression, the membrane-bound protease cleaves the cognate membrane-bound protease cleavage site of the membrane-cleavable chimeric protein, thereby releasing the secretable effector molecule from the cell membrane.

248. The method of embodiment 247, wherein the secretable effector molecule comprises a signal peptide or a signal-anchor sequence.

249. The method of embodiment 248, wherein the signal peptide comprises a native signal peptide native to the secretable effector molecule.

250. The method of embodiment 248, wherein the signal peptide comprises a non-native signal peptide or the signal-anchor sequence comprises a non-native signal-anchor sequence non-native to the secretable effector molecule.

251. The method of embodiment 250, wherein the non-native signal peptide or the non-native signal-anchor sequence is selected from the group consisting of: IL-12, IL-2, optimized IL-2, trypsiongen-2, *Gaussia* luciferase, CD5, human IgKVII, murine IgKVII, VSV-G, prolactin, serum albumin preprotein, azurocidin preprotein, osteonectin, CD33, IL-6, IL-8, CCL2, TIMP2, VEGFB, osteoprotegerin, serpin E1, GROalpha, CXCL12, IL-21, CD8, NKG2D, TNFR2, and GMCSF.

252. The method of any one of embodiments 247-250, wherein the secretable effector molecule is selected from a therapeutic class, wherein the therapeutic class is selected from the group consisting of: a cytokine, a chemokine, a homing molecule, a growth factor, a co-activation molecule, a tumor microenvironment modifier, a ligand, an antibody, a polynucleotide, a peptide, and an enzyme.

253. The method of embodiment 252, wherein the cytokine is selected from the group consisting of: IL-1-beta, IL-2, IL-4, IL-6, IL-7, IL-10, IL-12, an IL-12p70 fusion protein, IL-15, IL-17A, IL-18, IL-21, IL-22, Type I interferons, Interferon-gamma, and TNF-alpha.

254. The method of any one of embodiments 247-253, wherein the secretable effector molecule comprises IL-12, an IL-12p70 fusion protein, or IL-15.

255. The method of embodiment 254, wherein the secretable effector molecule comprises IL-15.

256. The method of embodiment 255, wherein the secretable effector molecule comprises the amino acid sequence of SEQ ID NO: 199.

257. The method of embodiment 255, wherein the secretable effector molecule comprises IL-15 and IL-15Rα sushi domain or an IL15/IL-15Rα sushi domain fusion protein.

258. The method of embodiment 257, wherein the secretable effector molecule comprises the amino acid sequence of SEQ ID NO: 202.

259. The method of embodiment 254, wherein the secretable effector molecule comprises IL-12 or an IL-12p70 fusion protein.

260. The method of embodiment 259, wherein the secretable effector molecule comprises the amino acid sequence of SEQ ID NO: 203.

261. The method of embodiment 252, wherein the chemokine is selected from the group consisting of: CCL21a, CXCL10, CXCL11, CXCL13, a CXCL10-CXCL11 fusion protein, CCL19, CXCL9, and XCL1.

262. The method of embodiment 252, wherein the homing molecule is selected from the group consisting of: anti-integrin alpha4,beta7; anti-MAdCAM; SDF1; and MMP-2.

263. The method of embodiment 252, wherein the growth factor is selected from the group consisting of: FLT3L and GM-CSF.

264. The method of embodiment 252, wherein the co-activation molecule is selected from the group consisting of: 4-1BBL and CD40L.

265. The method of embodiment 252, wherein the tumor microenvironment modifier is selected from the group consisting of: adenosine deaminase, a TGFbeta inhibitor, an immune checkpoint inhibitor, a VEGF inhibitor, and HPGE2.

266. The method of embodiment 265, wherein the TGF-beta inhibitor is selected from the group consisting of: an anti-TGFbeta peptide, an anti-TGFbeta antibody, a TGFb-TRAP, and a combination thereof.

267. The method of embodiment 265, wherein the immune checkpoint inhibitor is selected from the group consisting of: an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFa antibody, an anti-TREM1 antibody, and an anti-TREM2 antibody.

268. The method of embodiment 265, wherein the VEGF inhibitor comprises an anti-VEGF antibody, an anti-VEGF peptide, or a combination thereof.

269. The method of any one of embodiments 243-268, wherein the secretable effector molecule is a human-derived effector molecule.

270. The method of any one of embodiments 243-269, wherein the cognate protease cleavage site is cleavable by a protease selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, an MMP9 protease, and an NS3 protease.

271. The method of any one of embodiments 243-270, wherein the cognate protease cleavage site is cleavable by an ADAM17 protease.

272. The method of any one of embodiments 243-271, wherein the protease cleavage site comprises a first region having the amino acid sequence of PRAE (SEQ ID NO: 176).

273. The method of embodiment 272, wherein the protease cleavage site comprises a second region having the amino acid sequence of KGG (SEQ ID NO: 177).

274. The method of embodiment 273, wherein the first region is located N-terminal to the second region.

275. The method of any one of embodiments 243-274, wherein the protease cleavage site comprises the amino acid sequence of PRAEX$_1$X$_2$KGG (SEQ ID NO: 219), wherein X$_1$ is A, Y, P, S, or F, and wherein X$_2$ is V, L, S, I, Y, T, or A.

276. The method of any one of embodiments 243-275, wherein the protease cleavage site comprises the amino acid sequence of PRAEAVKGG (SEQ ID NO: 179).

277. The method of any one of embodiments 243-275, wherein the protease cleavage site comprises the amino acid sequence of PRAEALKGG (SEQ ID NO: 180).

278. The method of any one of embodiments 243-275, wherein the protease cleavage site comprises the amino acid sequence of PRAEYSKGG (SEQ ID NO: 181).

279. The method of any one of embodiments 243-275, wherein the protease cleavage site comprises the amino acid sequence of PRAEPIKGG (SEQ ID NO: 182).

280. The method of any one of embodiments 243-275, wherein the protease cleavage site comprises the amino acid sequence of PRAEAYKGG (SEQ ID NO: 183).

281. The method of any one of embodiments 243-275, wherein the protease cleavage site comprises the amino acid sequence of PRAESSKGG (SEQ ID NO: 184).

282. The method of any one of embodiments 243-275, wherein the protease cleavage site comprises the amino acid sequence of PRAEFTKGG (SEQ ID NO: 185).

283. The method of any one of embodiments 243-275, wherein the protease cleavage site comprises the amino acid sequence of PRAEAAKGG (SEQ ID NO: 186).

284. The method of any one of embodiments 243-274, wherein the protease cleavage site comprises the amino acid sequence of DEPHYSQRR (SEQ ID NO: 187).

285. The method of any one of embodiments 243-274, wherein the protease cleavage site comprises the amino acid sequence of PPLGPIFNPG (SEQ ID NO: 188).

286. The method of any one of embodiments 243-274, wherein the protease cleavage site comprises the amino acid sequence of PLAQAYRSS (SEQ ID NO: 189).

287. The method of any one of embodiments 243-274, wherein the protease cleavage site comprises the amino acid sequence of TPIDSSFNPD (SEQ ID NO: 190).

288. The method of any one of embodiments 243-274, wherein the protease cleavage site comprises the amino acid sequence of VTPEPIFSLI (SEQ ID NO: 191).

289. The method of any one of embodiments 243-274, wherein the protease cleavage site comprises the amino acid sequence of ITQGLAVSTISSFF (SEQ ID NO: 198).

290. The method of any one of embodiments 243-289, wherein the cell membrane tethering domain comprises a transmembrane-intracellular domain or a transmembrane domain.

291. The method of embodiment 290, wherein the transmembrane-intracellular domain and/or transmembrane domain is derived from PDGFR-beta, CD8, CD28, CD3zeta-chain, CD4, 4-1BB, OX40, ICOS, CTLA-4, PD-1, LAG-3, 2B4, LNGFR, NKG2D, EpoR, TNFR2, B7-1, or BTLA.

292. The method of any one of embodiments 243-291, wherein the cell membrane tethering domain comprises a post-translational modification tag, or motif capable of post-translational modification to modify the chimeric protein to include a post-translational modification tag, where the post-translational modification tag is capable of association with a cell membrane.

293. The method of embodiment 292, wherein the post-translational modification tag comprises a lipid-anchor domain, optionally wherein the lipid-anchor domain is selected from the group consisting of: a GPI lipid-anchor, a myristoylation tag, and a palmitoylation tag.

294. The method of any one of embodiments 243-291, wherein the cell membrane tethering domain comprises a cell surface receptor, or a cell membrane-bound portion thereof.

295. The method of any one of embodiments 243-294 wherein the protease is endogenous to the cell.

296. The method of embodiment 295, wherein the protease is selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, and an MMP9 protease.

297. The method of embodiment 296, wherein the protease is an ADAM17 protease.

298. The method of any one of embodiments 243-294 298, wherein the protease is heterologous to the cell.

299. The method of embodiment 298, wherein the protease is hepatitis C virus (HCV) nonstructural protein 3 (NS3).

300. The method of embodiment 299, wherein the protease cleavage site comprises an NS3 protease cleavage site.

301. The method of embodiment 300, wherein the NS3 protease cleavage site comprises a NS3/NS4A, a NS4A/NS4B, a NS4B/NS5A, or a NS5A/NS5B junction cleavage site.

302. The method of any one of embodiments 243-301, wherein the protease can be repressed by a protease inhibitor.

303. The method of embodiment 302, wherein the protease inhibitor is selected from the group consisting of: simeprevir, danoprevir, asunaprevir, ciluprevir, boceprevir, sovaprevir, paritaprevir, telaprevir, grazoprevir, glecaprevir, and voxiloprevir.

304. The method of any one of embodiments 243-303, wherein the protease further comprises a degron.

305. The method of any one of embodiments 243-303, wherein expression and/or localization of the protease is capable of regulation.

306. The method of embodiment 305, wherein the expression and/or localization is regulated by a cell state of the cell.

EXAMPLES

Below are examples of specific embodiments for carrying out the present invention. The examples are offered for illustrative purposes only, and are not intended to limit the scope of the present invention in any way. For example, the experiments described and performed below demonstrate the general utility of engineering cells to secrete payloads (e.g., effector molecules) and delivering those cells to induce an immunogenic response against tumors.

Efforts have been made to ensure accuracy with respect to numbers used (e.g., amounts, temperatures, etc.), but some experimental error and deviation should, of course, be allowed for.

Example 1—Regulated Cytokine Secretion Using Membrane-Cleavable System

A Membrane-Cleavable system is assessed for the ability to regulate the secretion of cytokines.

Methods

Engineering of IL-15 Secreting Cells:

Lentiviral vectors encoding membrane-cleavable IL-15 constructs are generated.

Lentivirus is produced using: Lenti-X 293T packaging cell line (Clontech, Cat #632180); LX293T Complete growth medium, without antibiotics; DMEM, hi-glucose; 1 mM Sodium Pyruvate; 10% FBS, heat-inactivated; Opti-Mem I Reduced Serum Media (Gibco/Thermo Fisher; Cat #31985); FuGene HD (Promega, Cat #E2311); Envelope, Packaging, and Transfer Vector plasmids; VSV-G-pseudo-typed envelope vector (pMD2.G); Packaging vector that contains Gag, Pol, Rev, and Tat that can be used with 2nd and 3rd generation transfer vectors (psMAX2). 293T(FT) cells from 90% confluent 10 cm dishes are lifted and dispensed at 1:3 dilution late in the afternoon the day before transfection and incubated cells as normal overnight at 37° C., 5% CO2 (cells should be 60-85% confluent the next day at time of transfection).

A transfection reaction is prepped for each 10 cm dish according to the protocol below:

1. Prep transfection reaction for each 10 cm dish in a separate 1.7 mL tube.
2. Add 900 uL Opti-Mem I at RT.
3. Add 9 ug vector backbone (containing gene of interest) per reaction.
4. Add 8 ug packaging vector per reaction.
5. Add 1 ug envelope vector per reaction (pMD2.G).
6. Mix thoroughly by quickly vortexing for 3 seconds.
7. Add 55 uL Fugene HD per reaction.
8. Mix by quickly pipetting up and down 20-30 times.
9. Let sit at RT for 10 min (allowing DNA complexes to form).
10. Slowly add mixture in dropwise manner around the dish, then mix by gently rocking back-forth and up-down for 5-10 seconds (do not swirl).
11. Place dish into virus incubator.

Viral supernatants are harvested on days 2 and 3 using a serological pipette. Cellular debris is removed using a Millipore steriflip 0.45 um filters. A Lenti-X Concentrator (Cat. Nos. 631231 & 631232) is used according to the protocol: 1) Combine 1 volume of Lenti-X Concentrator with 3 volumes of clarified supernatant. Mix by gentle inversion; 2) Incubate mixture on ice or at 4° C. for 30 minutes to overnight; (3) Centrifuge sample at 1,500×g for 45 minutes at 4° C.; (4) Carefully remove and discard supernatant, taking care not to disturb the pellet; (5) Gently resuspend the pellet in 1/10 to 1/100th of the original volume using sterile PBS+0.1% BSA.

Primary T cells are transduced using the viral supernatants according to the protocol below:

1. Activate T cells using Gibco (Thermo Fisher) Dynabeads Human T-Activator anti-CD3/anti-CD28 beads.
   a) Count the T cells—1e6 cells per well in a 24 well plate
   b) Wash dynabeads with OpTmizer media
   c) Vortex Dynabeads thoroughly immediately before use
   d) Transfer the desired volume of Dynabeads to a tube
   e) Add a 10× volume of PBS, and mix (vortex for 5 seconds, or keep on a roller for at least 5 min)
   f) Place the tube on a magnet for 1 min and discard the supernatant by aspiration
   g) Repeat washing of beads—for second wash, use OpTmizer media without IL-2
   h) Remove the tube from the magnet and resuspend the washed Dynabeads in the needed volume of OpTmizer Media with 100 U/mL IL-2 to reach 6e6 beads/mL
   i) Add T cell suspension to beads so that 1 mL contains 1e6 T cells and 3e6 Dynabeads per mL
   j) Plate 1 mL of mixture into each well of a 24-well plate
   k) Place the 24-well plate in a 37° C. incubator
   l) After 20 hrs, T cells are ready to be transduced
2. T cell transduction:
   a) Remove 500 ul of media by carefully pipetting from the top, ensuring not to disturb the settled T cells and beads
   b) Add the lentivirus mixture onto the cells drop by drop to each corresponding well
   c) Mix virus and cells by pipetting up and down gently
   d) Place the plate in a 37° C. incubator
   e) Add 500 ul of media back the next day
   f) Remove the CD3 dynabeads from each well after day 3 of transduction
      i) Vigorously mix the cells-dynabeads mixture by pipetting up and down
      ii) Transfer cells-dynabeads mixture into an eppendorf tube (1.5 mL)
      iii) Place the eppendorf tube to a magnet holder
      iv) Keep the eppendorf tube in a magnet holder and remove the media containing cells from eppendorf tube to another eppendorf tube Primary NK cells are transduced using the viral supernatants according to the protocol below:

1. Retronectin Coating of non-TC Treated 12 well plates (Day1). For 13 mL of total volume to coat one plate (final Retronectin concentration per well is 32 ug/mL volume corresponding to 8 ug/cm2 plate area):
   a. Thaw retronectin
   b. Take 0.416 mL from the original stock bottle (1 ug/ul concentration).

c. Add into 15 mL falcon tube and complete the volume to 13 mL with DPBS(1×)

d. Mix gently. Do not mix the solution vigorously. Do not vortex e. Transfer 1 mL retronectin solution into each well f. Incubate at 4° C. overnight. (1 day before Transduction)

2. Blocking Plate with 1% BSA solution (Day 2)

a. Collect Retronectin solution from each well and store at −20° C.

b. Block with 1% sterile BSA solution in PBS (1 mL/well) for 5-30 min at RT c. Aspirate the BSA solution and wash with DPBS once 3. NK transduction (Day 2)

a. Add 1 mL (0.5e6/mL) NK cells and add desired amount of viral titer to each on a 12-well plate b. Spin down the plate at 1200 g, 20 C, for 90 min c. Add 1 mL MACS NK media with cytokines into the wells d. Then transfer the plate to a 37° C. incubator Measurement of Surface-Bound IL-15:

Engineered cells are stained 7 days after transduction first with Polyclonal Rabbit an anti-Human IL-15 primary antibody (LS-C487337) for 1.5 hours at room temperature, and second with an anti-rabbit secondary antibody (labeled with Alexa Fluor 488) for 30 minutes. Surface-bound IL-15 is assessed by flow cytometry on a Beckman Coulter Flow Cytometer.

Measurement of Secreted IL-15:

Engineered cells (10^6) are plated 7 days after transduction in 1 mL fresh media. After 48 hours of incubation at 37 degrees, IL-15 secreted in the cell media is quantified by ELISA (Human IL-15 Quantikine ELISA Kit cat #D1500).

Determination of Protein Expression and Cleavage Efficiency

Figure 1B:
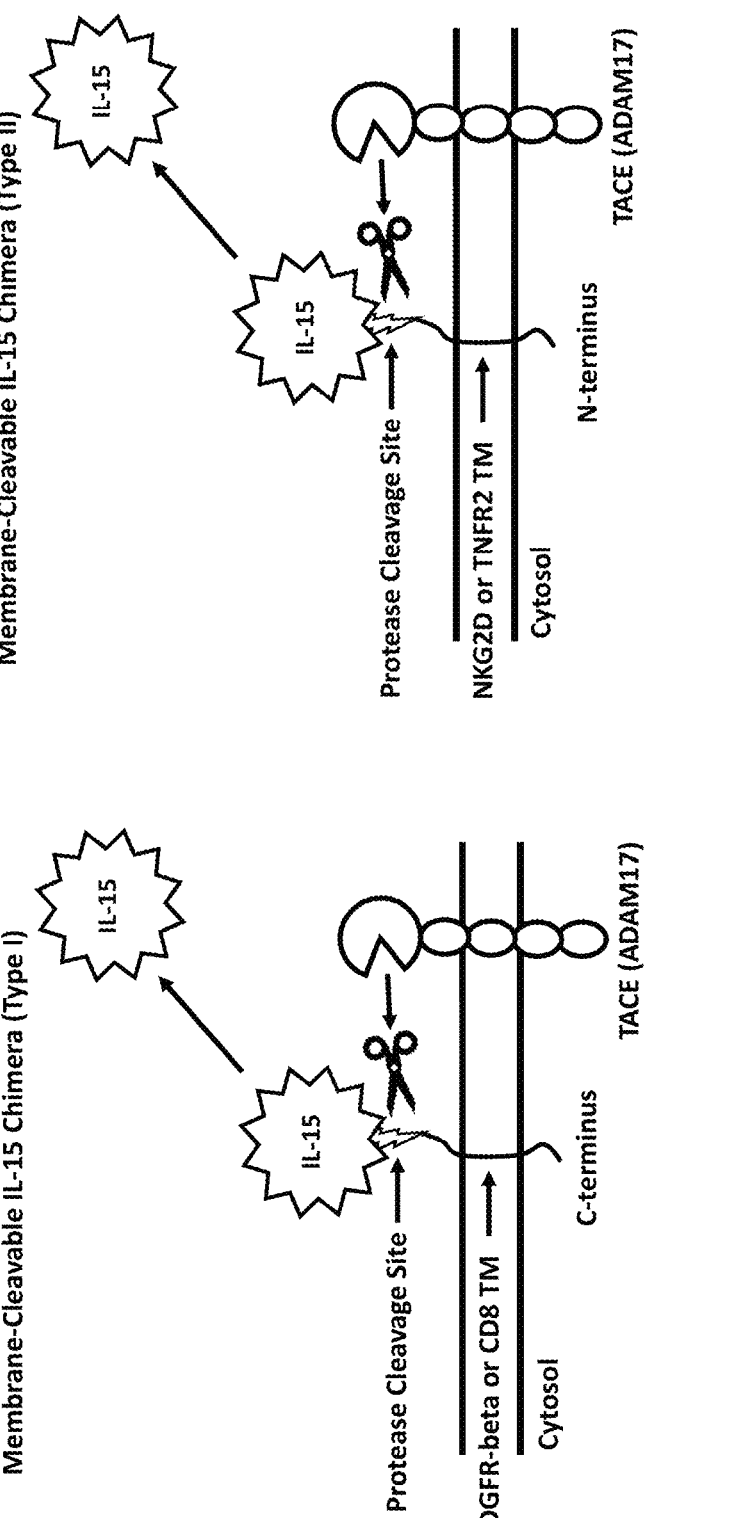
FIG. 1B illustrates a representative Membrane-Cleavable system for the regulated secretion of IL-15 in which IL-15 is expressed as a chimeric protein having a cleavage site capable of cleavage by TACE inserted between the IL-15 payload and membrane-tethering domain. The left panel illustrates a Type I transmembrane architecture (e.g., S-C-MT) through use of Type I transmembrane domains, such as PDGFR-beta and CD8. The right panel a Type II transmembrane architecture (e.g., MT-C-S) through use of Type II transmembrane domains, such as NKG2D and TNFR2.

A Membrane-Cleavable system is designed that uses a chimeric protein having the formula S-C-MT or MT-C-S (oriented from N-terminal to C-terminal), in which S refers to a secretable payload (e.g., an effector molecule), C refers to a protease cleavage site, and MT refers to a cell membrane tethering domain. FIG. 1A illustrates a schematic of the Membrane-Cleavable system described herein in which a desired payload is expressed as a chimeric protein in which a protease cleavage site is inserted between the payload and membrane-tethering domain. The left panel illustrates a schematic of the Membrane-Cleavable system using a transmembrane spanning architecture (e.g., the chimeric protein contains a transmembrane domain). The right panel illustrates a schematic of the Membrane-Cleavable system using a membrane-associated architecture (e.g., the chimeric protein contains a post-translational modification tag allowing association with a cell membrane). FIG. 1B illustrates a representative Membrane-Cleavable system for the regulated secretion of IL-15 in which IL-15 is expressed as a chimeric protein having a cleavage site capable of cleavage by TACE inserted between the IL-15 payload and membrane-tethering domain. The left panel illustrates a Type I transmembrane architecture (e.g., S-C-MT) through use of Type I transmembrane domains, such as PDGFR-beta and CD8. The right panel a Type II transmembrane architecture (e.g., MT-C-S) through use of Type II transmembrane domains, such as NKG2D and TNFR2.

Various protease cleavage site sequences based on a putative ADAM17 motif are assessed for expression and cleavage properties. Specifically, candidate protease cleavage site sequences presented in Table A with substitutions at the −1 and +1 position relative to the cleavage site (candidates #1-5) or with substitutions throughout the sequence (candidates #6-10) are examined. Various membrane tethering domain sequences are also assessed in the system, including Type I transmembrane architectures (e.g., S-C-MT) through use of Type I transmembrane domains, such as PDGFR-beta and CD8 transmembrane domain sequences, as well as inverting the orientation of the chimeric protein, such as constructing Type II transmembrane architectures (e.g., MT-C-S) through use of Type II transmembrane domains, such as NKG2D and TNFR2.

TABLE A

| Construct | P5 | P4 | P3 | P2 | P1 | P1' | P2' | P3' | P4 | P5' | FULL SEQ | SEQ ID NO |
|---|---|---|---|---|---|---|---|---|---|---|---|---|
| Pos Cntrl #1 | P | R | A | E | A | V | K | G | G | | PRAE AVKG G | 179 |
| Pos Cntrl #2 | P | R | A | E | A | L | K | G | G | | PRAE ALKG G | 180 |
| Candidate #1 | P | R | A | E | Y | S | K | G | G | | PRAE YSKG G | 181 |
| Candidate #2 | P | R | A | E | P | I | K | G | G | | PRAE PIKG G | 182 |
| Candidate #3 | P | R | A | E | A | Y | K | G | G | | PRAE AYKG G | 183 |
| Candidate #4 | P | R | A | E | S | S | K | G | G | | PRAE SSKG G | 184 |
| Candidate #5 | P | R | A | E | F | T | K | G | G | | PRAE FTKG G | 185 |
| Candidate #6 | D | E | P | H | Y | S | Q | R | R | | DEPH YSQR R | 187 |
| Candidate #7 | P | P | L | G | P | I | F | N | P | G | PPLG PIFN PG | 188 |
| Candidate #8 | P | L | A | Q | A | Y | R | S | S | | PLAQ AYRS S | 189 |
| Candidate #9 | T | P | I | D | S | S | F | N | P | D | TPID SSFN PD | 190 |
| Candidate #10 | V | T | P | E | P | I | F | S | L | I | VTPE PIFS LI | 191 |
| Neg Cntrl | P | R | A | E | A | A | K | G | G | | PRAE AAKG G | 186 |

The secretion properties for various Membrane-Cleavable systems featuring various combinations of protease cleavage sites and membrane tethering domains are assessed through analysis of surface-bound payload (e.g., surface-bound IL-15 by flow-cytometry) and secreted payload (e.g., secreted IL-15 by supernatant ELISA).

Properties assessed include:

Total protein expression (secreted+membrane bound)

Cleavage efficiency (ratio of secreted vs membrane bound cytokines, i.e., membrane release efficiency), including in various cell types of interest, such as T cells, NK cells, and HEK 293 cells A Membrane-Cleavable system demonstrating optimal total protein expression and the desired cleavage efficiency is determined.

Determination of Cell Type and Cell State Secretion Properties

Various protease cleavage site sequences based on a putative ADAM17 motif are assessed for secretion properties including protease specificity and secretion kinetics in different cell types and cell states. Specifically, candidate protease cleavage site sequences include those presented in Table A, as shown above. Various membrane tethering domain sequences are also assessed in the system, including Type I transmembrane architectures (e.g., S-C-MT) through use of Type I transmembrane domains, such as PDGFR-beta and CD8 transmembrane domain sequences, as well as inverting the orientation of the chimeric protein, such as constructing Type II transmembrane architectures (e.g., MT-C-S) through use of Type II transmembrane domains, such as NKG2D and TNFR2.

The secretion properties for various Membrane-Cleavable systems featuring various combinations of protease cleavage sites and membrane tethering domains are assessed through analysis of surface-bound payload (e.g., surface-bound IL-15 by flow-cytometry) and secreted payload (e.g., secreted IL-15 by supernatant ELISA).

Properties assessed include:

Secretion properties (e.g., specificity and kinetics), in cell types of interest, such as NK cells and T cells Secretion properties (e.g., specificity and kinetics), in various cell states, in particular cell states that may regulate protease expression and/or localization (e.g., +/−PMA or other activation states)

A Membrane-Cleavable system demonstrating the desired regulated secretion properties is determined. Specifically, a protease cleavage site and membrane tethering domain combination is determined demonstrating secretion kinetics for regulated secretion (membrane release) of the payload at a desired rate in cell types and cell states of interest.

Example 2—Regulated IL-15 Secretion with Various Linker/Cleavage Site/Transmembrane Domain Combinations Variations of Membrane-Cleavable systems, including three of the protease cleavage sites shown in Table A (SEQ ID NOs: 180, 187, and 191), various polypeptide linkers, various polypeptide linker orientations (i.e., a polypeptide linker N-terminal to the cleavage site and/or a polypeptide linker C-terminal to the cleavage site), and two transmembrane domains (a CD8 transmembrane domain and a B7-1 transmembrane domain) were assessed for the ability to regulate the secretion of a secretable payload, IL-15. The Membrane-Cleavable systems of this example include an orientation of, in the N-terminal to C-terminal direction, S-C-MT, in which S refers to the secretable payload, C refers to a protease cleavage site, and MT refers to a cell membrane tethering domain.

Engineering of IL-15 Secreting Cells:

Lentiviral vectors encoding membrane-cleavable IL-15 constructs, with varied linkers, linker orientations, and transmembrane domains were generated. Descriptions of the constructs are provided in Table B.

TABLE B

Description of Various Membrane-Cleavable IL-15 Constructs

| Construct | N Term Linker | Cleavage Site (SEQ ID NO) | C-Terminal Linker | TM Domain |
|---|---|---|---|---|
| SB03534 | None | 180 | None | B7-1 |
| SB03530 | None | 191 | None | B7-1 |
| SB03514 | None | 187 | None | B7-1 |
| SB03513 | None | 180 | SGGGGSGGGGSGGGGSGGGGS GGGSLQ (SEQ ID NO: 195) | B7-1 |
| SB03531 | None | 191 | SGGGGSGGGGSGGGGSGGGGS GGGSLQ (SEQ ID NO: 195) | B7-1 |
| SB03516 | None | 187 | SGGGGSGGGGSGGGGSGGGGS GGGSLQ (SEQ ID NO: 195) | B7-1 |
| SB03515 | None | 180 | TTTPAPRPPTPAPTIASQPLSLRP EACRPAAGGAVHTRGLDFACD (SEQ ID NO: 196) | B7-1 |
| SB03535 | None | 191 | TTTPAPRPPTPAPTIASQPLSLRP EACRPAAGGAVHTRGLDFACD (SEQ ID NO: 196) | CD8 |
| SB03537 | None | 187 | TTTPAPRPPTPAPTIASQPLSLRP EACRPAAGGAVHTRGLDFACD (SEQ ID NO: 196) | CD8 |
| SB03536 | SGGGGSGGGGSG (SEQ ID NO: 194) | 180 | GGGSGGGGSGGGSLQ (SEQ ID NO: 197) | CD8 |
| SB03532 | SGGGGSGGGGSG (SEQ ID NO: 194) | 191 | GGGSGGGGSGGGSLQ (SEQ ID NO: 197) | B7-1 |

TABLE B-continued

Description of Various Membrane-Cleavable IL-15 Constructs

| Construct | N Term Linker | Cleavage Site (SEQ ID NO) | C-Terminal Linker | TM Domain |
|---|---|---|---|---|
| SB03518 | SGGGGSGGGGSG (SEQ ID NO: 194) | 187 | GGGSGGGGSGGGSLQ (SEQ ID NO: 197) | B7-1 |
| SB03517 | SGGGGSGGGGSGGG GSGGGGSGGGSLQ (SEQ ID NO: 195) | 180 | None | B7-1 |
| SB03520 | SGGGGSGGGGSGGG GSGGGGSGGGSLQ (SEQ ID NO: 195) | 191 | None | B7-1 |
| SB03519 | SGGGGSGGGGSGGG GSGGGGSGGGSLQ (SEQ ID NO: 195) | 187 | None | B7-1 |

Figure 2:
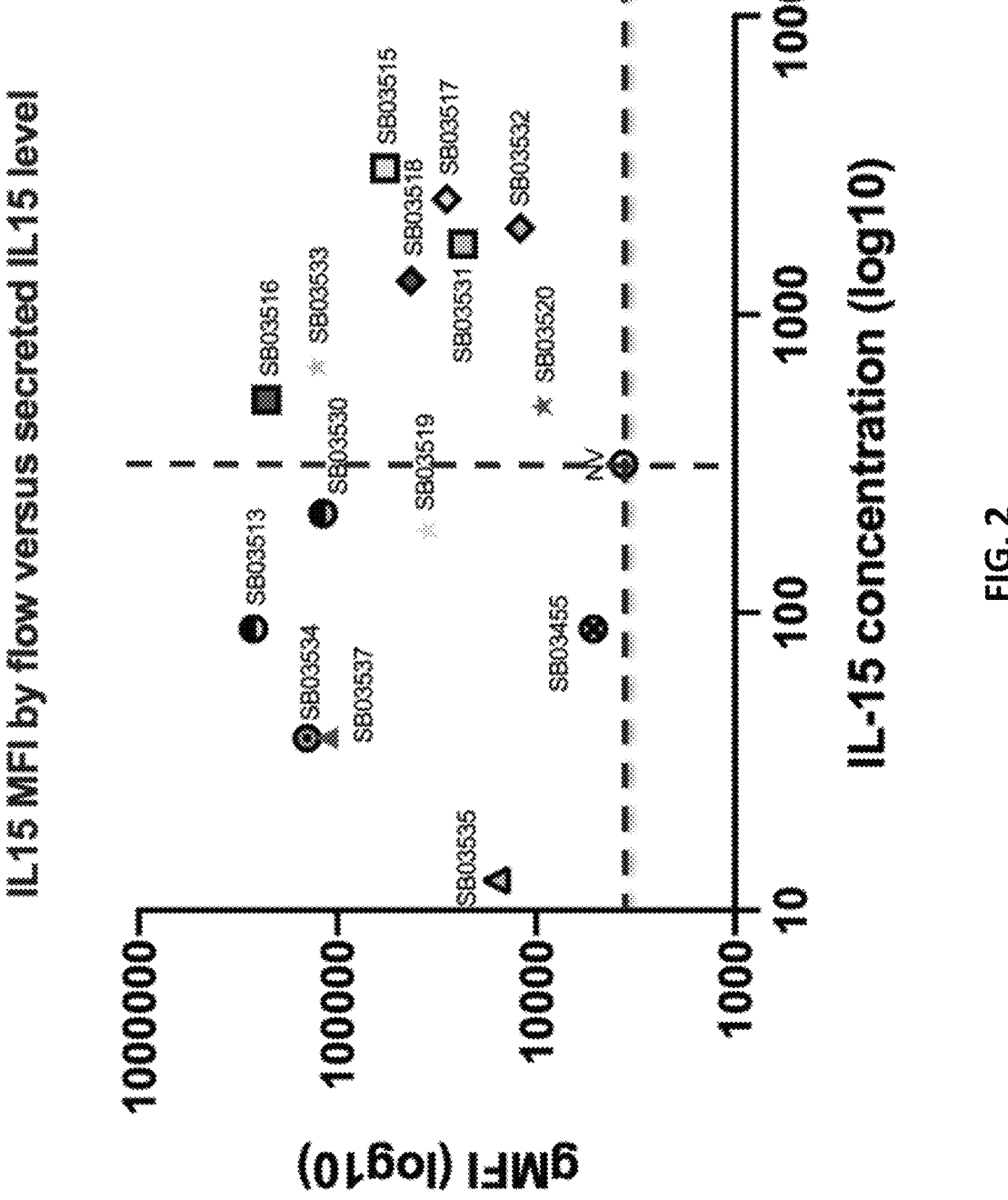
FIG. 2 provides a plot of membrane-bound expression as assayed by flow cytometry (calculated as geometric mean fluorescent intensity, "gMFI," y axis) and IL-15 secretion as determined by ELISA (measured as pg/ml, x-axis) for each Membrane-Cleavable IL-15 construct.

Lentivirus was produced as described in Example 1, encoding the constructs described in Table B. Primary NK cells were transduced with the lentiviruses by transduction methods described in Example 1. IL-15 membrane-bound expression and secretion were assayed as described in Example 1. A graph of the relationship of membrane-bound expression and secretion for each construct is provided in FIG. 2. Constructs SB03514 and SB03536 are not shown in the graph due to low expression levels. As shown in FIG. 2, the secretion levels for each construct widely vary. SB03516, SB03515, SB03533, SB03518, SB03517, SB03531, SB03532, and SB03520 have higher IL-15 secretion levels compared to a no virus control (NV). Of these constructs, SB03515, SB03517, SB03532, SB03531, and SB03518 demonstrated the highest secretion levels. As can be seen in FIG. 2, the linker type and orientation correlate with secretion level. For example, constructs including a single gly-ser linker (SEQ ID NO: 195) C-terminal to the cleavage site (see data points with a square shape), and constructs including a gly-ser linker (SEQ ID NO: 195) N-terminal to the cleavage site and a second gly-ser linker (SEQ ID NO: 197) C-terminal to the cleavage site (see data points with a diamond shape) had the highest secretion levels. Furthermore, use of a single gly-ser linker (SEQ ID NO: 195) N-terminal to the cleavage site (without a second gly-ser linker C-terminal to the cleavage site) correlated with an intermediate secretion level. Thus, the variation in linkers and linker orientation as shown in Table B provide the opportunity to select for a desired ratio of cell bound to secreted IL-15.

Example 3—Regulated IL-12 Secretion

Variations of Membrane-Cleavable systems, including three of the protease cleavage sites shown in Table A (SEQ ID NOs: 180, 187, and 191) were assessed for the ability to regulate the secretion of a secretable payload, IL-12, by NK cells and T cells. The Membrane-Cleavable systems of this example included an orientation of, in the N-terminal to C-terminal direction, S-C-MT, in which S refers to the secretable payload, C refers to a protease cleavage site, and MT refers to a cell membrane tethering domain.
Engineering of IL-12 Secreting Cells:
Lentiviral vectors encoding membrane-cleavable IL-12 constructs were generated. Descriptions of the constructs are provided in Table C.

TABLE C

Description of Various Membrane-Cleavable IL-12 Constructs

| Construct | N Term Linker | Cleavage Site | C-Terminal Linker | TM Domain |
|---|---|---|---|---|
| SB04182 | None | VTPEP IFSLI (SEQ ID NO: 191) | SGGGGSG GGGSGGG GSGGGGS GGGSLQ (SEQ ID NO: 195) | B7-1 |
| SB04183 | SGGGGSG GGGSG (SEQ ID NO: 194) | VTPEP IFSLI (SEQ ID NO: 191) | GGGSGGG GSGGGSL Q (SEQ ID NO: 197) | B7-1 |
| SB04184 | SGGGGSG GGGSG (SEQ ID NO: 194) | (SEQ ID NO: 187) | GGGSGGG GSGGGSL Q (SEQ ID NO: 197) | B7-1 |
| SB04185 | SGGGGSG GGGSG (SEQ ID NO: 194) | ITQGL AVSTI SSFF (SEQ ID NO: 198) | GGGSGGG GSGGGSL Q (SEQ ID NO: 197) | B7-1 |

Figure 3C:
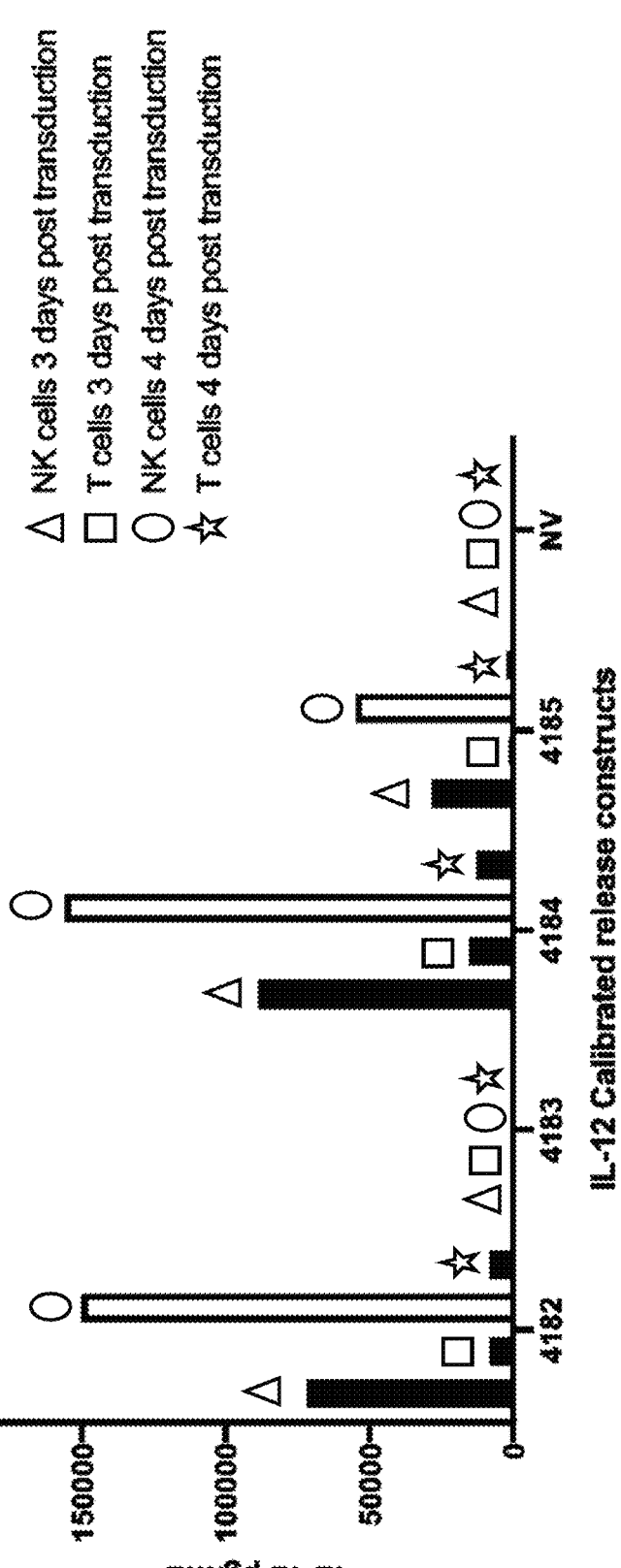

Lentivirus was produced as described in Example 1, encoding the constructs described in Table C. Constructs SB04183, SB04183, and SB04183 include cleavage sites described in Example 1. Construct SB04184 includes an ADAM17 cleavage site that is native to CD16. Primary NK cells were expanded and then transduced with the lentiviruses by transduction methods described in Example 1. IL-12 membrane-bound expression and secretion were assayed as described in Example 1. As shown FIG. 3A, a high level of membrane-bound IL-12 expression (at least 90% of cells positive) was achieved in NK cells with constructs SB04812, SB04184, and SB04185. Additionally, primary T cells were transduced with the lentiviruses by transduction methods described in Example 1. As shown in FIG. 3B, low to moderate membrane-bound IL-12 expression (about 20% to about 15% positive cells) was achieved in T cells with all constructs. As shown in FIG. 3C, a high level of IL-12 secretion (at least 50,000 pg/ml) was achieved in NK cells at 3 days post transduction and 4 days post-transduction for constructs SB04182 and SB04184. For construct SB04185, greater than 50,000 pg/ml of secreted IL-12 was measured at 4 days post-transduction. Additionally, a measurable amount of IL-12 was secreted from T cells with constructs SB04182 and SB04184.

Example 4—Regulated IL-15 Secretion

Variations of Membrane-Cleavable systems, including the protease cleavage sites of SEQ ID NO: 191, were assessed for the ability to regulate secretion of a secretable IL-15 payload. The Membrane-Cleavable systems of this example included an orientation of, in the N-terminal to C-terminal direction, S-C-MT, in which S refers to the secretable payload, C refers to a protease cleavage site, and MT refers to a cell membrane tethering domain.

Dual expression constructs were generated, which included a first promoter operably linked to the Membrane-Cleavable system, and a second promoter operably linked to a chimeric antigen receptor. Descriptions of the constructs are provided in Table D.

TABLE D

Description of Various Membrane-Cleavable IL-15 Constructs

| Construct | Promoter (S) | Secretable Effector (S) | Cleavage Site (C) | TM Domain (MT) |
|---|---|---|---|---|
| CAR/NFAT crIL15 | 5X NFAT minADEp | IL-15 | VTPEPI FSLI (SEQ ID NO: 191) | B7-1 |
| CAR/NFAT cr sushi IL15 | 5X NFAT minADEp | IL-15/ IL-15Rsushi | VTPEPI FSLI (SEQ ID NO: 191) | B7-1 |
| CAR/SV40 crIL15 | SV40 | IL-15 | VTPEPI FSLI (SEQ ID NO: 191) | B7-1 |

Figure 4B:
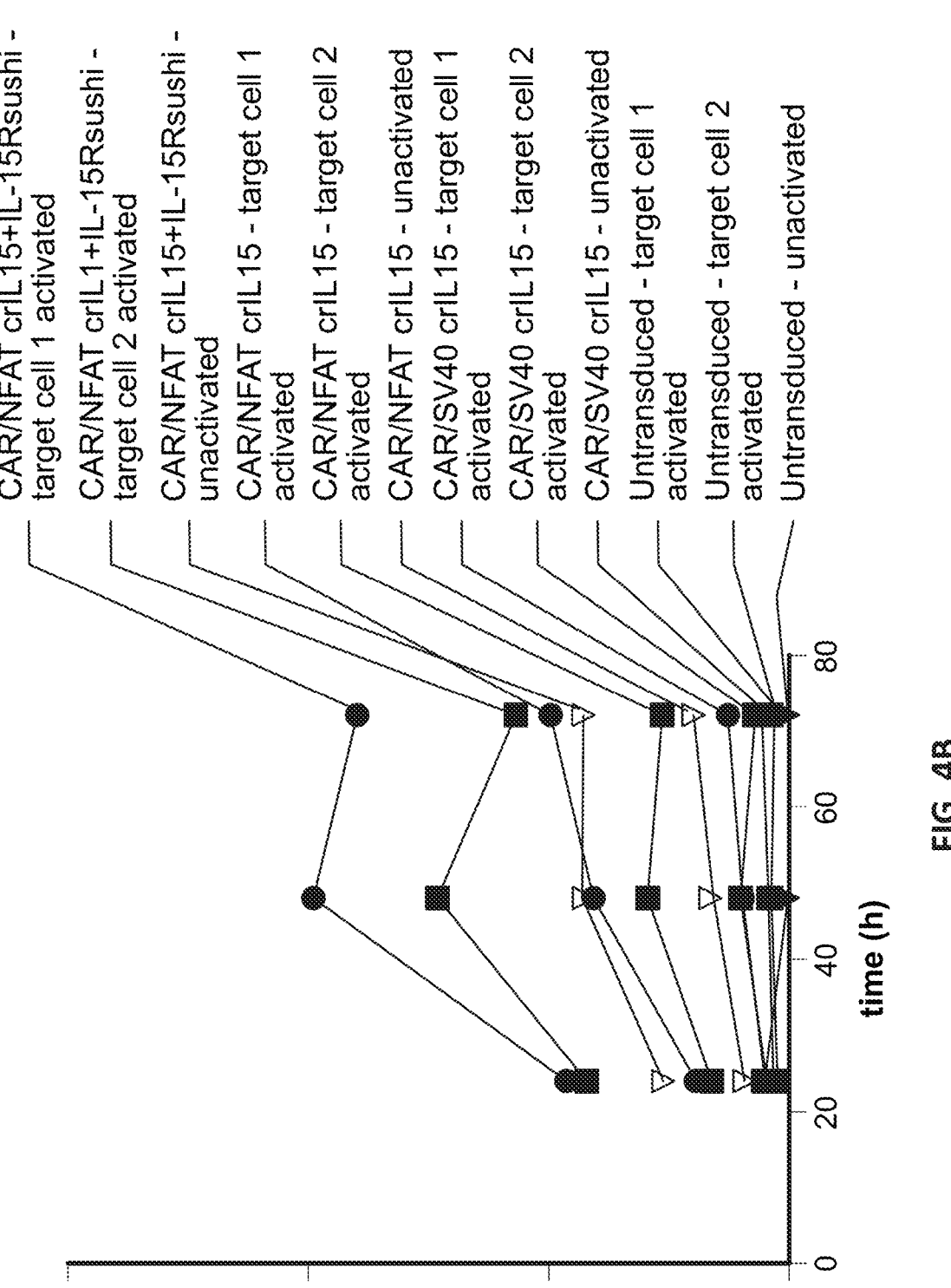

Lentivirus was produced as described in Example 1, encoding the constructs described in Table D. Primary, donor derived NK cells (expanded with IL-15/IL-21-expressing feeder cells) were transduced with each virus (or untransduced as a control). Next, 18 days after transduction, the NK cells were activated by co-culture with target cells that express the target antigen of the CAR (two different target cell lines were used, "target cell 1" and "target cell 2"). 24 hours after activation, IL-15 membrane-bound expression and secretion were assayed as described in Example 1. As shown FIG. 4A, membrane-bound IL-15 expression was detectable 24 hours after activation. Next, secretion levels were assayed as described in Example 1 at 24 hours, 48 hours, and 72 hours post-activation. As shown in FIG. 4B, all constructs achieved an increase in secreted IL-15 following the 24 hour time-point. Additionally, of the three constructs, the IL-15/IL-15Rsuhi construct achieved the highest levels of secretion.

Other Sequences

HIV-1 protease
(SEQ ID NO: 144):
PQVTLWQRPLVTIKIGGQLKEALLDTGADDTVLEEMSLPG

RWKPKMIGGIGGFIKVRQYDQILIEICGHKAIGTVLVGPT

PVNIIGRNLLTQIGCTLNF

Angiotensin converting enzyme (ACE)
(SEQ ID NO: 156):
MGAASGRRGPGLLLPLPLLLLLLPPQPALALDPGLQPGNFS

ADEAGAQLFAQSYNSSAEQVLFQSVAASWAHDTNITAENA

RRQEEAALLSQEFAEAWGQKAKELYEPIWQNFTDPQLRRI

IGAVRTLGSANLPLAKRQQYNALLSNMSRIYSTAKVCLPN

KTATCWSLDPDLTNILASSRSYAMLLFAWEGWHNAAGIPL

KPLYEDFTALSNEAYKQDGFTDTGAYWRSWYNSPTFEDDL

EHLYQQLEPLYLNLHAFVRRALHRRYGDRYINLRGPIPAH

LLGDMWAQSWENIYDMVVPFPDKPNLDVTSTMLQQGWNAT

HMFRVAEEFFTSLELSPMPPEFWEGSMLEKPADGREVVCH

ASAWDFYNRKDFRIKQCTRVTMDQLSTVHHEMGHIQYYLQ

YKDLPVSLRRGANPGFHEAIGDVLALSVSTPEHLHKIGLL

DRVTNDTESDINYLLKMALEKIAFLPFGYLVDQWRWGVFS

GRTPPSRYNFDWWYLRTKYQGICPPVTRNETHFDAGAKFH

VPNVTPYIRYFVSFVLQFQFHEALCKEAGYEGPLHQCDIY

RSTKAGAKLRKVLQAGSSRPWQEVLKDMVGLDALDAQPLL

KYFQPVTQWLQEQNQQNGEVLGWPEYQWHPPLPDNYPEGI

DLVTDEAEASKFVEEYDRTSQVVWNEYAEANWNYNTNITT

ETSKILLQKNMQIANHTLKYGTQARKFDVNQLQNTTIKRI

IKKVQDLERAALPAQELEEYNKILLDMETTYSVATVCHPN

GSCLQLEPDLTNVMATSRKYEDLLWAWEGWRDKAGRAILQ

FYPKYVELINQAARLNGYVDAGDSWRSMYETPSLEQDLER

LFQELQPLYLNLHAYVRRALHRHYGAQHINLEGPIPAHLL

GNMWAQTWSNIYDLVVPFPSAPSMDTTEAMLKQGWTPRRM

FKEADDFFTSLGLLPVPPEFWNKSMLEKPTDGREVVCHAS

AWDFYNGKDFRIKQCTTVNLEDLVVAHHEMGHIQYFMQYK

DLPVALREGANPGFHEAIGDVLALSVSTPKHLHSLNLLSS

EGGSDEHDINFLMKMALDKIAFIPFSYLVDQWRWRVFDGS

ITKENYNQEWWSLRLKYQGLCPPVPRTQGDFDPGAKFHIP

SSVPYIRYFVSFIIQFQFHEALCQAAGHTGPLHKCDIYQS

KEAGQRLATAMKLGFSRPWPEAMQLITGQPNMSASAMLSY

FKPLLDWLRTENELHGEKLGWPQYNWTPNSARSEGPLPDS

GRVSFLGLDLDAQQARVGQWLLLFLGIALLVATLGLSQRL

FSIRHRSLHRHSHGPQFGSEVELRHS

-continued

DENV NS3pro (NS2B/NS3) >sp|P33478|1475-2093
(SEQ ID NO: 157):
SGVLWDTPSPPEVERAVLDDGIYRIMQRGLLGRSQVGVGV

FQDGVFHTMWHVTRGAVLMYQGKRLEPSWASVKKDLISYG

GGWRFQGSWNTGEEVQVIAVEPGKNPKNVQTAPGTFKTPE

GEVGAIALDFKPGTSGSPIVNREGKIVGLYGNGVVTTSGT

YVSAIAQAKASQEGPLPEIEDEVFRKRNLTIMDLHPGSGK

TRRYLPAIVREAIRRNVRTLILAPTRVVASEMAEALKGMP

IRYQTTAVKSEHTGKEIVDLMCHATFTMRLLSPVRVPNYN

MIIMDEAHFTDPASIARRGYISTRVGMGEAAAIFMTATPP

GSVEAFPQSNAVIQDEERDIPERSWNSGYEWITDFPGKTV

WFVPSIKSGNDIANCLRKNGKRVIQLSRKTFDTEYQKTKN

NDWDYVVTTDISEMGANFRADRVIDPRRCLKPVILKDGPE

RVILAGPMPVTVASAAQRRGRIGRNQNKEGDQYVYMGQPL

NNDEDHAHWTEAKMLLDNINTPEGIIPALFEPEREKSAAI

DGEYRLRGEARKTFVELMRRGDLPVWLSYKVASEGFQYSD

RRWCFDGERNNQVLEENMDVEMWTKEGERKKLRPRWLDAR

TYSDPLALREFKEFAAGRR

DENV NS3pro (NS2B/NS3) >sp|P14340|1476-2093
(SEQ ID NO: 158):
AGVLWDVPSPPPVGKAELEDGAYRIKQKGILGYSQIGAGV

YKEGTFHTMWHVTRGAVLMHKGKRIEPSWADVKKDLISYG

GGWKLEGEWKEGEEVQVLALEPGKNPRAVQTKPGLFKTNA

GTIGAVSLDFSPGTSGSPIIDKKGKVVGLYGNGVVTRSGA

YVSAIAQTEKSIEDNPEIEDDIFRKRKLTIMDLHPGAGKT

KRYLPAIVREAIKRGLRTLILAPTRVVAAEMEEALRGLPI

RYQTPAIRAEHTGREIVDLMCHATFTMRLLSPVRVPNYNL

IIMDEAHFTDPASIAARGYISTRVEMGEAAGIFMTATPPG

SRDPFPQSNAPIMDEEREIPERSWSSGHEWVTDFKGKTVW

FVPSIKAGNDIAACLRKNGKKVIQLSRKTFDSEYVKTRTN

DWDFVVTTDISEMGANFKAERVIDPRRCMKPVILTDGEER

VILAGPMPVTHSSAAQRRGRIGRNPKNENDQYIYMGEPLE

NDEDCAHWKEAKMLLDNINTPEGIIPSMFEPEREKVDAID

GEYRLRGEARKTFVDLMRRGDLPVWLAYRVAAEGINYADR

RWCFDGIKNNQILEENVEVEIWTKEGERKKLKPRWLDAKI

YSDPLALKEFKEFAAGRK

DENV NS3pro (NS2B/NS3) >sp/Q99D35|1474-2092
(SEQ ID NO: 159):
SGVLWDVPSPPETQKAELEEGVYRIKQQGIFGKTQVGVGV

QKEGVFHTMWHVTRGAVLTHNGKRLEPNWASVKKDLISYG

GGWRLSAQWQKGEEVQVIAVEPGKNPKNFQTMPGIFQTTT

GEIGAIALDFKPGTSGSPIINREGKVVGLYGNGVVTKNGG

YVSGIAQTNAEPDGPTPELEEEMFKKRNLTIMDLHPGSGK

TRKYLPAIVREAIKRRLRTLILAPTRVVAAEMEEALKGLP

IRYQTTATKSEHTGREIVDLMCHATFTMRLLSPVRVPNYN

LIIMDEAHFTDPASIAARGYISTRVGMGEAAAIFMTATPP

GTADAFPQSNAPIQDEERDIPERSWNSGNEWITDFVGKTV

WFVPSIKAGNDIANCLRKNGKKVIQLSRKTFDTEYQKTKL

NDWDFVVTTDISEMGANFKADRVIDPRRCLKPVILTDGPE

RVILAGPMPVTVASAAQRRGRVGRNPQKENDQYIFMGQPL

NKDEDHAHWTEAKMLLDNINTPEGIIPALFEPEREKSAAI

DGEYRLKGESRKTFVELMRRGDLPVWLAHKVASEGIKYTD

RKWCFDGERNNQILEENMDVEIWTKEGEKKKLRPRWLDAR

TYSDPLALKEFKDFAAGRK

DENV NS3pro (NS2B/NS3) >sp/Q5UCB8|1475-2092
(SEQ ID NO: 160):
SGALWDVPSPAATQKAALSEGVYRIMQRGLFGKTQVGVGI

HIEGVFHTMWHVTRGSVICHETGRLEPSWADVRNDMISYG

GGWRLGDKWDKEEDVQVLAIEPGKNPKHVQTKPGLFKTLT

GEIGAVTLDFKPGTSGSPIINRKGKVIGLYGNGVVTKSGD

YVSAITQAERIGEPDYEVDEDIFRKKRLTIMDLHPGAGKT

KRILPSIVREALKRRLRTLILAPTRVVAAEMEEALRGLPI

RYQTPAVKSEHTGREIVDLMCHATFTTRLLSSTRVPNYNL

IVMDEAHFTDPSSVAARGYISTRVEMGEAAAIFMTATPPG

TTDPFPQSNSPIEDIEREIPERSWNTGFDWITDYQGKTVW

FVPSIKAGNDIANCLRKSGKKVIQLSRKTFDTEYPKTKLT

DWDFVVTTDISEMGANFRAGRVIDPRRCLKPVILPDGPER

VILAGPIPVTPASAAQRRGRIGRNPAQEDDQYVFSGDPLK

NDEDHAHWTEAKMLLDNIYTPEGIIPTLFGPEREKTQAID

GEFRLRGEQRKTFVELMRRGDLPVWLSYKVASAGISYKDR

EWCFTGERNNQILEENMEVEIWTREGEKKKLRPKWLDARV

YADPMALKDFKEFASGRK

PEST (two copies of residues 277-307 of
human IKBa; SEQ ID NO: 161):
LQMLPESEDEESYDTESEFTEFTEDELPYDDGSLQMLPES

EDEESYDTESEFTEFTEDELPYDD

GRR (residues 352-408 of human p105;
SEQ ID NO: 162):
EIKDKEEVQRKRQKLMPNFSDSFGGGSGAGAGGGGMFGSG

GGGGGTGSTGPGYSFPH

DRR (residues 210-295 of yeast Cdc34;
SEQ ID NO: 163):
IDDENGSVILQDDDYDDGNNHIPFEDDDVYNYNDNDDDDE

RIEFEDDDDDDDDDSIDNDSVMDRKQPHKAEDESEDVEDVE

RVSKKD

SNS (tandem repeat of SP2 and NB
(SP2-NB-SP2 of influenza A or
influenza B; e.g.,
SEQ ID NO: 164):
PESMREEYRKEGSKRIKCPDCEPFCNKRGSPESMREEYRKE -continued RPB (four copies of residues 1688-1702 of
yeast RPB; SEQ ID NO: 165):
RSYSPTSPNYSPTSPSGSYSPTSPNYSPTSPSGGSRSYSP

TSPNYSPTSPSGSYSPTSPNYSPTSPSG

SPmix (tandem repeat of SP1 and SP2
(SP2-SP1-SP2-SP1-SP2 of influenza A
virus M2 protein; SEQ ID NO: 166):
PESMREEYRKEGSSLLTEVETPGSPESMREEYRKEGSSLL

TEVETPGSPESMREEYRKE

NS2 (three copies of residues 79-93
of influenza A virus NS protein;
SEQ ID NO: 167):
LIEEVRHRLKTTENSGSLIEEVRHRLKTTENSGSLIEE

VRHRLKTTENSGS

ODC (residues 106-142 of ornithine
decarboxylase; SEQ ID NO: 168):
FPPEVEEQDDGTLPMSCAQESGMDRHPAACASARINV mouse ODC
(residues 422-461; SEQ ID NO: 169):
SHGFPPEVEEQAAGTLPMSCAQESGMDRHPAACASARINV SB03513
                               (SEQ ID NO: 210)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEKNIKEF

LQSFVHIVQMFINTSDEPHYSQRRLLPSWAITLISVNGIF

VICCLTYCFAPRCRERRRNERLRRESVRPV

SB03514
                               (SEQ ID NO: 211)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEKNIKEF

LQSFVHIVQMFINTSVTPEPIFSLILLPSWAITLISVNGI

FVICCLTYCFAPRCRERRRNERLRRESVRPV

SB03515
                               (SEQ ID NO: 212)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEKNIKEF

LQSFVHIVQMFINTSDEPHYSQRRSGGGGSGGGGSGGGGS

GGGGSGGGGSLQLLPSWAITLISVNGIFVICCLTYCFAPRC

RERRRNERLRRESVRPV

SB03516
                               (SEQ ID NO: 213)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEKNIKEF

LQSFVHIVQMFINTSVTPEPIFSLISGGGGSGGGGSGGGG

SGGGGSGGGSLQLLPSWAITLISVNGIFVICCLTYCFAPR

CRERRRNERLRRESVRPV

SB03517

-continued (SEQ ID NO: 214)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEKNIKEF

LQSFVHIVQMFINTSSGGGGSGGGGSGDEPHYSQRRGGGS

GGGGSGGGGSLQLLPSWAITLISVNGIFVICCLTYCFAPRC

RERRRNERLRRESVRPV

SB03518
                               (SEQ ID NO: 215)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEKNIKEF

LQSFVHIVQMFINTSSGGGGSGGGGSGVTPEPIFSLIGGG

SGGGGSGGGSLQLLPSWAITLISVNGIFVICCLTYCFAPR

CRERRRNERLRRESVRPV

SB03519
                               (SEQ ID NO: 216)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEKNIKEF

LQSFVHIVQMFINTSSGGGGSGGGGSGGGGSGGGGSGGGS

LQDEPHYSQRRLLPSWAITLISVNGIFVICCLTYCFAPRC

RERRRNERLRRESVRPV

SB03520
                               (SEQ ID NO: 217)
AATMDWTWILFLVAAATRVHSNWVNVISDLKKIEDLIQSM

HIDATLYTESDVHPSCKVTAMKCFLLELQVISLESGDASI

HDTVENLIILANNSLSSNGNVTESGCKECEELEEK

Substitute Specification - CLEAN
NIKEFLQSFVHIVQMFINTSSGGGGSGGGGSGGGGSGGGG

SGGGSLQVTPEPIFSLILLPSWAITLISVNGIFVICCLTY

CFAPRCRERRRNERLRRESVRPV

5X NFAT minADEp promoter
                               (SEQ ID NO: 218)
GGGACTTTCCACTGGGGACTTTCCACTGGGGACTTTCCAC TGGGGACTTTCCACTGGGGACTTTCCACTCCTGCAGGagc tGGCGCGCCAGACGCTAGCGGGGGGCTATAAAAGGGGGTG

GGGGCGTTCGTCCTCACTCT

INTERPRETATIONS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

---

```
                          SEQUENCE LISTING

Sequence total quantity: 227
SEQ ID NO: 1            moltype = DNA  length = 31
FEATURE                Location/Qualifiers
misc_feature           1..31
                       note = Description of Artificial Sequence: Synthetic
                        oligonucleotide
source                 1..31
                       mol_type = other DNA
                       organism = synthetic construct
SEQUENCE: 1
agagggtata taatggaagc tcgacttcca g                               31

SEQ ID NO: 2            moltype = DNA  length = 52
FEATURE                Location/Qualifiers
misc_feature           1..52
                       note = Description of Artificial Sequence: Synthetic
                        oligonucleotide
source                 1..52
                       mol_type = other DNA
                       organism = synthetic construct
SEQUENCE: 2
gggaatttcc ggggactttc cgggaatttc cggggacttt ccgggaattt cc       52

SEQ ID NO: 3            moltype = DNA  length = 85
FEATURE                Location/Qualifiers
misc_feature           1..85
                       note = Description of Artificial Sequence: Synthetic
                        oligonucleotide
source                 1..85
                       mol_type = other DNA
                       organism = synthetic construct
SEQUENCE: 3
caccagacag tgacgtcagc tgccagatcc catggccgtc atactgtgac gtctttcaga  60
caccccattg acgtcaatgg gagaa                                       85

SEQ ID NO: 4            moltype = DNA  length = 90
FEATURE                Location/Qualifiers
misc_feature           1..90
                       note = Description of Artificial Sequence: Synthetic
                        oligonucleotide
source                 1..90
                       mol_type = other DNA
                       organism = synthetic construct
SEQUENCE: 4
ggaggaaaaa ctgtttcata cagaaggcgt ggaggaaaaa ctgtttcata cagaaggcgt  60
ggaggaaaaa ctgtttcata cagaaggcgt                                 90

SEQ ID NO: 5            moltype = DNA  length = 115
FEATURE                Location/Qualifiers
misc_feature           1..115
                       note = Description of Artificial Sequence: Synthetic
                        polynucleotide
source                 1..115
                       mol_type = other DNA
                       organism = synthetic construct
SEQUENCE: 5
aggatgtcca tattaggaca tctaggatgt ccatattagg acatctagga tgtccatatt  60
aggacatcta ggatgtccat attaggacat ctaggatgtc catattagga catct      115

SEQ ID NO: 6            moltype = DNA  length = 115
FEATURE                Location/Qualifiers
misc_feature           1..115
                       note = Description of Artificial Sequence: Synthetic
                        polynucleotide
source                 1..115
                       mol_type = other DNA
                       organism = synthetic construct
SEQUENCE: 6
agtatgtcca tattaggaca tctaccatgt ccatattagg acatctacta tgtccatatt  60
aggacatctt gtatgtccat attaggacat ctaaaatgtc catattagga catct      115
```

-continued

```
SEQ ID NO: 7              moltype = DNA   length = 48
FEATURE                   Location/Qualifiers
misc_feature              1..48
                          note = Description of Artificial Sequence: Synthetic
                           oligonucleotide
source                    1..48
                          mol_type = other DNA
                          organism = synthetic construct
SEQUENCE: 7
tgagtcagtg actcagtgag tcagtgactc agtgagtcag tgactcag                 48

SEQ ID NO: 8              moltype = DNA   length = 120
FEATURE                   Location/Qualifiers
misc_feature              1..120
                          note = Description of Artificial Sequence: Synthetic
                           polynucleotide
source                    1..120
                          mol_type = other DNA
                          organism = synthetic construct
SEQUENCE: 8
agatcaaagg gtttaagatc aaagggctta agatcaaagg gtataagatc aaagggccta  60
agatcaaagg gactaagatc aaagggttta agatcaaagg gcttaagatc aaagggccta  120

SEQ ID NO: 9              moltype = DNA   length = 32
FEATURE                   Location/Qualifiers
misc_feature              1..32
                          note = Description of Artificial Sequence: Synthetic
                           oligonucleotide
source                    1..32
                          mol_type = other DNA
                          organism = synthetic construct
SEQUENCE: 9
gtctagacgt ctagacgtct agacgtctag ac                                 32

SEQ ID NO: 10             moltype = DNA   length = 24
FEATURE                   Location/Qualifiers
misc_feature              1..24
                          note = Description of Artificial Sequence: Synthetic
                           oligonucleotide
source                    1..24
                          mol_type = other DNA
                          organism = synthetic construct
SEQUENCE: 10
cagacacaga cacagacaca gaca                                          24

SEQ ID NO: 11             moltype = DNA   length = 65
FEATURE                   Location/Qualifiers
misc_feature              1..65
                          note = Description of Artificial Sequence: Synthetic
                           oligonucleotide
source                    1..65
                          mol_type = other DNA
                          organism = synthetic construct
SEQUENCE: 11
ggatccggta ctcgagatct gcgatctaag taagcttggc attccggtac tgttggtaaa  60
gccac                                                               65

SEQ ID NO: 12             moltype = DNA   length = 588
FEATURE                   Location/Qualifiers
misc_feature              1..588
                          note = Description of Artificial Sequence: Synthetic
                           polynucleotide
source                    1..588
                          mol_type = other DNA
                          organism = synthetic construct
SEQUENCE: 12
gttgacattg attattgact agttattaat agtaatcaat tacggggtca ttagttcata  60
gcccatatat ggagttccgc gttacataac ttacggtaaa tggcccgcct ggctgaccgc  120
ccaacgaccc ccgcccattg acgtcaataa tgacgtatgt tcccatagta acgccaatag  180
ggactttcca ttgacgtcaa tgggtggagt atttacggta aactgcccac ttggcagtac  240
atcaagtgta tcatatgcca agtacgcccc ctattgacgt caatgacggt aaatggcccg  300
cctggcatta tgcccagtac atgaccttat gggactttcc tacttggcag tacatctacg  360
tattagtcat cgctattacc atggtgatgc ggttttggca gtacatcaat gggcgtggat  420
agcggtttga ctcacgggga tttccaagtc tccaccccat tgacgtcaat gggagtttgt  480
tttggcacca aaatcaacgg gactttccaa aatgtcgtaa caactccgcc ccattgacgc  540
aaatgggcgg taggcgtgta cggtgggagg tctatataag cagagctc                588

SEQ ID NO: 13             moltype = DNA   length = 1179
```

-continued

```
FEATURE              Location/Qualifiers
misc_feature         1..1179
                     note = Description of Artificial Sequence: Synthetic
                     polynucleotide
source               1..1179
                     mol_type = other DNA
                     organism = synthetic construct SEQUENCE: 13
ggctccggtg cccgtcagtg ggcagagcgc acatcgccca cagtccccga gaagttggggg   60
ggaggggtcg gcaattgaac cggtgcctag agaaggtggc gcggggtaaa ctgggaaagt  120
gatgccgtgt actggctccg ccttttttccc gagggtgggg gagaaccgta tataagtgca  180
gtagtcgccg tgaacgttct tttttcgcaac gggtttgccg ccagaacaca ggtaagtgcc  240
gtgtgtggtt cccgcgggcc tggcctcttt acgggttatg gcccttgcgt gccttgaatt  300
acttccacct ggctgcagta cgtgattctt gatcccgacg ttcgggttgg aagtgggtgg  360
gagagttcga ggccttgcgc ttaaggagcc ccttcgcctc gtgcttgagt tgaggcctgg  420
cctgggcgct ggggccgccg cgtgcgaatc tggtggcacc ttcgcgcctg tctcgctgct  480
ttcgataagt ctctagccat ttaaaatttt tgatgacctg ctgcgacgct tttttttctgg  540
caagatagtc ttgtaaatgc gggccaagat ctgcacactg gtatttcggt ttttggggcc  600
gcgggcggcg acggggcccg tgcgtcccag cgcacatgtt cggcgaggcg gggcctgcga  660
gcgcgaccac cgagaatcgg acgggggtag tctcaagctg gccggcctgc tctggtgcct  720
gtcctcgcgc cgccgtgtat cgccccgccc cgggcggcaa ggctggcccg gtcggcacca  780
gttgcgtgag cggaaagatg gccgcttccc ggtcctgctg caggggagctc aaaatggagg  840
acgcggcgct cgggagagcg ggcgggtgag tcacccacac aaaggaaaag ggcctttccg  900
tcctcagccg tcgcttcatg tgactccacg gagtaccggg cgccgtccag gcacctcgat  960
tagttctcga gctttttggag tacgtcgtct ttaggttggg gggaggggtt ttatgcgatg 1020
gagtttcccc acactgagtg ggtggagact gaagttaggc cagcttggca cttgatgtaa 1080
ttctccttgg aatttgccct ttttgagttt ggatcttggt tcattctcaa gcctcagaca 1140
gtggttcaaa gttttttttct tccatttcag gtgtcgtga                       1179

SEQ ID NO: 14           moltype = DNA   length = 544
FEATURE                 Location/Qualifiers
misc_feature            1..544
                        note = Description of Artificial Sequence: Synthetic
                        polynucleotide
source                  1..544
                        mol_type = other DNA
                        organism = synthetic construct SEQUENCE: 14
ggatctgcga tcgctccggt gcccgtcagt gggcagagcg cacatcgccc acagtccccg   60
agaagttggg gggaggggtc ggcaattgaa ccggtgccta gagaaggtgg cgcggggtaa  120
actgggaaag tgatgtcgtg tactggctcc gcctttttcc cgagggtggg ggagaaccgt  180
atataagtgc agtagtcgcc gtgaacgttc tttttcgcaa cgggtttgcc gccagaacac  240
agctgaagct tcgaggggct cgcatctctc cttcacgcgc cgccgccct acctgaggcc  300
gccatccacg ccggttgagt cgcgttctgc cgcctcccgc ctgtggtgcc tcctgaactg  360
cgtccgccgt ctaggtaagt ttaaagctca ggtcgagacc gggcctttgt ccggcgctcc  420
cttggagcct acctagactc agccggctct ccacgctttg cctgaccctg cttgctcaac  480
tctacgtctt tgtttcgttt tctgttctgc gccgttacag atccaagctg tgaccggcgc  540
ctac                                                              544

SEQ ID NO: 15           moltype = DNA   length = 399
FEATURE                 Location/Qualifiers
misc_feature            1..399
                        note = Description of Artificial Sequence: Synthetic
                        polynucleotide
source                  1..399
                        mol_type = other DNA
                        organism = synthetic construct SEQUENCE: 15
tttatttagt ctccagaaaa aggggggaat gaaagacccc acctgtaggt ttggcaagct   60
aggatcaagg ttaggaacag agagacagca gaatatgggc caaacaggat atctgtggta  120
agcagttcct gccccggctc agggccaaga acagttggaa cagcagaata tgggccaaac  180
aggatatctg tggtaagcag ttcctgcccc ggctcagggc caagaacaga tggtccccag  240
atgcggtccc gccctcagca gtttctagag aaccatcaga tgtttccagg gtgccccaag  300
gacctgaaat gaccctgtgc cttatttgaa ctaaccaatc agttcgcttc tcgcttctgt  360
tcgcgcgctt ctgctccccg agctcaataa aagagccca                         399

SEQ ID NO: 16           moltype = DNA   length = 511
FEATURE                 Location/Qualifiers
misc_feature            1..511
                        note = Description of Artificial Sequence: Synthetic
                        polynucleotide
source                  1..511
                        mol_type = other DNA
                        organism = synthetic construct SEQUENCE: 16
ggggttgggg ttgcgccttt tccaaggcag ccctgggttt gcgcagggac gcggctgctc   60
tgggcgtggt tccgggaaac gcagcggcgc cgacctgggg tctcgcacat tcttcacgtc  120
cgttcgcagc gtcacccgga tcttcgccgc taccttgtgg gcccccccgg cgacgcttcc  180
tgctccgccc ctaagtcggg aaggttcctt gcggttcgcg gcgtgccgga cgtgacaaac  240
```

```
ggaagccgca cgtctcacta gtaccctcgc agacggacag cgccagggag caatggcagc   300
gcgccgaccg cgatgggctg tggccaatag cggctgctca gcggggcgcg ccgagagcag   360
cggccgggaa ggggcggtgc gggaggcggg gtgtggggcg gtagtgtggg ccctgttcct   420
gcccgcgcg tgttccgcat tctgcaagcc tccggagcgc acgtcggcag tcggctccct    480
cgttgaccga atcaccgacc tctctcccca g                                  511

SEQ ID NO: 17          moltype = DNA   length = 408
FEATURE                Location/Qualifiers
misc_feature           1..408
                       note = Description of Artificial Sequence: Synthetic
                        polynucleotide
source                 1..408
                       mol_type = other DNA
                       organism = synthetic construct
SEQUENCE: 17
gtaacgccat tttgcaaggc atggaaaaat accaaaccaa gaatagagaa gttcagatca   60
agggcgggta catgaaaata gctaacgttg ggccaaacag gatatctgcg gtgagcagtt   120
tcggccccgg cccgggggcca agaacagatg gtcaccgcag tttcggcccc cgcccgaggc  180
caagaacaga tggtccccag atatggccca accctcagca gtttcttaag acccatcaga   240
tgtttccagg ctcccccaag gacctgaaat gaccctgcgc cttatttgaa ttaaccaatc   300
agcctgcttc tcgcttctgt tcgcgcgctt ctgcttcccg agctctataa aagagctcac   360
aaccctcac tcggcgcgcc agtcctccga cagactgagt cgcccggg                 408

SEQ ID NO: 18          moltype = DNA   length = 344
FEATURE                Location/Qualifiers
misc_feature           1..344
                       note = Description of Artificial Sequence: Synthetic
                        polynucleotide
source                 1..344
                       mol_type = other DNA
                       organism = synthetic construct
SEQUENCE: 18
ctgtggaatg tgtgtcagtt agggtgtgga aagtccccag gctccccagc aggcagaagt   60
atgcaaagca tgcatctcaa ttagtcagca accaggtgtg gaaagtcccc aggctcccca   120
gcaggcagaa gtatgcaaag catgcatctc aattagtcag caaccatagt cccgcccta    180
actccgccca tcccgcccct aactccgccc agttccgccc attctccgcc ccatggctga   240
ctaatttttt ttatttatgc agaggccgag gccgcctctg cctctgagct attccagaag   300
tagtgaggag gcttttttgg aggcctaggc ttttgcaaaa agct                    344

SEQ ID NO: 19          moltype = DNA   length = 1229
FEATURE                Location/Qualifiers
misc_feature           1..1229
                       note = Description of Artificial Sequence: Synthetic
                        polynucleotide
source                 1..1229
                       mol_type = other DNA
                       organism = synthetic construct
SEQUENCE: 19
gcgccgggtt ttggcgcctc ccgcgggcgc cccctcctc acggcgagcg ctgccacgtc    60
agacgaaggg cgcaggagcg ttcctgatcc ttccgcccgg acgctcagga cagcggcccg   120
ctgctcataa gactcggcct tagaaccca gtatcagcag aaggacattt taggacggga    180
cttgggtgac tctagggcac tggtttttctt tccagagagc ggaacaggcg aggaaaagta   240
gtcccttctc ggcgattctg cggagggatc tccgtggggc ggtgaacgcc gatgattata   300
taaggacgcg ccgggtgtgg cacagctagt tccgtcgcag ccgggatttg ggtcgcggtt   360
cttgtttgtg gatcgctgtg atcgtcactt ggtgagttgc gggctgctgg gctggccggg   420
gctttcgtgg ccgccgggcc gctcggtggg acggaagcgt gtggagagac cgccaagggc   480
tgtagtctgg gtccgcgagc aaggttgccc tgaactgggg gttgggggga cgcacaaaa    540
tggcggctgt tcccgagtct tgaatggaag acgcttgtaa ggcgggctgt gaggtcgttg   600
aaacaaggtg gggggcatgg tgggcggcaa gaacccaagg tcttgaggcc ttcgctaatg   660
cgggaaagct cttattcggg tgagatgggc tggggcacca tctggggacc ctgacgtgaa   720
gtttgtcact gactggagaa ctcgggtttg tcgtctggtt gcggggcgg cagttatgcg    780
gtgccgttgg gcagtgcacc cgtacctttg ggagcgcgcg cctcgtcgtg tcgtgacgtc   840
acccgttctg ttggcttata atgcaggggtg gggccacctg ccggtaggtg tgcggtaggc   900
ttttctccgt cgcaggacgc agggttcggg cctagggtag gctctcctga atcgacaggc   960
gccggacctc tggtgagggg agggataagt gaggcgtcag tttctttggt cggttttatg   1020
tacctatctt cttaagtagc tgaagctccg gttttgaact atgcgctcgg ggttggcgag   1080
tgtgttttgt gaagtttttt aggcacctt tgaaatgtaa tcatttgggt caatatgtaa     1140
ttttcagtgt tagactagta aagcttctgc aggtcgactc tagaaaattg tccgctaaat   1200
tctggccgtt tttggctttt ttgttagac                                     1229

SEQ ID NO: 20          moltype = DNA   length = 1179
FEATURE                Location/Qualifiers
misc_feature           1..1179
                       note = Description of Artificial Sequence: Synthetic
                        polynucleotide
source                 1..1179
                       mol_type = other DNA
                       organism = synthetic construct
```

```
SEQUENCE: 20
ggctccggtg cccgtcagtg ggcagagcgc acatcgccca cagtccccga gaagttgggg    60
ggaggggtcg gcaattgaac cggtgcctag agaaggtggc gcggggtaaa ctggaaagt    120
gatgtcgtgt actggctccg ccttttttcc gagggtgggg gagaaccgta tataagtgca   180
gtagtcgccg tgaacgttct ttttcgcaac gggtttgccg ccagaacaca ggtaagtgcc   240
gtgtgtggtt cccgcgggcc tggcctcttt acgggttatg gcccttgcgt gccttgaatt   300
acttccacct ggctgcagta cgtgattctt gatcccgagc ttcgggttgg aagtgggtgg   360
gagagttcga ggccttgcgc ttaaggagcc ccttcgcctc gtgcttgagt tgaggcctgg   420
cctgggcgct ggggccgccg cgtgcgaatc tggtggcacc ttcgcgcctg tctcgctgct   480
ttcgataagt ctctagccat ttaaaatttt tgatgacctg ctgcgacgct ttttttctgg   540
caagatagtc ttgtaaatgc gggccaagat ctgcacactg gtatttcggt ttttggggcc   600
gcgggcggcg acggggcccg tgcgtcccag cgcacatgtt cggcgaggcg gggcctgcga   660
gcgcggccac cgagaatcgg acggggtag tctcaagctg gccggcctgc tctggtgcct    720
ggtctcgcgc cgccgtgtat cgccccgccc tgggcggcaa ggctggcccg gtcggcacca   780
gttgcgtgag cggaaagatg gccgcttccc ggccctgctg cagggagctc aaaatggagg   840
acgcggcgct cgggagagcg ggcgggtgag tcacccacac aaaggaaaag ggcctttccg    900
tcctcagccg tcgcttcatg tgactccacg gagtaccggg gcgtccag gcacctcgat     960
tagttctcga gcttttggag tacgtcgtct ttaggttggg gggagggtt ttatgcgatg    1020
gagtttcccc acactgagtg ggtggagact gaagttaggc cagcttggca cttgatgtaa   1080
ttctccttgg aatttgccct ttttgagttt ggatcttggt tcattctcaa gcctcagaca   1140
gtggttcaaa gttttttct tccatttcag gtgtcgtga                           1179

SEQ ID NO: 21          moltype = DNA  length = 1718
FEATURE                Location/Qualifiers
misc_feature           1..1718
                       note = Description of Artificial Sequence: Synthetic
                        polynucleotide
source                 1..1718
                       mol_type = other DNA
                       organism = synthetic construct
SEQUENCE: 21
actagttatt aatagtaatc aattacgggg tcattagttc atagcccata tatggagttc    60
cgcgttacat aacttacggt aaatggcccg cctggctgac cgcccaacga ccccgcccca   120
ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc cccctattga cgtcaatgac ggtaaatggc ccgcctggca ttatgcccag   300
tacatgacct tatgggactt tcctacttgg cagtacatct acgtattagt catcgctatt   360
accatggtcg aggtgagccc cacgttctgc ttcactctcc catctcccc ccctcccca    420
cccccaattt tgtatttatt tatttttaa ttattttgtg cagcgatggg gcgggggggg   480
ggggggggc gcgcgccagg cggggcgggg cggggcgagg ggcggggcgg ggcgaggcgg    540
agaggtgcgg cggcagccaa tcagagcggc gcgctccgaa agtttccttt tatggcgagg   600
cggcggcggc ggcggcccta taaaagcga agcgcgcggc gggcggggag tcgctgcgac    660
gctgccttcg ccccgtgccc cgctccgccg ccgcctcgcg ccgcccgcgc cggctcggac   720
tgaccgcgtt actcccacag gtgagcgggc gggacggccc ttctcctccg ggctgtaatt   780
agcgcttggt ttaatgacgg cttgtttctt ttctgtggct gcgtgaaagc cttgagggc    840
tccgggaggg ccctttgtgc ggggggagc gctcgggggg tgcgtgcgtg tgtgtgtgcg    900
tggggagcgc gcgcgtgcggc tccgcgctgc ccggcggctg tgagcgctgc gggcgcgcg    960
cggggctttg tgcgctccgc agtgtgcgcg aggggagcgc ggccggcggg ggtgccccgc   1020
ggtgcggggg gggctgcgag gggaacaaag gctgcgtgcg gggtgtgtgc gtggggggt    1080
gagcagggg tgtgggcgcg tcggtcgggc tgcaaccccc cctgcacccc cctccccgag   1140
ttgctgagca cggcccggct tcgggtgcgg ggctccgtac ggggcgtggc gcggggctcg   1200
ccgtgccggg cggggggtgg cggcaggtgg gggtgccggg cggggcgggg ccgcctcggg   1260
ccgggggagg ctcgggggag gggcgcggcg gcccccgagg cgccggcggc tgtcgaggcg   1320
cggcgagccg cagccattgc cttttatggt aatcgtgcga gagggcgcag ggacttcctt   1380
tgtcccaaat ctgtgcggag ccgaaatctg ggaggcgccg ccgcacccc tctagcgggc   1440
gcggggcgaa gcggtgcggc gccggcagga aggaaatggg cggggagggc cttcgtgcgt   1500
cgccgcgccg ccgtcccctt ctccctctcc agcctcgggg ctgtccgcgg ggggacggct   1560
gccttcgggg gggacggggc agggcggggt tcggcttctg gcgtgtgacc ggcggctcta   1620
gagcctctgc taaccatgtt catgccttct tcttttttcct acagctcctg ggcaacgtgc   1680
tggttattgt gctgtctcat catttttggca aagaattc                          1718

SEQ ID NO: 22          moltype = DNA  length = 212
FEATURE                Location/Qualifiers
misc_feature           1..212
                       note = Description of Artificial Sequence: Synthetic
                        polynucleotide
source                 1..212
                       mol_type = other DNA
                       organism = synthetic construct
SEQUENCE: 22
gggcagagcg cacatcgccc acagtccccg agaagttggg gggagggtc ggcaattgaa     60
ccggtgccta gagaaggtgg cgcggggtaa actgggaaag tgatgtcgtg tactggctcc   120
gccttttttcc cgagggtggg ggagaaccgt atataagtgc agtagtcgcc gtgaacgttc   180
tttttcgcaa cgggtttgcc gccagaacac ag                                 212
```

```
SEQ ID NO: 23           moltype = DNA  length = 2379
FEATURE                 Location/Qualifiers
misc_feature            1..2379
                        note = Description of Artificial Sequence: Synthetic
                         polynucleotide
source                  1..2379
                        mol_type = other DNA
                        organism = synthetic construct
SEQUENCE: 23
ccactagttc catgtcctta tatggactca tctttgccta ttgcgacaca cactcaatga    60
acacctacta cgcgctgcaa agagccccgc aggcctgagg tgcccccacc tcaccactct   120
tcctattttt gtgtaaaaat ccagcttctt gtcaccacct ccaaggaggg ggaggaggag   180
gaaggcaggt tcctctaggc tgagccgaat gcccctctgt ggtcccacgc cactgatcgc   240
tgcatgccca ccacctgggt acacacagtc tgtgattccc ggagcagaac ggaccctgcc   300
cacccggtct tgtgtgctac tcagtggaca gacccaaggc aagaaagggt gacaaggaca   360
gggtcttccc aggctggctt tgagttccta gcaccgcccc gcccccaatc ctctgtggca   420
catggagtct tggtccccag agtcccccag cggcctccag atggtctggg agggcagttc   480
agctgtggct gcgcatagca gacatacaac ggacggtggg cccagaccca ggctgtgtag   540
acccagcccc cccgcccccgc agtgcctagg tcacccacta acgccccagg cctggtcttg   600
gctgggcgtg actgttaccc tcaaaagcag gcagctccag ggtaaaaggt gccctgccct   660
gtagagccca ccttccttcc cagggctgcg gctgggtagg tttgtagcct tcatcacggg   720
ccacctccag ccactggacc gctggcccct gccctgtcct ggggagtgtg gtcctgcgac   780
ttctaagtgg ccgcaagcca cctgactccc ccaacaccac actctacctc tcaagcccag   840
gtctctccct agtgacccac ccagcacatt tagctagctg agcccacag ccagaggtcc    900
tcaggccctg ctttcagggc agttgctctg aagtcggcaa gggggagtga ctgcctggcc   960
actccatgcc ctccaagagc tccttctgca ggagcgtaca gaaccaggg ccctggcacc   1020
cgtgcagacc ctgcccacc ccacctgggc gctcagtgcc caagagatgt ccacacctag   1080
gatgtcccgc ggtgggtggg gggcccgaga gacgggcagg ccggggcag gcctggccat    1140
gcggggccga accgggcact gcccagcgtg gggcgcgggg gccacggcgc ggcgccccga   1200
ccccgggcc cagcacccca aggcggccaa cgccaaaact ctccctcctc ctcttcctca    1260
atctcgctct cgctcttttt ttttttcgca aaaggagggg agaggggta aaaaaatgct    1320
gcactgtgcg gcgaagccgg tgagtgagcg gcgcggggcc aatcagcgtg cgccgttccg   1380
aaagttgcct tttatggctc gagcggccgc ggcggcgccc tataaaaccc agcggcgcga   1440
cgcgccacca ccgccgagac cgcgtccgcc ccgcgagcac agagcctcgc ctttgccgat   1500
ccgccgcccg tccacacccg ccgccaggta agcccggcca gccgaccggg gcaggcggct   1560
cacggcccgg ccgcaggcgg ccgcggcccc ttcgcccgtg cagagccgcc gtctgggccg   1620
cagcggggggg cgcatggggg gggaaccgga ccgccgtggg gggcgcggga gaagcccctg   1680
ggcctccgga gatgggggac accccacgcc agttcggagg cgcgaggccg cgctcgggag   1740
gcgcgctccg ggggtgccgc tctcggggcg ggggcaaccg gcggggtctt tgtctgagcc   1800
gggctcttgc caatggggat cgcagggtgg gcgcggcgga gccccgcca ggcccggtgg    1860
gggctggggc gccattgcgc gtgcgcgctg gtcctttggg cgctaactgc gtgcgcgctg   1920
ggaattggcg ctaattgcgc gtgcgcgctg ggactcaagg cgctaactgc gcgtgcgttc   1980
tggggcccgg ggtgccgcgg cctgggctgg ggcgaaggcg ggctcggccg gaaggggtgg   2040
ggtcgccgcg gctcccgggc gcttgcgcgc acttcctgcc cgagccgctg gccgcccgag   2100
ggtgtggccg ctgcgtgcgc gcgcgccgac ccggcgctgt ttgaaccggg cggaggcggg   2160
gctggcgccc ggttgggagg gggttggggc ctggcttcct gccgcgcgcc gcgggacgc    2220
ctccgaccag tgtttgcctt ttatggtaat aacgcggccg gcccggcttc ctttgtcccc   2280
aatctgggcg cgcgccggcg ccccctggcg gcctaaggac tcggcgcgcc ggaagtggcc   2340
agggcggggg cgacctcggc tcacagcgcg cccggctat                          2379

SEQ ID NO: 24           moltype = DNA  length = 529
FEATURE                 Location/Qualifiers
misc_feature            1..529
                        note = Description of Artificial Sequence: Synthetic
                         polynucleotide
source                  1..529
                        mol_type = other DNA
                        organism = synthetic construct
SEQUENCE: 24
gttgatttcc ttcatccctg gcacacgtcc aggcagtgtc gaatccatct ctgctacagg    60
ggaaaacaaa taacatttga gtccagtgga gaccgggagc agaagtaaag ggaagtgata   120
accccagag cccggaagcc tctggaggct gagacctcgc cccccttgcg tgataggggc    180
tacggagcca catgaccaag gcactgtcgc ctccgcacgt gtgagagtgc agggccccaa   240
gatggctgcc aggcctcgag gcctgactct tctatgtcac ttccgtaccg gcgagaaagg   300
cgggccctcc agccaatgag gctgcggggc gggccttcac cttgataggc actcgagtta   360
tccaatggtg cctgcgggcc ggagcgacta ggaactaacg tcatgccgag ttgctgagcg   420
ccggcagggg gggccggggc ggccaaacca atgcgatgcc cggggcggag tcgggcgctc   480
tataagttgt cgataggcgg gcactccgcc ctagtttcta aggaccatg                529

SEQ ID NO: 25           moltype = DNA  length = 794
FEATURE                 Location/Qualifiers
misc_feature            1..794
                        note = Description of Artificial Sequence: Synthetic
                         polynucleotide
source                  1..794
                        mol_type = other DNA
                        organism = synthetic construct
```

```
SEQUENCE: 25
agttccccaa ctttcccgcc tctcagcctt tgaaagaaag aaaggggagg gggcaggccg    60
cgtgcagtcg cgagcggtgc tgggctccgg ctccaattcc ccatctcagt cgctcccaaa   120
gtccttctgt ttcatccaag cgtgtaaggg tccccgtcct tgactcccta gtgtcctgct   180
gcccacagtc cagtcctggg aaccagcacc gatcacctcc catcgggcca atctcagtcc   240
cttccccct acgtcggggc ccacacgctc ggtgcgtgcc cagttgaacc aggcggctgc   300
ggaaaaaaaa aagcggggag aaagtagggc ccggctacta gcggttttac gggcgcacgt   360
agctcaggcc tcaagacctt gggctgggac tggctgagcc tggcgggagg cggggtccga   420
gtcaccgcct gccgccgcgc ccccggtttc tataaattga gcccgcagcc tcccgcttcg   480
ctctctgctc ctcctgttcg acagtcagcc gcatcttctt ttgcgtcgcc aggtgaagac   540
gggcggagag aaacccggga ggctagggac ggcctgaagg cggcagggc gggcgcaggc    600
cggatgtgtt cgcgccgctg cggggtgggc ccgggcggcc tccgcattgc aggggcgggc   660
ggaggacgtg atgcggcgcg ggctgggcat ggaggcctgg tggggagggg gaggggaggc   720
gtgggtgtcg gccggggcca ctaggcgctc actgttctct ccctccgcgc agccgagcca   780
catcgctgag acac                                                     794

SEQ ID NO: 26          moltype = DNA  length = 532
FEATURE                Location/Qualifiers
misc_feature           1..532
                       note = Description of Artificial Sequence: Synthetic
                        polynucleotide
source                 1..532
                       mol_type = other DNA
                       organism = synthetic construct
SEQUENCE: 26
agtgcggtta ccagcggaaa tgcctcgggg tcagaagtcg caggagagat agacagctgc    60
tgaaccaatg ggaccagcgg atggggcgga tgttatctac cattggtgaa cgttagaaac   120
gaatagcagc caatgaatca gctggggggg cggagcagtg acgtttattg cggaggggc    180
cgcttcgaat cggcggcggc cagcttggtg gcctgggcca atgaacggcc tccaacgagc   240
agggccttca ccaatcggcg gcctccacga cggggctggg ggagggtata taagccgagt   300
aggcgacggt gaggtcgacg ccggccaaga cagcacagac agattgacct attggggtgt   360
ttcgcgagtg tgagagggaa gcgccgcggc ctgtatttct agacctgccc ttcgcctggt   420
tcgtggccgc ttgtgacccc gggccctgc cgcctgcaag tcggaaattg cgctgtgctc    480
ctgtgctacg gcctgtggct ggactgcctg ctgctgccca actggctggc ac           532

SEQ ID NO: 27          moltype = DNA  length = 701
FEATURE                Location/Qualifiers
misc_feature           1..701
                       note = Description of Artificial Sequence: Synthetic
                        polynucleotide
source                 1..701
                       mol_type = other DNA
                       organism = synthetic construct
SEQUENCE: 27
tagtttcatc accaccgcca cccccccgcc ccccgccat ctgaaagggt tctaggggat    60
ttgcaacctc tctcgtgtgt ttcttctttc cgagaagcgc cgccacacga gaaagctggc   120
cgcgaaagtc gtgctggaat cacttccaac gaaaccccag gcatagatgg gaaagggtga   180
agaacacgtt gccatggcta ccgtttcccc ggtcacggaa taaacgctct ctaggatccg   240
gaagtagttc cgccgcgacc tctctaaaag gatggatgtg ttctctgctt acattcattg   300
gacgttttcc cttagaggcc aaggccgccc aggcaaaggg gcggtcccac gcgtgagggg   360
cccgcgggagc catttgattg gagaaaaagct gcaaaccctg accaatcgga aggagccacg   420
cttcgggcat cggtcaccgc acctggacag ctccgattgg tggacttccg cccccccctca   480
cgaatcctca ttgggtgccg tgggtgcgtg gtgcggcgcg attggtgggt tcatgtttcc   540
cgtcccccgc ccgcgagaag tgggggtgaa aagcggcccg acctgcttgg ggtgtagtgg   600
gcggaccgcg cggctggagg tgtgaggatc cgaacccagg ggtgggggt ggaggcggct    660
cctgcgatcg aaggggactt gagactcacc ggccgcacgt c                       701

SEQ ID NO: 28          moltype = DNA  length = 465
FEATURE                Location/Qualifiers
misc_feature           1..465
                       note = Description of Artificial Sequence: Synthetic
                        polynucleotide
source                 1..465
                       mol_type = other DNA
                       organism = synthetic construct
SEQUENCE: 28
gggccgccca ctcccccttc tctctcagggt ccctgtcccc tccagtgaat cccagaagac   60
tctggagagt tctgagcagg gggcggcact ctggcctctg attggtccaa ggaaggctgg   120
ggggcaggac gggaggcgaa aaccctggaa tattcccgac ctggcagcct catcgagctc   180
ggtgattggc tcagaaggga aaaggcgggt ctccgtgacg acttataaaa gcccaggggc   240
aagcggtccg gataacggct agcctgagga gctgctgcga cagtccacta ccttttttcga   300
gagtgactcc cgttgtccca aggcttccca gagcgaacct gtgcggctgc aggcaccggc   360
gcgtcgagtt tccggcgtcc ggaaggaccg agctcttctc gcggatccag tgttccgttt   420
ccagccccca atctcagagc ggagccgaca gagagcaggg aaccc                    465
```

```
SEQ ID NO: 29            moltype = DNA  length = 538
FEATURE                  Location/Qualifiers
misc_feature             1..538
                         note = Description of Artificial Sequence: Synthetic
                          polynucleotide
source                   1..538
                         mol_type = other DNA
                         organism = synthetic construct
SEQUENCE: 29
gccccacccc cgtccgcgtt acaaccggga ggcccgctgg gtcctgcacc gtcaccctcc  60
tccctgtgac cgcccacctg atacccaaac aactttctcg cccctccagt ccccagctcg  120
ccgagcgctt gcggggagcc acccagcctc agtttcccca gccccgggcg gggcgagggg  180
cgatgacgtc atgccggcgc gcggcattgt ggggcggggc gaggcggggc gccgggggga  240
gcaacactga gacgccattt tcggcggcgg gagcggcgca ggcggccgag cgggactggc  300
tgggtcggct gggctgctgg tgcgaggagc cgcggggctg tgctcggcgg ccaaggggac  360
agcgcgtggg tggccgagga tgctgcgggg cggtagctcc ggcgccctc gctggtgact  420
gctgccgcgt gcctcacaca gccgaggcgg gctcggcgca cagtcgctgc tccgcgctcg  480
cgcccggcgg cgctccaggt gctgacagcg cgagagagcg cggcctcagg agcaacac  538

SEQ ID NO: 30            moltype = DNA  length = 1091
FEATURE                  Location/Qualifiers
misc_feature             1..1091
                         note = Description of Artificial Sequence: Synthetic
                          polynucleotide
source                   1..1091
                         mol_type = other DNA
                         organism = synthetic construct
SEQUENCE: 30
ttccagagct ttcgaggaag gtttcttcaa ctcaaattca tccgcctgat aattttctta  60
tattttccta aagaaggaag agaagcgcat agaggagaag ggaaataatt ttttaggagc  120
ctttcttacg gctatgagga atttggggct cagttgaaaa gcctaaactg cctctcggga  180
ggttgggcgc ggcgaactac tttcagcggc gcacggagac ggcgtctacg tgaggggtga  240
taagtgacgc aacactcgtt gcataaattt gcgctccgcc agcccggagc atttaggggc  300
ggttggcttt gttgggtgag cttgtttgtg tccctgtggg tggacgtggt tggtgattgg  360
caggatcctg gtatccgcta acaggtactg gcccacagcc gtaaagacct gcggggggcgt  420
gagagggggg aatgggtgag gtcaagctgg aggcttcttg gggttgggtg ggccgctgag  480
gggaggggag ggcgaggtga cgcgacaccc ggcctttctg ggagagtggg ccttgttgac  540
ctaaggggga cgagggcagt tggcacgcgc acgcgccgac agaaactaac agacattaac  600
caacagcgat tccgtcgcgt ttacttggga ggaaggcgga aaagaggtag tttgtgtggc  660
ttctggaaac cctaaatttg gaatcccagt atgagaatgg tgtcccttct tgtgtttcaa  720
tgggattttt acttcgcgag tcttgtgggt ttggttttgt tttcagtttg cctaacaccg  780
tgcttaggtt tgaggcagat tggagttcgg tcggggggagt ttgaatatcc ggaacagtta  840
gtggggaaag ctgtggacgc ttggtaagag agcgctctgg attttccgct gttgacgttg  900
aaacccttgaa tgacgaattt cgtattaagt gacttagcct tgtaaaattg aggggaggct  960
tgcggaatat taacgtattt aaggcatttt gaaggaatag ttgctaattt tgaagaatat  1020
taggtgtaaa agcaagaaat acaatgatcc tgaggtgaca cgcttatgtt ttacttttaa  1080
actaggtcac c                                                        1091

SEQ ID NO: 31            moltype = DNA  length = 66
FEATURE                  Location/Qualifiers
source                   1..66
                         mol_type = other DNA
                         organism = Homo sapiens
SEQUENCE: 31
atgtgtcacc agcagctcgt tatatcctgg tttagtttgg tgtttctcgc ttcacccctg  60
gtggca                                                              66

SEQ ID NO: 32            moltype = DNA  length = 66
FEATURE                  Location/Qualifiers
misc_feature             1..66
                         note = Description of Artificial Sequence: Synthetic
                          oligonucleotide
source                   1..66
                         mol_type = other DNA
                         organism = synthetic construct
SEQUENCE: 32
atgtgccatc agcaactcgt catctcctgg ttctcccttg tgttcctcgc ttcccctctg  60
gtcgcc                                                              66

SEQ ID NO: 33            moltype = DNA  length = 42
FEATURE                  Location/Qualifiers
misc_feature             1..42
                         note = Description of Artificial Sequence: Synthetic
                          oligonucleotide
source                   1..42
                         mol_type = other DNA
                         organism = synthetic construct
```

-continued

```
SEQUENCE: 33
atgcaactgc tgtcatgtat cgcactcatc ctggcgctgg ta                        42

SEQ ID NO: 34          moltype = DNA   length = 60
FEATURE                Location/Qualifiers
source                 1..60
                       mol_type = other DNA
                       organism = Homo sapiens
SEQUENCE: 34
atgtatcgga tgcaactttt gagctgcatc gcattgtctc tggcgctggt gacaaattcc  60

SEQ ID NO: 35          moltype = DNA   length = 45
FEATURE                Location/Qualifiers
source                 1..45
                       mol_type = other DNA
                       organism = Homo sapiens
SEQUENCE: 35
atgaatctct tgctcatact tacgtttgtc gctgctgccg ttgcg                     45

SEQ ID NO: 36          moltype = DNA   length = 51
FEATURE                Location/Qualifiers
source                 1..51
                       mol_type = other DNA
                       note = Gaussia Luciferase
                       organism = Gaussia sp.
SEQUENCE: 36
atgggcgtga aggtcttgtt tgcccttatc tgcatagctg ttgcggaggc g             51

SEQ ID NO: 37          moltype = DNA   length = 72
FEATURE                Location/Qualifiers
source                 1..72
                       mol_type = other DNA
                       organism = Homo sapiens
SEQUENCE: 37
atgccgatgg ggagccttca acctttggca acgctttatc ttctggggat gttggttgct  60
agttgccttg gg                                                         72

SEQ ID NO: 38          moltype = DNA   length = 63
FEATURE                Location/Qualifiers
source                 1..63
                       mol_type = other DNA
                       organism = Mus musculus
SEQUENCE: 38
atggaaactg acacgttgtt gctgtgggta ttgctcttgt gggtcccagg atctacgggc  60
gac                                                                   63

SEQ ID NO: 39          moltype = DNA   length = 66
FEATURE                Location/Qualifiers
source                 1..66
                       mol_type = other DNA
                       organism = Homo sapiens
SEQUENCE: 39
atggatatga gggttcccgc ccagcttttg gggctgcttt tgttgtggct tcgaggggct  60
cggtgt                                                                66

SEQ ID NO: 40          moltype = DNA   length = 48
FEATURE                Location/Qualifiers
misc_feature           1..48
                       note = Description of Unknown: VSV-G sequence
source                 1..48
                       mol_type = other DNA
                       organism = unidentified
SEQUENCE: 40
atgaagtgtc tgttgtacct ggcgtttctg ttcattggtg taaactgt                 48

SEQ ID NO: 41          moltype = DNA   length = 84
FEATURE                Location/Qualifiers
source                 1..84
                       mol_type = other DNA
                       organism = Homo sapiens
SEQUENCE: 41
atgaatatca aaggaagtcc gtggaagggt agtctcctgc tgctcctcgt atctaacctt  60
ctcctttgtc aatccgtggc accc                                           84

SEQ ID NO: 42          moltype = DNA   length = 54
FEATURE                Location/Qualifiers
source                 1..54
                       mol_type = other DNA
                       organism = Homo sapiens
```

-continued

```
SEQUENCE: 42
atgaaatggg taacattcat atcacttctc tttctgttca gctctgcgta ttct          54

SEQ ID NO: 43          moltype = DNA   length = 57
FEATURE                Location/Qualifiers
source                 1..57
                       mol_type = other DNA
                       organism = Homo sapiens
SEQUENCE: 43
atgacaaggc ttactgtttt ggctctcctc gctggactct tggcttcctc ccgagca       57

SEQ ID NO: 44          moltype = DNA   length = 51
FEATURE                Location/Qualifiers
source                 1..51
                       mol_type = other DNA
                       organism = Homo sapiens
SEQUENCE: 44
atgagggctt ggatttttt tctgctctgc cttgccggtc gagccctggc g              51

SEQ ID NO: 45          moltype = DNA   length = 48
FEATURE                Location/Qualifiers
source                 1..48
                       mol_type = other DNA
                       organism = Homo sapiens
SEQUENCE: 45
atgcctcttc tgcttttgct tcctcttttg tgggcaggtg ccctcgca                 48

SEQ ID NO: 46          moltype = DNA   length = 87
FEATURE                Location/Qualifiers
source                 1..87
                       mol_type = other DNA
                       organism = Homo sapiens
SEQUENCE: 46
atgaactctt tctcaacctc tgcgtttggt ccggtcgctt tctcccttgg gctcctgctt    60
gtcttgccag cagcgtttcc tgcgcca                                        87

SEQ ID NO: 47          moltype = DNA   length = 60
FEATURE                Location/Qualifiers
source                 1..60
                       mol_type = other DNA
                       organism = Homo sapiens
SEQUENCE: 47
atgacaagta aactggcggt agccttgctc gcggcctttt tgatttccgc agccctttgt    60

SEQ ID NO: 48          moltype = DNA   length = 69
FEATURE                Location/Qualifiers
source                 1..69
                       mol_type = other DNA
                       organism = Homo sapiens
SEQUENCE: 48
atgaaggtaa gtgcagcgtt gctttgcctt ctcctcattg cagcgacctt tattcctcaa    60
gggctggcc                                                            69

SEQ ID NO: 49          moltype = DNA   length = 78
FEATURE                Location/Qualifiers
source                 1..78
                       mol_type = other DNA
                       organism = Homo sapiens
SEQUENCE: 49
atgggagcgg cagctagaac acttcgactt gcccttgggc tcttgctcct tgcaaccctc    60
cttagacctg ccgacgca                                                  78

SEQ ID NO: 50          moltype = DNA   length = 63
FEATURE                Location/Qualifiers
source                 1..63
                       mol_type = other DNA
                       organism = Homo sapiens
SEQUENCE: 50
atgtcaccgt tgttgcggag attgctgttg ccgcacttt tgcaactggc tcctgctcaa     60
gcc                                                                  63

SEQ ID NO: 51          moltype = DNA   length = 63
FEATURE                Location/Qualifiers
source                 1..63
                       mol_type = other DNA
                       organism = Homo sapiens
SEQUENCE: 51
atgaataacc tgctctgttg tgcgctcgtg ttcctggaca tttctataaa atggacaacg    60
caa                                                                  63
```

-continued

```
SEQ ID NO: 52          moltype = DNA  length = 69
FEATURE                Location/Qualifiers
source                 1..69
                       mol_type = other DNA
                       organism = Homo sapiens
SEQUENCE: 52
atgcaaatgt ctcctgccct tacctgtctc gtacttggtc ttgcgctcgt atttggagag   60
ggatcagcc                                                           69

SEQ ID NO: 53          moltype = DNA  length = 102
FEATURE                Location/Qualifiers
source                 1..102
                       mol_type = other DNA
                       organism = Homo sapiens
SEQUENCE: 53
atggcaaggg ctgcactcag tgctgccccg tctaatccca gattgcttcg agttgcattg   60
cttcttctgt tgctggttgc agctggtagg agagcagcgg gt                      102

SEQ ID NO: 54          moltype = DNA  length = 63
FEATURE                Location/Qualifiers
source                 1..63
                       mol_type = other DNA
                       organism = Homo sapiens
SEQUENCE: 54
atgaatgcaa aagtcgtggt cgtgctggtt ttggttctga cggcgttgtg tcttagtgat   60
ggg                                                                 63

SEQ ID NO: 55          moltype = DNA  length = 66
FEATURE                Location/Qualifiers
misc_feature           1..66
                       note = Description of Artificial Sequence: Synthetic
                        oligonucleotide
source                 1..66
                       mol_type = other DNA
                       organism = synthetic construct
SEQUENCE: 55
atggaacgca ttgtgatctg cctgatggtc atcttcctgg gcaccttagt gcacaagtcg   60
agcagc                                                              66

SEQ ID NO: 56          moltype = DNA  length = 1626
FEATURE                Location/Qualifiers
source                 1..1626
                       mol_type = other DNA
                       organism = Homo sapiens
SEQUENCE: 56
atgtgccatc agcagcttgt catatcttgg ttttcacttg tattcctggc cagccctttg    60
gttgcgatct gggagctcaa gaaggatgtg tacgttgtag agctggactg gtaccccgat   120
gctcccggtg agatggtcgt tttgacatgt gacactccag aagaggacgg tattacgtgg   180
actctggacc agtcctccga agttcttggt tctggtaaga ctctgactat ccaggtgaaa   240
gaatttgggg atgcgggaca atacacatgc cacaagggag gcgaggtgtt gtctcatagt   300
ttgctgcttc tccacaagaa agaggatgga atctggagca ccgacatact caaggatcaa   360
aaggaaccca aaaataagac atttctgcga tgtgaggcta agaactatag tggccgcttc   420
acttgttggt ggctgactac catcagcaca gatctcacgt tttcagtaaa aagtagtaga   480
ggttcaagtg atcctcaagg ggtaacgtgc ggtgctgcaa cactgtctgc tgaacgcgta   540
agaggagata ataaggagta cgagtattcc gtagaatgcc aagaggacag tgcttgtcct   600
gcggccgagg agtctctccc aatagaagtg atggtggacg cggtgcataa actgaaatat   660
gagaactaca caagcagttt ttttataaga gatatcatca gcccgatcc gccgaagaat   720
ttgcaactta aaccgcttaa aaactcacgc caggttgaag tatcctggga gtatccggat   780
acatggtcaa caccacacag ctatttttcc cttaccttct gtgtgcaggt ccaagggaag   840
agcaaaaggg agaagaagga cagggtattc actgataaaa cttccgcgac ggtcatctgc   900
cgaaaaaacg ctagtatatc tgtacgggcg caggataggc actatagttc ttcttggtct   960
gagtgggcct cagttccgtg ctctggggga ggaagtggag gagggtccgg cggtggaagc  1020
gggggaggga gtcgcaactt gccagtggct acaccagatc caggcatgtt tccatgtctg  1080
catcattccc agaatctcct gagagcggtg tcaaatatgc tccaaaaagc gagacaaaca  1140
ctggaatttt acccgtgtac cagtgaggag attgatcacg aggacataac caaggacaag  1200
acctcaactg tagaagcgtg tttgccgctg gagttgacta agaatgagtc ctgcctcaat  1260
tccagagaaa cttcattcat tactaacggc agttgtcttg catcccggaa aacgtccttt  1320
atgatggccc tttgccttag ttcaatttac gaggatctta aaatgtatca agtggagttt  1380
aaaaccatga atgctaaact tcttatggac cccaaacgac aaattttttct ggatcagaat  1440
atgcttgccg tgatagacga actcatgcag gcgcttaatt ttaactccga aacagttcca  1500
caaaaatcta gccttgaaga acctgatttt tataaaacga agattaaact gtgtatcctg  1560
ctgcatgcct ttcgcatccg agctgtcaca atcgataggc ttatgtccta ccttaacgcg  1620
agctag                                                             1626

SEQ ID NO: 57          moltype = DNA  length = 1623
FEATURE                Location/Qualifiers
```

```
misc_feature          1..1623
                      note = Description of Artificial Sequence: Synthetic
                       polynucleotide
source                1..1623
                      mol_type = other DNA
                      organism = synthetic construct
SEQUENCE: 57
atgtgccatc agcaactcgt catctcctgg ttctcccttg tgttcctcgc ttcccctctg   60
gtcgccattt gggaactgaa gaaggacgtc tacgtggtcg agctggattg gtacccggac  120
gcccctggag aaatggtcgt gctgacttgc gatacgccag aagaggacgg cataacctgg  180
accctggatc agagctccga ggtgctcgga agcggaaaga ccctgaccat tcaagtcaag  240
gagttcggcg acgcgggcca gtacacttgc cacaagggtg gcgaagtgct gtcccactcc  300
ctgctgctgc tgcacaagaa agaggatgga atctggtcca ctgacatcct caaggaccaa  360
aaagaaccga agaacaagac cttcctccgc tgcgaagcca agaactacag cggtcggttc  420
acctgttggt ggctgacgac aatctccacc gacctgactt tctccgtgaa gtcgtcacgg  480
ggatcaagcg atcctcaggg cgtgacctgt ggagccgcca ctctgtccgc cgagagagtc  540
aggggagaca acaaggaata tgagtactcc gtggaatgcc aggaggacag cgcctgccct  600
gccgcggaag agtccctgcc tatcgaggtc atggtcgatg ccgtgcataa gctgaaatac  660
gagaactaca cttcctcctt ctttatccgc gacatcatca agcctgaccc ccccaagaac  720
ttgcagctga agccactcaa gaactcccgc caagtggaag tgtcttggga atatccagac  780
acttggagca ccccgcactc atacttctcg ctcactttct gtgtgcaagt gcagggaaag  840
tccaaacggg agaagaaaga ccgggtgttc accgacaaaa cctccgccac tgtgatttgt  900
cggaagaacg cgtcaatcag cgtccgggcg caggatagat actactcgtc ctcctggagc  960
gaatgggcca gcgtgccttg ttccggtggc ggatcaggcg gaggttcagg aggaggctcc  1020
ggaggaggtt cccggaacct ccctgtggca accccgacc ctggaatgtt cccgtgccta  1080
caccactccc aaaacctcct gagggctgtg tcgaacatgt tgcagaaggc ccgccagacc  1140
cttgagttct acccctgcac ctcggaagaa attgatcacg aggacatcac caaggacaag  1200
acctcgaccg tggaagcctg cctgccgctg gaactgacca agaacgaatc gtgtctgaac  1260
tcccgcgaga caagctttat cactaacggc agctgcctgg cgtcgagaaa gacctcattc  1320
atgatggcgc tctgtctttc ctcgatctac gaagatctga agatgtatca ggtcgagttc  1380
aagaccatga acgccaagct gctcatggac ccgaagcggc agatcttcct ggaccagaat  1440
atgctcgccg tgattgatga actgatgcag gccctgaatt tcaactccga gactgtgcct  1500
caaaagtcca gcctggaaga accggacttc tacaagacca agatcaagct gtgcatcctg  1560
ttgcacgctt tccgcattcg agccgtgacc attgaccgcg tgatgtccta cctgaacgcc  1620
agt                                                               1623

SEQ ID NO: 58          moltype = DNA   length = 1635
FEATURE                Location/Qualifiers
source                 1..1635
                       mol_type = other DNA
                       organism = Mus musculus
SEQUENCE: 58
atgtgtccac agaagctgac aataagttgg tttgccattg tcctcctggt gagcccactc   60
atggcaatgt gggaactcga aaaggatgtc tacgtggtag aagtagattg gactccagac  120
gcgccagggg agacagtgaa tttgacatgt gacacaccag aagaagatga cattacatgg  180
acatctgacc aacgccatgg cgtaataggg agtgggaaaa cactcacgat cacagttaaa  240
gagttcttgg atgctggtca atatacttgc cataaaggcg cagacact cagccactca  300
catttgcttt tgcataaaaa agagaatggc atttggagca ctgaaatact taagaacttt  360
aagaacaaga catttctcaa gtgtgaggcc cctaattaca gcggcaggtt cacgtgctca  420
tggctggtcc agcgcaacat ggacctcaag tttaacataa aatcttcttc ctcttcacct  480
gactccagag ctgttacttg cggcatggct tctctgacg cagaaaaagt aacgttggat  540
caaagagact acgaaaagta ctctgtttct tgtcaagagg atgttacgtg cccgacggcc  600
gaagaaacgc ttccaattga actcgcgttg gaagctcgcc aacaaaacaa gtatgaaaac  660
tacagtacaa gcttctttat acgggatata attaaacccg atccccccaa gaacttgcaa  720
atgaaaccac ttaagaacag ccaggtggaa gtttcctggg agtatccaga ctcatggagt  780
actcctcaca gctattttc tctgaaattc tttgtaagga tacaacggaa gaaagagaag  840
atgaaagaga ccgaggaggg ttgtaatcag aagggagcgt ttctcgtgga gaaacgtct  900
accgaagtcc aatgtaaagg tggcaatgtg tgcgtccaag ctcaggatag atactataat  960
tcaagttgct ccaagtgggc ctgtgttcca tgccgcgttc ggagcggggg aggtagcgga  1020
ggaggtagtg ggggtgggtc aggaggaggg agtcgagtta tccggtgtc aggccccgca  1080
cgctgctga gccagagtcg caacctcctt aagacaacag atgacatggt gaaaacagca  1140
cgcgaaaagc ttaaacacta ctcttgtacg gcggaggata ttgatcacga ggatattacc  1200
cgagaccaaa ctagcacttt gaaaacctgt ctgcccttg aacttcataa aaatgagagc  1260
tgtctggcta cacgagagac gtcaagtacg actaggggca gctgtctccc gccgcaaaag  1320
acaagcctca tgatgacgct ctgtttgggt tccatttacg aggacttgaa aatgtatcaa  1380
acggagttcc aggctataaa tgcgcgcgttg cagaaccata accatcaaca aattatactt  1440
gataaaggca tgttggtggc gattgatgaa ctcatgcaga gtctcaatca caacggggaa  1500
acgttgagac agaaaccccc agtcggtgaa gcggacccat atcgagtaaa aatgaagctc  1560
tgcattctgc ttcacgcatt cagcactaga gttgttacca tcaaccgggt aatgggatat  1620
ctctccagtg cgtag                                                  1635

SEQ ID NO: 59          moltype = DNA   length = 465
FEATURE                Location/Qualifiers
misc_feature           1..465
                       note = Description of Artificial Sequence: Synthetic
                        polynucleotide
source                 1..465
                       mol_type = other DNA
                       organism = synthetic construct
```

```
SEQUENCE: 59
atggaacgca ttgtgatctg cctgatggtc atcttcctgg gcaccttagt gcacaagtcg    60
agcagccagg gacaggacag gcacatgatt agaatgcgcc agctcatcga tatcgtggac   120
cagttgaaga actacgtgaa cgacctggtg cccgagttcc tgccggcccc cgaagatgtg   180
gaaaccaatt gcgaatggtc ggcattttcc tgctttcaaa aggcacagct caagtccgct   240
aacaccggga acaacgaacg gatcatcaac gtgtccatca aaaagctgaa gcggaagcct   300
ccctccacca acgccggacg gaggcagaag cataggctga cttgcccgtc atgcgactcc   360
tacgagaaga agccgccgaa ggagttcctg gagcggttca agtcgctcct gcaaaagatg   420
attcatcagc acctgtcctc ccggactcat gggtctgagg attca               465

SEQ ID NO: 60          moltype = DNA  length = 2163
FEATURE                Location/Qualifiers
misc_feature           1..2163
                       note = Description of Artificial Sequence: Synthetic
                       polynucleotide
source                 1..2163
                       mol_type = other DNA
                       organism = synthetic construct
SEQUENCE: 60
atgtgccatc agcaactcgt catctcctgg ttctcccttg tgttcctcgc ttcccctctg    60
gtcgccattt gggaactgaa gaaggacgtc tacgtggtcg agctggattg gtacccggac   120
gcccctggag aaatggtcgt gctgacttgc gatacgcacg aagaggacgg cataacctgg   180
accctggatc agagctccga ggtgctcgga agcggaaaga ccctgaccat tcaagtcaag   240
gagttcggcg acgcgggcca gtacacttgc cacaagggtg gcgaagtgct gtcccactcc   300
ctgctgctgc tgcacaagaa agaggatgga atctggtcca ctgacatcct caaggaccaa   360
aaagaaccga agaacaagac cttcctccgc tgcgaagcca agaactacag cggtcggttc   420
acctgttggt ggctgacgac aatctccacc gacctgactt tctccgtgaa gtcgtcacgg   480
ggatcaagcg atcctcaggg cgtgacctgt ggagccgcca ctctgtccgc cgagagagtc   540
aggggagaca acaaggaata tgagtactcc gtggaatgcc aggaggacag cgcctgccct   600
gccgcggaag agtccctgcc tatcgaggtc atggtcgatg ccgtgcataa gctgaaatac   660
gagaactaca cttcctcctt ctttatccgc gacatcatca agcctgaccc ccccaagaac   720
ttgcagctga agccactcaa gaactcccgc caagtggaag tgtcttggga atatccagac   780
acttggagca ccccgcactc atacttctcg ctcactttct gtgtgcaagt gcagggaaag   840
tccaaacggg agaagaaaga ccgggtgttc accgacaaaa cctccgccac tgtgatttgt   900
cggaagaacg cgtcaatcag cgtccgggcg caggatagat actactcgtc ctcctggagc   960
gaatgggcca gcgtgccttg ttccggtggc ggatcaggcg gaggttcagg aggaggctcc  1020
ggaggaggtt cccggaacct ccctgtggca accccgacc ctggaatgtt cccgtgccta  1080
caccactccc aaaacctcct gagggctgtg tcgaacatgt tgcagaaggc ccgccagacc  1140
cttgagttct accctgcac ctcggaagaa attgatcacg agacatcac caaggacaag  1200
acctcgaccg tggaagcctg cctgccgctg gaactgacca agaacgaatc gtgtctgaac  1260
tcccgcgaga caagctttat cactaacggc agctgcctgg cgtcgagaaa gacctcattc  1320
atgatggcgc tctgtctttc ctcgatctac gaagatctga agatgtatca ggtcgagttc  1380
aagaccatga acgccaagct gctcatggac ccgaagcggc agatcttcct ggaccagaat  1440
atgctcgccg tgattgatga actgatgcag gccctgaatt tcaactccga gactgtgcct  1500
caaaagtcca gcctggaaga accggacttc tacaagacca agatcaagct gtgcatcctg  1560
ttgcacgctt tccgcattcg agccgtgacc attgaccgcg tgatgtccta cctgaacgcc  1620
agtagacgga aacgcggaag cggagagggc agaggctgc tgcttacatg cggggacgtg  1680
gaagagaacc ccggtccgat ggaacgcatt gtgatctgcc tgatggtcat cttcctgggc  1740
accttagtgc acaagtcgag cagccaggga caggacaggc acatgattag aatgcgccag  1800
ctcatcgata tcgtggacca gttgaagaac tacgtgaacg acctggtgcc cgagttcctg  1860
ccggcccccg aagatgtgga aaccaattgc gaatggtcgg cattttcctg ctttcaaaag  1920
gcacagctca gtccgctaa caccgggaac aacgaacgga tcatcaacgt gtccatcaaa  1980
aagctgaagc ggaagcctcc ctccaccaac gccggacgga ggcagaagca taggctgact  2040
tgcccgtcat gcgactccta cgagaagaag ccgccgaagg agttcctgga gcggttcaag  2100
tcgctcctgc aaaagatgat tcatcagcac ctgtcctccc ggactcatgg gtctgaggat  2160
tca                                                          2163

SEQ ID NO: 61          moltype = DNA  length = 2103
FEATURE                Location/Qualifiers
source                 1..2103
                       mol_type = other DNA
                       organism = Homo sapiens
SEQUENCE: 61
atgtgccatc agcagcttgt catatcttgg ttttcacttg tattcctggc cagccctttg    60
gttgcgatct gggagctcaa gaaggatgtg tacgttgtag agctggactg gtaccccgat   120
gctcccggtg agatggtcgt tttgacatgt gacactccag aagaggacgg tattacgtgg   180
actctggacc agtcctccga agttcttggt tctggtaaga ctctgactat ccaggtgaaa   240
gaatttgggg atgcgggaca atacacatgc cacaagggag gcgaggtgtt gtctcatagt   300
ttgctgcttc tccacaagaa agaggatgga atctggagcc ccgacatact caaggatcaa   360
aaggaaccca aaaataagac atttctgcga tgtgaggcta agaactatag tggccgcttc   420
acttgttggt ggctgactac catcagcaca gatctcacgt tttcagtaaa aagtagtaga   480
ggttcaagta tcctcaaggg ggtaacgtgc ggtgctgcaa cactgtctgc tgaacgcgta   540
agaggagata ataaggagta cgagtattcc gtagaatgcc aagaggacag tgcttgtcct   600
gcggccggag agtctctccc aatagaagtg atggtggacg cggtgcataa actgaaatat   660
gagaactaca caagcagttt ttttataaga gatatcatca gcccgatcc gccgaagaat   720
ttgcaactta aaccgcttaa aaactcacgc caggttgaag tatcctggga gtatccggat   780
acatggtcaa caccacacag ctattttcc cttaccttct gtgtgcaggt ccaagggaag   840
agcaaaaggg agaagaagga cagggtattc actgataaaa cttccgcgac ggtcatctgc   900
cgaaaaaacg ctagtatatc tgtacgggcg caggataggt actatagttc ttcttggtct   960
```

-continued

```
gagtgggcct cagttccgtg ctctggggga ggaagtggag gagggtccgg cggtggaagc  1020
gggggaggga gtcgcaactt gccagtggct acaccagatc caggcatgtt tccatgtctg  1080
catcattccc agaatctcct gagagcggtg tcaaatatgc tccaaaaagc gagacaaaca  1140
ctggaatttt acccgtgtac cagtgaggag attgatcacg aggacataac caaggacaag  1200
acctcaactg tagaagcgtg tttgccgctg gagttgacta agaatgagtc ctgcctcaat  1260
tccagagaaa cttcattcat tactaacggc agttgtcttg catcccggaa aacgtccttt  1320
atgatggccc tttgccttag ttcaatttac gaggatctta aaatgtatca agtggagttt  1380
aaaaccatga atgctaaact tcttatggac cccaaacgac aaattttct ggatcagaat  1440
atgcttgccg tgatagacga actcatgcag gcgcttaatt ttaactccga aacagttcca  1500
caaaaatcta gccttgaaga acctgatttt tataaaacga agattaaact gtgtatcctg  1560
ctgcatgcct ttcgcatccg agctgtcaca atcgataggg ttatgtccta ccttaacgcg  1620
agccggcgca agaggggttc cggagaggga aggggtagtc tgctcacctg cggcgatgtt  1680
gaagaaaatc ctggtcccat ggcgcaaagt ctggctcttt cactcctgat cctggtcttg  1740
gccttcggga ttccgaggac ccaaggaagt gatggtggcg cccaagattg ttgccttaaa  1800
tacagccagc ggaaaatacc cgcgaaagtg gtcaggagtt atagaaaaca ggagccttcc  1860
ctgggttgta gtatccccgc catactttc ctcccgagaa aacggagcca ggccgaactg  1920
tgcgctgacc ctaaggaact ttgggtgcaa caacttatgc aacacctgga taagacacct  1980
tctcctcaaa agccagctca gggctgccga aaagatagag gcgcctcaaa aaccggaaaa  2040
aagggcaaag gttctaaagg atgtaagcgg actgaacgct ctcaaacgcc taaagggccg  2100
tag                                                                 2103

SEQ ID NO: 62            moltype = DNA  length = 2109
FEATURE                  Location/Qualifiers
source                   1..2109
                         mol_type = other DNA
                         organism = Mus musculus
SEQUENCE: 62
atgtgtccac agaagctgac aataagttgg tttgccattg tcctcctggt gagcccactc  60
atggcaatgt gggaactcga aaaggatgtc tacgtggtag aagtagattg gactccagac  120
gcgccagggg agacagtgaa tttgacatgt gacacaccag aagaagatga cattacatgg  180
acatctgacc aacgccatgg cgtaataggg agtgggaaaa cactcacgat cacagttaaa  240
gagttcttgg atgctggtca atatacttgc cataaaggcg gcgagacact cagccactca  300
catttgcttt tgcataaaaa agagaatggc atttggagca ctgaaatact taagaacttt  360
aagaacaaga catttctcaa gtgtgaggcc cctaattaca gcggcaggtt cacgtgctca  420
tggctggtcc agcgcaacat ggacctcaag tttaacataa aatcttcttc ctcttccct  480
gactccagag ctgttacttg cggcatggct tctctgagcg cagaaaaagt aacgttggat  540
caaagagact acgaaaagta ctctgtttct tgtcaagagg atgttacgtg cccgacggcc  600
gaagaaacgc ttccaattga actcgcgttg gaagctcgcc aacaaaacaa gtatgaaaac  660
tacagtacaa gcttctttat acgggatata attaaacccg atccccccaa gaacttgcaa  720
atgaaaccac ttaagaacag ccaggtggaa gtttcctggg agtatccaga ctcatggagt  780
actcctcaca gctatttttc tctgaaattc tttgtaagga tacaacggaa gaaagagaag  840
atgaaagaga ccgaggaggg ttgtaatcag aagggagcgt ttctcgtgga gaaaacgtct  900
accgaagtcc aatgtaaagg tggcaatgtg tgcgtccaag ctcaggatag atactataat  960
tcaagttgct ccaagtgggc ctgtgttcca tgccgcgttc ggagcggggg aggtagcgga  1020
ggaggtagtg ggggtgggtc aggaggaggg agtccggtgtc aggccccgca  1080
cgctgcttga gccagagtcg caacctcctt aagacaacag atgacatggt gaaaacagca  1140
cgcgaaaagc ttaaacacta ctcttgtacg gcggaggata ttgatcacga ggatattacc  1200
cgagaccaaa ctagcacttt gaaaacctgt ctgccccttg aacttcataa aaatgagagc  1260
tgtctggcta cacgagagac gtcaagtacg actaggggca gctgtctccc gccgcaaaag  1320
acaagcctca tgatgacgct ctgtttgggt tccatttacg aggacttgaa aatgtatcaa  1380
acggagttcc aggctataaa tgcggcgttg cagaaccata accatcaaca aattatactt  1440
gataaaggca tgttggtggc gattgatgaa ctcatgcaga gtctcaatca caacggggaa  1500
acgttgagac agaaacccccc agtcggtgaa gcggacccat atcgagtaaa aatgaagctc  1560
tgcattctgc ttcacgcatt cagcactaga gttgttacca tcaaccgggt aatgggatat  1620
ctctccagtg cgcggcgcaa gagggggttcc ggagaggaaa ggggtagtct gctcacctgc  1680
ggcgatgttg aagaaaatcc tggtcccatg gcgcaaatga tgacccttc cctgctgagt  1740
cttgcctcg cgctctgcat cccgtggacg caggggtctg atgggggggg ccaagactgt  1800
tgcctgaagt attcacaaaa aaagataccg tactctattg tcagagggta caggaagcaa  1860
gaaccctcct tgggttgccc tataccagca attctttct ccccacgcaa gcattccaaa  1920
ccagaactgt gtgcgaaccc cgaggagggt tgggtacaga acttgatgcg aaggcttgac  1980
cagcccccag cccctggcaa gcagtcacct gggtgcagaa aaaacagagg tacttcaaag  2040
agcggcaaga aaggcaaagg gagtaaagga tgtaaaagaa cggagcagac ccagccttca  2100
cgaggctag                                                           2109

SEQ ID NO: 63            moltype = DNA  length = 2109
FEATURE                  Location/Qualifiers
source                   1..2109
                         mol_type = other DNA
                         organism = Mus musculus
SEQUENCE: 63
atggcgcaaa tgatgaccct ttccctgctg agtcttgtcc tcgcgctctg catcccgtgg  60
acgcaggggg ctgatggggg gggccaagac tgttgcctga gtattcaca aaaaaagata  120
ccgtactcta ttgtcagagg gtacaggaag caagaacccc ccttgggttg ccctatacca  180
gcaattcttt tctccccacg caagcattcc aaaccagaac tgtgtgcgaa ccccgaggag  240
ggttgggtac agaacttgat gcgaaggctt gaccagcccc cagcccctgg caagcagtca  300
cctgggtgca gaaaaaacag aggtacttca aagagcggca agaaaggcaa agggagtaaa  360
ggatgtaaaa gaacggagca gacccagcct tcacgaggcc ggcgcaagag gggttccgga  420
gagggaaggg gtagtctgct cacctgcggc gatgttgaag aaaatcctgg tcccatgtgt  480
ccacagaagc tgacaataag ttggtttgcc attgtcctcc tggtgagccc actcatggca  540
```

```
atgtgggaac tcgaaaagga tgtctacgtg gtagaagtag attggactcc agacgcgcca   600
ggggagacag tgaatttgac atgtgacaca ccagaagaag atgacattac atggacatct   660
gaccaacgcc atggcgtaat agggagtggg aaaacactca cgatcacagt taaagagttc   720
ttggatgctg tcaatatac ttgccataaa ggcggcgaga cactcagcca ctcacatttg   780
cttttgcata aaaaagagaa tggcatttgg agcactgaaa tacttaagaa ctttaagaac   840
aagacatttc tcaagtgtga ggcccctaat tacagcggca ggttcacgtg ctcatggctg   900
gtccagcgca acatggacct caagtttaac ataaaatctt cttcctcttc acctgactcc   960
agagctgtta cttgcggcat ggcttctctg agcgcagaaa aagtaacgtt ggatcaaaga  1020
gactacgaaa agtactctgt ttcttgtcaa gaggatgtta cgtgcccgac ggccgaagaa  1080
acgcttccaa ttgaactcgc gttggaagct cgccaacaaa acaagtatga aaactacagt  1140
acaagcttct ttatacggga tataattaaa cccgatcccc ccaagaactt gcaaatgaaa  1200
ccacttaaga acagccaggt ggaagtttcc tgggagtatc cagactcatg gagtactcct  1260
cacagctatt tttctctgaa attctttgta aggatacaac ggaagaaaga gaagatgaaa  1320
gagaccgagg agggttgtaa tcagaaggga gcgtttctcg tggagaaaac gtctaccgaa  1380
gtccaatgta aaggtggcaa tgtgtgcgtc caagctcagg atagatacta taattcaagt  1440
tgctccaagt gggcctgtgt tccatgccgc gttcggagcg ggggaggtag cggaggaggt  1500
agtgggggtg ggtcaggagg agggagtcga gttatcccgg tgtcaggccc cgcacgctgc  1560
ttgagccaga gtcgcaacct ccttaagaca acagatgaca tggtgaaaac agcacgcgaa  1620
aagcttaaac actactcttg tacggcggag gatattgatc acgaggatat tacccgagac  1680
caaaactagca ctttgaaaac ctgtctgccc cttgaacttc ataaaaatga gagctgtctg  1740
gctacacgag agacgtcaag tacgactagg ggcagctgtc tcccgccgca aaagacaagc  1800
ctcatgatga cgctctgttt gggttccatt tacgaggact tgaaaatgta tcaaacggag  1860
ttccaggcta taaatgcggc gttgcagaac cataaccatc aacaaattat acttgataaa  1920
ggcatgttgg tggcgattga tgaactcatg cagagtctca atcacaacgg ggaaacgttg  1980
agacagaaac ccccagtcgg tgaagcggac ccatatcgag taaaaatgaa gctctgcatt  2040
ctgcttcacg cattcagcac tagagttgtt accatcaacc gggtaatggg atatctctcc  2100
agtgcgtag                                                            2109
```

```
SEQ ID NO: 64            moltype = DNA  length = 465
FEATURE                  Location/Qualifiers
source                   1..465
                         mol_type = other DNA
                         organism = Mus musculus
SEQUENCE: 64
atgtttcatg tgtccttcag gtacatattt ggtatcccac cacttatatt ggtgctcttg   60
cctgtaacca gctctgaatg tcatataaaa gacaaggagg gcaaagcata cgagtccgta  120
ttgatgatct caatcgatga acttgacaag atgacaggga ccgattctaa ttgtccaaat  180
aacgagccaa acttctttcg gaaacacgtg tgtgatgata caaaagaagc tgctttttctt  240
aacagagctg ccagaaaact caagcagttc ctcaagatga atatatccga ggaatttaac  300
gtgcatctcc tcacagtatc tcagggaact caaacccttg taaactgcac ttctaaggag  360
gagaagaatg tcaaagagca gaagaaaaat gatgcatgtt ttttgaaacg gctgttgagg  420
gagatcaaaa catgctggaa taaaatcctc aagggctcaa tttag               465
```

```
SEQ ID NO: 65            moltype = DNA  length = 1428
FEATURE                  Location/Qualifiers
source                   1..1428
                         mol_type = other DNA
                         organism = Homo sapiens
SEQUENCE: 65
atggaaacag acacattgct gctttgggta ttgttgctct gggtgcctgg atcaacagga   60
aactgggtaa acgtaatttc agatctgaag aagatcgagg accttattca atccatgcac  120
atcgatgcca ctctctacac cgaaagcgac gttcacccat cttgcaaggt gaccgctatg  180
aaatgtgaat tgttggaact tcaggtaatt tctctggaga gcggcgatgc ctcaatacat  240
gacaccgttg aaaatcttat catccttgct aatgattcac tctctagtaa tgggaacgta  300
acagagagcg ggtgtaagga gtgtgaagaa ctggaggaga aaaacattaa ggaattttg  360
cagtcattcg tccatatagt gcaaatgttc ataaacactt ccagaagaaa gcgaggctct  420
ggggaggggc gaggctctct gctgacctgt ggggatgtag aagagaatcc aggtcccatg  480
gaccggctga ccagctcatt cctgcttctg attgtgccag cctacgtgct ctccatcaca  540
tgtcctcccc caatgagcgt cgagcatgct gacatctggg tgaagtcata ctccttgtac  600
agcagagaga gatacatttg taattccgga ttcaagcgca aggccggcac ctcctctctga  660
acagagtgcg tccttaacaa agcaaccaac gtagcacatt ggaccacacc atccttgaag  720
tgcatacagg aacctaaatc ttgcgataag actcatactt gtccaccttg tccagcccca  780
gaactgcttg gcggaccctc agtatttttg ttcccaccaa agccaaaaga cacactcatg  840
atatccagaa ctcctgaggt gacctgtgtc gttgtagacg tttcccacga agatcctgaa  900
gtaaaattca actggtacgt ggatggggtc gaagtccata acgccaagac taaaccaagg  960
gaggaacagt ataactctac ttaccgagta gtttctgtgt tgaccgtgct gcaccaggac  1020
tggttgaacg gaaggagta caaatgcaag gtgagcaata agctctgcc cgcaccaatc  1080
gaaaagacaa tatctaaggc caaggggcag ccacgagagc cccaggtata cacactgcca  1140
ccctcacgcg atgaattgac taagaaccag gtttccctga cctgtcttgt aaaaggtttc  1200
taccccttccg acatagctgt tgagtgggaa agtaacgggc agccagagaa caattacaag  1260
acaactccac ccgttcttga tagcgatgga tcattttttc tgtattccaa actcactgtc  1320
gataaaagtc gctggcagca aggcaatgtt tttagctgct cagtcatgca cgaagcactg  1380
cataatcact acacacaaaa aagtttgtcc cttagccctg gtaagtag              1428
```

```
SEQ ID NO: 66            moltype = DNA  length = 1080
FEATURE                  Location/Qualifiers
source                   1..1080
                         mol_type = other DNA
                         organism = Homo sapiens
```

```
SEQUENCE: 66
atgtactcaa tgcagttggc ctcctgtgta acattgacct tggtcctctt ggtcaacagc   60
aattggatcg atgtacgcta cgacttggag aagattgagt cccttataca gagtatacac  120
atagatacaa ccttgtatac tgacagtgac ttccatccca gctgtaaagt gactgcaatg  180
aactgttttt tgttggagtt gcaagtaatt ctgcatgaat acagcaacat gaccctcaat  240
gaaaccgtta ggaatgtcct ttatctcgca aattctactc tgagtagcaa taagaatgtt  300
gccgaaagcg gctgcaagga gtgcgaagaa ctggaggaaa aaactttcac cgagtttctc  360
cagagtttca tcagaattgt ccaaatgttc attaatacaa gtagtggtgg tgggagcggg  420
ggtggaggca gtgggggagg tgggagcgga ggtggagggt ccggaggggg gagccttcaa  480
ggcactactt gtcctccacc cgtatccatc gagcacgccg atattcgagt taaaaattat  540
agtgttaata gcagagaacg atacgtctgc aactcagggt ttaagagaaa ggccggaact  600
tcaactctca tagaatgcgt gattaataag aatactaacg tcgcacattg gactactccc  660
agtctcaagt gcatacgcga tccatctctc gctcattact caccagtacc tacagtggtt  720
actcctaagg tgacctctca gcccgaatca ccatctccca gcgcaaaaga gcctgaggcc  780
ttttctccta aatcagacac tgctatgact acagaaacag ccataatgcc aggaagccgg  840
ctgacaccat ctcaaactac cagcgcaggc acaactggga ctggctccca caaaagctca  900
cgcgcaccaa gtctcgccgc aacaatgaca ttggagccta cagccagcac atctcttaga  960
atcacagaaa tttctcccca cagtagcaag atgaccaagg tggcaattag taccagcgtc 1020
cttcttgtag gagctggagt tgtgatggca tttttggcat ggtatatcaa aagcaggtag 1080

SEQ ID NO: 67          moltype = DNA  length = 489
FEATURE                Location/Qualifiers
source                 1..489
                       mol_type = other DNA
                       organism = Mus musculus
SEQUENCE: 67
atgaagatcc tcaagccata catgcgaaac actagtatta gctgttactt gtgttttctg   60
ctgaatagtc attttttgac tgaagcagga atccatgtat ttatactcgg ttgtgtgtct  120
gtaggtctgc caaagactga ggctaattgg attgacgtgc gctatgatct tgaaaaaata  180
gagtccttga ttcaatcaat acacatcgat accactctct acaccgacag tgatttccat  240
ccttcctgca aggtaacagc tatgaattgc ttcctcctgg agctccaagt cattctccat  300
gagtactcca acatgacttt gaacgaaact gtaagaaacg tattgtatct ggctaatagc  360
accttgtcta gtaacaaaaa tgtggcagag agcggctgca aagaatgtga agaattggaa  420
gagaaaacat ttacagagtt cctgcaatcc tttattcgca tcgtccaaat gtttatcaat  480
acctcttag                                                          489

SEQ ID NO: 68          moltype = DNA  length = 438
FEATURE                Location/Qualifiers
source                 1..438
                       mol_type = other DNA
                       organism = Mus musculus
SEQUENCE: 68
atgtattcca tgcaacttgc cagttgtgta acccttactc tcgtcctgct cgttaattcc   60
gctggtgcta actggataga tgttcgatac gatctggaaa agattgagtc ccttatccaa  120
tccattcata tagataccac cctttatact gacagcgact tccatccttc ttgcaaggtg  180
accgctatga attgtttcct gctggaactc caagttattc tgcatgaata ctctaatatg  240
acacttaacg agaccgtaag aaatgttctc tatctcgca atagtacttt gagctcaaat  300
aagaacgtgg ccgagtctgg gtgtaaggaa tgcgaagagc tggaagaaaa gacattcacc  360
gagtttctcc agtctttcat acggattgtg cagatgttta tcaacacatc agattacaaa  420
gacgacgatg ataagtag                                                438

SEQ ID NO: 69          moltype = DNA  length = 579
FEATURE                Location/Qualifiers
source                 1..579
                       mol_type = other DNA
                       organism = Mus musculus
SEQUENCE: 69
atggcagcca tgtctgagga ctcttgtgtg aactttaaag aaatgatgtt catagacaat   60
acactctact ttatacctga ggagaatgga gatttggaat ctgacaactt tggcaggctg  120
cattgcacta ccgcagttat ccgaaacatc aacgatcagg tactgtttgt tgataaaaga  180
caacctgtat tcgaggacat gaccgacata gatcagtctg cctcagagcc ccagactagg  240
cttatcatct atatgtacaa ggacagcgaa gtacgaggcc tggctgttac actctcagtc  300
aaagactcta agatgagcac cctgtcatgc aagaacaaaa ttatcagttt tgaggagatg  360
gacccacctg aaaacataga tgacattcag tcagacctca tttttttca aaagcgggta  420
ccaggacaca acaaaatgga atttgaatca tcactctacg aaggacattt ccttgcatgc  480
cagaaagagg atgacgcatt caaattgatc ctgaaaaaaa aggacgaaaa tggtgataaa  540
tcagtcatgt ttacattgac caatcttcac caaagttag                         579

SEQ ID NO: 70          moltype = DNA  length = 579
FEATURE                Location/Qualifiers
source                 1..579
                       mol_type = other DNA
                       organism = Mus musculus
SEQUENCE: 70
atggctgcaa tgtctgaaga tagctgtgtc aactttaagg agatgatgtt cattgataat   60
actttgtact ttatacctga agaaaatgga gaccttgagt cagacaactt cgggagactg  120
cactgcacaa ctgccgttat ccgaaacata aatgatcaag tattgttcgt ggacaaaaga  180
caaccagtct ttgaggatat gacagacatc gaccaatccg catctgaacc tcagactagg  240
ctgatcatct atatgtacgc cgactccgaa gtaagaggcc ttgctgtgac acttagtgtt  300
```

```
aaggatagta agatgagcac actgtcctgt aagaataaga ttatatcttt tgaagagatg   360
gaccctcccg agaacataga tgacatccag agcgacttga tcttctttca gaagcgagtg   420
ccaggccata acaagatgga atttgaatca tctctttatg aaggccattt cctcgcatgt   480
caaaaggagg acgatgcctt caagctcatt ctgaaaaaaa aagacgagaa cggtgataag   540
agcgtgatgt tcactctgac aaatctgcac cagtcatag                          579

SEQ ID NO: 71            moltype = DNA   length = 534
FEATURE                  Location/Qualifiers
source                   1..534
                         mol_type = other DNA
                         organism = Homo sapiens
SEQUENCE: 71
atgtatcgca tgcaactcct gtcctgcatt gctctgagct tggctttggt aaccaactca   60
tacttcggga aactggagag taaactctcc gtaatcagga atcttaatga ccaagtattg   120
tttattgacc agggcaaccg cccgttgttc gaggatatga ctgattctga ctgtcgggat   180
aacgctccga gaactatctt tatcatttca atgtacaagg acagccaacc gcggggtatg   240
gctgtgacaa tcagtgtcaa atgtgagaag atttccacgc tgtcctgcga aaacaagata   300
atttctttca aagaaatgaa cccccctgac aatataaagg atacaaagag tgatatcatc   360
ttctttcaga ggtccgtgcc cggccacgat aataagatgc aatttgaaag ttcatcttat   420
gaggggtact ttttggcatg cgagaaagaa agggatctct tcaagttgat cctgaagaag   480
gaggacgaat gggcgaccg ctccatcatg ttcacagtcc agaacgagga ctag           534

SEQ ID NO: 72            moltype = DNA   length = 534
FEATURE                  Location/Qualifiers
source                   1..534
                         mol_type = other DNA
                         organism = Homo sapiens
SEQUENCE: 72
atgtaccgca tgcagctcct gagttgtatt gccctttccc tcgctctcgt taccaattct   60
tacttcggta agcttgcctc taaactctct gttattagga acttgaacga ccaagtcctt   120
ttcatagacc aagggaacag accactgttt gaagatatga cggatagcga ttgccgagat   180
aatgcccta ggacgatttt tatcattagt atgtatgcgg actctcaacc gaggggatg     240
gccgttacta taagtgtgaa atgcgagaaa atatcaacgc tcagttgtga gaacaaaatc   300
ataagtttca aggagatgaa tccacctgat aacatcaaac ataccaagtc tgatattata   360
tttttccaac gaagtgttcc gggacacgat aacaaaatgc aatttgagag ctcctcatac   420
gagggctact cctcgcgtg tgagaaagaa agggatttgt ttaagcttat cctcaagaaa   480
gaggacgagt gggggatcg gagcataatg tttaccgtac agaatgagga ctag           534

SEQ ID NO: 73            moltype = DNA   length = 441
FEATURE                  Location/Qualifiers
source                   1..441
                         mol_type = other DNA
                         organism = Mus musculus
SEQUENCE: 73
atggagcgga cactcgtgtg tcttgtcgta attttctcg ggacagtcgc acacaagtcc    60
tcaccccagt gtcctgatcg ccttctcata cgcctccgac atttgatcga cattgtagag   120
cagtcaaaa tttacgagaa tgacctcgat cccgagcttt tgagtgctcc caagacgtt     180
aagggtcatt gcgagcacgc agcttttgct tgcttccaga aggccaagtt gaaaccaagc   240
aaccctggta ataataagac tttcatcatc gacttggtcg cccaactccg aaggaggctg   300
cctgcccggc gcggaggaaa aaaacaaaag catattgcaa agtgtccttc atgtgattca   360
tacgaaaagc ggactcccaa agagttcttg gaaaggttga aatggcttct tcagaagatg   420
attcatcaac atttgtcata g                                             441

SEQ ID NO: 74            moltype = DNA   length = 564
FEATURE                  Location/Qualifiers
source                   1..564
                         mol_type = other DNA
                         organism = Homo sapiens
SEQUENCE: 74
atgaccaaca aatgccttt gcaaattgcc ctgcttttgt gttttagcac taccgcattg     60
agcatgtcat ataacctcct cggcttcctt cagagatcat caaactttca gtgtcagaaa   120
ctgctttggc aacttaatgg caggctcgaa tattgtctga aagatcggat gaatttcgac   180
attccagaag aaataaaaca gcttcaacaa ttccagaaag aggacgccgc cctgactatt   240
tacgagatgc tccagaatat cttcgccatt ttccggcaag acagctcatc cacggggtgg   300
aatgagacta ttgtagaaaa tcttctggct aatgtgtacc atcaaattaa tcacctcaaa   360
acggtgcttg aggaaaaact tgaaaaggaa gatttcacac ggggcaagtt gatgtcctcc   420
ctgcacctta aacgatacta cggcaggatt cttcattact tgaaggctaa ggagtatagc   480
cattgcgcgt ggacaattgt acgggtagaa atactgcgaa acttttattt catcaaccgg   540
ctcactggat accttagaaa ttag                                          564

SEQ ID NO: 75            moltype = DNA   length = 549
FEATURE                  Location/Qualifiers
source                   1..549
                         mol_type = other DNA
                         organism = Mus musculus
SEQUENCE: 75
atgaacaatc ggtggatact ccacgccgca tttctcctct gctttagcac gacggccctg    60
tccatcaact acaaacagct tcagttgcag gagcggacta acataaggaa gtgccaggaa   120
ctgctggaac agcttaatgg taaaattaat cttacatacc gagctgactt caaaattcct   180
```

```
atggaaatga ccgagaagat gcagaaatcc tacacggcat tcgccatcca ggaaatgctc   240
cagaacgtat ttctcgtgtt ccgcaataat ttctcttcta cgggttggaa cgaaaccatt   300
gttgttagac tgcttgacga actgcatcag caaaccgtgt tccttaaaac cgtgcttgag   360
gagaagcagg aggagcgcct gacttgggag atgtctagta ccgcacttca cttgaaatcc   420
tactactggc gcgttcagcg gtatctgaag ctgatgaagt ataactcata cgcctggatg   480
gtagtgcgcg cagagatctt cagaaacttt cttatcatcc ggcgactgac ccgaaacttt   540
cagaattag                                                          549

SEQ ID NO: 76              moltype = DNA   length = 501
FEATURE                    Location/Qualifiers
source                     1..501
                           mol_type = other DNA
                           organism = Homo sapiens
SEQUENCE: 76
atgaagtaca ctagctatat attggccttc cagctttgca tcgtattggg tagcctcgga   60
tgctattgcc aagacccgta tgtcaaagaa gccgaaaatc tcaaaaagta tttcaatgcc   120
ggacactcag acgtcgcgga taacggtaca ctgtttcttg gcatcctgaa aaattggaag   180
gaagagagtg acagaaaaat aatgcagtca caaatagtgt ccttttactt taagctgttc   240
aaaaatttca aggatgacca aagtatccag aagagtgttg aaactatcaa agaggacatg   300
aatgtgaaat tctttaacag taataagaag aagcgcgatg acttcgagaa actcactaat   360
tacagcgtaa cggatcttaa cgtccaacgc aaggcaatcc acgagcttat acaggtaatg   420
gctgagctta gtcccgcagc caagacaggg aagagaaaaa ggtctcaaat gctttttcgg   480
ggccggcgag cttcacaata g                                             501

SEQ ID NO: 77              moltype = DNA   length = 468
FEATURE                    Location/Qualifiers
source                     1..468
                           mol_type = other DNA
                           organism = Mus musculus
SEQUENCE: 77
atgaacgcta cgcattgcat cctcgcactc caattgttcc tcatggctgt gtcagggtgt   60
tactgtcacg gtactgtcat agaaagcctc gaatccctga ataactattt taacagtagc   120
ggtatagatg tagaagaaaa gtctctcttt cttgacatct ggaggaattg gcaaaaggat   180
ggagacatga agattctcca atctcagatt atatcatttt acttgaggct ttttgaggtt   240
ctgaaggata accaggcgat cagcaataat atcagcgtaa ttgaatctca ccttattaca   300
acatttttct caaattccaa ggcaaagaaa gatgctttca tgtctatcgc gaaatttgag   360
gtgaacaatc ctcaggtaca aaggcaagcc tttaacgagc tgattagagt tgtacatcag   420
ttgttgcccg aaagtagtct tagaaaacgc aaacggagcc gatgctag              468

SEQ ID NO: 78              moltype = DNA   length = 570
FEATURE                    Location/Qualifiers
source                     1..570
                           mol_type = other DNA
                           organism = Mus musculus
SEQUENCE: 78
atggcaaggt tgtgcgcttt tctcatggta ctggctgtgc tctcctattg gcctacttgt   60
tctctgggat gcgacttgcc acagacccac aatctgcgga ataagagggc tctgactctg   120
ctggtgcaaa tgagacggct ctctccactt agctgtttga aagatagaaa ggatttcggg   180
ttcccccagg agaaggtgga tgcccagcag atcaagaagg cacaggctat ccccgtcctt   240
tccgagctga cccagcaaat tttgaacatc tttacaagta aggatagttc agctgcatgg   300
aataccacac ttttggattc tttttgtaac gatctgcatt agcagctgaa cgatctccag   360
ggatgcctga tgcagcaagt cggcgtgcaa gaatttccac tcacccagga ggacgctctg   420
ctcgcagtgc gaaagtattt tcaccgaatt accgtgtacc tccgggagaa aaagcattca   480
ccctgcgctt gggaagtagt cagggccgaa gtatggagag cccttagtag ctccgctaat   540
gtactgggcc ggttgcggga agagaaatag                                   570

SEQ ID NO: 79              moltype = DNA   length = 405
FEATURE                    Location/Qualifiers
source                     1..405
                           mol_type = other DNA
                           organism = Homo sapiens
SEQUENCE: 79
atggcgcaaa gtctggctct ttcactcctg atcctggtct tggccttcgg gattccgagg   60
acccaaggaa gtgatggtgg cgcccaagat tgttgcctta aatacagcca gcggaaaata   120
cccgcgaaag tggtcaggag ttatagaaaa caggagcctt ccctgggttg tagtatcccc   180
gccatacttt tcctcccgag aaaacggagc caggccgaac tgtgcgctga ccctaaggaa   240
ctttgggtgc aacaacttat gcaacacctg ataagacac cttctcctca aaagccagct    300
cagggctgcc gaaaagatag aggcgcctca aaaaccggaa aaaagggcaa aggttctaaa   360
ggatgtaagc ggactgaacg ctctcaaacg cctaaagggc cgtag                 405

SEQ ID NO: 80              moltype = DNA   length = 402
FEATURE                    Location/Qualifiers
source                     1..402
                           mol_type = other DNA
                           organism = Mus musculus
SEQUENCE: 80
atggcgcaaa tgatgaccct ttccctgctg agtcttgtcc tcgcgctctg catcccgtgg   60
acgcagggg ctgatggggg gggccaagac tgttgcctga agtattcaca aaaaaagata   120
ccgtactcta ttgtcagagg gtacaggaag caagaaccct ccttgggttg ccctatacca   180
```

```
gcaattctttt tctccccacg caagcattcc aaaccagaac tgtgtgcgaa ccccgaggag    240
ggttgggtac agaacttgat gcgaaggctt gaccagcccc cagcccctgg caagcagtca    300
cctgggtgca gaaaaaacag aggtacttca aagagcggca agaaaggcaa agggagtaaa    360
ggatgtaaaa gaacggagca gacccagcct tcacgaggct ag                       402

SEQ ID NO: 81              moltype = DNA   length = 309
FEATURE                    Location/Qualifiers
source                     1..309
                           mol_type = other DNA
                           organism = Homo sapiens
SEQUENCE: 81
atggcgcaaa gtctggctct ttcactcctg atcctggtct tggccttcgg gattccgagg    60
acccaaggaa gtgatggtgg cgcccaagat tgttgcctta aatacagcca gcggaaaata    120
cccgcgaaag tggtcaggag ttatagaaaa caggagcctt ccctgggttg tagtatcccc    180
gccatacttt tcctccccga gaaaacggagc caggccgaac tgtgcgctga ccctaaggaa    240
ctttgggtgc aacaacttat gcaacacctg gataagacac cttctcctca aaagccagct    300
cagggctag                                                            309

SEQ ID NO: 82              moltype = DNA   length = 309
FEATURE                    Location/Qualifiers
source                     1..309
                           mol_type = other DNA
                           organism = Mus musculus
SEQUENCE: 82
atggcgcaaa tgatgaccct ttccctgctg agtcttgtcc tcgcgctctg catcccgtgg    60
acgcaggggt ctgatggggg gggccaagac tgttgcctga agtattcaca aaaaaagata    120
ccgtactcta ttgtcagagg gtacaggaag caagaaccct ccttgggttg ccctatacca    180
gcaattcttt tctccccacg caagcattcc aaaccagaac tgtgtgcgaa ccccgaggag    240
ggttgggtac agaacttgat gcgaaggctt gaccagcccc cagcccctgg caagcagtca    300
cctgggtag                                                            309

SEQ ID NO: 83              moltype = DNA   length = 327
FEATURE                    Location/Qualifiers
source                     1..327
                           mol_type = other DNA
                           organism = Mus musculus
SEQUENCE: 83
atggcacccc gcgtcacacc cttgcttgct ttttctctgc ttgtcctctg gaccttcccc    60
gctcctaccc ttggaggagc caatgatgcc gaggattgct gcctgagtgt tacacaaagg    120
ccaataccag ggaatatagt gaaggcattc cggtatctgc tcaatgaaga tgggtgcaga    180
gtccccgcag ttgtctttac aacattgcga ggttaccagc tttgtgctcc cccagaccag    240
ccttgggtag atcgcattat tcgccggttg aagaagagct cagcaaagaa taagggcaat    300
tccacacgga gaagccccgt ctcctag                                        327

SEQ ID NO: 84              moltype = DNA   length = 381
FEATURE                    Location/Qualifiers
source                     1..381
                           mol_type = other DNA
                           organism = Mus musculus
SEQUENCE: 84
atgaaatcag cagtcctttt cttgctcggg attattttttc tggaacaatg tggagtgagg    60
ggaacactcg taataagaaa cgctcggtgc tcatgcatat caacatcacg gggcactatc    120
cactacaaat ccctgaagga tctgaagcag ttcgccccaa gccctaactg taacaagacc    180
gaaattatcg caactctcaa aaatggagat cagacttgtc ttgacccaga ttcagcaaat    240
gtcaagaagc tgatgaaaga gtgggaaaag aagatttcac aaaaaaaaaa gcaaaaacgc    300
ggcaagaaac atcaaaagaa catgaaaaac aggaaaccta agactcccca gtcaaggaga    360
agatcccgca agacaaccta g                                              381

SEQ ID NO: 85              moltype = DNA   length = 303
FEATURE                    Location/Qualifiers
source                     1..303
                           mol_type = other DNA
                           organism = Mus musculus
SEQUENCE: 85
atgaacagaa aagttaccgc tatagcactt gctgccataa tatgggccac cgcagctcaa    60
gggttcctga tgttcaagca gggccgatgc ctctgcattg ccctggaat gaaggccgtg    120
aaaatggccg aaatagaaaa agctagtgtc atataccct ctaacggttg cgataaagtc    180
gaggttatag tcacaatgaa agctcataaa cgccaacgct gcctcgaccc ccggtctaag    240
caggctaggc tcataatgca agcaatcgag aagaaaaact ttcttagacg gcaaaacatg    300
tag                                                                  303

SEQ ID NO: 86              moltype = DNA   length = 297
FEATURE                    Location/Qualifiers
source                     1..297
                           mol_type = other DNA
                           organism = Mus musculus
SEQUENCE: 86
atgaacccat ctgccgccgt tattttctgt ctgatactcc ttgggctgag tggcacacaa    60
ggcataccccc tcgcccgcac agtccggtgt aattgtatac atattgacga cggccctgtt    120
```

```
agaatgcggg ccatcggtaa gctggagatt ataccagcaa gccttagttg tcccagggtt    180
gaaatcatag caactatgaa aaaaaacgac gaacaaagat gtttgaatcc cgagagcaag    240
acaatcaaaa accttatgaa agcatttagt caaaaacgct ctaaacgcgc tccatag       297

SEQ ID NO: 87          moltype = DNA  length = 297
FEATURE                Location/Qualifiers
source                 1..297
                       mol_type = other DNA
                       organism = Homo sapiens
SEQUENCE: 87
atgaatcaga cggcaatcct tatatgctgc cttatattcc ttactctctc agggatacaa    60
ggggtaccac tttctcggac tgttcgctgc acttgcattt caatatctaa ccaacctgta    120
aatccgcgga gcctggaaaa attggagatt atacctgctt ctcaattctg ccctcgggtg    180
gaaatcatcg ccactatgaa gaagaagggc gagaaaaggt gtctgaatcc agagtcaaag    240
gcaatcaaaa acctgctgaa agcggtgtca aaggaacggt ccaagagatc accctag       297

SEQ ID NO: 88          moltype = DNA  length = 534
FEATURE                Location/Qualifiers
source                 1..534
                       mol_type = other DNA
                       organism = Mus musculus
SEQUENCE: 88
atgaacagga aagtaacagc cattgcattg gctgccatca tctgggccac cgcagcacag    60
ggttttctga tgtttaagca agggcgctgt ctctgtatag gcccaggcat gaaggccgtg    120
aagatggcag agattgagaa ggcatctgtg atttatcctt ctaacgggtg cgataaagtc    180
gaagttattg tgacaatgaa ggcacacaaa cgccaacggt gtttggaccc acgatctaaa    240
caggcaagat tgattatgca agccatcgag aaaaagaact ttctccgaag gcaaaatatg    300
atccctttgg ctcggacagt gcggtgtaac tgtattcaca tcgacgatgg gccagtacgg    360
atgagagcaa taggaaagct cgaaatcata cccgcctcat tgtcttgtcc cagggtggaa    420
ataatcgcca ctatgaaaaa gaacgatgaa cagaggtgtc tcaacccaga gagtaagact    480
atcaagaacc ttatgaaggc attcagtcag aagaggtcaa agcgagcacc atag          534

SEQ ID NO: 89          moltype = DNA  length = 345
FEATURE                Location/Qualifiers
source                 1..345
                       mol_type = other DNA
                       organism = Homo sapiens
SEQUENCE: 89
atgagacttc tcatattggc gcttctcggg atatgttctc ttacggcata catagttgag    60
ggggtgggat ctgaggttag cgataaacga acttgtgtta gtcttacaac acagaggctt    120
ccagtctcca ggataaaaac atatacgata actgagggat ctctcagagc ggtcatcttc    180
ataacgaaga ggggcctgaa ggtctgtgct gacccacaag cgacttgggt aagggacgtt    240
gtgcggagca tggacaggaa gagcaatact cgcaacaaca tgatccaaac caaacctacg    300
ggcacccaac agtcaaccaa tactgcggta acattgacgg ggtag                    345

SEQ ID NO: 90          moltype = DNA  length = 345
FEATURE                Location/Qualifiers
source                 1..345
                       mol_type = other DNA
                       organism = Mus musculus
SEQUENCE: 90
atgcgcctcc ttctgctgac ttttctgggt gtatgttgcc tgacaccctg ggtcgtagaa    60
ggagtaggaa ccgaggttct ggaagagtcc tcatgtgtaa acttgcagac acaacgactc    120
cccgtccaaa aaatcaagac ctatataatc tgggaggggg caatgcgggc cgtcattttc    180
gtgactaaac gaggtctcaa aatctgcgcc gaccccgagg ctaagtgggt gaaggcagcc    240
attaagaccg tggatgggag agccagcacc agaaagaaca tggccgaaac agtacctact    300
ggcgcacagc ggtcaacctc aactgctata accttgacag gatag                    345

SEQ ID NO: 91          moltype = DNA  length = 513
FEATURE                Location/Qualifiers
misc_feature           1..513
                       note = Description of Unknown: m_sCD40L #1 sequence
source                 1..513
                       mol_type = other DNA
                       organism = unidentified
SEQUENCE: 91
atggagactg acactctgct tctgtgggtg ttgctgctgt gggtgcctgg cagtacaggc    60
gatatgcaac gaggtgacga ggaccctcaa atcgccgccc atgtagtctc tgaagctaat    120
agcaacgctg catccgtctt gcagtgggca aagaaaggct actatactat gaagtccaac    180
ttggtaatgc ttgaaaacgg caagcagttg actgtcaaga gagagggact ttattacgtc    240
tatacccaag tcacattctg tagcaatcga gaacctcct cacagaggcc tttttatagtg    300
ggactctggc ttaaaccaag tagcggctct gagcgcatac tgttgaaagc cgcaaacaca    360
cacagctctt cccaactctg cgagcagcaa tccgtgcatc tcggtggagt atttgagctt    420
caagccggtg cctcagtgtt tgtgaacgtc actgaggcct cccaggtcat acatcgagtt    480
gggttcagct ccttcggctt gctcaagctc tag                                 513
```

-continued

```
SEQ ID NO: 92            moltype = DNA  length = 588
FEATURE                  Location/Qualifiers
misc_feature             1..588
                         note = Description of Unknown: m_sCD40L #2 sequence
source                   1..588
                         mol_type = other DNA
                         organism = unidentified
SEQUENCE: 92
atggaaactg atacattgct gctctgggtt ttgctgctct gggtgcctgg gagtacaggc  60
gacatgagga ggcagttcga ggatctcgtt aaggatatta cccttaataa ggaggagaag  120
aaagaaaact cttttgagat gcaacgaggg gacgaagatc ctcagatcgc tgctcacgtg  180
gtctctgaag ctaacagcaa cgccgcttct gtcctccagt gggccaagaa aggttattac  240
accatgaaat caaaccttgt aatgcttgaa aacgggaaac agcttacagt gaagagggaa  300
ggtctttact acgtctatac ccaggtaacc ttctgctcaa acagagaacc atcaagccag  360
aggccattca tagtggggct ctggctcaaa ccttccagtg gcagcgagag aatcttgttg  420
aaagctgcta atacacatag tagtagccag ctttgcgagc aacagtcagt ccacctcggg  480
ggggtgtttg agttgcaagc aggggcctca gtattcgtga atgtcactga ggcttcccag  540
gtaattcaca gggtaggctt tagttcattc ggtttgctga agctttag                588

SEQ ID NO: 93            moltype = DNA  length = 849
FEATURE                  Location/Qualifiers
misc_feature             1..849
                         note = Description of Unknown: m_sCD40L #3 sequence
source                   1..849
                         mol_type = other DNA
                         organism = unidentified
SEQUENCE: 93
atgcgaagaa tgcagcttct gctccttatt gctctgagtc tcgcccttgt caccaactcc  60
ggggacagaa tgaaacaaat cgaggacaaa attgaagaaa tactgagtaa aatatatcac  120
atcgaaaacg aaattgcacg cattaagaaa ttgattggcg aacgcaccag tggcggctct  180
ggtggcaccg gaggttcagg cgggaccggg ggctctgaca aagtcgaaga ggaggttaac  240
cttcatgagg actttgtgtt catcaagaag ctgaaacggt gcaataaagg agaaggttct  300
ttgagcctcc ttaattgcga agagatgcga cgacagttcg aggatctggt taaggacatt  360
acacttaata aggaagagaa aaaggagaac tctttcgaaa tgcagcgcgg cgatgaagat  420
ccccagatag ccgcccatgt cgtctctgag gccaactcta acgcagcatc cgtcctccag  480
tgggctaaga aaggatatta tactatgaaa agcaatttgg tcatgctcga aaacggtaaa  540
cagctcactg ttaagagaga aggcctctat tacgtatata ctcaagtaac tttctgttct  600
aataggggaac cctcctctca aagacctttt atcgtaggac tctggttgaa accaagtagc  660
ggtagtgaaa ggattctgct caaagcagct aatactcact ccagcagtca actgtgcgaa  720
caacaaagcg ttcacctcgg ggggcgtcttt gaacttcagg caggtgccag tgttttcgtc  780
aacgtaacag aagcatccca ggtaattcat cgagtagggt tttctagctt tggtttgctg  840
aagctgtag                                                           849

SEQ ID NO: 94            moltype = DNA  length = 2160
FEATURE                  Location/Qualifiers
misc_feature             1..2160
                         note = Description of Unknown: anti-CD40_FGK4.5 sequence
source                   1..2160
                         mol_type = other DNA
                         organism = unidentified
SEQUENCE: 94
atggaaactg atcgcctgtt gctctgggta cttcttctgt gggtgcctgg gtccactggt  60
gacactgtac ttcacaaatc acccgctttg gccgtttctc ctggtgaacg ggtcacaatt  120
agttgccgag cttccgattc tgtatctact cttatgcatt ggtatcaaca aaaacctggt  180
cagcagccaa aattgctcat ttatcttgct agtcacttgg agtccggcgt acctgctcga  240
ttcagcggta gtgggtctgg cacagatttc actttgacca tagatcccgt ggaggccgat  300
gacactgcaa cctactattg ccagcaatcc tggaacgacc cttggacttt cggcggcggc  360
accaagctgg aactcaagcg agcagatgct gccccaaccg ttagtatatt cccaccctca  420
accgaacaac tcgccacagg aggcgctagt gtcgtgtgtc ttatgaacaa tttctatccca  480
cgagacatta gcgtcaagtg gaaaattgat gggacagaaa ggcgagatgg agttttggat  540
tcagtaacag accaggattc aaaggattct acctatagca tgagctccac cttgagcctg  600
accaaagctg attatgaatc tcataacctg tatacttgtg aagtggtgca taagacttct  660
agctcaccag tggttaaatc ttttaaccgc aacgaatgtc agccaagagg ggttccgtaa  720
gagggaaggg gtagtctgct cacctgcggc gatgttgaag aaaatcctgg tcccatggac  780
attcggctct ctttggtatt cctggtactt tttataaagg gggtgcaatg tgaagtccag  840
ctcgtggaaa gcggtgggggg cctggttcag cccggtcgca gccttaaact tagttgcgca  900
gcatccggat ttacattttc tgactataac atggcctggg ttcgacaggc acccaaaaaa  960
gggctggagt gggtcgcaac tatcatatac gatggttccc gtacatacta tagagattca  1020
gtgaagggggc gctttacaat aagcagggac aatgctaagt ctaccttgta tcttcagatg  1080
gactccctga ggagcgaaga tacagcaaca tattattgtg ctacaaaccg ctggttgctg  1140
cttcattatt tcgactactg gggtcagggc gtcatggtaa ctgtatcaag cgccgagacc  1200
acagcccctt ctgtatatcc attggcacca ggtactgctc tgaaatccaa ctcaatggta  1260
accccttggat gtctggttaa gggttatttt cccgagcccg tcacagttac ttggaactct  1320
gggccccttt ctagcggagt ccatacctttt cccgccgttt tgcagagtgg tctgtacacc  1380
cttacctcaa gcgtcacagt tccatctagc acatggagct cccagcagt aacttgtaat  1440
gtggcccatc cagcctcctc aactaaggta gataaaaaga tcgttccag agaatgcaat  1500
ccatgtggat gcaccgggtc tgaggtcagc agtgtgttca ttttcccacc caagactaaa  1560
gatgtattga ctattactct tacacccaaa gtaacctgcg tggtggttga tattagtcaa  1620
```

```
aatgatcccg aggtacggtt ctcttggttt atcgacgacg tcgaagtaca tacagctcag   1680
acacacgctc ccgagaaaca aagcaattcc actcttagga gcgtgtccga gttgccaatc   1740
gtacataggg attggcttaa tggcaagacc tttaagtgta aggtcaattc aggggcattc   1800
cccgcaccaa tagagaagag tataagcaaa cccgagggga cacccagagg tccacaggtc   1860
tatacaatgg ctccccccaa ggaagagatg acccaaagtc aagtctcaat tacatgtatg   1920
gtgaagggct tttatccacc cgacatatac actgagtgga agatgaatgg acagccccaa   1980
gagaattata aaaacactcc ccctaccatg gacaccgacg ggtcctattt tctttatagt   2040
aaattgaacg tgaaaaagga gacctggcaa caaggcaaca ctttcacctg ctccgttctt   2100
cacgagggcc tgcataatca tcataccgaa aagtctctca gtcattctcc aggtaagtag   2160
```

SEQ ID NO: 95           moltype = DNA   length = 528
FEATURE                 Location/Qualifiers
source                  1..528
                        mol_type = other DNA
                        organism = Homo sapiens SEQUENCE: 95
```
atggaaacag atacgttgct gttgtgggta cttctccttt gggtccctgg cagcacaggg   60
gacgagaata gtttcgaaat gcagaagggc gaccagaacc cacagatcgc ggctcacgtt   120
atatcagaag caagtagtaa gaccacttcc gtacttcagt gggctgaaaa aggatattac   180
accatgtcca acaatctcgt gacactggag aacggtaaac aacttacggt gaaacgacag   240
ggcctctatt acatctacgc tcaggtgaca ttctgctcaa atagggaggc ttctagtcaa   300
gcgcccttca tcgccagcct gtgcctcaaa tctcccgggc ggttcgaacg aatcctgttg   360
cgagcggcca atacccatag ctcagctaaa ccttgcggcc agcagagtat tcatcttggt   420
ggtgtgtttg aacttcagcc gggagcatct gtgttcgtca acgtaacgga ccctagccaa   480
gtgtctcatg ggacaggttt tacatccttc ggactcctca agttgtag             528
```

SEQ ID NO: 96           moltype = DNA   length = 540
FEATURE                 Location/Qualifiers
source                  1..540
                        mol_type = other DNA
                        organism = Homo sapiens SEQUENCE: 96
```
atgacagttc tcgcgccagc ttggagtccc accacatact tgcttttgct tctgcttctg   60
tcctctggca tgagtgggac ccaagattgt tcctttcaac attccccaat tagttctgat   120
tttgcagtga agattagaga gctctcagac tatctgctgc aagattatcc tgtcacagtc   180
gcttcaaacc tgcaagacga agagctctgc ggtgccttgt ggcggttggt cttggctcaa   240
agatggatgg agagactgaa aaccgtagca ggcagcaaga tgcagggtct cctggaaagg   300
gtgaacacgg aaatccattt tgtgaccaag tgcgcgttcc agccccaccc gagttgtctc   360
cggtttgttc aaacgaatat atcccggttg ctccaggaaa cctcagaaca actggtggct   420
ttgaaaccct ggatcacaag acaaaacttt agtcggtgcc tcgaactcca gtgccaacca   480
gattcttcta cacttccccc cccgtggtcc ccgcgcccgt tggaagcaac ggccccatag   540
```

SEQ ID NO: 97           moltype = DNA   length = 876
FEATURE                 Location/Qualifiers
source                  1..876
                        mol_type = other DNA
                        organism = Homo sapiens SEQUENCE: 97
```
atggcctgga gtcctctgtt tctgactctt ataactcact gtgccggcag ttgggctata   60
cccccctcatg tacagaagtc tgtaaacaac gacatgattg taaccgacaa taatggcgca   120
gtgaaattcc cacaactgtg taagttctgt gatgtacggt ttagtacatg cgacaatcaa   180
aaaagctgta tgtctaactg ctctattaca tccatatgtg aaaaacctca ggaggtgtgt   240
gttgccgttt ggcgaaaaaa tgatgagaat atcacactgg agacagtatg tcatgaccct   300
aaactgccat accatgattt catactggag gacgccgcca gtcctaagtg cattatgaaa   360
gagaaaaaga aacccggtga aacattcttt atgtgctctt gtagctctga cgagtgtaac   420
gacaacatta tattcagcga ggagtacaat acaagcaacc ccgatatacc acctcacgta   480
caaaaaagtg tcaacaacga tatgattgtt accgacaata acggagctgt taagtttcct   540
cagttgtgca agtctgcga tgtacgattc tctacctgcg acaaccaaaa gtcatgtatg   600
tctaactgtt ccataaacctc catctgcgag aagccccagg aagtctgcgt cgccgtgtgg   660
cggaaaaacg acgagaatat cactcttgaa accgtttgtc atgatcctaa actgccctat   720
cacgacttta ttctggaaga tgctgcttcc cctaagtgta tcatgaaaga aaagaagaaa   780
cctggggaga cattctttat gtgttcatgc tcctccgatg agtgtaacga caatatcatc   840
ttctctgagg aatacaacac ttctaaccct gattag                          876
```

SEQ ID NO: 98           moltype = DNA   length = 2178
FEATURE                 Location/Qualifiers
source                  1..2178
                        mol_type = other DNA
                        organism = Homo sapiens SEQUENCE: 98
```
atggcctggt ccctctcttt tctgaccctc atcacacact gtgcaggctc atgggctgag   60
accgtcttga cccagtcccc aggaactttg tctctgtctc ctggtgaaag agctaccctt   120
agttgtcgag cctctctcagtc ccttggttct agctatctcg cttggtacca gcaaaagcca   180
ggccaggccc cacgactgct gatctacgga gcatcttcac gggctcccgg cattcccgat   240
cgattttccg gatctggtag tggtacagat ttcacactga ccatatctcg cctggagccc   300
gaggactttg ctgtttatta ttgtcagcag tacgccgatt ctcctatcac ttttggacag   360
ggaacccgcc tggagattaa gcgcacagta gcagctccat ccgtctttat ctttccacca   420
tcagatgaac agctcaagag tgggaccgca agtgtagtat gcctgctgaa caatttttac   480
cctagagagg ccaaagtgca gtggaaggtg ataacgcccc tccagagtgg caatagtcaa   540
```

-continued

```
gaaagtgtta ctgagcaaga tagtaaggac tctacatact cttttgagttc tacttttgacc    600
ctgtcaaaag cagattatga aaaacataag gtgtatgcat gtgaagttac acaccaaggg    660
ttgtcctctc cagttacaaa atcttttaat agaggagagt gccgccgcaa acgcggtagt    720
ggagaaggtc gaggctcact cttgacctgt ggcgacgtgg aagaaaatcc cggtcctatg    780
gattggactt ggagggtatt ttgtcttttg gcagtaacac ctggagctca cccccaagta    840
cagctcgtcc aatctggtgc cgaggttaaa aagcctggaa gttcagtgaa ggtctcttgc    900
aaggcatctg gatacacctt ttcatctaac gtcatatcct gggtacggca agccccagga    960
cagggacttg agtggatggg aggggtcatc cccatcgtgg acattgctaa ttacgctcag   1020
cgattcaaag ggcgggttac tataactgcc gacgagtcta cctcaactac ctacatggag   1080
ttgtcctctc tccgctccga ggacactgct gtatattact gtgccagcac tctcgggttg   1140
gtgttggatg ccatggacta ttggggacaa ggaaccctgg tgacagttag ctccgcaagc   1200
actaaaggcc cttctgtttt tcccttggca ccttgtagta ggtctacctc tgagtctaca   1260
gcagcacttg gatgcttggt taaggactat tttcccgagc cagttacagt ctcttggaac   1320
agtggtgccc tcacaagtgg ggttcatacc ttccccgcag tcctccagag tagtggcctt   1380
tacagcctct catcagttgt gactgttcct agttcatcac tcggtactaa gacatataca   1440
tgtaacgtag accacaagcc aagcaacaca aaagtagaca aacgagtcga atctaagtat   1500
ggaccccctt gtccctcctg tcctgctccc gagttccttg ggggcccttc cgtgttcttg   1560
tttcctccca agcccaagga taccctcatg atctcacgaa ccccagaggt aacatgtgtg   1620
gttgttgacg taagtcagga agatcccgaa gtgcaattta attggtacgt ggatggcgtc   1680
gaagtccata acgctaaaac aaaaccccga gaggaacaat tcaattccac atatcgggtg   1740
gtgagtgtat tgaccgttct tcaccaagat tggctgaacg gcaaggagta taagtgtaaa   1800
gtaagcaaca aaggtctgcc aagtagcata gaaaaaacaa tatctaaagc taagggccaa   1860
ccaagggaac cacaagtata tacattgccc ccctctcagg aagagatgac aaaagaatcaa   1920
gttagcctga cctgtttggt aaaggggttc tatccctcag atatagcagt cgagtgggaa   1980
tctaacggca gcccgagaa taattataaa acaacccccc ctgtgttgga ctcagacggc   2040
agcttcttc tctattcacg gctcactgtt gataagtccc gatggcagga ggggaatgtt   2100
ttcagctgta gcgtgatgca cgaagctctc cacaaccact atacacagaa aagtttgtct   2160
ttgtcccttg gaaaatag                                                  2178
```

```
SEQ ID NO: 99         moltype = DNA  length = 1062
FEATURE               Location/Qualifiers
source                1..1062
                      mol_type = other DNA
                      organism = Homo sapiens
SEQUENCE: 99
atgagtacat cctttccaga gctggatctg gagaattttg agtatgacga cagtgccgaa    60
gcctgctacc tcggggacat agtcgcattc gggacaatct ttttgtctgt attttacgcc   120
ctggtgttta catttggcct ggttggaaat ctgttggtcg tactcgctct caccaattcc   180
cgaaaaccca aaagtataac agacatatac ctgttgaatc tggcactgag tgacctttg    240
ttcgtcgcca cccttccttt ttggacacac taccttatca gtcacgaggg gcttcataat   300
gctatgtgca agctcactac tgccttcttc tttatcggat tcttcggggg tatctttttt   360
atcacagtta ttagcattga ccgatacctt gccagtagtgc tcgcagccaa ctcaatgaac   420
aaccgcaccg tgcagcatgg agtgactatt tccttggtg tgtgggccgc tgctatactt   480
gtcgccagcc ctcaattcat gtttaccaaa aggaaagaca atgagtgcct cggagattac   540
cctgaggtgt tgcaagaaat gtggcctgta cttcgaaata gcgaagtgaa tatactcggc   600
tttgctcttc tctgctcat catgtcattc tgttattttc gaataatcca aacattgttc   660
agctgtaaga accgaaagaa agcccgcgcc gtacgcctga ttctgctcgt tgtgttcgcc   720
tttttctgt tttggactcc ttacaacata atgatattcc tggagactct caaattctat   780
aacttttttc cctcctgtga tatgaaaagg gaccttagat tggctctcag tgtcactgaa   840
acagtagcct ttagccattg ttgtctcaac cctttcatat atgcatttgc aggggaaaag   900
ttccggcggt atctcggaca tttgtatcgg aagtgcttgg ccgtgttgtg tggtcatcct   960
gtccataccg gattctctcc tgagagtcaa cggagccgcc aagattcaat cctgtccagt   1020
ttcactcact atacttcaga gggggatggc agccttctgc tc                      1062
```

```
SEQ ID NO: 100        moltype = DNA  length = 1458
FEATURE               Location/Qualifiers
misc_feature          1..1458
                      note = Description of Unknown: Kyneurinase #1 sequence
source                1..1458
                      mol_type = other DNA
                      organism = unidentified
SEQUENCE: 100
atggagaccg acactttgtt gctgtgggta ctttttgttgt gggtcccagg atctaccggg    60
gatatggaac cctctcctct tgaactgcca gtagacgccg tgcgccgcat tgcagccgag   120
ttgaattgcg atccaacaga tgaacgcgtt gccctgaggc tcgacgaaga ggataaaattg   180
tcacatttca ggaactgctt ttacattcca aagatgaggg atcttccatc catagatctt   240
agcctcgtgt ccgaggatga cgatgccata tatttttcttg ggaacagtct tgggttgcag   300
ccaaaaatgg tacggacata tctcgaagag gagctggaca aatgggctaa aatgggtgct   360
tacggccacg acgtgggaaa acgcccctgg atagttggag acgaatctat cgtgagtctt   420
atgaaagata tagttggagc acatgagaaa gaaattgcac tgatgaatgc ccttactatc   480
aatctgcatc tcctcttgct ttcattcttt aagcccactc ctaaacgcca caaatactt   540
ttggaagcaa aagcctttcc aagcgaccac tacgctattg agtcacaaat acaactccat   600
ggacttgatg tggaaaagtc tatgcggatg gtaaaaccac gcgaaggcga ggagaccctt   660
cgaatggagg acatacttga ggtcatcgaa gaagaaggag atagtatagc agttatcctt   720
ttcagcgggc tgcacttcta cacaggtcaa ctctttaaca ttccagctat tactaaggca   780
ggccacgcta aaggatgctt cgtgggcttt gaccttgcac acgcagtagg aaacgtagag   840
ctccgcttgc acgattgggg cgttgatttc gcctgctggt gttcatataa gtatcttaac   900
tcaggagctg gtgggttggc aggcgcattc gtacacgaga aacacgctca taccgtaaag   960
cctgcactgg tagggtggtt cggacacgat ctctctaccc gcttcaatat ggataataaa   1020
```

```
ctccagctta tacctggcgc caatggattc aggatctcaa atcctcctat tttgctcgtt   1080
tgcagtttgc acgcatctct tgaggtgttc cagcaggcta ccatgactgc actccgccgg   1140
aagtcaatcc ttttgaccgg atacttggag tatatgctga aacattatca ctcaaaagat   1200
aacactgaga ataagggccc catagtaaac attatcactc catctcgggc tgaagagcgc   1260
ggctgccaac tcacattgac tttttccatt cccaagaagt cagtgttcaa agagttggag   1320
aaacgggggg ttgtatgtga taagcgggag ccagatgaa tccgcgttgc cccagtcccc   1380
ctctataatt cttttcacga tgtatacaag tttattagac tgctgacaag tatcttggac   1440
tcatctgagc gatcttag                                                   1458
```

```
SEQ ID NO: 101           moltype = DNA   length = 1395
FEATURE                  Location/Qualifiers
misc_feature             1..1395
                         note = Description of Unknown: Kyneurinase #2 sequence
source                   1..1395
                         mol_type = other DNA
                         organism = unidentified
SEQUENCE: 101
atggaaccct ctcctcttga actgccagta gacgccgtgc gccgcattgc agccgagttg   60
aattgcgatc caacagatga acgcgttgcc ctgaggctcg acgaagagga taaattgtca   120
catttcagga actgctttta cattccaaag atgagggatc ttccatccat agatcttagc   180
ctcgtgtccg aggatgacga tgccatatat tttcttggga acagtcttgg gttgcagcca   240
aaaatggtac ggacatatct cgaagaggac ctggacaaat gggctaaaat gggtgcttac   300
ggccacgacg tgggaaaacg cccctggata gttggcgacg aatctatcgt gagtcttatg   360
aaagatatag ttggagcaca tgagaaagaa attgcactga tgaatgccct tactatcaat   420
ctgcatctcc tcttgctttc attctttaag cccactccta aacgccacaa aatacttttg   480
gaagcaaaag cctttccaag cgaccactac gctattgagt cacaaataca actccatgga   540
cttgatgtgg aaaagtctat gcggatggta aaaccacgcg aaggcgagga gacccttcga   600
atggaggaca tacttgaggt catcgaagaa gaaggagata gtatagcagt tatcctttc    660
agcgggctgc acttctacac aggtcaactc tttaacattc cagctattac taaggcaggc   720
cacgctaaag gatgcttcgt gggctttgac cttgcacacg cagtaggaaa cgtagagctc   780
cgcttgcacg attggggcgt tgatttcgcc tgctggtgtt catataagta tcttaactca   840
ggagctggtg ggttggcagg cgcattcgta cacgagaaac acgctcatac cgtaaagcct   900
gcactggtag ggtggttcgg cacgatctc tctacccgct tcaatatgga taataaactc   960
cagcttatac ctggcgccaa tggattcagg atctcaaatc ctcctatttt gctcgtttgc   1020
agtttgcacg catctcttga ggtgttccag caggctacca tgactgcact ccgccggaag   1080
tcaatccttt tgaccggata cttggagtat atgctgaaac attatcactc aaaagataac   1140
actgagaata agggccccat agtaaacatt atcactccat ctcgggctga gagcgcggc    1200
tgccaactca cattgacttt ttccattccc aagaagtcag tgttcaaaga gttggagaaa   1260
cggggggttg tatgtgataa gcgggagcca gatggaatcc gcgttgcccc agtccccctc   1320
tataattctt ttcacgatgt atacaagttt attagactgc tgacaagtat cttggactca   1380
tctgagcgat cttag                                                     1395
```

```
SEQ ID NO: 102           moltype = DNA   length = 573
FEATURE                  Location/Qualifiers
misc_feature             1..573
                         note = Description of Unknown: VEGF sequence
source                   1..573
                         mol_type = other DNA
                         organism = unidentified
SEQUENCE: 102
atgaatttct tgctgagctg ggtgcattgg acactcgcat tgttgctgta cttgcaccat   60
gccaagtggt cccaggctgc acccactact gagggcgagc aaaagtctca tgaggtgatt   120
aaatttatgg acgtttacca acgatcatac tgtcggccaa tcgaaaccct cgtagatata   180
ttccaggagt acccagacga gatcgaatac attttcaagc cctcatgtgt cccattgatg   240
cgatgtgctg ggtgctgtaa cgacgaagca cttgaatgtg tccccacctc cgagagtaac   300
atcacaatgc aaataatgag aatcaagccc caccaatccc aacatatcgg tgaaatgtca   360
ttccttcagc attcccgctg cgagtgccgg cctaagaagg accgcaccaa accagagaac   420
cattgtgaac cctgttctga gagacggaag cacttgttcg tacaggaccc tcaaacatgc   480
aagtgcagct gtaagaatac cgactcacgg tgtaaagcta ggcaactgga gcttaatgaa   540
aggacctgcc gatgcgataa acccaggagg taa                                 573
```

```
SEQ ID NO: 103           moltype = DNA   length = 426
FEATURE                  Location/Qualifiers
misc_feature             1..426
                         note = Description of Unknown: GM-CSF sequence
source                   1..426
                         mol_type = other DNA
                         organism = unidentified
SEQUENCE: 103
atgtggttgc agaatttgct cttcctgggg attgtggtct acagcctctc cgcacctacc   60
cgctctccta tcacagttac aagaccctgg aaacatgtgg aggccattaa agaagcattg   120
aatttgttgg acgatatgcc cgtcaccctg aatgaagaag tagaagttgt ttctaatgag   180
ttcagcttta aaaaattgac ctgtgtgcag acacggctta aaattttga caggggactt   240
agaggaaact ttactaagct gaaggggca cttaacatga cagcttctta ttatcagacc   300
tattgtcctc caacacctga aaccgactgt gaaacacagg taaccactta cgccgatttt   360
attgattctt tgaaaacatt cctcaccgat ataccatttg agtgtaagaa gccaggccaa   420
aagtag                                                               426
```

```
SEQ ID NO: 104           moltype = DNA   length = 822
```

-continued

```
FEATURE          Location/Qualifiers
misc_feature     1..822
                 note = Description of Unknown: Anti-PD1 sequence
source           1..822
                 mol_type = other DNA
                 organism = unidentified
SEQUENCE: 104
atggaaactg acacacttct tctgtgggtc ttgctcctgt gggtcccagg ctctactggt    60
gacagtcctg ataggccatg gaacccacct acctttagtc cagccttgct cgtcgtaacc   120
gaaggggaca acgctacatt cacctgctct tttagcaata cttctgagag ttttcatgta   180
gtctggcatc gggagagtcc atccggacaa acagatactt tggccgcttt tccagaggat   240
aggtctcaac ctgggcaaga cgcaaggttt cgagtcacac agcttcctaa cgggagagat   300
tttcacatgt ctgtagttcg ggcacgccga aatgattctg gcacatatgt ttgcggtgtg   360
atctcacttg ctccaaagat tcaaataaag gagagccttc gcgccgagtt gcgggtgact   420
gagcgggagc ccaagtcctg cgacaaaacc catacttgtc caccctgtgg cggcgggtca   480
tccggtggcg ggtctggggg gcaaccaaga gagccacagg tatatactct tcccccccagc   540
agagaagaaa tgacaaaaaa ccaagtgtcc ctgacatgtc tggttaaagg attttatccc   600
agtgacattg ctgtagaatg ggaatccaat ggtcaacccg agaataacta caaaaccact   660
cctccagtat tggacagtga cggttccttc ttcctctatt ccaaacttac agtggataaa   720
tcccgctggc agcaagggaa tgtattcagc tgtagtgtca tgcacgaagc tcttcataac   780
cattatacac agaaatctct ttccctgagc ccaggtaaat ag                      822

SEQ ID NO: 105     moltype = DNA   length = 1116
FEATURE            Location/Qualifiers
source             1..1116
                   mol_type = other DNA
                   organism = Mus musculus
SEQUENCE: 105
atggagactg atacactttt gctctgggtt ttgctcttgt gggtaccagg gtctactgga    60
gatgcacaaa ctcctgcatt caacaagcct aaggtagagc ttcatgtcca tttggacgga   120
gccataaaac ctgaaaccat actctatttc ggcaagaaac ggggtatagc acttcccgct   180
gataccgtgg aagagttgag aaatatcatt ggcatggaca aacctcttag cctgcctggc   240
tttcttgcaa agttcgacta ctatatgcca gttatagcag ggtgtagaga agcaataaag   300
cgaatcgcct atgagttcgt tgagatgaag gctaaagaag gagttgttta cgtggaagtc   360
cggtactcac ctcatctgct tgctaatagc aaggtggacc caatgccatg gaatcaaact   420
gaaggtgatg taaccctga cgatgtggtc gatttggtca atcaaggtct ccaagaaggc   480
gagcaggctt tcggcattaa ggtaagaagt atattgtgct gtatgcgaca tcaaccttca   540
tggtccctga aggtcctcga attgtgcaaa aagtacaatc aaaaaacagt ggtcgcaatg   600
gatctcgctg gagatgagac catagaaggt tcctctcttt tccccggtca tgtcgaagca   660
tatgaagggg ctgtcaaaaa tggtatccac cgcaccgtcc acgcagggga agtagggtcc   720
ccagaagtag tcagggaagc cgttgacatt ttgaaaacag aaagagtcgg gcatggctac   780
catacaatag aggacgaagc cttgtacaat cgacttttga aagaaaatat gcacttcgag   840
gtctgtccct ggagttcata tctcaccgga gcatgggacc caaaacaac ccacgccgtc   900
gtacgcttca agaatgataa ggcaaactac agtttgaata cagatgatcc actgatattc   960
aagtcaacac ttgacactga ctaccagatg acaaaaaaag atatgggttt caccgaagaa  1020
gagttcaaga gattgaacat taacgcagca aaaagctcct tcctgccaga ggaagagaaa  1080
aaagaattgc ttgaaaggtt gtatcgagaa taccaa                            1116

SEQ ID NO: 106     moltype = DNA   length = 1056
FEATURE            Location/Qualifiers
source             1..1056
                   mol_type = other DNA
                   organism = Mus musculus
SEQUENCE: 106
atggcacaaa ctccagcttt taataagccc aaagtggaac ttcatgttca tctggatggg    60
gcaattaagc ccgaaactat attgtacttt ggcaaaaaga ggggtattgc cctgccagca   120
gataccgttg aggagcttcg caacatcatt gggatggaca agccctctc tctgccaggt   180
tttctcgcta aattcgatta ttatatgcct gttattgctg gttgccggga ggccatcaag   240
aggatagcct acgagtttgt tgagatgaag gccaaagagg gcgtggtgta cgtagaggtc   300
agatacagcc ctcacctgct tgccaacagc aaggtggacc caatgccctg gaaccaaacc   360
gaggggatg tcactcccga cgacgttgta gacctcgtaa atcagggcct tcaagagggc   420
gagcaggcat ttggcataaa agtccggtct atactctgct gtatgaggca caaacctcc   480
tggtctttgg aggtacttga gttgtgtaag aaatacaatc aaaagactgt agtcgccatg   540
gatcttgcag gcgatgaaac catcgagggt agctccttgt tccctggaca tgttgaagcc   600
tacgaggggg ccgtaaaaaa tgggatacac aggactgtcc acgctggtga agtcggaagc   660
ccagaggtgg taagggaggc agttgacata ctcaagacag agcgggttgg acacggatac   720
cacacaattg aggacgaggc cctgtataac cgcctcctca aagagaacat gcattttgag   780
gtgtgtcctt ggtccagcta cctgactggt gcttgggacc ctaaaacaac tcacgccgtg   840
gtccggttca gaaacgataa agccaattac tctttgaata ccgacgaccc cctcatattc   900
aaatcaacat ggataccga ctaccaaatg accaaaaagg atatgggtt tactgaagag   960
gagttcaaga ggctcaacat aaatgccgct aaatcctcct ttctccccga ggaagaaaaa  1020
aaagaactcc ttgagcggct gtatagggag tatcaa                            1056

SEQ ID NO: 107     moltype = DNA   length = 966
FEATURE            Location/Qualifiers
source             1..966
                   mol_type = other DNA
                   organism = Mus musculus
```

```
SEQUENCE: 107
atggaaacag atacactctt gctctgggta ctgcttctgt gggtccccgg ctctactggg    60
gatgaagatg atgtaactac tacagaagaa ctcgctcccg ctcttgtccc cccacccaag   120
ggtacctgcg ccggttggat ggctggcatc ccaggacatc caggtcacaa cggtacccc    180
ggaagagatg gtcgggatgg aactcccggc gagaaggacg aaaaagggga tgcagggctt   240
ctgggaccta aaggtgaaac aggggacgtt ggaatgactg gtgcagaagg gcctcgcggc   300
tttcctggca cccctgggag gaaaggagag cccggagagc tccagagaac tgaacctcgg   360
cctgcactca ctataactac ttcccctaat cttgggaccc gcgagaacaa cgccgatcag   420
gttacacctg taagccatat cgggtgcccc aatactaccc agcaagggag tcccgtgttc   480
gcaaagcttt tggctaaaaa ccaagcatcc ctgtgtaaca ctactcttaa ttggcattca   540
caagacggtg ctggtagctc ttatctttct caggggctgc ggtacgaaga agataagaag   600
gaattggttg tggattctcc aggactctat tatgtctttc tcgaattgaa gctcagtccc   660
accttcacaa acactggaca caaagtccag ggctgggtaa gtctggtact ccaagcaaag   720
ccccaggttg acgatttcga caatttggca ctcaccgtag agcttttccc atgctccatg   780
gaaaataaac ttgttgatcg gtcatggtca cagctcttgc tgcttaaggc agggcatcgc   840
ctctcagtgg gtctgagagc ttatttgcat ggtgcacaag atgcttacag ggattgggaa   900
ttgtcctacc caaacactac aagtttcggg ttgttccttg tcaaacctga taacccatgg   960
gagtag                                                             966

SEQ ID NO: 108          moltype = DNA   length = 900
FEATURE                 Location/Qualifiers
source                  1..900
                        mol_type = other DNA
                        organism = Mus musculus
SEQUENCE: 108
atggaaactg atacactcct cctgtgggtc cttcttttgt gggtgcccgg atcaaccggc    60
gatggctgga tggcaggcat cccaggacac ccaggacaca acggtactcc aggtcgagac   120
ggtcgggatg ggactcctgg ggagaaaggc gagaaggggg acgctggttt gctcggtcct   180
aaggggaaa ccgggatgt aggaatgaca ggggctgaag ggcctcgggg atttcctggg   240
acaccaggca ggaagggtga accaggggag gccctccagc gcaccgagcc acggccagct   300
ctgaccataa caacaagtcc aaacctgggc acacgcgaaa acaatgctga ccaggtgact   360
cctgtaagtc acatcggatg ccctaacact acacaacagg gctctcctgt atttgcaaag   420
cttctcgcaa aaaatcaagc atcactttgt aatacaaccc tgaactggca ttctcaggac   480
ggagcagggt cctcttattt gtctcaaggg ctccgctacg aagaagataa aaaggaattg   540
gttgttgaca gtccaggttt gtattatgtg tttttggaac ttaagctgtc accaaccttc   600
actaacaccg gccacaaggt ccaaggctgg gttagtcttg ttttgcaagc caaacctcaa   660
gtggatgatt ttgacaatct ggctttgact gttgagcttt ttccatgcag tatggagaat   720
aaaactggttg atcggtcatg gtcacagctc cttctgctca aggccggaca taggctgagt   780
gtgggacttc gggcctactt gcacggcgcc caggacgcat accgagactg ggaactcagc   840
taccctaaca caacttcttt tgggttgttc cttgtcaaac ccgataatcc ttgggaatag   900

SEQ ID NO: 109          moltype = DNA   length = 870
FEATURE                 Location/Qualifiers
source                  1..870
                        mol_type = other DNA
                        organism = Mus musculus
SEQUENCE: 109
atggagactg atactttgct cctgtgggtt cttctcctgt gggttcctgg ttccacaggg    60
gatatgcatg tcaatggcaa ggtagcactc gtgactgggg ctgcacaggg tatcgggaaa   120
gcttttgccg aggccctgtt gctgcatggc gccaaggtcg ctttggtaga ttggaacttg   180
gaggctgcag ttaaatgcaa agctgcactc gacgaacaat ttgagcctca aaaaaccctc   240
tttgtgcagt gtgacgttgc tgaccaaaag caactcaggg acacattcag gaaggtcgta   300
gaccatttcg gacgcctcga tatactcgtt aataatgccg gggtaaacaa cgaaaagaac   360
tgggaacaaa cattgcaaat caacctggta agtgtcatta gcggaactta tctgggtctt   420
gattatatga gcaagcagaa cggggggcgag ggcgggatca ttatcaacat gtcaagtctt   480
gccggattga tgccagttgc tcagcagcct gtttactgtg ccagcaagca cggtattatt   540
gggtttaccc ggagtgccgc catggccgca aatcttatga agagtggggt aagactgaat   600
gttatctgcc caggtttcgt agatacccca atcctggaga gcatcgagaa ggaggaaaat   660
atgggacaat acattgaata aaagatcaa atcaaggcta tgatgaagtt ctacggggtt   720
ctgcatccat ccacaattgc caacgggctc attaatctga ttggaggacga cgccttgaac   780
ggagctataa tgaaaatcac agcttccaaa ggcattcact ccaagatta tgatatatca   840
cccttgcttg tcaaggctcc tctgacaagt                                   870

SEQ ID NO: 110          moltype = DNA   length = 807
FEATURE                 Location/Qualifiers
source                  1..807
                        mol_type = other DNA
                        organism = Mus musculus
SEQUENCE: 110
atgcatgtca atggcaaggt agcactcgtg actggggctg cacagggtat cgggaaagct    60
tttgccgagg ccctgttgct gcatggcgcc aaggtcgctt tggtagattg gaacttggag   120
ctggagtta aatgcaaagc tgcactcgac gaacaatttg agcctcaaaa aaccctcttt   180
gtgcagtgtg acgttgctga ccaaaagcaa ctcaggacaa cattcaggaa ggtcgtagac   240
catttcggac gcctcgatat actcgttaat aatgccgggg taaacaacga aaagaactgg   300
gaacaaacat tgcaaatcaa cctggtaagt gtcattagcg gaacttatct gggtcttgat   360
tatatgagca gcagaacgg gggcgagggc gggatcatta tcaacatgtc aagtcttgcc   420
ggattgatgc cagttgctca gcagcctgtt tactgtgcca gcaagcacgg tattattggg   480
tttacccgga gtgccgccat ggccgcaaat cttatgaaga gtggggtaag actgaatgtt   540
atctgcccag gtttcgtaga taccccaatc ctggagagca tcgagaagga ggaaaatatg   600
```

-continued

```
ggacaataca ttgaatataa agatcaaatc aaggctatga tgaagttcta cggggttctg    660
catccatcca caattgccaa cgggctcatt aatctgattg aggacgacgc cttgaacgga    720
gctataatga aaatcacagc ttccaaaggc attcacttcc aagattatga tatatcaccc    780
ttgcttgtca aggctcctct gacaagt                                         807

SEQ ID NO: 111          moltype =    length =
SEQUENCE: 111
000

SEQ ID NO: 112          moltype = AA   length = 22
FEATURE                 Location/Qualifiers
REGION                  1..22
                        note = Description of Unknown: IL-12 sequence
source                  1..22
                        mol_type = protein
                        organism = Homo sapiens
SEQUENCE: 112
MCHQQLVISW FSLVFLASPL VA                                               22

SEQ ID NO: 113          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 113
MQLLSCIALI LALV                                                        14

SEQ ID NO: 114          moltype = AA   length = 20
FEATURE                 Location/Qualifiers
source                  1..20
                        mol_type = protein
                        organism = Homo sapiens
SEQUENCE: 114
MYRMQLLSCI ALSLALVTNS                                                  20

SEQ ID NO: 115          moltype = AA   length = 15
FEATURE                 Location/Qualifiers
source                  1..15
                        mol_type = protein
                        organism = Homo sapiens
SEQUENCE: 115
MNLLLILTFV AAAVA                                                       15

SEQ ID NO: 116          moltype = AA   length = 17
FEATURE                 Location/Qualifiers
source                  1..17
                        mol_type = protein
                        note = Gaussia Luciferase
                        organism = Gaussia sp.
SEQUENCE: 116
MGVKVLFALI CIAVAEA                                                     17

SEQ ID NO: 117          moltype = AA   length = 24
FEATURE                 Location/Qualifiers
source                  1..24
                        mol_type = protein
                        organism = Homo sapiens
SEQUENCE: 117
MPMGSLQPLA TLYLLGMLVA SCLG                                             24

SEQ ID NO: 118          moltype = AA   length = 21
FEATURE                 Location/Qualifiers
source                  1..21
                        mol_type = protein
                        organism = Mus musculus
SEQUENCE: 118
METDTLLLWV LLLWVPGSTG D                                                21

SEQ ID NO: 119          moltype = AA   length = 22
FEATURE                 Location/Qualifiers
source                  1..22
                        mol_type = protein
                        organism = Homo sapiens
SEQUENCE: 119
MDMRVPAQLL GLLLLWLRGA RC                                               22

SEQ ID NO: 120          moltype = AA   length = 16
```

-continued

```
FEATURE              Location/Qualifiers
REGION               1..16
                     note = Description of Unknown: VSV-G sequence
source               1..16
                     mol_type = protein
                     organism = unidentified
SEQUENCE: 120
MKCLLYLAFL FIGVNC                                              16

SEQ ID NO: 121       moltype = AA  length = 28
FEATURE              Location/Qualifiers
source               1..28
                     mol_type = protein
                     organism = Homo sapiens
SEQUENCE: 121
MNIKGSPWKG SLLLLLVSNL LLCQSVAP                                 28

SEQ ID NO: 122       moltype = AA  length = 18
FEATURE              Location/Qualifiers
source               1..18
                     mol_type = protein
                     organism = Homo sapiens
SEQUENCE: 122
MKWVTFISLL FLFSSAYS                                            18

SEQ ID NO: 123       moltype = AA  length = 19
FEATURE              Location/Qualifiers
source               1..19
                     mol_type = protein
                     organism = Homo sapiens
SEQUENCE: 123
MTRLTVLALL AGLLASSRA                                           19

SEQ ID NO: 124       moltype = AA  length = 17
FEATURE              Location/Qualifiers
source               1..17
                     mol_type = protein
                     organism = Homo sapiens
SEQUENCE: 124
MRAWIFFLLC LAGRALA                                            17

SEQ ID NO: 125       moltype = AA  length = 16
FEATURE              Location/Qualifiers
source               1..16
                     mol_type = protein
                     organism = Homo sapiens
SEQUENCE: 125
MPLLLLLPLL WAGALA                                             16

SEQ ID NO: 126       moltype = AA  length = 29
FEATURE              Location/Qualifiers
source               1..29
                     mol_type = protein
                     organism = Homo sapiens
SEQUENCE: 126
MNSFSTSAFG PVAFSLGLLL VLPAAFPAP                                29

SEQ ID NO: 127       moltype = AA  length = 20
FEATURE              Location/Qualifiers
source               1..20
                     mol_type = protein
                     organism = Homo sapiens
SEQUENCE: 127
MTSKLAVALL AAFLISAALC                                          20

SEQ ID NO: 128       moltype = AA  length = 23
FEATURE              Location/Qualifiers
source               1..23
                     mol_type = protein
                     organism = Homo sapiens
SEQUENCE: 128
MKVSAALLCL LLIAATFIPQ GLA                                      23

SEQ ID NO: 129       moltype = AA  length = 26
FEATURE              Location/Qualifiers
source               1..26
                     mol_type = protein
                     organism = Homo sapiens
```

-continued

```
SEQUENCE: 129
MGAAARTLRL ALGLLLLATL LRPADA                                      26

SEQ ID NO: 130          moltype = AA  length = 21
FEATURE                 Location/Qualifiers
source                  1..21
                        mol_type = protein
                        organism = Homo sapiens
SEQUENCE: 130
MSPLLRRLLL AALLQLAPAQ A                                           21

SEQ ID NO: 131          moltype = AA  length = 21
FEATURE                 Location/Qualifiers
source                  1..21
                        mol_type = protein
                        organism = Homo sapiens
SEQUENCE: 131
MNNLLCCALV FLDISIKWTT Q                                           21

SEQ ID NO: 132          moltype = AA  length = 23
FEATURE                 Location/Qualifiers
source                  1..23
                        mol_type = protein
                        organism = Homo sapiens
SEQUENCE: 132
MQMSPALTCL VLGLALVFGE GSA                                         23

SEQ ID NO: 133          moltype = AA  length = 34
FEATURE                 Location/Qualifiers
source                  1..34
                        mol_type = protein
                        organism = Homo sapiens
SEQUENCE: 133
MARAALSAAP SNPRLLRVAL LLLLLVAAGR RAAG                             34

SEQ ID NO: 134          moltype = AA  length = 21
FEATURE                 Location/Qualifiers
source                  1..21
                        mol_type = protein
                        organism = Homo sapiens
SEQUENCE: 134
MNAKVVVVLV LVLTALCLSD G                                           21

SEQ ID NO: 135          moltype = AA  length = 22
FEATURE                 Location/Qualifiers
REGION                  1..22
                        note = Description of Unknown: IL-21 sequence
source                  1..22
                        mol_type = protein
                        organism = unidentified
SEQUENCE: 135
MERIVICLMV IFLGTLVHKS SS                                          22

SEQ ID NO: 136          moltype = AA  length = 21
FEATURE                 Location/Qualifiers
REGION                  1..21
                        note = Description of Unknown: CD8 sequence
source                  1..21
                        mol_type = protein
                        organism = unidentified
SEQUENCE: 136
MALPVTALLL PLALLLHAAR P                                           21

SEQ ID NO: 137          moltype = AA  length = 21
FEATURE                 Location/Qualifiers
REGION                  1..21
                        note = Description of Artificial Sequence: Synthetic peptide
source                  1..21
                        mol_type = protein
                        organism = synthetic construct
SEQUENCE: 137
MALPVTALLL PLALLLHAAR P                                           21

SEQ ID NO: 138          moltype = AA  length = 21
FEATURE                 Location/Qualifiers
REGION                  1..21
                        note = Description of Unknown: GCMSF sequence
```

```
source                   1..21
                         mol_type = protein
                         organism = unidentified
SEQUENCE: 138
MLLVTSLLLC ELPHPAFLLI P                                            21

SEQ ID NO: 139           moltype = DNA   length = 63
FEATURE                  Location/Qualifiers
misc_feature             1..63
                         note = Description of Unknown: CD8 sequence
source                   1..63
                         mol_type = other DNA
                         organism = unidentified
SEQUENCE: 139
atggccttac cagtgaccgc cttgctcctg ccgctggcct tgctgctcca cgccgccagg  60
ccg                                                               63

SEQ ID NO: 140           moltype = DNA   length = 63
FEATURE                  Location/Qualifiers
misc_feature             1..63
                         note = Description of Artificial Sequence: Synthetic
                          oligonucleotide
source                   1..63
                         mol_type = other DNA
                         organism = synthetic construct
SEQUENCE: 140
atggcgctcc cggtgacagc acttctcttg cctcttgccc tgctgttgca tgccgcgcgc  60
cca                                                               63

SEQ ID NO: 141           moltype = DNA   length = 63
FEATURE                  Location/Qualifiers
misc_feature             1..63
                         note = Description of Unknown: GCMSF sequence
source                   1..63
                         mol_type = other DNA
                         organism = unidentified
SEQUENCE: 141
atgttgctcg tgacatccct cttgctttgt gagttgcctc atcccgcatt cctgctcatc  60
cca                                                               63

SEQ ID NO: 142           moltype = AA   length = 10
FEATURE                  Location/Qualifiers
REGION                   1..10
                         note = Description of Unknown: cleavage site sequence
source                   1..10
                         mol_type = protein
                         organism = Hepacivirus C
SEQUENCE: 142
DEMEECSQHL                                                        10

SEQ ID NO: 143           moltype = AA   length = 9
FEATURE                  Location/Qualifiers
REGION                   1..9
                         note = Description of Unknown: cleavage site sequence
source                   1..9
                         mol_type = protein
                         organism = Hepacivirus C
SEQUENCE: 143
EDVVPCSMG                                                         9

SEQ ID NO: 144           moltype = AA   length = 99
FEATURE                  Location/Qualifiers
source                   1..99
                         mol_type = protein
                         organism = Human immunodeficiency virus 1
SEQUENCE: 144
PQVTLWQRPL VTIKIGGQLK EALLDTGADD TVLEEMSLPG RWKPKMIGGI GGFIKVRQYD  60
QILIEICGHK AIGTVLVGPT PVNIIGRNLL TQIGCTLNF                         99

SEQ ID NO: 145           moltype = AA   length = 19
FEATURE                  Location/Qualifiers
REGION                   1..8
                         note = Description of Unknown: cleavage site sequence
source                   1..19
                         mol_type = protein
                         organism = unidentified
SEQUENCE: 145
EDANSEPLFA ERKDABCYL                                              19
```

-continued

```
SEQ ID NO: 146              moltype = AA  length = 4
FEATURE                     Location/Qualifiers
REGION                      1..4
                            note = Description of Unknown: cleavage site sequence
source                      1..4
                            mol_type = protein
                            organism = unidentified
SEQUENCE: 146
YVAD                                                                        4

SEQ ID NO: 147              moltype = AA  length = 5
FEATURE                     Location/Qualifiers
REGION                      1..5
                            note = Description of Unknown: cleavage site sequence
source                      1..5
                            mol_type = protein
                            organism = unidentified
SEQUENCE: 147
VDVAD                                                                       5

SEQ ID NO: 148              moltype = AA  length = 4
FEATURE                     Location/Qualifiers
REGION                      1..4
                            note = Description of Unknown: cleavage site sequence
source                      1..4
                            mol_type = protein
                            organism = unidentified
SEQUENCE: 148
DEVD                                                                        4

SEQ ID NO: 149              moltype = AA  length = 4
FEATURE                     Location/Qualifiers
REGION                      1..4
                            note = Description of Unknown: cleavage site sequence
source                      1..4
                            mol_type = protein
                            organism = unidentified
SEQUENCE: 149
VEHD                                                                        4

SEQ ID NO: 150              moltype = AA  length = 5
FEATURE                     Location/Qualifiers
REGION                      1..5
                            note = Description of Unknown: cleavage site sequence
source                      1..5
                            mol_type = protein
                            organism = unidentified
VARIANT                     5
                            note = X can be any amino acid
SEQUENCE: 150
LGHDX                                                                       5

SEQ ID NO: 151              moltype = AA  length = 5
FEATURE                     Location/Qualifiers
REGION                      1..5
                            note = Description of Unknown: cleavage site sequence
source                      1..5
                            mol_type = protein
                            organism = unidentified
SEQUENCE: 151
LQTDG                                                                       5

SEQ ID NO: 152              moltype = AA  length = 8
FEATURE                     Location/Qualifiers
REGION                      1..8
                            note = Description of Unknown: cleavage site sequence
source                      1..8
                            mol_type = protein
                            organism = unidentified
SEQUENCE: 152
EVNLDAEF                                                                    8

SEQ ID NO: 153              moltype = AA  length = 7
FEATURE                     Location/Qualifiers
REGION                      1..7
                            note = Description of Unknown: cleavage site sequence
source                      1..7
                            mol_type = protein
                            organism = unidentified
```

-continued

```
SEQUENCE: 153
PQGIAGQ                                                                       7

SEQ ID NO: 154        moltype = AA   length = 7
FEATURE               Location/Qualifiers
REGION                1..7
                      note = Description of Unknown: cleavage site sequence
source                1..7
                      mol_type = protein
                      organism = unidentified
SEQUENCE: 154
ENLYFQS                                                                       7

SEQ ID NO: 155        moltype = AA   length = 5
FEATURE               Location/Qualifiers
REGION                1..5
                      note = Description of Unknown: cleavage site sequence
source                1..5
                      mol_type = protein
                      organism = unidentified
MOD_RES               1
                      note = Abz is linked with histidine
SEQUENCE: 155
HPFHL                                                                         5

SEQ ID NO: 156        moltype = AA   length = 1306
FEATURE               Location/Qualifiers
source                1..1306
                      mol_type = protein
                      organism = Homo sapiens
SEQUENCE: 156
MGAASGRRGP GLLLPLPLLL LLPPQPALAL DPGLQPGNFS ADEAGAQLFA QSYNSSAEQV    60
LFQSVAASWA HDTNITAENA RRQEEAALLS QEFAEAWGQK AKELYEPIWQ NFTDPQLRRI   120
IGAVRTLGSA NLPLAKRQQY NALLSNMSRI YSTAKVCLPN KTATCWSLDP DLTNILASSR   180
SYAMLLFAWE GWHNAAGIPL KPLYEDFTAL SNEAYKQDGF TDTGAYWRSW YNSPTFEDDL   240
EHLYQQLEPL YLNLHAFVRR ALHRRYGDRY INLRGPIPAH LLGDMWAQSW ENIYDMVVPF   300
PDKPNLDVTS TMLQQGWNAT HMFRVAEEFF TSLELSPMPP EFWEGSMLEK PADGREVVCH   360
ASAWDFYNRK DFRIKQCTRV TMDQLSTVHH EMGHIQYYLQ YKDLPVSLRR GANPGFHEAI   420
GDVLALSVST PEHLHKIGLL DRVTNDTESD INYLLKMALE KIAFLPFGYL VDQWRWGVFS   480
GRTPPSRYNF DWWYLRTKYQ GICPPVTRNE THFDAGAKFH VPNVTPYIRY FVSFVLQFQF   540
HEALCKEAGY EGPLHQCDIY RSTKAGAKLR KVLQAGSSRP WQEVLKDMVG LDALDAQPLL   600
KYFQPVTQWL QEQNQQNGEV LGWPEYQWHP PLPDNYPEGI DLVTDEAEAS KFVEEYDRTS   660
QVVWNEYAEA NWNYNTNITT ETSKILLQKN MQIANHTLKY GTQARKFDVN QLQNTTIKRI   720
IKKVQDLERA ALPAQELEEY NKILLDMETT YSVATVCHPN GSCLQLEPDL TNVMATSRKY   780
EDLLWAWEGW RDKAGRAILQ FYPKYVELIN QAARLNGYVD AGDSWRSMYE TPSLEQDLER   840
LFQELQPLYL NLHAYVRRAL HRHYGAQHIN LEGPIPAHLL GNMWAQTWSN IYDLVVPFPS   900
APSMDTTEAM LKQGWTPRRM FKEADDFFTS LGLLPVPPEF WNKSMLEKPT DGREVVCHAS   960
AWDFYNGKDF RIKQCTTVNL EDLVVAHHEM GHIQYFMQYK DLPVALREGA NPGFHEAIGD  1020
VLALSVSTPK HLHSLNLLSS EGGSDEHDIN FLMKMALDKI AFIPFSYLVD QWRWRVFDGS  1080
ITKENYNQEW WSLRLKYQGL CPPVPRTQGD FDPGAKFHIP SSVPYIRYFV SFIIQFQFHE  1140
ALCQAAGHTG PLHKCDIYQS KEAGQRLATA MKLGFSRPWP EAMQLITGQP NMSASAMLSY  1200
FKPLLDWLRT ENELHGEKLG WPQYNWTPNS ARSEGPLPDS GRVSFLGLDL DAQQARVGQW  1260
LLLFLGIALL VATLGLSQRL FSIRHRSLHR HSHGPQFGSE VELRHS                 1306

SEQ ID NO: 157        moltype = AA   length = 619
FEATURE               Location/Qualifiers
source                1..619
                      mol_type = protein
                      organism = Dengue virus
SEQUENCE: 157
SGVLWDTPSP PEVERAVLDD GIYRIMQRGL LGRSQVGVGV FQDGVFHTMW HVTRGAVLMY    60
QGKRLEPSWA SVKKDLISYG GGWRFQGSWN TGEEVQVIAV EPGKNPKNVQ TAPGTFKTPE   120
GEVGAIALDF KPGTSGSPIV NREGKIVGLY GNGVVTTSGT YVSAIAQAKA SQEGPLPEIE   180
DEVFRKRNLT IMDLHPGSGK TRRYLPAIVR EAIRRNVRTL ILAPTRVVAS EMAEALKGMP   240
IRYQTTAVKS EHTGKEIVDL MCHATFTMRL LSPVRVPNYN MIIMDEAHFT DPASIARRGY   300
ISTRVGMGEA AAIFMTATPP GSVEAFPQSN AVIQDEERDI PERSWNSGYE WITDFPGKTV   360
WFVPSIKSGN DIANCLRKNG KRVIQLSRKT FDTEYQKTKN NDWDYVVTTD ISEMGANFRA   420
DRVIDPRRCL KPVILKDGPE RVILAGPMPV TVASAAQRRG RIGRNQNKEG DQYVYMGQPL   480
NNDEDHAHWT EAKMLLDNIN TPEGIIPALF EPEREKSAAI DGEYRLRGEA RKTFVELMRR   540
GDLPVWLSYK VASEGFQYSD RRWCFDGERN NQVLEENMDV EMWTKEGERK KLRPRWLDAR   600
TYSDPLALRE FKEFAAGRR                                                619

SEQ ID NO: 158        moltype = AA   length = 618
FEATURE               Location/Qualifiers
source                1..618
                      mol_type = protein
                      organism = Dengue virus
```

```
SEQUENCE: 158
AGVLWDVPSP PPVGKAELED GAYRIKQKGI LGYSQIGAGV YKEGTFHTMW HVTRGAVLMH   60
KGKRIEPSWA DVKKDLISYG GGWKLEGEWK EGEEVQVLAL EPGKNPRAVQ TKPGLFKTNA  120
GTIGAVSLDF SPGTSGSPII DKKGKVVGLY GNGVVTRSGA YVSAIAQTEK SIEDNPEIED  180
DIFRKRKLTI MDLHPGAGKT KRYLPAIVRE AIKRGLRTLI LAPTRVVAAE MEEALRGLPI  240
RYQTPAIRAE HTGREIVDLM CHATFTMRLL SPVRVPNYNL IIMDEAHFTD PASIAARGYI  300
STRVEMGEAA GIFMTATPPG SRDPFPQSNA PIMDEEREIP ERSWSSGHEW VTDFKGKTVW  360
FVPSIKAGND IAACLRKNGK KVIQLSRKTF DSEYVKTRTN DWDFVVTTDI SEMGANFKAE  420
RVIDPRRCMK PVILTDGEER VILAGPMPVT HSSAAQRRGR IGRNPKNEND QYIYMGEPLE  480
NDEDCAHWKE AKMLLDNINT PEGIIPSMFE PEREKVDAID GEYRLRGEAR KTFVDLMRRG  540
DLPVWLAYRV AAEGINYADR RWCFDGIKNN QILEENVEVE IWTKEGERKK LKPRWLDAKI  600
YSDPLALKEF KEFAAGRK                                                618

SEQ ID NO: 159         moltype = AA  length = 619
FEATURE                Location/Qualifiers
source                 1..619
                       mol_type = protein
                       organism = Dengue virus
SEQUENCE: 159
SGVLWDVPSP PETQKAELEE GVYRIKQQGI FGKTQVGVGV QKEGVFHTMW HVTRGAVLTH   60
NGKRLEPNWA SVKKDLISYG GGWRLSAQWQ KGEEVQVIAV EPGKNPKNFQ TMPGIFQTTT  120
GEIGAIALDF KPGTSGSPII NREGKVVGLY GNGVVTKNGG YVSGIAQTNA EPDGPTPELE  180
EEMFKKRNLT IMDLHPGSGK TRKYLPAIVR EAIKRRLRTL ILAPTRVVAA EMEEALKGLP  240
IRYQTTATKS EHTGREIVDL MCHATFTMRL LSPVRVPNYN LIIMDEAHFT DPASIAARGY  300
ISTRVGMGEA AAIFMTATPP GTADAFPQSN APIQDEERDI PERSWNSGNE WITDFVGKTV  360
WFVPSIKAGN DIANCLRKNG KKVIQLSRKT FDTEYQKTKL FDTEYPKTKL ISEMGANFKA  420
DRVIDPRRCL KPVILTDGPE RVILAGPMPV TVASAAQRRG RVGRNPQKEN DQYIFMGQPL  480
NKDEDHAHWT EAKMLLDNIN TPEGIIPALF EPEREKSAAI DGEYRLKGES RKTFVELMRR  540
GDLPVWLAHK VASEGIKYTD RKWCFDGERN NQILEENMDV EIWTKEGEKK KLRPRWLDAR  600
TYSDPLALKE FKDFAAGRK                                               619

SEQ ID NO: 160         moltype = AA  length = 618
FEATURE                Location/Qualifiers
source                 1..618
                       mol_type = protein
                       organism = Dengue virus
SEQUENCE: 160
SGALWDVPSP AATQKAALSE GVYRIMQRGL FGKTQVGVGI HIEGVFHTMW HVTRGSVICH   60
ETGRLEPSWA DVRNDMISYG GGWRLGDKWD KEEDVQVLAI EPGKNPKHVQ TKPGLFKTLT  120
GEIGAVTLDF KPGTSGSPII NRKGKVIGLY GNGVVTKSGD YVSAITQAER IGEPDYEVDE  180
DIFRKKRLTI MDLHPGAGKT KRILPSIVRE ALKRRLRTLI LAPTRVVAAE MEEALRGLPI  240
RYQTPAVKSE HTGREIVDLM CHATFTTRLL SSTRVPNYNL IVMDEAHFTD PSSVAARGYI  300
STRVEMGEAA AIFMTATPPG TTDPFPQSNS PIEDIEREIP ERSWNTGFDW ITDYQGKTVW  360
FVPSIKAGND IANCLRKSGK KVIQLSRKTF DTEYPKTKLT DWDFVVTTDI SEMGANFRAG  420
RVIDPRRCLK PVILPDGPER VILAGPIPVT PASAAQRRGR IGRNPAQEDD QYVFSGDPLK  480
NDEDHAHWTE AKMLLDNIYT PEGIIPTLFG PEREKTQAID GEFRLRGEQR KTFVELMRRG  540
DLPVWLSYKV ASAGISYKDR EWCFTGERNN QILEENMEVE IWTREGEKKK LRPKWLDARV  600
YADPMALKDF KEFASGRK                                                618

SEQ ID NO: 161         moltype = AA  length = 64
FEATURE                Location/Qualifiers
REGION                 1..64
                       note = Description of Artificial Sequence: Synthetic
                        polypeptide
source                 1..64
                       mol_type = protein
                       organism = synthetic construct
SEQUENCE: 161
LQMLPESEDE ESYDTESEFT EFTEDELPYD DGSLQMLPES EDEESYDTES EFTEFTEDEL   60
PYDD                                                               64

SEQ ID NO: 162         moltype = AA  length = 57
FEATURE                Location/Qualifiers
source                 1..57
                       mol_type = protein
                       organism = Homo sapiens
SEQUENCE: 162
EIKDKEEVQR KRQKLMPNFS DSFGGGSGAG AGGGGMFGSG GGGGGTGSTG PGYSFPH      57

SEQ ID NO: 163         moltype = AA  length = 86
FEATURE                Location/Qualifiers
REGION                 1..86
                       note = Description of Unknown: Yeast Cdc34 sequence
source                 1..86
                       mol_type = protein
                       organism = unidentified
SEQUENCE: 163
IDDENGSVIL QDDDYDDGNN HIPFEDDDVY NYNDNDDDDE RIEFEDDDDD DDDSIDNDSV   60
MDRKQPHKAE DESEDVEDVE RVSKKD                                        86
```

```
SEQ ID NO: 164          moltype = AA  length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 164
PESMREEYRK EGSKRIKCPD CEPFCNKRGS PESMREEYRK E                      41

SEQ ID NO: 165          moltype = AA  length = 68
FEATURE                 Location/Qualifiers
REGION                  1..68
                        note = Description of Artificial Sequence: Synthetic
                         polypeptide
source                  1..68
                        mol_type = protein
                        organism = synthetic construct
SEQUENCE: 165
RSYSPTSPNY SPTSPSGSYS PTSPNYSPTS PSGGSRSYSP TSPNYSPTSP SGSYSPTSPN  60
YSPTSPSG                                                           68

SEQ ID NO: 166          moltype = AA  length = 59
FEATURE                 Location/Qualifiers
REGION                  1..59
                        note = Description of Artificial Sequence: Synthetic
                         polypeptide
source                  1..59
                        mol_type = protein
                        organism = synthetic construct
SEQUENCE: 166
PESMREEYRK EGSSLLTEVE TPGSPESMRE EYRKEGSSLL TEVETPGSPE SMREEYRKE   59

SEQ ID NO: 167          moltype = AA  length = 51
FEATURE                 Location/Qualifiers
REGION                  1..51
                        note = Description of Artificial Sequence: Synthetic
                         polypeptide
source                  1..51
                        mol_type = protein
                        organism = synthetic construct
SEQUENCE: 167
LIEEVRHRLK TTENSGSLIE EVRHRLKTTE NSGSLIEEVR HRLKTTENSG S           51

SEQ ID NO: 168          moltype = AA  length = 37
FEATURE                 Location/Qualifiers
REGION                  1..37
                        note = Description of Unknown: ODC sequence
source                  1..37
                        mol_type = protein
                        organism = unidentified
SEQUENCE: 168
FPPEVEEQDD GTLPMSCAQE SGMDRHPAAC ASARINV                           37

SEQ ID NO: 169          moltype = AA  length = 40
FEATURE                 Location/Qualifiers
source                  1..40
                        mol_type = protein
                        organism = Mus musculus
SEQUENCE: 169
SHGFPPEVEE QAAGTLPMSC AQESGMDRHP AACASARINV                        40

SEQ ID NO: 170          moltype = DNA  length = 65
FEATURE                 Location/Qualifiers
misc_feature            1..65
                        note = Description of Artificial Sequence: Synthetic
                         oligonucleotide
source                  1..65
                        mol_type = other DNA
                        organism = synthetic construct
SEQUENCE: 170
taggcgtgta cggtgggagg cctatataag cagagctcgt ttagtgaacc gtcagatcgc  60
ctgga                                                             65
```

-continued

```
SEQ ID NO: 171          moltype = DNA  length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 171
tctagagggt atataatggg ggcca                                           25

SEQ ID NO: 172          moltype = DNA  length = 63
FEATURE                 Location/Qualifiers
misc_feature            1..63
                        note = Description of Artificial Sequence: Synthetic
                         oligonucleotide
source                  1..63
                        mol_type = other DNA
                        organism = synthetic construct
SEQUENCE: 172
ttcgcatatt aaggtgacgc gtgtggcctc gaacaccgag cgaccctgca gcgacccgct   60
taa                                                                  63

SEQ ID NO: 173          moltype = DNA  length = 659
FEATURE                 Location/Qualifiers
misc_feature            1..659
                        note = Description of Artificial Sequence: Synthetic
                         polynucleotide
source                  1..659
                        mol_type = other DNA
                        organism = synthetic construct
SEQUENCE: 173
gacattgatt attgactagt tattaatagt aatcaattac ggggtcatta gttcatagcc   60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt acgccccta ttgacgtcaa tgacggtaaa tggcccgcct   300
ggcattatgc ccagtacatg accttatggg actttcctac ttggcagtac atctacgtat  360
tagtcatcgc tattaccatg gtcgaggtga gccccacgtt ctgcttcact ctccccatct  420
ccccccctc cccacccca attttgtatt tatttatttt ttaattattt tgtgcagcga   480
tggggggcggg gggggggggg gggcgcgcgc caggcggggc ggggcgggggc gaggggcggg  540
gcggggcgag gcggagaggt gcggcggcag ccaatcagag cggcgcgctc cgaaagtttc  600
ctttatggc gaggcggcgg cggcggcggc cctataaaaa gcgaagcgcg cggcgggcg    659

SEQ ID NO: 174          moltype = DNA  length = 251
FEATURE                 Location/Qualifiers
misc_feature            1..251
                        note = Description of Artificial Sequence: Synthetic
                         polynucleotide
source                  1..251
                        mol_type = other DNA
                        organism = synthetic construct
SEQUENCE: 174
tgtttgctgc ttgcaatgtt tgcccatttt agggtggaca caggacgctg tggtttctga   60
gccaggggggc gactcagatc ccagccagtg gacttagccc ctgtttgctc ctccgataac  120
tggggtgacc ttggttaata ttcaccagca gcctcccccg ttgcccctct ggatccactg  180
cttaaatacg gacgaggaca gggccctgtc tcctcagctt caggcaccac cactgacctg  240
ggacagtgaa t                                                        251

SEQ ID NO: 175          moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 175
FNVLMVHKRS HTGERPLQCE ICGFTCRQKG NLLRHIKLHT GEKPFKCHLC NYACQRRDAL   60

SEQ ID NO: 176          moltype = AA  length = 4
FEATURE                 Location/Qualifiers
REGION                  1..4
                        note = Description of Unknown: cleavage site sequence
source                  1..4
                        mol_type = protein
                        organism = unidentified
```

-continued

```
SEQUENCE: 176
PRAE                                                                   4

SEQ ID NO: 177         moltype =   length =
SEQUENCE: 177
000

SEQ ID NO: 178         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
VARIANT                5
                       note = X can be A, Y, P, S, or F
VARIANT                6
                       note = X can be V, L, S, I, Y  or T
SEQUENCE: 178
PRAEXXKGG                                                              9

SEQ ID NO: 179         moltype = AA  length = 9
FEATURE                Location/Qualifiers
REGION                 1..9
                       note = Description of Unknown: cleavage site sequence
source                 1..9
                       mol_type = protein
                       organism = unidentified
SEQUENCE: 179
PRAEAVKGG                                                              9

SEQ ID NO: 180         moltype = AA  length = 9
FEATURE                Location/Qualifiers
REGION                 1..9
                       note = Description of Unknown: cleavage site sequence
source                 1..9
                       mol_type = protein
                       organism = unidentified
SEQUENCE: 180
PRAEALKGG                                                              9

SEQ ID NO: 181         moltype = AA  length = 9
FEATURE                Location/Qualifiers
REGION                 1..9
                       note = Description of Unknown: cleavage site sequence
source                 1..9
                       mol_type = protein
                       organism = unidentified
SEQUENCE: 181
PRAEYSKGG                                                              9

SEQ ID NO: 182         moltype = AA  length = 9
FEATURE                Location/Qualifiers
REGION                 1..9
                       note = Description of Unknown: cleavage site sequence
source                 1..9
                       mol_type = protein
                       organism = unidentified
SEQUENCE: 182
PRAEPIKGG                                                              9

SEQ ID NO: 183         moltype = AA  length = 9
FEATURE                Location/Qualifiers
REGION                 1..9
                       note = Description of Unknown: cleavage site sequence
source                 1..9
                       mol_type = protein
                       organism = unidentified
SEQUENCE: 183
PRAEAYKGG                                                              9

SEQ ID NO: 184         moltype = AA  length = 9
FEATURE                Location/Qualifiers
REGION                 1..9
                       note = Description of Unknown: cleavage site sequence
source                 1..9
                       mol_type = protein
                       organism = unidentified
```

-continued

```
SEQUENCE: 184
PRAESSKGG                                                                9

SEQ ID NO: 185         moltype = AA   length = 9
FEATURE                Location/Qualifiers
REGION                 1..9
                       note = Description of Unknown: cleavage site sequence
source                 1..9
                       mol_type = protein
                       organism = unidentified
SEQUENCE: 185
PRAEFTKGG                                                                9

SEQ ID NO: 186         moltype = AA   length = 9
FEATURE                Location/Qualifiers
REGION                 1..9
                       note = Description of Unknown: cleavage site sequence
source                 1..9
                       mol_type = protein
                       organism = unidentified
SEQUENCE: 186
PRAEAAKGG                                                                9

SEQ ID NO: 187         moltype = AA   length = 9
FEATURE                Location/Qualifiers
REGION                 1..9
                       note = Description of Unknown: cleavage site sequence
source                 1..9
                       mol_type = protein
                       organism = unidentified
SEQUENCE: 187
DEPHYSQRR                                                                9

SEQ ID NO: 188         moltype = AA   length = 10
FEATURE                Location/Qualifiers
REGION                 1..10
                       note = Description of Unknown: cleavage site sequence
source                 1..10
                       mol_type = protein
                       organism = unidentified
SEQUENCE: 188
PPLGPIFNPG                                                               10

SEQ ID NO: 189         moltype = AA   length = 9
FEATURE                Location/Qualifiers
REGION                 1..9
                       note = Description of Unknown: cleavage site sequence
source                 1..9
                       mol_type = protein
                       organism = unidentified
SEQUENCE: 189
PLAQAYRSS                                                                9

SEQ ID NO: 190         moltype = AA   length = 10
FEATURE                Location/Qualifiers
REGION                 1..10
                       note = Description of Unknown: cleavage site sequence
source                 1..10
                       mol_type = protein
                       organism = unidentified
SEQUENCE: 190
TPIDSSFNPD                                                               10

SEQ ID NO: 191         moltype = AA   length = 10
FEATURE                Location/Qualifiers
REGION                 1..10
                       note = Description of Unknown: cleavage site sequence
source                 1..10
                       mol_type = protein
                       organism = unidentified
SEQUENCE: 191
VTPEPIFSLI                                                               10

SEQ ID NO: 192         moltype = AA   length = 21
FEATURE                Location/Qualifiers
REGION                 1..21
                       note = Description of Unknown: NKG2D sequence
```

```
source                  1..21
                        mol_type = protein
                        organism = unidentified
SEQUENCE: 192
PFFFCCFIAV AMGIRFIIMV A                                          21

SEQ ID NO: 193          moltype = DNA  length = 63
FEATURE                 Location/Qualifiers
misc_feature            1..63
                        note = Description of Unknown: NKG2D sequence
source                  1..63
                        mol_type = other DNA
                        organism = unidentified
SEQUENCE: 193
cccttcttct tctgttgctt tatcgccgtg gccatgggca tccgcttcat cattatggtg  60
gcc                                                             63

SEQ ID NO: 194          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 194
SGGGGSGGGG SG                                                    12

SEQ ID NO: 195          moltype = AA  length = 27
FEATURE                 Location/Qualifiers
REGION                  1..27
                        note = Description of Artificial Sequence: Synthetic peptide
source                  1..27
                        mol_type = protein
                        organism = synthetic construct
SEQUENCE: 195
SGGGGSGGGG SGGGGSGGGG SGGGGSLQ                                   27

SEQ ID NO: 196          moltype = AA  length = 45
FEATURE                 Location/Qualifiers
REGION                  1..45
                        note = Description of Artificial Sequence: Synthetic
                         polypeptide
source                  1..45
                        mol_type = protein
                        organism = synthetic construct
SEQUENCE: 196
TTTPAPRPPT PAPTIASQPL SLRPEACRPA AGGAVHTRGL DFACD                45

SEQ ID NO: 197          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 197
GGGSGGGGSG GGSLQ                                                 15

SEQ ID NO: 198          moltype = AA  length = 14
FEATURE                 Location/Qualifiers
REGION                  1..14
                        note = Description of Unknown: cleavage site sequence
source                  1..14
                        mol_type = protein
                        organism = unidentified
SEQUENCE: 198
ITQGLAVSTI SSFF                                                  14

SEQ ID NO: 199          moltype = AA  length = 135
FEATURE                 Location/Qualifiers
source                  1..135
                        mol_type = protein
                        organism = Homo sapiens
SEQUENCE: 199
MVLGTIDLCS CFSAGLPKTE ANWVNVISDL KKIEDLIQSM HIDATLYTES DVHPSCKVTA  60
MKCFLLELQV ISLESGDASI HDTVENLIIL ANNSLSSNGN VTESGCKECE ELEEKNIKEF  120
LQSFVHIVQM FINTS                                                 135

SEQ ID NO: 200          moltype = AA  length = 267
```

-continued

```
FEATURE              Location/Qualifiers
source               1..267
                     mol_type = protein
                     organism = Homo sapiens
SEQUENCE: 200
MAPRRARGCR TLGLPALLLL LLLRPPATRG ITCPPPMSVE HADIWVKSYS LYSRERYICN   60
SGFKRKAGTS SLTECVLNKA TNVAHWTTPS LKCIRDPALV HQRPAPPSTV TTAGVTPQPE  120
SLSPSGKEPA ASSPSSNNTA ATTAAIVPGS QLMPSKSPST GTTEISSHES SHGTPSQTTA  180
KNWELTASAS HQPPGVYPQG HSDTTVAIST STVLLCGLSA VSLLACYLKS RQTPPLASVE  240
MEAMEALPVT WGTSSRDEDL ENCSHHL                                      267

SEQ ID NO: 201       moltype = AA   length = 65
FEATURE              Location/Qualifiers
source               1..65
                     mol_type = protein
                     organism = Homo sapiens
SEQUENCE: 201
ITCPPPMSVE HADIWVKSYS LYSRERYICN SGFKRKAGTS SLTECVLNKA TNVAHWTTPS   60
LKCIR                                                               65

SEQ ID NO: 202       moltype = AA   length = 217
FEATURE              Location/Qualifiers
source               1..217
                     mol_type = protein
                     organism = Homo sapiens
SEQUENCE: 202
MDWTWILFLV AAATRVHSNW VNVISDLKKI EDLIQSMHID ATLYTESDVH PSCKVTAMKC   60
FLLELQVISL ESGDASIHDT VENLIILANN SLSSNGNVTE SGCKECEELE EKNIKEFLQS  120
FVHIVQMFIN TSSGGSGGGG SGGGSGGGGS LQITCPPPMS VEHADIWVKS YSLYSRERYI  180
CNSGFKRKAG TSSLTECVLN KATNVAHWTT PSLKCIR                           217

SEQ ID NO: 203       moltype = AA   length = 541
FEATURE              Location/Qualifiers
REGION               1..541
                     note = Description of Unknown: IL-12 (IL-12p70) sequence
source               1..541
                     mol_type = protein
                     organism = Homo sapiens
SEQUENCE: 203
MCHQQLVISW FSLVFLASPL VAIWELKKDV YVVELDWYPD APGEMVVLTC DTPEEDGITW   60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GSGGGSGGGS GGGSRNLPVA TPDPGMFPCL  360
HHSQNLLRAV SNMLQKARQT LEFYPCTSEE IDHEDITKDK TSTVEACLPL ELTKNESCLN  420
SRETSFITNG SCLASRKTSF MMALCLSSIY EDLKMYQVEF KTMNAKLLMD PKRQIFLDQN  480
MLAVIDELMQ ALNFNSETVP QKSSLEEPDF YKTKIKLCIL LHAFRIRAVT IDRVMSYLNA  540
S                                                                  541

SEQ ID NO: 204       moltype = AA   length = 46
FEATURE              Location/Qualifiers
REGION               1..46
                     note = Description of Unknown: transmembrane domain sequence
source               1..46
                     mol_type = protein
                     organism = unidentified
SEQUENCE: 204
LLPSWAITLI SVNGIFVICC LTYCFAPRCR ERRRNERLRR ESVRPV                  46

SEQ ID NO: 205       moltype = AA   length = 21
FEATURE              Location/Qualifiers
source               1..21
                     mol_type = protein
                     organism = Homo sapiens
SEQUENCE: 205
IYIWAPLAGT CGVLLLSLVI T                                             21

SEQ ID NO: 206       moltype = AA   length = 27
FEATURE              Location/Qualifiers
source               1..27
                     mol_type = protein
                     organism = Homo sapiens
SEQUENCE: 206
IYIWAPLAGT CGVLLLSLVI TLYCNHR                                       27

SEQ ID NO: 207       moltype = AA   length = 28
FEATURE              Location/Qualifiers
```

-continued

```
source                  1..28
                        mol_type = protein
                        organism = Homo sapiens
SEQUENCE: 207
IYIWAPLAGT CGVLLLSLVI TLYCNHRN                                    28

SEQ ID NO: 208          moltype = AA  length = 45
FEATURE                 Location/Qualifiers
REGION                  1..45
                        note = Description of Unknown: CD8 hinge sequence
source                  1..45
                        mol_type = protein
                        organism = unidentified
SEQUENCE: 208
TTTPAPRPPT PAPTIALQPL SLRPEACRPA AGGAVHTRGL DFACD                 45

SEQ ID NO: 209          moltype = AA  length = 86
FEATURE                 Location/Qualifiers
REGION                  1..86
                        note = Description of Unknown: CD8 hinge sequence
source                  1..86
                        mol_type = protein
                        organism = unidentified
SEQUENCE: 209
AAAFVPVFLP AKPTTTPAPR PPTPAPTIAS QPLSLRPEAC RPAAGGAVHT RGLDFACDIY  60
IWAPLAGTCG VLLLSLVITL YCNHRN                                      86

SEQ ID NO: 210          moltype = AA  length = 190
FEATURE                 Location/Qualifiers
REGION                  1..190
                        note = Description of Artificial Sequence: Synthetic
                         polypeptide
source                  1..190
                        mol_type = protein
                        organism = synthetic construct
SEQUENCE: 210
AATMDWTWIL FLVAAATRVH SNWVNVISDL KKIEDLIQSM HIDATLYTES DVHPSCKVTA  60
MKCFLLELQV ISLESGDASI HDTVENLIIL ANNSLSSNGN VTESGCKECE ELEEKNIKEF  120
LQSFVHIVQM FINTSDEPHY SQRRLLPSWA ITLISVNGIF VICCLTYCFA PRCRERRRNE  180
RLRRESVRPV                                                        190

SEQ ID NO: 211          moltype = AA  length = 191
FEATURE                 Location/Qualifiers
REGION                  1..191
                        note = Description of Artificial Sequence: Synthetic
                         polypeptide
source                  1..191
                        mol_type = protein
                        organism = synthetic construct
SEQUENCE: 211
AATMDWTWIL FLVAAATRVH SNWVNVISDL KKIEDLIQSM HIDATLYTES DVHPSCKVTA  60
MKCFLLELQV ISLESGDASI HDTVENLIIL ANNSLSSNGN VTESGCKECE ELEEKNIKEF  120
LQSFVHIVQM FINTSVTPEP IFSLILLPSW AITLISVNGI FVICCLTYCF APRCRERRRN  180
ERLRRESVRP V                                                      191

SEQ ID NO: 212          moltype = AA  length = 217
FEATURE                 Location/Qualifiers
REGION                  1..217
                        note = Description of Artificial Sequence: Synthetic
                         polypeptide
source                  1..217
                        mol_type = protein
                        organism = synthetic construct
SEQUENCE: 212
AATMDWTWIL FLVAAATRVH SNWVNVISDL KKIEDLIQSM HIDATLYTES DVHPSCKVTA  60
MKCFLLELQV ISLESGDASI HDTVENLIIL ANNSLSSNGN VTESGCKECE ELEEKNIKEF  120
LQSFVHIVQM FINTSDEPHY SQRRSGGGGS GGGGSGGGGS GGGGSGGGSL QLLPSWAITL  180
ISVNGIFVIC CLTYCFAPRC RERRRNERLR RESVRPV                          217

SEQ ID NO: 213          moltype = AA  length = 218
FEATURE                 Location/Qualifiers
REGION                  1..218
                        note = Description of Artificial Sequence: Synthetic
                         polypeptide
source                  1..218
                        mol_type = protein
                        organism = synthetic construct
```

```
SEQUENCE: 213
AATMDWTWIL FLVAAATRVH SNWVNVISDL KKIEDLIQSM HIDATLYTES DVHPSCKVTA   60
MKCFLLELQV ISLESGDASI HDTVENLIIL ANNSLSSNGN VTESGCKECE ELEEKNIKEF  120
LQSFVHIVQM FINTSVTPEP IFSLISGGGG SGGGGSGGGG SGGGGSGGGS LQLLPSWAIT  180
LISVNGIFVI CCLTYCFAPR CRERRRNERL RRESVRPV                         218

SEQ ID NO: 214          moltype = AA  length = 217
FEATURE                 Location/Qualifiers
REGION                  1..217
                        note = Description of Artificial Sequence: Synthetic
                         polypeptide
source                  1..217
                        mol_type = protein
                        organism = synthetic construct
SEQUENCE: 214
AATMDWTWIL FLVAAATRVH SNWVNVISDL KKIEDLIQSM HIDATLYTES DVHPSCKVTA   60
MKCFLLELQV ISLESGDASI HDTVENLIIL ANNSLSSNGN VTESGCKECE ELEEKNIKEF  120
LQSFVHIVQM FINTSSGGGG SGGGGSGDEP HYSQRRGGGS GGGGSGGGSL QLLPSWAITL  180
ISVNGIFVIC CLTYCFAPRC RERRRNERLR RESVRPV                          217

SEQ ID NO: 215          moltype = AA  length = 218
FEATURE                 Location/Qualifiers
REGION                  1..218
                        note = Description of Artificial Sequence: Synthetic
                         polypeptide
source                  1..218
                        mol_type = protein
                        organism = synthetic construct
SEQUENCE: 215
AATMDWTWIL FLVAAATRVH SNWVNVISDL KKIEDLIQSM HIDATLYTES DVHPSCKVTA   60
MKCFLLELQV ISLESGDASI HDTVENLIIL ANNSLSSNGN VTESGCKECE ELEEKNIKEF  120
LQSFVHIVQM FINTSSGGGG SGGGGSGVTP EPIFSLIGGG SGGGGSGGGS LQLLPSWAIT  180
LISVNGIFVI CCLTYCFAPR CRERRRNERL RRESVRPV                         218

SEQ ID NO: 216          moltype = AA  length = 217
FEATURE                 Location/Qualifiers
REGION                  1..217
                        note = Description of Artificial Sequence: Synthetic
                         polypeptide
source                  1..217
                        mol_type = protein
                        organism = synthetic construct
SEQUENCE: 216
AATMDWTWIL FLVAAATRVH SNWVNVISDL KKIEDLIQSM HIDATLYTES DVHPSCKVTA   60
MKCFLLELQV ISLESGDASI HDTVENLIIL ANNSLSSNGN VTESGCKECE ELEEKNIKEF  120
LQSFVHIVQM FINTSSGGGG SGGGGSGGGG SGGGGSGGGS LQDEPHYSQR RLLPSWAITL  180
ISVNGIFVIC CLTYCFAPRC RERRRNERLR RESVRPV                          217

SEQ ID NO: 217          moltype = AA  length = 218
FEATURE                 Location/Qualifiers
REGION                  1..218
                        note = Description of Artificial Sequence: Synthetic
                         polypeptide
source                  1..218
                        mol_type = protein
                        organism = synthetic construct
SEQUENCE: 217
AATMDWTWIL FLVAAATRVH SNWVNVISDL KKIEDLIQSM HIDATLYTES DVHPSCKVTA   60
MKCFLLELQV ISLESGDASI HDTVENLIIL ANNSLSSNGN VTESGCKECE ELEEKNIKEF  120
LQSFVHIVQM FINTSSGGGG SGGGGSGGGG SGGGGSGGGS LQVTPEPIFS LILLPSWAIT  180
LISVNGIFVI CCLTYCFAPR CRERRRNERL RRESVRPV                         218

SEQ ID NO: 218          moltype = DNA  length = 140
FEATURE                 Location/Qualifiers
misc_feature            1..140
                        note = Description of Artificial Sequence: Synthetic
                         polynucleotide
source                  1..140
                        mol_type = other DNA
                        organism = synthetic construct
SEQUENCE: 218
gggactttcc actgggggact ttccactggg gactttccac tggggacttt ccactgggga   60
ctttccactc ctgcaggagc tggcgcgcca gacgctagcg gggggctata aaaggggggtg  120
ggggcgttcg tcctcactct                                              140
```

```
SEQ ID NO: 219          moltype = AA   length = 9
FEATURE                 Location/Qualifiers
source                  1..9
                        mol_type = protein
                        organism = synthetic construct
VARIANT                 5
                        note = X can be A, Y, P, S, or F
VARIANT                 6
                        note = X can be V, L, S, I, Y, T, or A
SEQUENCE: 219
PRAEXXKGG                                                                9

SEQ ID NO: 220          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 220
GSGSGSGSGG                                                               10

SEQ ID NO: 221          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 221
AEAAAKEAAA KEAAAKA                                                       17

SEQ ID NO: 222          moltype = AA   length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 222
KESGSVSSEQ LAQFRSLD                                                      18

SEQ ID NO: 223          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 223
EGKSSGSGSE SKST                                                          14

SEQ ID NO: 224          moltype = AA   length = 4
FEATURE                 Location/Qualifiers
REGION                  1..4
                        note = Description of Unknown: hairy-related basic
                         helix-loop-helix repressor domain motif
source                  1..4
                        mol_type = protein
                        organism = unidentified
SEQUENCE: 224
WRPW                                                                     4

SEQ ID NO: 225          moltype = AA   length = 5
FEATURE                 Location/Qualifiers
REGION                  1..5
                        note = Description of Unknown: cleavage site sequence
source                  1..5
                        mol_type = protein
                        organism = unidentified
VARIANT                 2
                        note = X can be G or A
SEQUENCE: 225
GXELR                                                                    5
```

```
SEQ ID NO: 226          moltype = AA  length = 6
FEATURE                 Location/Qualifiers
source                  1..6
                        mol_type = protein
                        organism = unidentified
MOD_RES                 1
                        note = Abz is linked with histidine
MOD_RES                 6
                        note = Lys(Dnp)
SEQUENCE: 226
HPFHLK                                                                6

SEQ ID NO: 227          moltype = AA  length = 4
FEATURE                 Location/Qualifiers
source                  1..4
                        mol_type = protein
                        organism = synthetic construct
SEQUENCE: 227
KEGS                                                                  4
```

What is claimed is:

1. A membrane-cleavable chimeric protein, oriented from N-terminal to C-terminal, having the formula:

S-C-MT or MT-C-S wherein

S comprises a secretable effector molecule,

C comprises a protease cleavage site, and

MT comprises a cell-membrane tethering domain, wherein S-C-MT or MT-C-S is configured to be expressed as a single polypeptide, and wherein the protease cleavage site comprises the amino acid sequence of PRAEYSKGG (SEQ ID NO: 181); or the amino acid sequence of PRAEPIKGG (SEQ ID NO: 182); or the amino acid sequence of PRAEAYKGG (SEQ ID NO: 183); or the amino acid sequence of PRAESSKGG (SEQ ID NO: 184); or the amino acid sequence of PRAEFTKGG (SEQ ID NO: 185); or the amino acid sequence of DEPHYSQRR (SEQ ID NO: 187); or the amino acid sequence of PPLGPIFNPG (SEQ ID NO: 188); or the amino acid sequence of PLAQAYRSS (SEQ ID NO: 189); or the amino acid sequence of TPIDSSFNPD (SEQ ID NO: 190); or the amino acid sequence of VTPEPIFSLI (SEQ ID NO: 191).

2. The membrane-cleavable chimeric protein of claim 1, wherein the secretable effector molecule comprises a signal peptide or signal-anchor sequence.

3. The membrane-cleavable chimeric protein of claim 1, wherein the secretable effector molecule is selected from a therapeutic class, wherein the therapeutic class is selected from the group consisting of a cytokine, a chemokine, a homing molecule, a growth factor, a co-activation molecule, a tumor microenvironment modifier, a ligand, an antibody, a peptide, and an enzyme.

4. The membrane-cleavable chimeric protein of claim 1, wherein the secretable effector molecule comprises IL-15, IL-12, or an IL-12p70 fusion protein.

5. The membrane-cleavable chimeric protein of claim 1, wherein the protease cleavage site is cleavable by a protease selected from the group consisting of: a Type 1 transmembrane protease, a Type II transmembrane protease, a GPI anchored protease, an ADAM8 protease, an ADAM9 protease, an ADAM10 protease, an ADAM12 protease, an ADAM15 protease, an ADAM17 protease, an ADAM19 protease, an ADAM20 protease, an ADAM21 protease, an ADAM28 protease, an ADAM30 protease, an ADAM33 protease, a BACE1 protease, a BACE2 protease, a SIP protease, an MT1-MMP protease, an MT3-MMP protease, an MT5-MMP protease, a furin protease, a PCSK7 protease, a matriptase protease, a matriptase-2 protease, an MMP9 protease, and an NS3 protease.

6. The membrane-cleavable chimeric protein of claim 1, wherein the protease cleavage site is cleavable by an ADAM17 protease.

7. The membrane-cleavable chimeric protein of claim 1, wherein the cell-membrane tethering domain comprises a transmembrane-intracellular domain or a transmembrane domain.

8. The membrane-cleavable chimeric protein of claim 1, wherein the cell-membrane tethering domain comprises a post-translational modification tag, or a motif capable of post-translational modification to modify the chimeric protein to include a post-translational modification tag, wherein the post-translational modification tag is capable of association with a cell membrane.

9. The membrane-cleavable chimeric protein of claim 1, wherein:

a) when expressed in a cell, the secretable effector molecule is tethered to a cell membrane of the cell; and/or b) when expressed in a cell expressing a protease capable of cleaving the protease cleavage site, the secretable effector molecule is released from the cell membrane; and/or c) the protease is an ADAM17 protease.

10. An engineered nucleic acid comprising an expression cassette comprising a promoter and an exogenous polynucleotide sequence encoding the membrane-cleavable chimeric protein of claim 1.

11. An expression vector comprising the engineered nucleic acid of claim 10.

12. An isolated cell comprising the membrane-cleavable chimeric protein of claim 1.

13. The isolated cell of claim 12, wherein the cell is selected from the group consisting of: a T cell, a CD8+ T cell, a CD4+ T cell, a gamma-delta T cell, a cytotoxic T lymphocyte (CTL), a regulatory T cell, a viral-specific T cell, a Natural Killer T (NKT) cell, a Natural Killer (NK) cell, a B cell, a tumor-infiltrating lymphocyte (TIL), an innate lymphoid cell, a mast cell, an eosinophil, a basophil, a neutrophil, a myeloid cell, a macrophage, a monocyte, a dendritic cell, an erythrocyte, a platelet cell, a human embryonic stem cell (ESC), an ESC-derived cell, a pluripotent stem cell, a mesenchymal stromal cell (MSC), an induced pluripotent stem cell (iPSC), and an iPSC-derived cell.

14. The isolated cell of claim 12, wherein the cell further comprises a protease capable of cleaving the protease cleavage site.

15. The isolated cell of claim 12, wherein the cell further comprises an antigen-recognizing receptor.

16. A composition comprising the membrane-cleavable chimeric protein of any one of claim 1 and a pharmaceutically acceptable carrier, pharmaceutically acceptable excipient, or a combination thereof.

17. A method of treating a subject in need thereof, the method comprising administering a therapeutically effective dose of the isolated cell of claim 12.

18. A method of inducing release of a membrane-tethered effector molecule, comprising:
  a) providing the isolated cell of claim 12; and
  b) culturing the cell under conditions suitable for expression of a protease and the membrane-cleavable chimeric protein,
    wherein upon expression, the membrane-cleavable chimeric protein is tethered to the cell membrane of the cell, and
    wherein, upon expression, the protease cleaves the cognate membrane-bound protease cleavage site of the membrane-cleavable chimeric protein, thereby releasing the secretable effector molecule from the cell membrane.

19. The membrane-cleavable chimeric protein of claim 2, wherein the signal peptide comprises a native signal peptide native to the secretable effector molecule or the signal peptide comprises a non-native signal peptide or the signal-anchor sequence comprises a non-native signal-anchor sequence non-native to the secretable effector molecule.

20. The membrane-cleavable chimeric protein of claim 19, wherein the non-native signal peptide or the non-native signal-anchor sequence is selected from the group consisting of IL-12, IL-2, trypsinogen-2, *Gaussia* luciferase, CF5, human IgKVII, murine IgKVII, VSV-G, prolactin, serum albumin preprotein, azurocidin preprotein, osteonectin, CD33, IL-6, IL-8, CCL2, TIMP2, VEGFβ, osteoprotegerin, serpin E1, GROα, CXCL12, IL-21, CD8, NKG2D, TNFR2, and GM-CSF.

21. The membrane-cleavable chimeric protein of claim 3, wherein
  the cytokine is selected from the group consisting of IL-1β, IL-2, IL-4, IL-6, IL-7, IL-10, IL-12, an IL-12p70 fusion protein, IL-15, IL-17A, IL-18, IL-21, IL-22, Type I interferons, Interferon-gamma, and TNFα;

the chemokine is selected from the group consisting of CCL21α, CXCL10, CXCL11, CXCL13, a CXCL10-CXCL11 fusion protein, CCL19, CXCL9, and XCL1;
  the homing molecule is selected from the group consisting of anti-integrin α4β7; anti-MAdCAM; SDF1; and MMP-2;
  the growth factor is selected from the group consisting of FLT3L and GM-CSF;
  the co-activation molecule is selected from the group consisting of 4-1BBL and CD40L;
  the tumor microenvironment modifier is selected from the group consisting of adenosine deaminase, a TGFβ inhibitor, an immune checkpoint inhibitor, a VEGF inhibitor, and HPGE2;
  the immune checkpoint inhibitor is selected from the group consisting of an anti-PD-1 antibody, an anti-PD-L1 antibody, an anti-PD-L2 antibody, an anti-CTLA-4 antibody, an anti-LAG-3 antibody, an anti-TIM-3 antibody, an anti-TIGIT antibody, an anti-VISTA antibody, an anti-KIR antibody, an anti-B7-H3 antibody, an anti-B7-H4 antibody, an anti-HVEM antibody, an anti-BTLA antibody, an anti-GAL9 antibody, an anti-A2AR antibody, an anti-phosphatidylserine antibody, an anti-CD27 antibody, an anti-TNFα antibody, an anti-TREM1 antibody, and an anti-TREM2 antibody; or
  the VEGF inhibitor comprises an anti-VEGF antibody, an anti-VEGF peptide, or a combination thereof.

22. The membrane-cleavable chimeric protein of claim 21, wherein the TGFβ inhibitor is selected from the group consisting of an anti-TGFβ peptide, an anti-TGFβ antibody, a TGFβ-TRAP, and a combination thereof.

23. The membrane-cleavable chimeric protein of claim 7, wherein the transmembrane-intracellular domain and/or transmembrane domain is derived from PDGFR-β, CD8, CD28, CD3 ζ-chain, CD4, 4-1BB, OX40, ICOS, CTLA-4, PD-1, LAG-3, 2B4, LNGFR, NKG2D, EpoR, TNFR2, B7-1, or BTLA.

24. The membrane-cleavable chimeric protein of claim 7, wherein the cell-membrane tethering domain comprises a cell-surface receptor or a cell-membrane-bound portion of the cell-surface receptor.

25. The membrane-cleavable chimeric protein of claim 8, wherein the post-translation modification tag comprises a lipid-anchor domain.

26. The membrane-cleavable chimeric protein of claim 25, wherein the lipid-anchor domain is selected from the group consisting of a GPI lipid-anchor, a myristoylation tag, and a palmitoylation tag.

27. The engineered nucleic acid of claim 10, wherein the promoter is selected from the group consisting of a constitutive promoter, an inducible promoter, a tissue-specific promoter, and a synthetic promoter.

28. The isolated cell of claim 14, wherein the protease is an endogenous protease.

29. The isolated cell of claim 28, wherein the protease is an ADAM17 protease.

30. The isolated cell of claim 15, wherein the antigen-recognizing receptor is a CAR.

\* \* \* \* \*